US006551814B1

(12) United States Patent
Coschigano

(10) Patent No.: US 6,551,814 B1
(45) Date of Patent: Apr. 22, 2003

(54) METHODS FOR BIOREMEDIATION BY DEGRADING TOLUENE

(75) Inventor: Peter W. Coschigano, The Plains, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 09/072,433

(22) Filed: May 4, 1998

Related U.S. Application Data

(60) Provisional application No. 60/046,845, filed on May 5, 1997.

(51) Int. Cl.[7] .............................. B09B 3/00; C12N 1/00; C12N 1/20; C02E 3/00
(52) U.S. Cl. ..................... 435/262.5; 210/600; 210/610; 435/243; 435/248; 435/252.1; 435/252.3; 435/252.4; 435/822
(58) Field of Search ................................ 210/601, 600, 210/606, 632, 198.1, 205, 928, 922, 909, 610; 435/243, 248, 252.1, 252.3, 252.31, 252.4, 262, 262.5, 264, 281, 68.1, 42, 822; 930/10, 200, 240

(56) References Cited

U.S. PATENT DOCUMENTS

| | | | |
|---|---|---|---|
| 4,283,390 A | 8/1981 | Koch et al. .................. | 424/122 |
| 4,683,195 A | 7/1987 | Mullis et al. .................. | 435/6 |
| 4,683,202 A | 7/1987 | Mullis .......................... | 435/91 |
| 4,919,813 A | 4/1990 | Weaver ....................... | 210/603 |
| 4,996,153 A * | 2/1991 | Cadmus et al. ............. | 435/209 |
| 5,017,495 A | 5/1991 | Yen et al. ................. | 435/320.1 |
| 5,037,551 A | 8/1991 | Barkley et al. ............. | 210/603 |
| 5,057,221 A | 10/1991 | Bryant et al. ................ | 210/610 |
| 5,139,945 A * | 8/1992 | Liu ............................. | 435/232 |
| 5,171,684 A | 12/1992 | Yen et al. ................. | 435/252.3 |
| 5,182,199 A | 1/1993 | Hartley ........................ | 435/162 |
| 5,232,596 A | 8/1993 | Castaldi ...................... | 210/603 |
| 5,277,815 A | 1/1994 | Beeman ...................... | 210/605 |
| 5,342,769 A | 8/1994 | Hunter et al. ............... | 435/166 |
| 5,369,031 A * | 11/1994 | Middleditch et al. ........ | 435/284 |
| 5,482,630 A | 1/1996 | Lee et al. .................... | 210/605 |
| 5,512,479 A | 4/1996 | Steffan ...................... | 435/262.5 |
| 5,519,134 A | 5/1996 | Acevedeo et al. .......... | 544/243 |
| 5,543,317 A | 8/1996 | Shields et al. ............ | 435/240.2 |
| 5,554,520 A | 9/1996 | Fowler et al. ............... | 435/165 |
| 5,556,536 A | 9/1996 | Turk .......................... | 210/150 |
| 5,560,737 A | 10/1996 | Schuring et al. ............ | 405/128 |
| 5,571,705 A | 11/1996 | Pierce ........................ | 435/174 |
| 5,585,272 A | 12/1996 | Pierce et al. ............. | 435/262.5 |
| 5,610,061 A | 3/1997 | Pierce ..................... | 435/252.1 |
| 5,610,065 A * | 3/1997 | Kelley et al. ................ | 435/264 |
| 5,849,566 A * | 12/1998 | Dale et al. ................... | 435/262 |

OTHER PUBLICATIONS

Bioremediation of Mixed Harardous Wastes, YES Technologies.
Blattner, et al. Analysis of the *Escherichia coli* genome. IV. DNA sequence of the region from 89.2 to 92.8 minutes. *Nucleic Acids Res.* 21:5408(1993).

Blattner, et al, The complete genome sequence of *Escherichia coli* K–12. *Science* (Wash. D.C.). 277:1453(1997).
Bertoni, et al. "Cloning of the genes for and characterization of the early stages of toluene and o–xylene catabolism in *Pseudomonas stutzer* OX1" *Applied Envir Microbiol* 62:3704–3711 (1996).
Boshart et al., "A Very Strong Enhancer Is Located Upstream of an Immediate Early Gene of Human Cytomegalovirus," *Cell* 41:521–530 (1985).
Coschigano et al., "Identification and sequence analysis of two regulatory genes involved in anaerobic toluene metabolism by strain T1," *Appl. Environ. Microbiol.* 63:652–660 (1997).
Coschigano et al., "Identification and Analysis of Genes Involved in Anaerobic Toluene Metabolism by Strain T1: Putative Role of a Glycine Free Radical," *Appl Environ Microbiol.* 64:1650–1656 (1998).
Coshigano and Young, ASM Abstract Q–406 (1994).
Coshigano and Young, ASM Abstract Q–138 (1995).
Dijkema et al., "Cloning and Expression of The Chromosomal Immune Interferon Gene of The Rat," *EMBO J.* 4:761–767 (1985).
Ditta et al., "Plasmids Related to The Broad Host Range Vector, pRK290, Useful for Gene Cloning and ofr Monitoring Gene Expression," *Plasmid* 13:149–153 (1985).
Doty et al., "Strand Separation and Specific Recombination in Deoxyribonucleic Acids: Physical Chemical Studies," *Proc. Natl. Acad. Sci. USA* 46:461–476 (1960).
Evans, et al., "Metabolites formed during anaerobic transformation of toluene and o–xylene and their proposed relationship to the initial steps of toluene mineralization" *Appl. Environ. Microbiol.* 58:496–501 (1992).
Franklin, et al. "Molecular and functional analysis of the TOL plasmid pWWO form *Pseudomonas putida* and cloning of genes for the entire regulated aromatic ring meta cleavage pathway" *Proc Natl Acad Sci, U.S.A.* 78:7458–7462 (1981).
Frazer et al., "Toluene Metabolism Under Anaerobic Conditions: A Review," *Anaerobe* 1:293–303 (1995).
Frey et al. (1994) "Adenosylmethionine–dependent Synthesis of the Glycyl Radical in Pyruvate Formate–lyase by Abstraction of the Glycine C–2 pro–S Hydrogen Atom," *J. Biol. Chem.* 269:12432–12437.
Fries et al., "Isolation, characterization and distribution of denitrifying toluene degraders from a variety of habitats," *Appl. Environ. Microbiol.* 60:2802–2810 (1994).
Furukawa, et al. "SAL–TOL in vivo recombinant plasmid pKF439" *J Bact* 162:1325–1328 (1985).

(List continued on next page.)

Primary Examiner—David M. Naff
Assistant Examiner—Deborah K. Ware
(74) Attorney, Agent, or Firm—Medlen & Carroll, LLP

(57) ABSTRACT

Compositions and methods for the degradation of compounds contained in a liquid or solid waste stream are provided. Genes encoding toluene-degrading enzymes are also provided. The enzymes have homology to the *E. coli* pyruvate formate lyase and pyruvate formate lyase activator.

8 Claims, 65 Drawing Sheets

OTHER PUBLICATIONS

Ghosal, et al. "Nucleotide sequence and expression of gene nahH of plasmid NAH7 and homology with gene xylE of TOL pWWO" *Gene* 55:19–28 (1987).

Gorman et al., "The Rous Sarcoma Virus Long Terminal Repeat is a Strong Promoter When Introduced Into A Variety of Eukaryotic Cells By DNA–mediated Transfection," *Proc. Natl. Acad. Sci. USA*, 79:6777–6781 (1982).

Harayama, et al. "Characterization of five genes in the upper–pathway operon of TOL Plasmid pWWO from *Pseudomonas putida* and identification of the gene products" *J Bact* 171:5048–5055 (1989).

Harayama, et al. "Gene order of the TOL catabolic plasmid upper pathway operon and oxidation of both toluene and benzyl by the alcohol by xylA product" *J Bact* 167:455–461 (1986).

Hirose, et al. "Construction of hybrid biphenyl (bph) and toluene (tod) genes for functional analysis of aromatic ring dioxygenases" *Gene* 138:27–33 (1994).

Horn, et al. "DNA sequence determination of the TOL plasmid (pWWO) xylGFJ genes of *Pseudomonas putida*: implications for the evolution of aromatic catabolism" *Mol. Microbiology* 5:2459–2474 (1991).

Inouye, et al. "Molecular cloning of regulatory gene xylR and operator–promoter regions of the xylABC and XylDEGF operons of the TOL plasmid" *J Bact* 155:1192–1199 (1983).

Inouye, et al. "Molecular cloning of TOL genes xylB and xylE in *Escherichia coli*" *J Bact* 145:1137–1143 (1981).

Inouye, et al. "Overproduction of the xylS gene product and activation of the xylDLEGF operon on the TOL plasmid" *J Bact* 169:3587 (1987).

Johnson and Olsen "Nucleotide sequence analysis of genes encoding a toluene/benzene–2–monooxygenase from Pseudomonas sp. strain JS150" *Applied Envir Microbiol* 61:3336–3346 (1995).

Keen et al. (1988) "Improved broad–host–range plasmids for DNA cloning in Gram–negative bacteria," *Gene* 70:191–197.

Keil et al., "Molecular analysis of regulatory ans structural xyl genes of the TOL plasmid pWW53–4" *J. General Microbiology* 133: 114 1158 (1987).

Kim et al., "Use of The Human Elongation Factor 1 α Promoter as a Versatile and Efficient Expression System," *Gene* 91:217–223 (1990).

Maniatis et al., "Regulation of Inducible and Tissue–Specific Gene Expression," *Science* 236:1237–1244 (1987).

Marmur and Lane, "Strand Separation and Specific Recombination in Deoxyribonucleic Acids: Biological Studies," *Proc. Natl. Acad. Sci. USA* 46:453–461 (1960).

Mizushima and Nagata, "pEF–BOS, a Powerful Mammalian Expression Vector," *Nuc. Acids Res.*, 18:5322 (1990).

Ogiwara et al. "Construction and analysis of a profile library characterizing groups of structurally known proteins," *Protein Sci.* 5:1991 (1996) abstract.

Olsen, et al. "A novel toluene–3–monooxygenase pathway cloned from *Pseudomonas pickettii* PKO1" *J Bact* 176:3749–3756 (1994).

Pérez–Martin and Lorenzo "VTR expression cassettes for engineering conditional phenotypes in Pseudomonas: activity on the Pu promoter of the TOL plasmid under limiting concentrations of the XylR activator protein" *Gene* 172:81–86 (1996).

Plaga et al., "Catalytic–site mapping of pyruvate formate lyase," *Eur. J. Biochem.* 178:445–450 (1988).

Rabus et al., "Complete oxidation of toluence under strictly anoxic conditions by a new sulfate–reducing bacterium," *Appl. Environ. Microbiol.* 59:1444–1451 (1993).

Ramos, et al. "Altered effector specificities in regulators of gene expression: TOL plasmid xylS mutants and their use to engineer expansion of the range of aromatics degraded by bacteria" *Proc Natl Acad Sci, U.S.A.* 83:8467–8471 (1986).

Rödel et al., "Primary structure of *Escherichia coli* pyruvate formate–lyase and pyruvate formate–lyase activating enzyme deduced from the DNA nucleotide sequences," *Eur. J. Biochem.* 177:153–158 (1988).

Sayler, et al. "Application of DNA–DNA colony hybridization to the detection of catabolic genotypes in environmental samples" *Applied Envir Microbiol* 49:1295–1303 (1985).

Shields, et al. "TOM, a new aromatic degradative plasmid from *Burkholderia* (*Pseudomonas*) *Cepacia* G4" *Applied Envir Microbiol* 61:1352–1356 (1995).

Toluene Fact Sheet, Agency for Toxic Substances and Disease Registry (1995).

Uetsuki et al., "Isolation and Characterization of the Human Chromosomal Gene for Polypeptide Chain ELongation Factor–1α ," *J. Biol. Chem.*, 264:5791–5798 (1989).

Voss et al. , "The Role of Enhancers in the Regulation of Cell–Type–Specific Transcriptional Control," *Trends Biochem. Sci.* 11:287–289 (1986).

Wagner et al., "The free radical in pyruvate formate–lyase is located on glycine–734," *Proc. Natl. Acad. Sci. U.S.A.* 89, 996–1000 (1992).

Wright and Olsen "Self–mobilization and organization of the genes encoding the toluene metabolic pathway of *Pseudomonas mendocina* KR1" *Applied Envir Microbiol* 60:235–242 (1994).

Yen and Karl "Identification of a new gene, tmoF, in the *Pseudomonas mendocina* KR1 gene cluster encoding toluene–4–monooxygenase" *Bact* 174:7253–7261 (1992).

Zylstra and Gibson "Toluene degradation by *Pseudomonas putida* F1" *J. Biol. Chem.* 264:14940–14946 (1989).

\* cited by examiner

FIG. 2A

```
              P  A  F  M  E  A  E  V  D  V  E  K  Y  E  R  I  V  L  N  L  L  S  N  A  F  K  F  S  P  D  G  G  R
1801    ATTCGCTGTTCGTTGAGTGCCGACTGGTGAAGAATCTTGCTCGGAAGAATTCAGGAGTATTCAGTGTCCTGGAATTCCAGCTGATCAACAGAGTGAAATTTCG    1900
              I  R  C  S  L  S  A  T  G  V  G  D  I  K  S  R  Q  F  G  G  T  G  L  G  L  T  I  V  K  D  F  V  C  L  H  G  G  V
1901    GCCGGTTTCGGCAAGGTGGGGATATCAAGTCCCGGAGGCGGAACGTTTGGCGGTACGGGCCTTGGACTATTGTGAAGGATTTGTGTCCCTGCATGGGGGGT    2000
              R  F  R  Q  G  G  D  I  K  S  R  Q  F  G  G  T  G  L  G  L  T  I  V  K  D  F  V  C  L  H  G  G  V
2001    TGTGGTCGTTCAGAGACGCTCCCGGAGGCGGGGCTTTATTCAGATGAATGCCGCTTCGGGTGTATGTAAATGCGGTTGCAAAGGCT    2100
              V  V  V  S  D  A  P  G  G  G  A  L  F  Q  I  E  L  P  R  N  A  P  S  G  V  V  N  A  V  A  K  A
2101    GGTGAATTAAGCCCTACATCTTTTGATATCAGCGCATGGGGACCTGGAGGGCGAGTCGAAATGACAAGCGCCAGTGAGCCAGTGATCGTCCTCGGATCC    2200
              G  E  L  S  P  T  S  F  D  I  S  A  W  G  L  E  G  R  S  E  W  T  S  A  E  G  A  S  D  R  P  R  I  L
2201    TGATTGTCGAAGATAACGTCGATATGCGCTGTTTTATAGGAGGGCGTCTCATTGACGAGTATCAGATCAGTGTTGCCGCTGATGGTGAGCAGGCACTGGA    2300
              I  V  E  D  N  V  D  M  R  C  F  I  G  R  V  L  I  D  E  Y  Q  I  S  V  A  A  D  G  E  Q  A  L  E
2301    GCTTATTACCTCCTCATCCCCCGGATCTGGTGCTTTCCCAAAGGTCAGCGATGATCAAGTCAGCTCTGGTTGAGAATAAATTGCTGCCGAGTCGGTTCAAGATTATGTTGTCAAGCCAT    2400
              L  I  T  S  S  P  P  D  L  V  I  T  D  L  M  M  P  K  V  S  G  L  L  V  K  E  M  R  S  R  G  D
2401    CTAGCCAATGTTCCTATACTCGTGCTTTCGGCCAAGGCGGATGATGGTTGAGAATAAATTGCTGCCGAGTCGGTTCAAGATTATGTTGTCAAGCCAT    2500
              L  A  N  V  P  I  L  V  L  S  A  K  A  D  D  G  L  R  I  K  L  L  A  E  S  V  Q  D  Y  V  K  P  F
2501    TCTCGGCTACGGAGTTGCGAGATCGGCAGATCATCGACAATGCCAGGAGTTGCAGCGAAGTTGCAGCGAATCTGAGTCCCGCCAGTCTATGAG    2600
              S  A  T  E  L  R  A  R  V  R  N  L  V  T  M  K  R  A  D  A  L  Q  R  A  L  D  S  Q  S  D  D  L
2601    ATCGCCAATTGACTCGGCAGATCATCGACAATGCCAGGAGTTGCAGCGAAGTTGCAGCGAATCTGAGTCCCGCCAGTCTATGAG    2700
              S  Q  L  T  R  Q  I  I  D  N  R  Q  E  L  Q  R  S  H  D  A  L  Q  E  S  E  S  R  W  R  A  V  Y  E
2701    AATTCTGCTGCAGTATTGTGTTGACAAATTGGACGGCTTGATTTGTCTGCGAATCAAGCATTCAAAAAATGGTTGGCTATGCCGAGGATGAGTTGC    2800
              N  S  A  A  G  I  V  L  T  N  L  D  G  L  I  L  S  A  N  Q  A  F  Q  K  M  V  G  Y  A  E  D  E  L  R
2801    GGGTGATTGAAATATCGGATCTCGTCCCCGAACATGATGTCCCGAACATGATGTCCCGCGTTCAAATCTGATCAGTGCCCGCGCTCGACGACTATCAAGT    2900
              V  I  E  I  S  D  L  V  P  E  H  D  R  E  K  I  R  S  R  V  S  N  L  I  S  G  R  V  D  D  Y  Q  V
2901    GCAAAGGCAATGCCGACGAAAGGACGCCGAATGATGTGGGCAAGATGATGGCAATGTGGGCAATGCTGGCCAATCAGTCCTCATACCTGGGCTGCTCATACCTGGCTGCTCATACCTGGCAAGGAGAGTCATCATGGCCTGATCATGGCCTG    3000
              Q  R  Q  C  R  R  K  D  G  R  M  M  A  N  V  R  A  S  L  I  P  G  L  A  N  Q  S  P  M  V  V  R
3001    ATTTTTGATGACATTACCGAAAGATTACGAACTGAAGCTGAACGACAGAGTCATGCTGTTACCGAGTCAAGGGAAAAGTGACCAGAGTCAAGGGAAAAGTTGACCAGAGTCATGCTGTTACCGCCAATGGGAGAAT    3100
```

```
         EcoR I                          BspLU11 I
                                         |
      GAATTCATCGTCGGCTACCACGCCGAAGATCCCAACATGTTCCCGCTGTATCCCGAACTGTCCCACATGG
      ├──┼──┼──┼──┼──┼──┼──┼──┼──┼──┼──┼──┼──┼──┼──┼──┼──┼──┼──┼──┼──┤  70
      CTTAAGTAGCAGCCGATGGTGCGGCTTCTAGGGTTGTACAAGGGCGACATAGGGCTTGACAGGGTGTACC
```

Glu Phe Ile Val Gly Tyr His Ala Glu Asp Pro Asn Met Phe Pro Leu Tyr Pro Glu Leu Ser His Met
  Asn Ser Ser Ser Ala Thr Thr Pro Lys Ile Pro Thr Cys Ser Arg Cys Ile Pro Asn Cys Pro Thr Trp
Arg Ile His Arg Arg Leu Pro Arg Arg Arg Ser Gln His Val Pro Ala Val Ser Arg Thr Val Pro His Gly
├──┼──┼──┼──┼──┼──┼──┼──┼──┼──┼──┼──┼──┼──┼──┼──┼──┼──┼──┼──┼──┤
Ser Asn Met Thr Pro • Trp Ala Ser Ser Gly Leu Met Asn Gly Ser Tyr Gly Ser Ser Asp Trp Met Ala
  Phe Glu Asp Asp Ala Val Val Gly Phe Ile Gly Val His Glu Arg Gln Ile Gly Phe Gln Gly Val His
    Ile • Arg Arg Ser Gly Arg Arg Leu Asp Trp Cys Thr Gly Ala Thr Asp Arg Val Thr Gly Cys Pro

```
                                           NgoM I
                                           Eag I
                         BspM I            Eco52 I
             RleA I      Bsg I             Nae I      Bgl I
             |           |                 |          |
      CCGTGCAGGACTACCTGCGGAGCGACTACTCGCCGCAGCCGGCCGACGAGGCGGCGGCGATCAATGAATA
      ├──┼──┼──┼──┼──┼──┼──┼──┼──┼──┼──┼──┼──┼──┼──┼──┼──┼──┼──┼──┼──┤ 140
      GGCACGTCCTGATGGACGCCTCGCTGATGAGCGGCGTCGGCCGGCTGCTCCGCCGCCGCTAGTTACTTAT
```

Ala Val Gln Asp Tyr Leu Arg Ser Asp Tyr Ser Pro Gln Pro Ala Asp Glu Ala Ala Ala Ile Asn Glu Tyr
  Pro Cys Arg Thr Thr Cys Gly Ala Thr Thr Arg Arg Ser Arg Pro Thr Arg Arg Arg Arg Ser Met Asn
    Arg Ala Gly Leu Pro Ala Glu Arg Leu Leu Ala Ala Ala Gly Arg Arg Gly Gly Gly Asp Gln • Ile
├──┼──┼──┼──┼──┼──┼──┼──┼──┼──┼──┼──┼──┼──┼──┼──┼──┼──┼──┼──┼──┤
  Thr Cys Ser • Arg Arg Leu Ser • Glu Gly Cys Gly Ala Ser Ser Ala Ala Ala Ile Leu Ser Tyr
Gly His Leu Val Val Gln Pro Ala Val Val Arg Arg Leu Arg Gly Val Leu Arg Arg Asp Ile Phe Val
  Arg Ala Pro Ser Gly Ala Ser Arg Ser Ser Ala Ala Ala Pro Arg Arg Pro Pro Pro Ser • His Ile

```
              ApaB I                                            Eag I
              |PstI                                             |Eco52 I
              ||                                                ||
      CTGGAAGCCGCATAGCCTGCAGAGCAAGTGTCAGCCCTATTTCGATCCGGCAGACCTCGGCCGCATGTAT
      ├──┼──┼──┼──┼──┼──┼──┼──┼──┼──┼──┼──┼──┼──┼──┼──┼──┼──┼──┼──┼──┤ 210
      GACCTTCGGCGTATCGGACGTCTCGTTCACAGTCGGGATAAAGCTAGGCCGTCTGGAGCCGGCGTACATA
```

Trp Lys Pro His Ser Leu Gln Ser Lys Cys Gln Pro Tyr Phe Asp Pro Ala Asp Leu Gly Arg Met Tyr
Thr Gly Ser Arg Ile Ala Cys Arg Ala Ser Val Ser Pro Ile Ser Ile Arg Gln Thr Ser Ala Ala Cys Ile
  Leu Glu Ala Ala • Pro Ala Glu Gln Val Ser Ala Leu Phe Arg Ser Gly Arg Pro Arg Pro His Val
├──┼──┼──┼──┼──┼──┼──┼──┼──┼──┼──┼──┼──┼──┼──┼──┼──┼──┼──┼──┼──┤
  Gln Phe Gly Cys Leu Arg Cys Leu Leu His • Gly • Lys Ser Gly Ala Ser Arg Pro Arg Met Tyr
    Pro Leu Arg Met Ala Gln Leu Ala Leu Thr Leu Gly Ile Glu Ile Arg Cys Val Glu Ala Ala His Ile
Ser Ser Ala Ala Tyr Gly Ala Ser Cys Thr Asp Ala Arg Asn Arg Asp Pro Leu Gly Arg Gly Cys Thr Asp

FIG. 5A

```
                Bce83 I                                                                    Pvu I
CGAGCCCTGCAAGGGCCTCAAGGACGCGATGCAGGCGAAATTCTTTACCTTCCTGATCTGTCACGCGATC
                                                                                                    630
GCTCGGGACGTTCCCGGAGTTCCTGCGCTACGTCCGCTTTAAGAAATGGAAGGACTAGACAGTGCGCTAG
```

Glu Pro Cys Lys Gly Leu Lys Asp Ala Met Gln Ala Lys Phe Phe Thr Phe Leu Ile Cys His Ala Ile
 Pro Ser Pro Ala Arg Ala Ser Arg Thr Arg Cys Arg Arg Asn Ser Leu Pro Ser • Ser Val Thr Arg Ser
  Arg Ala Leu Gln Gly Pro Gln Gly Arg Asp Ala Gly Glu Ile Leu Tyr Leu Pro Asp Leu Ser Arg Asp

Ser Gly Gln Leu Pro Arg Leu Ser Ala Ile Cys Ala Phe Asn Lys Val Lys Arg Ile Gln • Ala Ile
 Leu Gly Ala Leu Ala Glu Leu Val Arg His Leu Arg Phe Glu Lys Gly Glu Gln Asp Thr Val Arg Asp
  Arg Ala Arg Cys Pro Gly • Pro Arg Ser Ala Pro Ser Ile Arg • Arg Gly Ser Arg Asp Arg Ser Arg

```
                     EcoP15 I
         Eco47 III    BsrB I                    Bbs I                    BsaX I  Stu I         Sal I
GAGCGCTACGCGAGCGGCTACGCCCAGAAGGAAGACACCCTGCTGTGGCCGTACTACAAGGCCTCCGTCG
                                                                                                    700
CTCGCGATGCGCTCGCCGATGCGGGTCTTCCTTCTGTGGGACGACACCGGCATGATGTTCCGGAGGCAGC
```

Glu Arg Tyr Ala Ser Gly Tyr Ala Gln Lys Glu Asp Thr Leu Leu Trp Pro Tyr Tyr Lys Ala Ser Val
 Ser Ala Thr Arg Ala Ala Thr Pro Arg Arg Lys Thr Pro Cys Cys Gly Arg Thr Thr Arg Pro Pro Ser
  Arg Ala Leu Arg Glu Arg Leu Arg Pro Glu Gly Arg His Pro Ala Val Ala Val Leu Gln Gly Leu Arg Arg

Ser Arg • Ala Leu Pro • Ala Trp Phe Ser Ser Val Arg Ser His Gly Tyr • Leu Ala Glu Thr Thr
 Leu Ala Val Arg Ala Ala Val Gly Leu Leu Phe Val Gly Gln Gln Pro Arg Val Val Leu Gly Gly Asp
  Ala Ser Arg Ser Arg Ser Arg Gly Ser Pro Leu Cys Gly Ala Thr Ala Thr Ser Cys Pro Arg Arg Arg

```
                                                                              Psp1406 I
TCGACAAGAAATTCCAGCCGATGAGCCACATGGATGCGGTGGAACTCGTCGAGATGGAACGTTTGAAGAT
                                                                                                    770
AGCTGTTCTTTAAGGTCGGCTACTCGGTGTACCTACGCCACCTTGAGCAGCTCTACCTTGCAAACTTCTA
```

Val Asp Lys Lys Phe Gln Pro Met Ser His Met Asp Ala Val Glu Leu Val Glu Met Glu Arg Leu Lys Ile
 Ser Thr Arg Asn Ser Ser Arg • Ala Thr Trp Met Arg Trp Asn Ser Ser Arg Trp Asn Val • Arg
  Arg Gln Glu Ile Pro Ala Asp Glu Pro His Gly Cys Gly Gly Thr Arg Arg Asp Gly Thr Phe Glu Asp

Ser Leu Phe Asn Trp Gly Ile Leu Trp Met Ser Ala Thr Ser Ser Thr Ser Ile Ser Arg Lys Phe Ile
 Asp Val Leu Phe Glu Leu Arg His Ala Val His Ile Arg His Phe Glu Asp Leu His Phe Thr Gln Leu Asn
  Arg Cys Ser Ile Gly Ala Ser Ser Gly Cys Pro His Pro Pro Val Arg Arg Ser Pro Val Asn Ser Ser

FIG. 5D

```
                    Eag I
          BamH I    Eco52 I        Bbs I
          |         |              |
CAGCCAAGCGGATCCGCACGGCCGAGCCCTCCATCGTCTTCCGCTATTCCAAGAAGAACCGCGAGAAGAC
++++++++++|++++++++|+++++++++|++++++++|+++++++++|++++++++|+++++++++|   980
GTCGGTTCGCCTAGGCGTGCCGGCTCGGGAGGTAGCAGAAGGCGATAAGGTTCTTCTTGGCGCTCTTCTG
```

Ala Ala Lys Arg Ile Arg Thr Ala Glu Pro Ser Ile Val Phe Arg Tyr Ser Lys Lys Asn Arg Glu Lys Thr
 Gln Pro Ser Gly Ser Ala Arg Pro Ser Pro Pro Ser Ser Ser Ala Ile Pro Arg Arg Thr Ala Arg Arg
  Ser Gln Ala Asp Pro His Gly Arg Ala Leu His Arg Leu Pro Leu Phe Gln Glu Glu Pro Arg Glu Asp
++++++++++|++++++++|+++++++++|++++++++|+++++++++|++++++++|+++++++++|
 Ala Leu Arg Ile Arg Val Ala Ser Gly Glu Met Thr Lys Arg  •  Glu Leu Phe Phe Arg Ser Phe Val
Cys Gly Leu Pro Asp Ala Arg Gly Leu Gly Gly Asp Asp Glu Ala Ile Gly Leu Leu Val Ala Leu Leu Arg
 Leu Trp Ala Ser Gly Cys Pro Arg Ala Arg Trp Arg Arg Gly Ser Asn Trp Ser Ser Gly Arg Ser Ser

```
       Bbs I
       |
GCTGCGCTGGGTTTTCGAGTGCATCCGCGACGGACTCGGCTATCCGTCGATCAAGCACGACGAGATCGGC
++++++++++|++++++++|+++++++++|++++++++|+++++++++|++++++++|+++++++++|   1050
CGACGCGACCCAAAAGCTCACGTAGGCGCTGCCTGAGCCGATAGGCAGCTAGTTCGTGCTGCTCTAGCCG
```

Leu Arg Trp Val Phe Glu Cys Ile Arg Asp Gly Leu Gly Tyr Pro Ser Ile Lys His Asp Glu Ile Gly
Arg Cys Ala Gly Phe Ser Ser Ala Ser Ala Thr Asp Ser Ala Ile Arg Arg Ser Ser Thr Thr Arg Ser Ala
 Ala Ala Leu Gly Phe Arg Val His Pro Arg Arg Thr Arg Leu Ser Val Asp Gln Ala Arg Arg Asp Arg
++++++++++|++++++++|+++++++++|++++++++|+++++++++|++++++++|+++++++++|
 Ser Arg Gln Thr Lys Ser His Met Arg Ser Pro Ser Pro  •  Gly Asp Ile Leu Cys Ser Ser Ile Pro
  Gln Ala Pro Asn Glu Leu Ala Asp Ala Val Ser Glu Ala Ile Arg Arg Asp Leu Val Val Leu Asp Ala
 Ala Ala Ser Pro Lys Arg Thr Cys Gly Arg Arg Val Arg Ser Asp Thr Ser  •  Ala Arg Arg Ser Arg Cys

```
                                            Kas I
                                            |Nar I
                                            ||Ehe I
                            Bgl I           |||Bbe I
                            |               ||||
ACGGAGCAGATGAAGGAATACGCCAAGTTCAGCCTCAACGGCAACGGCGCCACCGACGAGGAAGCCCACA
++++++++++|++++++++|+++++++++|++++++++|+++++++++|++++++++|+++++++++|   1120
TGCCTCGTCTACTTCCTTATGCGGTTCAAGTCGGAGTTGCCGTTGCCGCGGTGGCTGCTCCTTCGGGTGT
```

Thr Glu Gln Met Lys Glu Tyr Ala Lys Phe Ser Leu Asn Gly Asn Gly Ala Thr Asp Glu Glu Ala His
 Arg Ser Arg  •  Arg Asn Thr Pro Ser Ser Ala Ser Thr Ala Thr Ala Pro Pro Thr Arg Lys Pro Thr
  His Gly Ala Asp Glu Gly Ile Arg Gln Val Gln Pro Gln Arg Gln Arg Arg His Arg Arg Gly Ser Pro Gln
++++++++++|++++++++|+++++++++|++++++++|+++++++++|++++++++|+++++++++|
Val Ser Cys Ile Phe Ser Tyr Ala Leu Asn Leu Arg Leu Pro Leu Pro Ala Val Ser Ser Ser Ala Trp Leu
 Arg Leu Leu His Leu Phe Val Gly Leu Glu Ala Glu Val Ala Val Ala Gly Gly Val Leu Phe Gly Val
  Pro Ala Ser Ser Pro Ile Arg Trp Thr  •  Gly  •  Arg Cys Arg Arg Trp Arg Arg Pro Leu Gly Cys

FIG. 5F

```
                                RleA I
                                |
ACTGGGTCAACGTGCTGTGCATGTCGCCCGGCATCCACGGTCGCCGCAAGACGCAAAAAACCCGTTCGGA
++++++++++++++++++++++++++++++++++++++++++++++++++++++++++++++++++++++ 1190
TGACCCAGTTGCACGACACGTACAGCGGGCCGTAGGTGCCAGCGGCGTTCTGCGTTTTTTGGGCAAGCCT
```

Asn Trp Val Asn Val Leu Cys Met Ser Pro Gly Ile His Gly Arg Arg Lys Thr Gln Lys Thr Arg Ser Glu
 Thr Gly Ser Thr Cys Cys Ala Cys Arg Pro Ala Ser Thr Val Ala Ala Arg Arg Lys Lys Pro Val Arg
  Leu Gly Gln Arg Ala Val His Val Ala Arg His Pro Arg Ser Pro Gln Asp Ala Lys Asn Pro Phe Gly
++++++++++++++++++++++++++++++++++++++++++++++++++++++++++++++++++++++
  Gln Thr Leu Thr Ser His Met Asp Gly Pro Met Trp Pro Arg Arg Leu Val Cys Phe Val Arg Glu Ser
 Val Pro Asp Val His Gln Ala His Arg Gly Ala Asp Val Thr Ala Ala Leu Arg Leu Phe Gly Thr Arg Phe
Ser Pro • Arg Ala Thr Cys Thr Ala Arg Cys Gly Arg Asp Gly Cys Ser Ala Phe Phe Gly Asn Pro

```
 EcoP15 I                          BstX I                          BsiW I
 |                                 |                               |
AGGTGGCGGCTCAATCTTCCCGGCCAAGCTGCTGGAAATCTCGCTCAATGACGGCTACGACTGGTCGTAC
++++++++++++++++++++++++++++++++++++++++++++++++++++++++++++++++++++++ 1260
TCCACCGCCGAGTTAGAAGGGCCGGTTCGACGACCTTTAGAGCGAGTTACTGCCGATGCTGACCAGCATG
```

Gly Gly Gly Ser Ile Phe Pro Ala Lys Leu Leu Glu Ile Ser Leu Asn Asp Gly Tyr Asp Trp Ser Tyr
Lys Val Ala Ala Gln Ser Ser Arg Pro Ser Cys Trp Lys Ser Arg Ser Met Thr Ala Thr Thr Gly Arg Thr
 Arg Trp Arg Leu Asn Leu Pro Gly Gln Ala Ala Gly Asn Leu Ala Gln • Arg Leu Arg Leu Val Val
++++++++++++++++++++++++++++++++++++++++++++++++++++++++++++++++++++++
 Pro Pro Pro Glu Ile Lys Gly Ala Leu Ser Ser Ser Ile Glu Ser Leu Ser Pro • Ser Gln Asp Tyr
  Thr Ala Ala • Asp Glu Arg Gly Leu Gln Gln Phe Asp Arg Glu Ile Val Ala Val Val Pro Arg Val
   Leu His Arg Ser Leu Arg Gly Pro Trp Ala Ala Pro Phe Arg Ala • His Arg Ser Arg Ser Thr Thr Arg

FIG. 5G

```
                    Age I
                        Bbs I                        Xmn I              Eco57 I
GCCGACATGCAACTCGGCCCGAAGACCGGTGATCTCTCGTCGCTGAAGTCCTTCGAGGATGTTTGGGAGG
─────┼─────┼─────┼─────┼─────┼─────┼─────┼─────┼─────┼─────┼─────┼─────┼ 1330
CGGCTGTACGTTGAGCCGGGCTTCTGGCCACTAGAGAGCAGCGACTTCAGGAAGCTCCTACAAACCCTCC

Ala Asp Met Gln Leu Gly Pro Lys Thr Gly Asp Leu Ser Ser Leu Lys Ser Phe Glu Asp Val Trp Glu
   Pro Thr Cys Asn Ser Ala Arg Arg Pro Val Ile Ser Arg Arg • Ser Pro Ser Arg Met Phe Gly Arg
  Arg Arg His Ala Thr Arg Pro Glu Asp Arg • Ser Leu Val Ala Glu Val Leu Arg Gly Cys Leu Gly Gly
─────┼─────┼─────┼─────┼─────┼─────┼─────┼─────┼─────┼─────┼─────┼─────┼
  Ala Ser Met Cys Ser Pro Gly Phe Val Pro Ser Arg Glu Asp Ser Phe Asp Lys Ser Ser Thr Gln Ser Ala
   Gly Val His Leu Glu Ala Arg Leu Gly Thr Ile Glu Arg Arg Gln Leu Gly Glu Leu Ile Asn Pro Leu
    Arg Cys Ala Val Arg Gly Ser Ser Arg His Asp Arg Thr Ala Ser Thr Arg Arg Pro His Lys Pro Pro

CTTTCCGCAAGCAGTATCAATATGCGATCAACCTCTGTATCAGCACCAAGGACGTGTCGCGCTACTTCGA
─────┼─────┼─────┼─────┼─────┼─────┼─────┼─────┼─────┼─────┼─────┼─────┼ 1400
GAAAGGCGTTCGTCATAGTTATACGCTAGTTGGAGACATAGTCGTGGTTCCTGCACAGCGCGATGAAGCT

Ala Phe Arg Lys Gln Tyr Gln Tyr Ala Ile Asn Leu Cys Ile Ser Thr Lys Asp Val Ser Arg Tyr Phe Glu
   Leu Ser Ala Ser Ser Ile Asn Met Arg Ser Thr Ser Val Ser Ala Pro Arg Thr Cys Arg Ala Thr Ser
    Phe Pro Gln Ala Val Ser Ile Cys Asp Gln Pro Leu Tyr Gln His Gln Gly Arg Val Ala Leu Leu Arg
─────┼─────┼─────┼─────┼─────┼─────┼─────┼─────┼─────┼─────┼─────┼─────┼
  Lys Arg Leu Cys Tyr • Tyr Ala Ile Leu Arg Gln Ile Leu Val Leu Ser Thr Asp Arg • Lys Ser
  Ser Glu Ala Leu Leu Ile Leu Ile Arg Asp Val Glu Thr Asp Ala Gly Leu Val His Arg Ala Val Glu Leu
    Lys Gly Cys Ala Thr Asp Ile His Ser • Gly Arg Tyr • Cys Trp Pro Arg Thr Ala Ser Ser Arg

Eco47 III    Pst I              Bcg I'
GCAGCGCTTCCTGCAGATGCCTTTCGTGTCCGCAATCGACGACGGCTGCATGGAACTCGGGATGGACGCC
─────┼─────┼─────┼─────┼─────┼─────┼─────┼─────┼─────┼─────┼─────┼─────→ 1470
CGTCGCGAAGGACGTCTACGGAAAGCACAGGCGTTAGCTGCTGCCGACGTACCTTGAGCCCTACCTGCGG

Gln Arg Phe Leu Gln Met Pro Phe Val Ser Ala Ile Asp Asp Gly Cys Met Glu Leu Gly Met Asp Ala
  Ser Ser Ala Ser Cys Arg Cys Leu Ser Cys Pro Gln Ser Thr Thr Ala Ala Trp Asn Ser Gly Trp Thr Pro
   Ala Ala Leu Pro Ala Asp Ala Phe Arg Val Arg Asn Arg Arg Arg Leu His Gly Thr Arg Asp Gly Arg
─────┼─────┼─────┼─────┼─────┼─────┼─────┼─────┼─────┼─────┼─────┼─────→
  Cys Arg Lys Arg Cys Ile Gly Lys Thr Asp Ala Ile Ser Ser Pro Gln Met Ser Ser Pro Ile Ser Ala
   Leu Ala Glu Gln Leu His Arg Glu His Gly Cys Asp Val Val Ala Ala His Phe Glu Pro His Val Gly
    Ala Ala Ser Gly Ala Ser Ala Lys Arg Thr Arg Leu Arg Arg Arg Ser Cys Pro Val Arg Ser Pro Arg Arg
```

FIG. 5H

```
                         Bcg I                                              PshA I              BssS I
                         |                    Van91 I                       |Pvu I              |Msp20 I
                         |                    |                             ||                  ||
         TGCGCCCTGTCCGAGCAGCCCAATGGCTGGCACAACCCGATCACGACGATCGTCGCGGCGAACTCCCTCG
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1540
         ACGCGGGACAGGCTCGTCGGGTTACCGACCGTGTTGGGCTAGTGCTGCTAGCAGCGCCGCTTGAGGGAGC

Cys Ala Leu Ser Glu Gln Pro Asn Gly Trp His Asn Pro Ile Thr Thr Ile Val Ala Ala Asn Ser Leu
             Ala Pro Cys Pro Ser Ser Pro Met Ala Gly Thr Thr Arg Ser Arg Arg Ser Ser Arg Arg Thr Pro Ser
           Leu Arg Pro Val Arg Ala Ala Gln Trp Leu Ala Gln Pro Asp His Asp Asp Arg Arg Gly Glu Leu Pro Arg
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
           Gln Ala Arg Asp Ser Cys Gly Leu Pro Gln Cys Leu Gly Ile Val Val Ile Thr Ala Ala Phe Glu Arg Thr
             Ala Gly Gln Gly Leu Leu Gly Ile Ala Pro Val Val Arg Asp Arg Arg Asp Asp Arg Arg Val Gly Glu
           Arg Gly Thr Arg Ala Ala Trp His Ser Ala Cys Gly Ser  •  Ser Ser Arg Arg Pro Ser Ser Gly Arg

Msc I                                       BseR I
                 |Msp20 I                                    |Xho I
                 ||                                          ||
                 || Xcm I                                    || Sci I
                 ||   |                                      ||   |
         TGGCCATCAAGAAACTGGTATTCGAGGAGAAGAAATACACCCTCGAGCAACTCAGCCAAGCGTTGAAGGC
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1610
         ACCGGTAGTTCTTTGACCATAAGCTCCTCTTCTTTATGTGGGAGCTCGTTGAGTCGGTTCGCAACTTCCG

Val Ala Ile Lys Lys Leu Val Phe Glu Glu Lys Lys Tyr Thr Leu Glu Gln Leu Ser Gln Ala Leu Lys Ala
             Trp Pro Ser Arg Asn Trp Tyr Ser Arg Arg Arg Asn Thr Pro Ser Ser Asn Ser Ala Lys Arg  •  Arg
               Gly His Gln Glu Thr Gly Ile Arg Gly Glu Glu Ile His Pro Arg Ala Thr Gln Pro Ser Val Glu Gly
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
             Ala Met Leu Phe Ser Thr Asn Ser Ser Phe Phe Tyr Val Arg Ser Cys Ser Leu Trp Ala Asn Phe Ala
           His Gly Asp Leu Phe Gln Tyr Glu Leu Leu Leu Phe Val Gly Glu Leu Leu Glu Ala Leu Arg Gln Leu Arg
           Pro Trp  •  Ser Val Pro Ile Arg Pro Ser Ser Ile Cys Gly Arg Ala Val  •  Gly Leu Thr Ser Pro

Kas I
                                                            |Nar I
                                                            ||Ehe I
                                       Sal I                |||Bbe I
                                       |                    ||||
         GAACTGGGAAGGTTTCGAGGAAATGCGCGTCGACTTCAAGCGGGCGCCGAAGTGGGGCAACGACGATGAT
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1680
         CTTGACCCTTCCAAAGCTCCTTTACGCGCAGCTGAAGTTCGCCCGCGGCTTCACCCCGTTGCTGCTACTA

Asn Trp Glu Gly Phe Glu Glu Met Arg Val Asp Phe Lys Arg Ala Pro Lys Trp Gly Asn Asp Asp Asp
             Arg Thr Gly Lys Val Ser Arg Lys Cys Ala Ser Thr Ser Ser Gly Arg Arg Ser Gly Ala Thr Thr Met Ile
           Glu Leu Gly Arg Phe Arg Gly Asn Ala Arg Arg Leu Gln Ala Gly Ala Glu Val Gly Gln Arg Arg  •
         ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
           Phe Gln Ser Pro Lys Ser Ser Ile Arg Thr Ser Lys Leu Arg Ala Gly Phe His Pro Leu Ser Ser Ser
             Val Pro Phe Thr Glu Leu Phe His Ala Asp Val Glu Leu Pro Arg Arg Leu Pro Ala Val Val Ile Ile
           Ser Ser Pro Leu Asn Arg Pro Phe Ala Arg Arg Ser  •  Ala Pro Ala Ser Thr Pro Cys Arg Arg His Asn
```

FIG. 5I

```
                                                              Fsp I
TACGCCGACGGTATCATCACCCGCTTCTACGAGGAAATCATCGGCGGCGAAATGCGCAAGATCACCAACT
----+----+----+----+----+----+----+----+----+----+----+----+----+----+ 1750
ATGCGGCTGCCATAGTAGTGGGCGAAGATGCTCCTTTAGTAGCCGCCGCTTTACGCGTTCTAGTGGTTGA
```

Tyr Ala Asp Gly Ile Ile Thr Arg Phe Tyr Glu Glu Ile Ile Gly Gly Glu Met Arg Lys Ile Thr Asn
 Thr Pro Thr Val Ser Ser Pro Ala Ser Thr Arg Lys Ser Ser Ala Ala Lys Cys Ala Arg Ser Pro Thr
Leu Arg Arg Arg Tyr His His Pro Leu Leu Arg Gly Asn His Arg Arg Arg Asn Ala Gln Asp His Gln Leu
----+----+----+----+----+----+----+----+----+----+----+----+----+----+
 •  Ala Ser Pro Ile Met Val Arg Lys  •  Ser Ser Ile Met Pro Pro Ser Ile Arg Leu Ile Val Leu  •
Val Gly Val Thr Asp Asp Gly Ala Glu Val Leu Phe Asp Asp Ala Ala Phe His Ala Leu Asp Gly Val
 Arg Arg Arg Tyr  •   •  Gly Ser Arg Arg Pro Phe  •  Arg Arg Arg Phe Ala Cys Ser  •  Trp Ser

```
                              BsrG I                              Bsp120 I
ACTCTGGTGGTCCGGTCATGCCGACTGGTCAGGCTGTCGGCCTGTACATGGAAGTCGGTTCGCGCACGGG
----+----+----+----+----+----+----+----+----+----+----+----+----+----+ 1820
TGAGACCACCAGGCCAGTACGGCTGACCAGTCCGACAGCCGGACATGTACCTTCAGCCAAGCGCGTGCCC
```

Tyr Ser Gly Gly Pro Val Met Pro Thr Gly Gln Ala Val Gly Leu Tyr Met Glu Val Gly Ser Arg Thr Gly
 Thr Leu Val Val Arg Ser Cys Arg Leu Val Arg Leu Ser Ala Cys Thr Trp Lys Ser Val Arg Ala Arg
Leu Trp Trp Ser Gly His Ala Asp Trp Ser Gly Cys Arg Pro Val His Gly Ser Arg Phe Ala His Gly
----+----+----+----+----+----+----+----+----+----+----+----+----+----+
Glu Pro Pro Gly Thr Met Gly Val Pro  •  Ala Thr Pro Arg Tyr Met Ser Thr Pro Glu Arg Val Pro
Val Arg Thr Thr Arg Asp His Arg Ser Thr Leu Ser Asp Ala Gln Val His Phe Asp Thr Arg Ala Arg Ala
Ser Gln His Asp Pro  •  Ala Ser Gln Asp Pro Gln Arg Gly Thr Cys Pro Leu Arg Asn Ala Cys Pro

```
 Apa I       Bgl I
CCCCACGCCGGACGGGCGCTTCGGGGGTGAAGCGGCAGACGACGGCGGCATTTCTCCCTACATGGGAACC
----+----+----+----+----+----+----+----+----+----+----+----+----+----+ 1890
GGGGTGCGGCCTGCCCGCGAAGCCCCCACTTCGCCGTCTGCTGCCGCCGTAAAGAGGGATGTACCCTTGG
```

Pro Thr Pro Asp Gly Arg Phe Gly Gly Glu Ala Ala Asp Asp Gly Gly Ile Ser Pro Tyr Met Gly Thr
 Ala Pro Arg Arg Thr Gly Ala Ser Gly Val Lys Arg Gln Thr Thr Ala Ala Phe Leu Pro Thr Trp Glu Pro
Pro His Ala Gly Arg Ala Leu Arg Gly  •  Ser Gly Arg Arg Arg Arg His Phe Ser Leu His Gly Asn
----+----+----+----+----+----+----+----+----+----+----+----+----+----+
Gly Val Gly Ser Pro Arg Lys Pro Pro Ser Ala Ala Ser Ser Pro Pro Met Glu Gly  •  Met Pro Val
 Gly Arg Arg Val Pro Ala Glu Pro Thr Phe Arg Cys Val Val Ala Ala Asn Arg Gly Val His Ser Gly
Gly Trp Ala Pro Arg Ala Ser Arg Pro His Leu Pro Leu Arg Arg Arg Cys Lys Glu Arg Cys Pro Phe Arg

FIG. 5J

```
                                                          Eco47 III
                                                          |
CAGCGCGAACCCGAGAAGCACCATGATCTTATCGTGCGCGTTTCCGGCTACAGCGCTCGGTTCGTAGACA
++++++++++++++++++++++++++++++++++++++++++++++++++++++++++++++++++++++ 2170
GTCGCGCTTGGGCTCTTCGTGGTACTAGAATAGCACGCGCAAAGGCCGATGTCGCGAGCCAAGCATCTGT
```

Gln Arg Glu Pro Glu Lys His His Asp Leu Ile Val Arg Val Ser Gly Tyr Ser Ala Arg Phe Val Asp
   Ser Ala Asn Pro Arg Ser Thr Met Ile Leu Ser Cys Ala Phe Pro Ala Thr Ala Leu Gly Ser • Thr
   Ala Ala Arg Thr Arg Glu Ala Pro • Ser Tyr Arg Ala Arg Phe Arg Leu Gln Arg Ser Val Arg Arg His

Cys Arg Ser Gly Ser Phe Cys Trp Ser Arg Ile Thr Arg Thr Glu Pro • Leu Ala Arg Asn Thr Ser Met
  Leu Ala Phe Gly Leu Leu Val Met Ile Lys Asp His Ala Asn Gly Ala Val Ala Ser Pro Glu Tyr Val
    Ala Arg Val Arg Ser Ala Gly His Asp • Arg Ala Arg Lys Arg Ser Cys Arg Glu Thr Arg Leu Cys

```
                                                          Xho I
                                                        [ Sci I
                                                        | |
TTCCGACCTATGGGCAGAACACCATCATCGCCCGTCAGGAACAGGATTTCAGCGCATCCGATCTCGAGTT
++++++++++++++++++++++++++++++++++++++++++++++++++++++++++++++++++++++ 2240
AAGGCTGGATACCCGTCTTGTGGTAGTAGCGGGCAGTCCTTGTCCTAAAGTCGCGTAGGCTAGAGCTCAA
```

Ile Pro Thr Tyr Gly Gln Asn Thr Ile Ile Ala Arg Gln Glu Gln Asp Phe Ser Ala Ser Asp Leu Glu Phe
  Phe Arg Pro Met Gly Arg Thr Pro Ser Ser Pro Val Arg Asn Arg Ile Ser Ala His Pro Ile Ser Ser
    Ser Asp Leu Trp Ala Glu His His Arg Pro Ser Gly Thr Gly Phe Gln Arg Ile Arg Ser Arg Val

Gly Val • Pro Cys Phe Val Met Met Ala Arg • Ser Cys Ser Lys Leu Ala Asp Ser Arg Ser Asn
Asn Arg Gly Ile Pro Leu Val Gly Asp Asp Gly Thr Leu Phe Leu Ile Glu Ala Cys Gly Ile Glu Leu Glu
  Glu Ser Arg His Ala Ser Cys Trp • Arg Gly Asp Pro Val Pro Asn • Arg Met Arg Asp Arg Thr

```
    Bce83 I
    |
CCTAAACGTCGAAATCTAGGACAAGCCACTCAAGGGGGGCAGCATCCCGTCCCCCTTTACCTTACGGTTG
++++++++++++++++++++++++++++++++++++++++++++++++++++++++++++++++++++++ 2310
GGATTTGCAGCTTTAGATCCTGTTCGGTGAGTTCCCCCCGTCGTAGGGCAGGGGGAAATGGAATGCCAAC
```

Leu Asn Val Glu Ile • Asp Lys Pro Leu Lys Gly Gly Ser Ile Pro Ser Pro Phe Thr Leu Arg Leu
Ser • Thr Ser Lys Ser Arg Thr Ser His Ser Arg Gly Ala Ala Ser Arg Pro Pro Leu Pro Tyr Gly Cys
  Pro Lys Arg Arg Asn Leu Gly Gln Ala Thr Gln Gly Gly Gln His Pro Val Pro Leu Tyr Leu Thr Val

Arg Phe Thr Ser Ile • Ser Leu Gly Ser Leu Pro Pro Leu Met Gly Asp Gly Lys Val Lys Arg Asn
   • Val Asp Phe Asp Leu Val Leu Trp Glu Leu Pro Ala Ala Asp Arg Gly Gly Lys Gly • Pro Gln
Gly Leu Arg Arg Phe Arg Pro Cys Ala Val • Pro Pro Cys Cys Gly Thr Gly Arg • Arg Val Thr Ala

FIG. 5L

```
CACGAAAAAACATGGAGGGCAGCAACATGGAAACAGGACAGAATTTGCAAAACCAGCCGCATACCGAGGT
                                                                      2380
GTGCTTTTTTGTACCTCCCGTCGTTGTACCTTTGTCCTGTCTTAAACGTTTTGGTCGGCGTATGGCTCCA
```

His Glu Lys Thr Trp Arg Ala Ala Thr Trp Lys Gln Asp Arg Ile Cys Lys Thr Ser Arg Ile Pro Arg
  Thr Lys Lys His Gly Gly Gln Gln His Gly Asn Arg Thr Glu Phe Ala Lys Pro Ala Ala Tyr Arg Gly
  Ala Arg Lys Asn Met Glu Gly Ser Asn Met Glu Thr Gly Gln Asn Leu Gln Asn Gln Pro His Thr Glu Val

Cys Ser Phe Val His Leu Ala Ala Val His Phe Cys Ser Leu Ile Gln Leu Val Leu Arg Met Gly Leu His
  Val Phe Phe Cys Pro Pro Cys Cys Cys Pro Phe Leu Val Ser Asn Ala Phe Gly Ala Ala Tyr Arg Pro
  Arg Phe Phe Met Ser Pro Leu Leu Met Ser Val Pro Cys Phe Lys Cys Phe Trp Gly Cys Val Ser Thr

```
GGGTACGGCGAGGCCGTGCCGGAGTTGCAAATGGCAAACCCCCGACCCCACCGATCCGCACCGTGGGCAA
                                                                      2450
CCCATGCCGCTCCGGCACGGCCTCAACGTTTACCGTTTGGGGGCTGGGGTGGCTAGGCGTGGCACCCGTT
```

Trp Val Arg Arg Gly Arg Ala Gly Val Ala Asn Gly Lys Pro Pro Thr Pro Pro Ile Arg Thr Val Gly Asn
  Gly Tyr Gly Glu Ala Val Pro Glu Leu Gln Met Ala Asn Pro Arg Pro His Arg Ser Ala Pro Trp Ala
  Gly Thr Ala Arg Pro Cys Arg Ser Cys Lys Trp Gln Thr Pro Asp Pro Thr Asp Pro His Arg Gly Gln

Thr Arg Arg Pro Arg Ala Pro Thr Ala Phe Pro Leu Gly Gly Val Gly Gly Ile Arg Val Thr Pro Leu
  Pro Tyr Pro Ser Ala Thr Gly Ser Asn Cys Ile Ala Phe Gly Arg Gly Trp Arg Asp Ala Gly His Ala Ile
  Pro Val Ala Leu Gly His Arg Leu Gln Leu His Cys Val Gly Ser Gly Val Ser Gly Cys Arg Pro Cys

|BsrD I    |Taq II'   |Nco I                              |Bpu10 I   |Bpm I
|          |          |                                   |          |
```
TGCACCGCCAACCGGCACGCCATGGGTGGCGTCTGGAAACGCTGGCTTAGGGACGTTGAAAACACGACCT
                                                                      2520
ACGTGGCGGTTGGCCGTGCGGTACCCACCGCAGACCTTTGCGACCGAATCCCTGCAACTTTTGTGCTGGA
```

Ala Pro Pro Thr Gly Thr Pro Trp Val Ala Ser Gly Asn Ala Gly Leu Gly Thr Leu Lys Thr Arg Pro
Met His Arg Gln Pro Ala Arg His Gly Trp Arg Leu Glu Thr Leu Ala • Gly Arg • Lys His Asp Leu
  Cys Thr Ala Asn Arg His Ala Met Gly Gly Val Trp Lys Arg Trp Leu Arg Asp Val Glu Asn Thr Thr

Ala Gly Gly Val Pro Val Gly His Thr Ala Asp Pro Phe Ala Pro Lys Pro Val Asn Phe Val Arg Gly
    Cys Arg Trp Gly Ala Arg Trp Pro His Arg Arg Ser Val Ser Ala • Pro Arg Gln Phe Cys Ser Arg
    His Val Ala Leu Arg Cys Ala Met Pro Pro Thr Gln Phe Arg Gln Ser Leu Ser Thr Ser Phe Val Val Gln

FIG. 5M

```
                EcoN I
                  BspM I
                    BssS I                              Tth111 I        Bpm I
G TCCAGGCACGAGGAAGGCAAACTAAGTTTCCGCGACCACGTCTGAACACCGGACAGACGTGGTTCACC
                                                                              2590
CGAGGTCCGTGCTCCTTCCGTTTGATTCAAAGGCGCTGGTGCAGACTTGTGGCCTGTCTGCACCAAGTGG
```

Ala Pro Gly Thr Arg Lys Ala Asn • Val Ser Ala Thr Thr Ser Glu His Arg Thr Asp Val Val His
 Leu Gln Ala Arg Gly Arg Gln Thr Lys Phe Pro Arg Pro Arg Leu Asn Thr Gly Gln Thr Trp Phe Thr
  Cys Ser Arg His Glu Glu Gly Lys Leu Ser Phe Arg Asp His Val • Thr Pro Asp Arg Arg Gly Ser Pro

Ala Gly Pro Val Leu Phe Ala Phe • Thr Glu Ala Val Val Asp Ser Cys Arg Val Ser Thr Thr • Arg
 Ser Trp Ala Arg Pro Leu Cys Val Leu Asn Gly Arg Gly Arg Arg Phe Val Pro Cys Val His Asn Val
  Glu Leu Cys Ser Ser Pro Leu Ser Leu Lys Arg Ser Trp Thr Gln Val Gly Ser Leu Arg Pro Glu Gly

```
                          Bpm I
                            BspH I
T CCAGACCACTGTAGTGATAGATCATGAAAACCTACTCCAGCGCAAATGGCCTGTTCGTCCCGGAAGTCG
                                                                              2660
A GGTCTGGTGACATCACTATCTAGTACTTTTGGATGAGGTCGCGTTTACCGGACAAGCAGGGCCTTCAGC
```

Leu Gln Thr Thr Val Val Ile Asp His Glu Asn Leu Leu Gln Arg Lys Trp Pro Val Arg Pro Gly Ser Arg
 Ser Arg Pro Leu • • • Ile Met Lys Thr Tyr Ser Ser Ala Asn Gly Leu Phe Val Pro Glu Val
  Pro Asp His Cys Ser Asp Arg Ser • Lys Pro Thr Pro Ala Gln Met Ala Cys Ser Ser Arg Lys Ser

Trp Val Val Thr Thr Ile Ser • Ser Phe Arg Ser Trp Arg Leu His Gly Thr Arg Gly Pro Leu Arg
  Gl. Leu Gly Ser Tyr His Tyr Ile Met Phe Val • Glu Leu Ala Phe Pro Arg Asn Thr Gly Ser Thr Ser
   G y Ser Trp Gln Leu Ser Leu Asp His Phe Gly Val Gly Ala Cys Ile Ala Gln Glu Asp Arg Phe Asp

```
                                        Bcg I      Bcg I'           EcoR V Bcg I'
A TCCCTACTACTATGTAAGTACGGAAAACCAGAGCTTCCTCGATAAATTTGCAAAGATATCGAAAAAGCA
                                                                              2730
T AGGGATGATGATACATTCATGCCTTTTGGTCTCGAAGGAGCTATTTAAACGTTTCTATAGCTTTTTCGT
```

Ser Leu Leu Leu Cys Lys Tyr Gly Lys Pro Glu Leu Pro Arg • Ile Cys Lys Asp Ile Glu Lys Ala
 Asp Pro Tyr Tyr Tyr Val Ser Thr Glu Asn Gln Ser Phe Leu Asp Lys Phe Ala Lys Ile Ser Lys Lys His
  Ile Pro Thr Thr Met • Val Arg Lys Thr Arg Ala Ser Ser Ile Asn Leu Gln Arg Tyr Arg Lys Ser

Asp Arg Ser Ser His Leu Tyr Pro Phe Gly Ser Ser Gly Arg Tyr Ile Gln Leu Ser Ile Ser Phe Ala
  Gly • • • Thr Leu Val Ser Phe Trp Leu Lys Arg Ser Leu Asn Ala Phe Ile Asp Phe Phe Cys
   Ile Gly Val Val Ile Tyr Thr Arg Phe Val Leu Ala Glu Glu Ile Phe Lys Cys Leu Tyr Arg Phe Leu Met

FIG. 5N

```
                Bcg I                              Bbs I
                |                                  |
TCCCGTCAATGTACTGGTGGTCGGCAAACAAGGCTGCGGCAAGTCTTCCCTAGTGCGGCAATACGCCGCC
++++++++++++++++++++++++++++++++++++++++++++++++++++++++++++++++++++++  2800
AGGGCAGTTACATGACCACCAGCCGTTTGTTCCGACGCCGTTCAGAAGGGATCACGCCGTTATGCGGCGG
```

Ser Arg Gln Cys Thr Gly Gly Arg Gln Thr Arg Leu Arg Gln Val Phe Pro Ser Ala Ala Ile Arg Arg
 Pro Val Asn Val Leu Val Val Gly Lys Gln Gly Cys Gly Lys Ser Ser Leu Val Arg Gln Tyr Ala Ala
 Ile Pro Ser Met Tyr Trp Trp Ser Ala Asn Lys Ala Ala Ala Ser Leu Pro • Cys Gly Asn Thr Pro Pro
 ++++++++++++++++++++++++++++++++++++++++++++++++++++++++++++++++++++++
Asp Arg • His Val Pro Pro Arg Cys Val Leu Ser Arg Cys Thr Lys Gly Leu Ala Ala Ile Arg Arg Arg
 Gly Thr Leu Thr Ser Thr Thr Pro Leu Cys Pro Gln Pro Leu Asp Glu Arg Thr Arg Cys Tyr Ala Ala
  Gly Asp Ile Tyr Gln His Asp Ala Phe Leu Ala Ala Ala Leu Arg Gly • His Pro Leu Val Gly Gly

```
                           BsaB I
                           |
GTCAACAGGCTACCCTTGGCGACCTTCCAGATCGGCATCCTGTCGGAGCCGGGGCAACTGTTTGGTGAAT
++++++++++++++++++++++++++++++++++++++++++++++++++++++++++++++++++++++  2870
CAGTTGTCCGATGGGAACCGCTGGAAGGTCTAGCCGTAGGACAGCCTCGGCCCCGTTGACAAACCACTTA
```

Arg Gln Gln Ala Thr Leu Gly Asp Leu Pro Asp Arg His Pro Val Gly Ala Gly Ala Thr Val Trp • Ile
 Val Asn Arg Leu Pro Leu Ala Thr Phe Gln Ile Gly Ile Leu Ser Glu Pro Gly Gln Leu Phe Gly Glu
  Ser Thr Gly Tyr Pro Trp Arg Pro Ser Arg Ser Ala Ser Cys Arg Ser Arg Gly Asn Cys Leu Val Asn
 ++++++++++++++++++++++++++++++++++++++++++++++++++++++++++++++++++++++
  • Cys Ala Val Arg Pro Ser Arg Gly Ser Arg Cys Gly Thr Pro Ala Pro Ala Val Thr Gln His Ile
 Thr Leu Leu Ser Gly Lys Ala Val Lys Trp Ile Pro Met Arg Asp Ser Gly Pro Cys Ser Asn Pro Ser Tyr
 Asp Val Pro • Gly Gln Arg Gly Glu Leu Asp Ala Asp Gln Arg Leu Arg Pro Leu Gln Lys Thr Phe

```
                                                           Mfe I
       Bsa I             Bpm I               Ear I         Mun I
       |                 |                   |             |
ACGCGCTGGAGAACGGGGAGACCCGTTACAAGCAGTTCCTCTTCCCCCAGGCCATCCAGACACCCAATTG
++++++++++++++++++++++++++++++++++++++++++++++++++++++++++++++++++++++  2940
TGCGCGACCTCTTGCCCCTCTGGGCAATGTTCGTCAAGGAGAAGGGGGTCCGGTAGGTCTGTGGGTTAAC
```

Arg Ala Gly Glu Arg Gly Asp Pro Leu Gln Ala Val Pro Leu Pro Pro Gly His Pro Asp Thr Gln Leu
 Tyr Ala Leu Glu Asn Gly Glu Thr Arg Tyr Lys Gln Phe Leu Phe Pro Gln Ala Ile Gln Thr Pro Asn Cys
  Thr Arg Trp Arg Thr Gly Arg Pro Val Thr Ser Ser Ser Ser Pro Arg Pro Ser Arg His Pro Ile
 ++++++++++++++++++++++++++++++++++++++++++++++++++++++++++++++++++++++
 Arg Ala Pro Ser Arg Pro Ser Gly Asn Cys Ala Thr Gly Arg Gly Gly Pro Trp Gly Ser Val Trp Asn
  Ala Ser Ser Phe Pro Ser Val Arg • Leu Cys Asn Arg Lys Gly Trp Ala Met Trp Val Gly Leu Gln
  Val Arg Gln Leu Val Pro Leu Gly Thr Val Leu Leu Glu Glu Glu Gly Leu Gly Asp Leu Cys Gly Ile Ala

FIG. 50

Taq II'
Ear I
BspLU11 I

```
CGTCATCCACCTTGAAGAGATCAATCGCCCCGAGCATCCGAAGGCGTTGAACATGTTGTTCTCCATTCTC
                                                                      3010
GCAGTAGGTGGAACTTCTCTAGTTAGCGGGGCTCGTAGGCTTCCGCAACTTGTACAACAAGAGGTAAGAG
```

Arg His Pro Pro • Arg Asp Gln Ser Pro Arg Ala Ser Glu Gly Val Glu His Val Val Leu His Ser
  Val Ile His Leu Glu Glu Ile Asn Arg Pro Glu His Pro Lys Ala Leu Asn Met Leu Phe Ser Ile Leu
Ala Ser Ser Thr Leu Lys Arg Ser Ile Ala Pro Ser Ile Arg Arg Arg • Thr Cys Cys Ser Pro Phe Ser

Arg • Gly Gly Gln Leu Ser • Asp Gly Arg Ala Asp Ser Pro Thr Ser Cys Thr Thr Arg Trp Glu Arg
  Thr Met Trp Arg Ser Ser Ile Leu Arg Gly Ser Cys Gly Phe Ala Asn Phe Met Asn Asn Glu Met Arg
Asp Asp Val Lys Phe Leu Asp Ile Ala Gly Leu Met Arg Leu Arg Gln Val His Gln Glu Gly Asn Glu

EcoP15 I
EcoICR I
Sac I

```
TCCGATGACCGTCAGGTATGGATGGACGAGCTCGGACTGCTGCAAGTAGCGCCCGGAGTCGTTTTCTTCG
                                                                      3080
AGGCTACTGGCAGTCCATACCTACCTGCTCGAGCCTGACGACGTTCATCGCGGGCCTCAGCAAAAGAAGC
```

Leu Arg • Pro Ser Gly Met Asp Gly Arg Ala Arg Thr Ala Ala Ser Ser Ala Arg Ser Arg Phe Leu Arg
  Ser Asp Asp Arg Gln Val Trp Met Asp Glu Leu Gly Leu Leu Gln Val Ala Pro Gly Val Val Phe Phe
    Pro Met Thr Val Arg Tyr Gly Trp Thr Ser Ser Asp Cys Cys Lys • Arg Pro Glu Ser Phe Ser Ser

Arg His Gly Asp Pro Ile Ser Pro Arg Ala Arg Val Ala Ala Leu Leu Ala Arg Leu Arg Lys Arg Arg
Glu Ser Ser Arg • Thr His Ile Ser Ser Ser Pro Ser Ser Cys Thr Ala Gly Pro Thr Thr Lys Lys Ala
  Gly Ile Val Thr Leu Tyr Pro His Val Leu Glu Ser Gln Gln Leu Tyr Arg Gly Ser Asp Asn Glu Glu

EcoR I

```
CAACGCTCAACGAAGGGTCCGAATTC
                           3106
GTTGCGAGTTGCTTCCCAGGCTTAAG
```

Asn Ala Gln Arg Arg Val Arg Ile
Ala Thr Leu Asn Glu Gly Ser Glu Phe
Gln Arg Ser Thr Lys Gly Pro Asn Ser

Leu Ala • Arg Leu Thr Arg Ile Gly
  Val Ser Leu Ser Pro Asp Ser Asn
Cys Arg Glu Val Phe Pro Gly Phe Glu

FIG. 5P

```
                    ApaB I
                     Sph I
                      Mfe I
                       Mun I  ApaB I     ApaB I          Afl II              BspM I
                       |      |          |               Bst98 I             |
                       |      |          |               |                   |
ATACGGCGACGCAGCGCATGCAATTGATGCACTTGCTGCGGTCGAGCTTAAGCACCTGCTTGCGCCCGGT
├────┼────┼────┼────┼────┼────┼────┼────┼────┼────┼────┼────┼────┼────┤ 70
TATGCCGCTGCGTCGCGTACGTTAACTACGTGAACGACGCCAGCTCGAATTCGTGGACGAACGCGGGCCA

Ile Arg Arg Arg Ser Ala Cys Asn  •  Cys Thr Cys Cys Gly Arg Ala  •  Ala Pro Ala Cys Ala Arg
 Tyr Gly Asp Ala Ala His Ala Ile Asp Ala Leu Ala Ala Val Glu Leu Lys His Leu Leu Ala Pro Gly
  Asn Thr Ala Thr Gln Arg Met Gln Leu Met His Leu Leu Arg Ser Ser Leu Ser Thr Cys Leu Arg Pro Val
├────┼────┼────┼────┼────┼────┼────┼────┼────┼────┼────┼────┼────┼────┤
Ile Arg Arg Arg Leu Ala His Leu Gln His Val Gln Gln Pro Arg Ala  •  Ala Gly Ala Gln Ala Arg Asp
 Tyr Pro Ser Ala Ala Cys Ala Ile Ser Ala Ser Ala Ala Thr Ser Ser Leu Cys Arg Ser Ala Gly Pro
  Val Ala Val Cys Arg Met Cys Asn Ile Cys Lys Ser Arg Asp Leu Lys Leu Val Gln Lys Arg Gly Thr

Age I                                              Ace III
                          |                                                  |
CCATCAAGAAGCTGCGATGCACCGGTTGGGCAGACCGTTGCACACCGTCCGCAGCTCACGCAACGATCAC
├────┼────┼────┼────┼────┼────┼────┼────┼────┼────┼────┼────┼────┼────┤ 140
GGTAGTTCTTCGACGCTACGTGGCCAACCCGTCTGGCAACGTGTGGCAGGCGTCGAGTGCGTTGCTAGTG

Ser Ile Lys Lys Leu Arg Cys Thr Gly Trp Ala Asp Arg Cys Thr Pro Ser Ala Ala His Ala Thr Ile Thr
 Pro Ser Arg Ser Cys Asp Ala Pro Val Gly Gln Thr Val Ala His Arg Pro Gln Leu Thr Gln Arg Ser
  His Gln Glu Ala Ala Met His Arg Leu Gly Arg Pro Leu His Thr Val Arg Ser Ser Arg Asn Asp His
├────┼────┼────┼────┼────┼────┼────┼────┼────┼────┼────┼────┼────┼────┤
 Met Leu Phe Ser Arg His Val Pro Gln Ala Ser Arg Gln Val Gly Asp Ala Ala  •  Ala Val Ile Val
  Gly Asp Leu Leu Gln Ser Ala Gly Thr Pro Cys Val Thr Ala Cys Arg Gly Cys Ser Val Cys Arg Asp Arg
   Trp  •  Ser Ala Ala Ile Cys Arg Asn Pro Leu Gly Asn Cys Val Thr Arg Leu Glu Arg Leu Ser  •

Van91 I
                     |
GGTTGTAATAGTATTCCTTGCCCACCTTTTGGGTTTCAGGGTTGTGGCACCACGGACATCTCAATGGGCA
├────┼────┼────┼────┼────┼────┼────┼────┼────┼────┼────┼────┼────┼────┤ 210
CCAACATTATCATAAGGAACGGGTGGAAAACCCAAAGTCCCAACACCGTGGTGCCTGTAGAGTTACCCGT

Val Val Ile Val Phe Leu Ala His Leu Leu Gly Phe Arg Val Val Ala Pro Arg Thr Ser Gln Trp Ala
   Arg Leu  •   •  Tyr Ser Leu Pro Thr Phe Trp Val Ser Gly Leu Trp His His Gly His Leu Asn Gly Gln
    Gly Cys Asn Ser Ile Pro Cys Pro Pro Phe Gly Phe Gln Gly Cys Gly Thr Thr Asp Ile Ser Met Gly
├────┼────┼────┼────┼────┼────┼────┼────┼────┼────┼────┼────┼────┼────┤
 Thr Thr Ile Thr Asn Arg Ala Trp Arg Lys Pro Lys Leu Thr Thr Ala Gly Arg Val Asp  •  His Ala
   Asn Tyr Tyr Tyr Glu Lys Gly Val Lys Gln Thr Glu Pro Asn His Cys Trp Pro Cys Arg Leu Pro Cys
    Pro Gln Leu Leu Ile Gly Gln Gly Gly Lys Pro Asn  •  Pro Gln Pro Val Val Ser Met Glu Ile Pro Leu
```

FIG. 6A

```
ACCCTTCAAGAACACCGTCGTCCGNAATCCAGGACCGTCTTGCAGGCTAAAACGCTGTATTTCGGTGACT
                                                                      280
TGGGAAGTTCTTGTGGCAGCAGGCNTTAGGTCCTGGCAGAACGTCCGATTTTGCGACATAAAGCCACTGA
```

Thr Leu Gln Glu His Arg Arg Pro ??? Ser Arg Thr Val Leu Gln Ala Lys Thr Leu Tyr Phe Gly Asp
  Pro Phe Lys Asn Thr Val Val Arg Asn Pro Gly Pro Ser Cys Arg Leu Lys Arg Cys Ile Ser Val Thr
   Asn Pro Ser Arg Thr Pro Ser Ser ??? Ile Gln Asp Arg Leu Ala Gly • Asn Ala Val Phe Arg • Leu

Val Arg • Ser Cys Arg Arg Gly ??? Asp Leu Val Thr Lys Cys Ala Leu Val Ser Tyr Lys Pro Ser •
  Gly Lys Leu Phe Val Thr Thr Arg ??? Gly Pro Gly Asp Gln Leu Ser Phe Arg Gln Ile Glu Thr Val
   Gly Glu Leu Val Gly Asp Asp ??? Ile Trp Ser Arg Arg Ala Pro • Phe Ala Thr Asn Arg His Ser

```
                                                                    Bcg I
                                                                    |
AATGGAATTTTCACGTCAGCCCCAGAATCGCATGTTGGAAACGTCATCCGTCCGGTATCAATCGGCTCGC
                                                                      350
TTACCTTAAAAGTGCAGTCGGGGTCTTAGCGTACAACCTTTGCAGTAGGCAGGCCATAGTTAGCCGAGCG
```

• Trp Asn Phe His Val Ser Pro Arg Ile Ala Cys Trp Lys Arg His Pro Ser Gly Ile Asn Arg Leu Ala
 Asn Gly Ile Phe Thr Ser Ala Pro Glu Ser His Val Gly Asn Val Ile Arg Pro Val Ser Ile Gly Ser
  Met Glu Phe Ser Arg Gln Pro Gln Asn Arg Met Leu Glu Thr Ser Ser Val Arg Tyr Gln Ser Ala Arg

His Phe Lys • Thr Leu Gly Leu Ile Ala His Gln Phe Arg • Gly Asp Pro Ile Leu Arg Ser Ala
Leu Pro Ile Lys Val Asp Ala Gly Ser Asp Cys Thr Pro Phe Thr Met Arg Gly Thr Asp Ile Pro Glu Ser
  Ile Ser Asn Glu Arg • Gly Trp Phe Arg Met Asn Ser Val Asp Asp Thr Arg Tyr • Asp Ala Arg

```
      BsaM I    BstB I
      Bsm I    Csp45 I      Bcg I
      |        |            |
TGTGCGAGCATTCATTTCGAACGATTACGCCTCCGCCCAAATCCGGCGGCGGAGGCCGATCCACCACGAC
                                                                      420
ACACGCTCGTAAGTAAAGCTTGCTAATGCGGAGGCGGGTTTAGGCCGCCGCCTCCGGCTAGGTGGTGCTG
```

Val Arg Ala Phe Ile Ser Asn Asp Tyr Ala Ser Ala Gln Ile Arg Arg Arg Pro Ile His His Asp
Leu Cys Glu His Ser Phe Arg Thr Ile Thr Pro Pro Lys Ser Gly Gly Gly Gly Arg Ser Thr Thr Thr
  Cys Ala Ser Ile His Phe Glu Arg Leu Arg Leu Arg Pro Asn Pro Ala Ala Glu Ala Asp Pro Pro Arg

Thr Arg Ala Asn Met Glu Phe Ser • Ala Glu Ala Trp Ile Arg Arg Arg Leu Gly Ile Trp Trp Ser
   His Ser Cys Glu Asn Arg Val Ile Val Gly Gly Gly Leu Asp Pro Pro Pro Arg Asp Val Val Val
 Gln Ala Leu Met • Lys Ser Arg Asn Arg Arg Arg Gly Phe Gly Ala Ala Ser Ala Ser Gly Gly Arg Gly

FIG. 6B

```
                    |EcoP15 I                      |Bgl I
                    |                              |
CATAGAAGTGAATCTTGTAAGGGTTCATTGAACTTCCGCCCTGCTGGCGGCGTCAATAAGTGCGATCACC
++++++++|++++++++|++++++++|++++++++|++++++++|++++++++|++++++++|++++++++  490
GTATCTTCACTTAGAACATTCCCAAGTAACTTGAAGGCGGGACGACCGCCGCAGTTATTCACGCTAGTGG
```

His Arg Ser Glu Ser Cys Lys Gly Ser Leu Asn Phe Arg Pro Ala Gly Gly Val Asn Lys Cys Asp His
  Ile Glu Val Asn Leu Val Arg Val His  •  Thr Ser Ala Leu Leu Ala Ala Ser Ile Ser Ala Ile Thr
Pro  •  Lys  •  Ile Leu  •  Gly Phe Ile Glu Leu Pro Pro Cys Trp Arg Arg Gln  •  Val Arg Ser Pro

Trp Leu Leu Ser Asp Gln Leu Pro Glu Asn Phe Lys Arg Gly Ala Pro Pro Thr Leu Leu His Ser  •  Trp
Met Ser Thr Phe Arg Thr Leu Thr  •  Gln Val Glu Ala Arg Ser Ala Ala Asp Ile Leu Ala Ile Val
  Tyr Phe His Ile Lys Tyr Pro Asn Met Ser Ser Gly Gly Gln Gln Arg Arg  •  Tyr Thr Arg Asp Gly

```
                                      |Mlu113 I
                                      |  Sac II
                                      |   |Uba1221 I
                                      |   ||              |Uba1221 I
                                      |   ||              |
AGTCGGTGTGGTGATTTCCCTCATGTATTCGTTTGTCACCGCGGCTCAGCTAAAATATGCAAATAAA
++++++++|++++++++|++++++++|++++++++|++++++++|++++++++|++++++++>  557
TCAGCCACACCACTAAAGGGAGTACATAAGCAAACAGTGGCGCCGAGTCGATTTTATACGTTTATTT
```

Gln Ser Val Trp  •  Phe Pro Ser Cys Ile Arg Leu Ser Pro Arg Leu Ser  •  Asn Met Gln Ile Lys
  Ser Arg Cys Gly Asp Phe Pro His Val Phe Val Cys His Arg Gly Ser Ala Lys Ile Cys Lys  •
    Val Gly Val Val Ile Ser Leu Met Tyr Ser Phe Val Thr Ala Ala Gln Leu Lys Tyr Ala Asn Lys

Asp Thr His His Asn Gly Glu His Ile Arg Lys Asp Gly Arg Ser Leu  •  Phe Ile Cys Ile Phe
Leu Arg His Pro Ser Lys Gly  •  Thr Asn Thr Gln  •  Arg Pro Glu Ala Leu Ile His Leu Tyr Phe
  Thr Pro Thr Thr Ile Glu Arg Met Tyr Glu Asn Thr Val Ala Ala  •  Ser Phe Tyr Ala Phe Leu

FIG. 6C

```
TutD.T1      MF--------PLYPELSHMAVQDYLRSDYSPQPADEAAAI  32
PflD.coli    MTNRISRLKTALFANTREISLERALLYTASHRQTEGEPVI  40
Pfl.Clostrid MFKQWEGFQDGEWTN---DVNVRDFIQKNY--KEYTGDKSF  36

TutD.T1      ----------------NEYW---------------------  37
PflD.coli    LR---------RAKATAYILEHVEISI--RDEELIAGNRT   69
Pfl.Clostrid LKGPTEKTKKVWDKAVSLILEELKKGILDVDTETISGINS   76

TutD.T1      -KPHS--LQSKCQP---YFDPADLGRM---YQVSSMEAPS   67
PflD.coli    VKPRAGIMSPEMDP---YWLLKELD-------QFPTRPQDR  100
Pfl.Clostrid FKP--GYLDKDNEVIVGFQTDAPLKRITNPFGGIRMAEQS  114

TutD.T1      -----FASG------YNSIVPPY------ETVLEDGLLAR   90
PflD.coli    -----FAISEEDKRIYREELFPYWEKRSMKDFINGQMTDE  135
Pfl.Clostrid LKEYGFKISDEMHNIFTN----YRKTHNQGVF--DAYSEE  148

TutD.T1      IK--------LAEKHIAEAQADMST-FPWNGTKGLDN-IAK  121
PflD.coli    VKAATNTQIFSINQTDKGQGHIIIDYPRLLNHGLGELVAQ  175
Pfl.Clostrid TRIARSAGVLTGLPDAYGRGRIIGDYRRVALYGIDFLI--  187

TutD.T1      IDN---------WKAMVIACKAVISWARRQGRLCKIVAE  151
PflD.coli    MQQHCQQQPENHFYQAALLLLEASQKHILRYAELAETMA  215
Pfl.Clostrid ------QEKKKDLSNLKGDMLDELI-------RLREEVSE  213

TutD.T1      NFET-DPKRQAELLEIADICQRIPAEPCKGLKDAMQAKFF  190
PflD.coli    NC-T-DAQRREELLTIAEISRHNAQHKPQTFWQACQ--LF  251
Pfl.Clostrid QIRALDEIKKMALSYGVDISRPAVNAK-----EAAQFLYF  248

TutD.T1      TFLICHAIERYASGYAQ----KEDTLLWPYYKASVVDKKF  226
PflD.coli    WYM--NIILQYESNASSLSLGRFDQYMLPFYQTSLTQG--  288
Pfl.Clostrid GYLAGVK----ENNGAAMSLGRTSTFLDIYIERDLEQGLI  284
```

FIG. 7A

```
TutD.T1       QPMSHMDAVELVEMERLKISEHGAGKSRAYREIFPGSNDL  266
PflD.coli     EDAAFLK--ELLESLWVKCNDIVLLRSTSSARYFAGFPTG  325
Pfl.Clostrid  TED---EAQEVIDQFIIKLRLVRHLRTPEYNELFAGDPTW  321

TutD.T1       FILTVGGTNAKGEDACNDMTDAILEAAKRI-RTAEPSIVF  305
PflD.coli     YTALLGGLTENGRSAVNVLSFLCLDAYQSV-QLPQPNLGV  364
Pfl.Clostrid  VTESIAGVGIDGRSLVTKNSFRYLHTLINLGSAPEPNMTV  361

TutD.T1       RYSKKNREKTLRWVFECIRDGLGYPSIKHDEIGTEQMKEY  345
PflD.coli     RTNALIDTPFLMKTAETIRFGTGIPQIFNDEVVVP-----  400
Pfl.Clostrid  LWSENLPESFKKFCAE-MSILTDSIQYENDDIMRPI---Y  397

TutD.T1       AKFSLNGNGATDEEAHNWVNVLCMSPGIHGRRKTQKTRSE  385
PflD.coli     ---AFLNRGVSLEDARDYSVVGCVELSIPGR-----TYGL  431
Pfl.Clostrid  GD-------------DYAIACVSAMRVGK---------   415

TutD.T1       GGGSIF----PA-KLLEISLNDGYDWSYADMQLGPKTGDL  420
PflD.coli     HDIAMF----NLLKVMEICLHE-----------NEGN    453
Pfl.Clostrid  -DMQFFGARCNLAKCLLAINGGVD-EKKGIKVVPDIEPI  452

TutD.T1       SS-LKSFEDVWEAFRKQYQYAINLCISTKDVSRYFEQRFL  459
PflD.coli     AA-L-TYEGLLEQIRAKISHYITLMVEGSNICDIGHRDWA  491
Pfl.Clostrid  TDEVLDYEKVKENYFKVLEYMAGLYVNTMNIIHFMHDKY- 492

TutD.T1       QMPFVSAIDDGCMELGMDACALSEQPNGWH----NPITTI  495
PflD.coli     PVPLLSSFISDCLEKGRD---ITDGGARYNFSGVQGIGIA 528
Pfl.Clostrid  ------AYEASQMAL----------HDTKVGRLMAFGIA  514

TutD.T1       VAANSLVAIKKLVFEEKKYTLEQLSQALKANWEGFEEMRV 535
PflD.coli     NLSDSLHALKGMVFEQQRLSFDELLSVLKANFATPEGEKV 568
Pfl.Clostrid  GFSVAADSLSAIRYAKVKPIREN---GITVDFVKEGD--- 549
```

FIG. 7B

```
TutD.T1      D - - - F K R A P K W G N D D D Y A D G I I T R F Y E E I I G G E M R K I T N Y   572
PflD.coli    R A R L I N R F E K Y G N D I D E V D N I S A E L L R H Y C K - E V E K Y Q N P   607
Pfl.Clostrid - - - - - - - F P K Y G N D D D R V D S I A V E I V E K F - S D E L K K H P T Y   580

TutD.T1      S G G P V M P T G Q A V G L Y M E V G S R T G P T P D G R F G G E A A D D G G I   612
PflD.coli    R G G Y F T P G S Y T V S A H V P L G S V V G A T P D G R F A G E Q L A D G G L   647
Pfl.Clostrid R N A K H T L S V L T I T S N V M Y G K K T G T T P D G R K V G E P L A P G A -   620

TutD.T1      S P Y M G T D K K G P T A V L R S V S K V Q K N - - Q K G N L L N Q R L S V P I   650
PflD.coli    S P M L G Q D A Q G P T A V L K S V S K L D N T L L S N G T L L N V K F T P A T   687
Pfl.Clostrid N P M H G R D M E G A L A S L N S V A K V P Y V C C E D G V S N T F S I V P D A   659

TutD.T1      M R S K H G F E I - - W N S Y M K T W H D L N I D H V Q F N V V S T D E M R A A   688
PflD.coli    L E G E A G L R K - - L A D F L R A F T Q L K L Q H I Q F N V V N A D T L R E A   725
Pfl.Clostrid L G N D H D V R I N N L V S I M G G Y F G Q G A H L N V N V L N R E T L I D A   699
                                           *
TutD.T1      Q R E P E K H H D L I V R V S G Y S A R F V D I P T Y G Q N T I I A R Q E Q D F   728
PflD.coli    Q Q R P Q D Y A G L V V R V A G Y S A F F V E L S K E I Q D D I I R R T A H Q L   765
Pfl.Clostrid M N N P D K Y P T L T I R V S G Y A V N F N R L S K D H Q K E V I S R T F H E -   739

TutD.T1      S A S D L E F L N V E I                                                           740
PflD.coli                                                                                     765
Pfl.Clostrid - - - - - - - - - - K L                                                          740
```

FIG. 7C pUC129

ATG ACC ATG ATT ACG CCA AGC TTG CAT GCA TCG GTA CCG GGC CCC
met thr met ile thr pro ser leu his ala ser val pro gly pro /HindIII\/-SphI\      /-NsiI-\      /-KpnI\/-ApaI\

/-XhoI\/-SalI-\      /-ClaI-\/HindIII\/EcoRV\/EcoRI\/-PstI-\/SmaI-\/
CCC TCG AGG TCG ACG GTA TCG ATA AGC TTG ATA TCG AAT TCC TGC AGC CCG GGG
pro ser arg ser thr val ser ile ser leu ile ser asn ser cys ser pro gly /---NotI--\
/---BstXI---\
/-EagI\      /-SacII\      /-SacI-\/EcoRI\

-BamHI\/-SpeI-\/XbaI-\
GAT CCA CTA GTT CTA GAG CGG CCG CCA CCG CGG TGG AGC TCG AAT TCA
asp pro leu val leu glu arg pro pro arg trp ser ser asn ser

```
            Uba1221 I
                    Uba1221 I
                         Mlu113 I
                            Sac II
TTTATTTGCATATTTTAGCTGAGCCGCGGTGACAAACGAATACATGAGGGAAATCACCACACCGACTGGT
├──┼──┼──┼──┼──┼──┼──┼──┼──┼──┼──┼──┼──┼──┼──┼──┼──┼──┼──┼──┼──┤ 70
AAATAAACGTATAAAATCGACTCGGCGCCACTGTTTGCTTATGTACTCCCTTTAGTGGTGTGGCTGACCA
```

Phe Ile Cys Ile Phe • Leu Ser Arg Gly Asp Lys Arg Ile His Glu Gly Asn His His Thr Asp Trp
 Leu Phe Ala Tyr Phe Ser • Ala Ala Val Thr Asn Glu Tyr Met Arg Glu Ile Thr Thr Pro Thr Gly
  Leu Tyr Leu His Ile Leu Ala Glu Pro Arg • Gln Thr Asn Thr • Gly Lys Ser Pro His Arg Leu Val
├──┼──┼──┼──┼──┼──┼──┼──┼──┼──┼──┼──┼──┼──┼──┼──┼──┼──┼──┼──┤
Lys Ile Gln Met Asn • Ser Leu Arg Pro Ser Leu Arg Ile Cys Ser Pro Phe • Trp Val Ser Gln His
 Lys Asn Ala Tyr Lys Leu Gln Ala Ala Thr Val Phe Ser Tyr Met Leu Ser Ile Val Val Gly Val Pro
  • Lys Cys Ile Lys Ala Ser Gly Arg His Cys Val Phe Val His Pro Phe Asp Gly Cys Arg Ser Thr

```
                          Bgl I                             EcoP15 I
GATCGCACTTATTGACGCCGCCAGCAGGGCGGAAGTTCAATGAACCCTTACAAGATTCACTTCTATGGTC
├──┼──┼──┼──┼──┼──┼──┼──┼──┼──┼──┼──┼──┼──┼──┼──┼──┼──┼──┼──┤ 140
CTAGCGTGAATAACTGCGGCGGTCGTCCCGCCTTCAAGTTACTTGGGAATGTTCTAAGTGAAGATACCAG
```

• Ser His Leu Leu Thr Pro Pro Ala Gly Arg Lys Phe Asn Glu Pro Leu Gln Asp Ser Leu Leu Trp Ser
 Asp Arg Thr Tyr • Arg Arg Gln Gln Gly Gly Ser Ser Met Asn Pro Tyr Lys Ile His Phe Tyr Gly
  Ile Ala Leu Ile Asp Ala Ala Ser Arg Ala Glu Val Gln • Thr Leu Thr Arg Phe Thr Ser Met Val
├──┼──┼──┼──┼──┼──┼──┼──┼──┼──┼──┼──┼──┼──┼──┼──┼──┼──┼──┼──┤
Asp Cys Lys Asn Val Gly Gly Ala Pro Arg Phe Asn Leu Ser Gly Lys Cys Ser Glu Ser Arg His Asp
 Ser Arg Val • Gln Arg Arg Trp Cys Pro Pro Leu Glu Ile Phe Gly • Leu Ile • Lys • Pro Arg
  Ile Ala Ser Ile Ser Ala Ala Leu Leu Ala Ser Thr • His Val Arg Val Leu Asn Val Glu Ile Thr

```
                                              BstB I          BsaM I
                                Bcg I         Csp45 I         Bsm I
GTGGTGGATCGGCCTCCGCCGCCGGATTTGGGCGGAGGCGTAATCGTTCGAAATGAATGCTCGCACAGCG
├──┼──┼──┼──┼──┼──┼──┼──┼──┼──┼──┼──┼──┼──┼──┼──┼──┼──┼──┼──┤ 210
CACCACCTAGCCGGAGGCGGCGGCCTAAACCCGCCTCCGCATTAGCAAGCTTTACTTACGAGCGTGTCGC
```

Trp Trp Ile Gly Leu Arg Arg Arg Ile Trp Ala Glu Ala • Ser Phe Glu Met Asn Ala Arg Thr Ala
 Arg Gly Gly Ser Ala Ser Ala Ala Gly Phe Gly Arg Arg Arg Asn Arg Ser Lys • Met Leu Ala Gln Arg
  Val Val Asp Arg Pro Pro Pro Asp Leu Gly Gly Gly Val Ile Val Arg Asn Glu Cys Ser His Ser
├──┼──┼──┼──┼──┼──┼──┼──┼──┼──┼──┼──┼──┼──┼──┼──┼──┼──┼──┼──┤
His His Ile Pro Arg Arg Arg Ile Gln Ala Ser Ala Tyr Asp Asn Ser Ile Phe Ala Arg Val Ala
 Pro Pro Asp Ala Glu Ala Ala Pro Asn Pro Arg Leu Arg Leu Arg Glu Phe His Ile Ser Ala Cys Arg
  Thr Thr Ser Arg Gly Gly Gly Gly Ser Lys Pro Pro Pro Thr Ile Thr Arg Phe Ser His Glu Cys Leu Ser

FIG. 12A

Bcg I'

AGCCGATTGATACCGGACGGATGACGTTTCCAACATGCGATTCTGGGGCTGACGTGAAAATTCCATTAGT
TCGGCTAACTATGGCCTGCCTACTGCAAAGGTTGTACGCTAAGACCCCGACTGCACTTTTAAGGTAATCA  280

Ser Arg Leu Ile Pro Asp Gly • Arg Phe Gln His Ala Ile Leu Gly Leu Thr • Lys Phe His •
 Ala Asp • Tyr Arg Thr Asp Asp Val Ser Asn Met Arg Phe Trp Gly • Arg Glu Asn Ser Ile Ser
  Glu Pro Ile Asp Thr Gly Arg Met Thr Phe Pro Thr Cys Asp Ser Gly Ala Asp Val Lys Ile Pro Leu Val

Leu Arg Asn Ile Gly Ser Pro His Arg Lys Trp Cys Ala Ile Arg Pro Ser Val His Phe Asn Trp • Asp
 Ala Ser Gln Tyr Arg Val Ser Ser Thr Glu Leu Met Arg Asn Gln Pro Gln Arg Ser Phe Glu Met Leu
  Gly Ile Ser Val Pro Arg Ile Val Asn Gly Val His Ser Glu Pro Ala Ser Thr Phe Ile Gly Asn Thr

Acc III
                                                    BspE I

CACCGAAATACAGCGTTTTAGCCTGCAAGACGGTCCTGGATTCCGGACGACGGTGTTCTTGAAGGGTTGC
GTGGCTTTATGTCGCAAAATCGGACGTTCTGCCAGGACCTAAGGCCTGCTGCCACAAGAACTTCCCAACG  350

Ser Pro Lys Tyr Ser Val Leu Ala Cys Lys Thr Val Leu Asp Ser Gly Arg Arg Cys Ser • Arg Val Ala
 His Arg Asn Thr Ala Phe • Pro Ala Arg Arg Ser Trp Ile Pro Asp Asp Gly Val Leu Glu Gly Leu
  Thr Glu Ile Gln Arg Phe Ser Leu Gln Asp Gly Pro Gly Phe Arg Thr Thr Val Phe Leu Lys Gly Cys

Gly Phe Tyr Leu Thr Lys Ala Gln Leu Val Thr Arg Ser Glu Pro Arg Arg His Glu Gln Leu Thr Ala
 • Arg Phe Val Ala Asn • Gly Ala Leu Arg Asp Gln Ile Gly Ser Ser Pro Thr Arg Ser Pro Asn Gly
  Val Ser Ile Cys Arg Lys Leu Arg Cys Ser Pro Gly Pro Asn Arg Val Val Thr Asn Lys Phe Pro Gln

Van91 I                                           Ace III

CCATTGAGATGTCCGTGGTGCCACAACCCTGAAACCCAAAAGGTGGGCAAGGAATACTATTACAACCGTG
GGTAACTCTACAGGCACCACGGTGTTGGGACTTTGGGTTTTCCACCCGTTCCTTATGATAATGTTGGCAC  420

His • Asp Val Arg Gly Ala Thr Thr Leu Lys Pro Lys Arg Trp Ala Arg Asn Thr Ile Thr Thr Val
 Pro Ile Glu Met Ser Val Val Pro Gln Pro • Asn Pro Lys Gly Gly Gln Gly Ile Leu Leu Gln Pro •
  Pro Leu Arg Cys Pro Trp Cys His Asn Pro Glu Thr Gln Lys Val Gly Lys Glu Tyr Tyr Tyr Asn Arg

Trp Gln Ser Thr Arg Pro Ala Val Val Arg Phe Gly Leu Leu His Ala Leu Phe Val Ile Val Val Thr
 Met Ser Ile Asp Thr Thr Gly Cys Gly Gln Phe Gly Phe Pro Pro Cys Pro Ile Ser Asn Cys Gly His
  Gly Asn Leu His Gly His His Trp Leu Gly Ser Val Trp Phe Thr Pro Leu Ser Tyr • • Leu Arg Ser

FIG. 12B

```
                                        Age I
ATCGTTGCGTGAGCTGCGGACGGTGTGCAACGGTCTGCCCAACCGGTGCATCGCAGCTTCTTGATGGACC
+----+----+----+----+----+----+----+----+----+----+----+----+----+----+ 490
TAGCAACGCACTCGACGCCTGCCACACGTTGCCAGACGGGTTGGCCACGTAGCGTCGAAGAACTACCTGG

Ile Val Ala  *  Ala Ala Asp Gly Val Gln Arg Ser Ala Gln Pro Val His Arg Ser Phe Leu Met Asp
   Ser Leu Arg Glu Leu Arg Thr Val Cys Asn Gly Leu Pro Asn Arg Cys Ile Ala Ala Ser  *  Trp Thr
  Asp Arg Cys Val Ser Cys Gly Arg Cys Ala Thr Val Cys Pro Thr Gly Ala Ser Gln Leu Leu Asp Gly Pro
 Ile Thr Ala His Ala Ala Ser Pro Thr Cys Arg Asp Ala Trp Thr Cys Arg Leu Lys Lys Ile Ser Arg
   Asp Asn Arg Ser Ser Arg Val Thr His Leu Pro Arg Gly Leu Arg His Met Ala Ala Glu Gln His Val
    Arg Gln Thr Leu Gln Pro Arg His Ala Val Thr Gln Gly Val Pro Ala Asp Cys Ser Arg Ser Pro Gly

Mfe I
           Afl II                              Mun I       Sph I
           Bst98 I              ApaB I         ApaB I      ApaB I
GGGCGCAAGCCAGGTGCTTAAGCTCGACCGCAGCAAGTGCATCAATTGCATGCGCTGCGTCGCCGTATGC
+----+----+----+----+----+----+----+----+----+----+----+----+----+----+ 560
CCCGCGTTCGGTCCACGAATTCGAGCTGGCGTCGTTCACGTAGTTAACGTACGCGACGCAGCGGCATACG

Arg Ala Gln Ala Arg Cys Leu Ser Ser Thr Ala Ala Ser Ala Ser Ile Ala Cys Ala Ala Ser Pro Tyr Ala
    Gly Arg Lys Pro Gly Ala  *  Ala Arg Pro Gln Gln Val His Gln Leu His Ala Leu Arg Arg Arg Met
    Gly Ala Ser Gln Val Leu Lys Leu Asp Arg Ser Lys Cys Ile Asn Cys Met Arg Cys Val Ala Val Cys
  Ala Cys Ala Leu His Lys Leu Glu Val Ala Ala Leu Ala Asp Ile Ala His Ala Ala Asp Gly Tyr Ala
   Pro Arg Leu Gly Pro Ala  *  Ala Arg Gly Cys Cys Thr Cys  *  Asn Cys Ala Ser Arg Arg Ile Gly
   Pro Ala Leu Trp Thr Ser Leu Ser Ser Arg Leu Leu His Met Leu Gln Met Arg Gln Thr Ala Thr His

Age I           Tth111 I
CTCACCGGTAGCCGCGACTCTGTCGGGATGGAAATGACACTCGACGAGATTTTGCGCGAGGTCTTGTCCG
+----+----+----+----+----+----+----+----+----+----+----+----+----+----+ 630
GAGTGGCCATCGGCGCTGAGACAGCCCTACCTTTACTGTGAGCTGCTCTAAAACGCGCTCCAGAACAGGC

Ser Pro Val Ala Ala Thr Leu Ser Gly Trp Lys  *  His Ser Thr Arg Phe Cys Ala Arg Ser Cys Pro
 Pro His Arg  *  Pro Arg Leu Cys Arg Asp Gly Asn Asp Thr Arg Arg Asp Phe Ala Arg Gly Leu Val Arg
   Leu Thr Gly Ser Arg Asp Ser Val Gly Met Glu Met Thr Leu Asp Glu Ile Leu Arg Glu Val Leu Ser
   Glu Gly Thr Ala Ala Val Arg Asp Pro His Phe His Cys Glu Val Leu Asn Gln Ala Leu Asp Gln Gly
     *  Arg Tyr Gly Arg Ser Gln Arg Ser Pro Phe Ser Val Arg Arg Ser Lys Ala Arg Pro Arg Thr Arg
    Arg Val Pro Leu Arg Ser Glu Thr Pro Ile Ser Ile Val Ser Ser Ser Ile Lys Arg Ser Thr Lys Asp Ser
```

FIG. 12C

```
                                                                              BsaM I
                                                                       Ear I  Bsm I
ATGAGCCTTTCTACCGCAATAGCGGGGGCGGAGTGACGATCAGCGGAGGCGATCCTCTCTTCCACCCTGC
                                                                              ──── 700
TACTCGGAAAGATGGCGTTATCGCCCCCGCCTCACTGCTAGTCGCCTCCGCTAGGAGAGAAGGTGGGACG
```

Met Ser Leu Ser Thr Ala Ile Ala Gly Ala Glu • Arg Ser Ala Glu Ala Ile Leu Ser Ser Thr Leu
   • Ala Phe Leu Pro Gln • Arg Gly Arg Ser Asp Asp Gln Arg Arg Arg Ser Ser Leu Pro Pro Cys
Asp Glu Pro Phe Tyr Arg Asn Ser Gly Gly Gly Val Thr Ile Ser Gly Gly Asp Pro Leu Phe His Pro Ala

Ile Leu Arg Glu Val Ala Ile Ala Pro Ala Ser His Arg Asp Ala Ser Ala Ile Arg Glu Glu Val Arg Cys
His Ala Lys Arg Gly Cys Tyr Arg Pro Arg Leu Ser Ser • Arg Leu Arg Asp Glu Arg Gly Gly Gln
 Ser Gly Lys • Arg Leu Leu Pro Pro Pro Thr Val Ile Leu Pro Pro Ser Gly Arg Lys Trp Gly Ala

```
        BscE I
        BssH II                            Nru I
           BscE I                             Pvu I
ATTCACATTGGAACTAGCGCGCAAGATCAAGGAACGCGGCGTCCATGTCGCGATCGAGACTTCCTGCTTC
                                                                         ──── 770
TAAGTGTAACCTTGATCGCGCGTTCTAGTTCCTTGCGCCGCAGGTACAGCGCTAGCTCTGAAGGACGAAG
```

His Ser His Trp Asn • Arg Ala Arg Ser Arg Asn Ala Ala Ser Met Ser Arg Ser Arg Leu Pro Ala Ser
 Ile His Ile Gly Thr Ser Ala Gln Asp Gln Gly Thr Arg Arg Pro Cys Arg Asp Arg Asp Phe Leu Leu
  Phe Thr Leu Glu Leu Ala Arg Lys Ile Lys Glu Arg Gly Val His Val Ala Ile Glu Thr Ser Cys Phe

Glu Cys Gln Phe • Arg Ala Leu Asp Leu Phe Ala Ala Asp Met Asp Arg Asp Leu Ser Gly Ala Glu
Met • Met Pro Val Leu Ala Cys Ser • Pro Val Arg Arg Gly His Arg Ser Arg Ser Lys Arg Ser Gly
 Asn Val Asn Ser Ser Ala Arg Leu Ile Leu Ser Arg Pro Thr Trp Thr Ala Ile Ser Val Glu Gln Lys

```
       BstX I                                          Sal I
CCAAAAAAATGGGCGACTATCCAGCCGCTACTTAAACTCGTCGATCTTTTCATCGTCGACCTGAAATCGC
                                                                         ──── 840
GGTTTTTTTACCCGCTGATAGGTCGGCGATGAATTTGAGCAGCTAGAAAAGTAGCAGCTGGACTTTAGCG
```

Gln Lys Asn Gly Arg Leu Ser Ser Arg Tyr Leu Asn Ser Ser Ile Phe Ser Ser Ser Thr • Asn Arg
Pro Lys Lys Met Gly Asp Tyr Pro Ala Ala Thr • Thr Arg Arg Ser Phe His Arg Arg Pro Glu Ile Ala
 Pro Lys Lys Trp Ala Thr Ile Gln Pro Leu Leu Lys Leu Val Asp Leu Phe Ile Val Asp Leu Lys Ser

Trp Phe Phe Pro Arg Ser Asp Leu Arg • Lys Phe Glu Asp Ile Lys Glu Asp Asp Val Gln Phe Arg
 Leu Phe Ile Pro Ser • Gly Ala Ala Val • Val Arg Arg Asp Lys • Arg Arg Gly Ser Ile Ala
Gly Phe Phe His Ala Val Ile Trp Gly Ser Ser Leu Ser Thr Ser Arg Lys Met Thr Ser Arg Phe Asp Ser

FIG. 12D

```
                              Msp20 I
                               | Msc I
                               |  | Msp20 I
                               |  |  |
TGAATCGGAAAAAGCATGAGGAAACTGTTGGCTGGCCACTGCAACCCATACTCGACAATATCGAGCATCT
+----+----+----+----+----+----+----+----+----+----+----+----+----+----+ 910
ACTTAGCCTTTTTCGTACTCCTTTGACAACCGACCGGTGACGTTGGGTATGAGCTGTTATAGCTCGTAGA
```

• Ile Gly Lys Ser Met Arg Lys Leu Leu Ala Gly His Cys Asn Pro Tyr Ser Thr Ile Ser Ser Ile
  Glu Ser Glu Lys Ala • Gly Asn Cys Trp Leu Ala Thr Ala Thr His Thr Arg Gln Tyr Arg Ala Ser
Leu Asn Arg Lys Lys His Glu Glu Thr Val Gly Trp Pro Leu Gln Pro Ile Leu Asp Asn Ile Glu His Leu
+----+----+----+----+----+----+----+----+----+----+----+----+----+----+
Gln Ile Pro Phe Leu Met Leu Phe Ser Asn Ala Pro Trp Gln Leu Gly Tyr Glu Val Ile Asp Leu Met Glu
 Ser Asp Ser Phe Ala His Pro Phe Gln Gln Ser Ala Val Ala Val Trp Val Arg Cys Tyr Arg Ala Asp
  Phe Arg Phe Phe Cys Ser Ser Val Thr Pro Gln Gly Ser Cys Gly Met Ser Ser Leu Ile Ser Cys Arg

```
CATACAAGCCAAGGCCAATATCCGCATACACATTCCTGTAATCCCTGGATTCAACGACTCACCAATGGAT
+----+----+----+----+----+----+----+----+----+----+----+----+----+----+ 980
GTATGTTCGGTTCCGGTTATAGGCGTATGTGTAAGGACATTAGGGACCTAAGTTGCTGAGTGGTTACCTA
```

Ser Tyr Lys Pro Arg Pro Ile Ser Ala Tyr Thr Phe Leu • Ser Leu Asp Ser Thr Thr His Gln Trp Ile
 His Thr Ser Gln Gly Gln Tyr Pro His Thr His Ser Cys Asn Pro Trp Ile Gln Arg Leu Thr Asn Gly
  Ile Gln Ala Lys Ala Asn Ile Arg Ile His Ile Pro Val Ile Pro Gly Phe Asn Asp Ser Pro Met Asp
+----+----+----+----+----+----+----+----+----+----+----+----+----+----+
Tyr Leu Gly Leu Gly Ile Asp Ala Tyr Val Asn Arg Tyr Asp Arg Ser Glu Val Val • Trp His Ile
 • Val Leu Trp Pro Trp Tyr Gly Cys Val Cys Glu Gln Leu Gly Gln Ile • Arg Ser Val Leu Pro Asn
  Met Cys Ala Leu Ala Leu Ile Arg Met Cys Met Gly Thr Ile Gly Pro Asn Leu Ser Glu Gly Ile Ser

```
                                          Pvu II
                                           |
TTCGAGGATTACATCGCTTACTTGGGTCGCCATGCCGCGCAGCTGGATGGCGTAGACATTCTAAATTATC
+----+----+----+----+----+----+----+----+----+----+----+----+----+----+ 1050
AAGCTCCTAATGTAGCGAATGAACCCAGCGGTACGGCGCGTCGACCTACCGCATCTGTAAGATTTAATAG
```

Ser Arg Ile Thr Ser Leu Thr Trp Val Ala Met Pro Arg Ser Trp Met Ala • Thr Phe • Ile Ile
 Phe Arg Gly Leu His Arg Leu Leu Gly Ser Pro Cys Arg Ala Ala Gly Trp Arg Arg His Ser Lys Leu Ser
  Phe Glu Asp Tyr Ile Ala Tyr Leu Gly Arg His Ala Ala Gln Leu Asp Gly Val Asp Ile Leu Asn Tyr
+----+----+----+----+----+----+----+----+----+----+----+----+----+----+
Glu Leu Ile Val Asp Ser Val Gln Thr Ala Met Gly Arg Leu Gln Ile Ala Tyr Val Asn • Ile Ile
 Arg Pro Asn Cys Arg Lys Ser Pro Asp Gly His Arg Ala Ala Pro His Arg Leu Cys Glu Leu Asn Asp
Lys Ser Ser • Met Ala • Lys Pro Arg Trp Ala Ala Cys Ser Ser Pro Thr Ser Met Arg Phe • •

FIG. 12E

```
                                                    BstX I
              BsrB I                                |    Ear I
              |                                     |    |
    ACGTCTATGGAGAAGGCAAGTACCGCTCCTTGGGCCGGGAAAATGAATACCAGTATTTTGGCGTGGAAGA
    ────────┼────┼────┼────┼────┼────┼────┼────┼────┼────┼────┼────┼──── 1120
    TGCAGATACCTCTTCCGTTCATGGCGAGGAACCCGGCCCTTTTACTTATGGTCATAAAACCGCACCTTCT
```

Thr Ser Met Glu Lys Ala Ser Thr Ala Pro Trp Ala Gly Lys Met Asn Thr Ser Ile Leu Ala Trp Lys
  Arg Leu Trp Arg Arg Gln Val Pro Leu Leu Gly Pro Gly Lys • Ile Pro Val Phe Trp Arg Gly Arg
 His Val Tyr Gly Glu Gly Lys Tyr Arg Ser Leu Gly Arg Glu Asn Glu Tyr Gln Tyr Phe Gly Val Glu Glu

Val Asp Ile Ser Phe Ala Leu Val Ala Gly Gln Ala Pro Phe Ile Phe Val Leu Ile Lys Ala His Phe Leu
  Arg Arg His Leu Leu Cys Thr Gly Ser Arg Pro Gly Pro Phe His Ile Gly Thr Asn Gln Arg Pro Leu
   Thr • Pro Ser Pro Leu Tyr Arg Glu Lys Pro Arg Ser Phe Ser Tyr Trp Tyr Lys Pro Thr Ser Ser

```
                                    NgoM I
                       Nru I        |Nae I   BssS I                     Pvu I
                       |            |   |    |                          |
    GAACCCACCCGAAAAGGTAGTGCCACTCGCGAAAGGTTTGAAACTCGCCGGCATCACGAGCGTAACGATC
    ────────┼────┼────┼────┼────┼────┼────┼────┼────┼────┼────┼────┼──── 1190
    CTTGGGTGGGCTTTTCCATCACGGTGAGCGCTTTCCAAACTTTGAGCGGCCGTAGTGCTCGCATTGCTAG
```

Arg Thr His Pro Lys Arg • Cys His Ser Arg Lys Val • Asn Ser Pro Ala Ser Arg Ala • Arg Ser
  Glu Pro Thr Arg Lys Gly Ser Ala Thr Arg Glu Arg Phe Glu Thr Arg Arg His His Glu Arg Asn Asp
   Asn Pro Pro Glu Lys Val Val Pro Leu Ala Lys Gly Leu Lys Leu Ala Gly Ile Thr Ser Val Thr Ile

Val Trp Gly Phe Leu Tyr His Trp Glu Arg Phe Thr Gln Phe Glu Gly Ala Asp Arg Ala Tyr Arg Asp
Ser Gly Val Arg Phe Pro Leu Ala Val Arg Ser Leu Asn Ser Val Arg Arg Cys • Ser Arg Leu Ser Arg
  Phe Gly Gly Ser Phe Thr Thr Gly Ser Ala Phe Pro Lys Phe Ser Ala Pro Met Val Leu Thr Val Ile

```
                                                     Nru I
                                                     |    Taq II'
                                                     |    |
    GGCGGGTTGGTCGGGATCACAGCGGACAGACACAAGAGTAGTCGCGACGCTGGGACTGGGTGTATTGCAT
    ────────┼────┼────┼────┼────┼────┼────┼────┼────┼────┼────┼────┼──── 1260
    CCGCCCAACCAGCCCTAGTGTCGCCTGTCTGTGTTCTCATCAGCGCTGCGACCCTGACCCACATAACGTA
```

Ala Gly Trp Ser Gly Ser Gln Arg Thr Asp Thr Arg Val Val Ala Thr Leu Gly Leu Gly Val Leu His
Arg Arg Val Gly Arg Asp His Ser Gly Gln Thr Gln Glu • Ser Arg Arg Trp Asp Trp Val Tyr Cys Ile
  Gly Gly Leu Val Gly Ile Thr Ala Asp Arg His Lys Ser Ser Arg Asp Ala Gly Thr Gly Cys Ile Ala

Ala Pro Gln Asp Pro Asp Cys Arg Val Ser Val Leu Thr Thr Ala Val Ser Pro Ser Pro Thr Asn Cys
  Arg Thr Pro Arg Ser • Leu Pro Cys Val Cys Ser Tyr Asp Arg Arg Gln Ser Gln Thr Tyr Gln Met
   Pro Pro Asn Thr Pro Ile Val Ala Ser Leu Cys Leu Leu Leu Arg Ser Ala Pro Val Pro His Ile Ala Tyr

```
                    Bsa I                                    BstX I
                    |                                        |
          GATCAAGGAGACCGCCATGAACGACATCGTAAGCGCCAAGGTTCTGGAATATAAAGGAAAGAAGCTCAAT
          ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1540
          CTAGTTCCTCTGGCGGTACTTGCTGTAGCATTCGCGGTTCCAAGACCTTATATTTCCTTTCTTCGAGTTA
```

Asp Gln Gly Asp Arg His Glu Arg His Arg Lys Arg Gln Gly Ser Gly Ile  •  Arg Lys Glu Ala Gln
  Ile Lys Glu Thr Ala Met Asn Asp Ile Val Ser Ala Lys Val Leu Glu Tyr Lys Gly Lys Lys Leu Asn
Arg Ser Arg Arg Pro Pro  •  Thr Thr Ser  •  Ala Pro Arg Phe Trp Asn Ile Lys Glu Arg Ser Ser Ile
```
          ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
```
Ser  •  Pro Ser Arg Trp Ser Arg Cys Arg Leu Arg Trp Pro Glu Pro Ile Tyr Leu Phe Ser Ala  •  Asn
  Ile Leu Ser Val Ala Met Phe Ser Met Thr Leu Ala Leu Thr Arg Ser Tyr Leu Pro Phe Phe Ser Leu
Asp Leu Leu Gly Gly His Val Val Asp Tyr Ala Gly Leu Asn Gln Phe Ile Phe Ser Leu Leu Glu Ile

```
                                           Eag I
                                           Eco52 I
                    Ear I                  |        Eco57 I   BssS I
                    |                      |        |         |
          TTCACGCCGGAAGATCCGGCTGAAGAGACAATTCCGGCCGACGAGTTGCACGAGCATCTGCAAAAGCCTT
          ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1610
          AAGTGCGGCCTTCTAGGCCGACTTCTCTGTTAAGGCCGGCTGCTCAACGTGCTCGTAGACGTTTTCGGAA
```

Phe His Ala Gly Arg Ser Gly  •  Arg Asp Asn Ser Gly Arg Arg Val Ala Arg Ala Ser Ala Lys Ala Phe
  Phe Thr Pro Glu Asp Pro Ala Glu Glu Thr Ile Pro Ala Asp Glu Leu His Glu His Leu Gln Lys Pro
Ser Arg Arg Lys Ile Arg Leu Lys Arg Gln Phe Arg Pro Thr Ser Cys Thr Ser Ile Cys Lys Ser Leu
```
          ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
```
  •  Ala Pro Leu Asp Pro Gln Leu Ser Leu Glu Pro Arg Arg Thr Ala Arg Ala Asp Ala Phe Ala Lys
Lys Val Gly Ser Ser Gly Ala Ser Ser Val Ile Gly Ala Ser Ser Asn Cys Ser Cys Arg Cys Phe Gly Glu
Glu Arg Arg Phe Ile Arg Ser Phe Leu Cys Asn Arg Gly Val Leu Gln Val Leu Met Gln Leu Leu Arg

```
                                                           NgoM I
                                                           Nae I
                                        Eco57 I            |       EcoR I
                                        |                  |       |
          CGACGGCGAGGACCAAGCGCCTGAAGGAGCGTTGCCGCTGGAAACACGCATCTGCCGGCGAATTCATTGA
          ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1680
          GCTGCCGCTCCTGGTTCGCGGACTTCCTCGCAACGGCGACCTTTGTGCGTAGACGGCCGCTTAAGTAACT
```

Asp Gly Glu Asp Gln Ala Pro Glu Gly Ala Leu Pro Leu Glu Thr Arg Ile Cys Arg Arg Ile His  •
Ser Thr Ala Arg Thr Lys Arg Leu Lys Glu Arg Cys Arg Trp Lys His Ala Ser Ala Gly Glu Phe Ile Glu
Arg Arg Arg Gly Pro Ser Ala  •  Arg Ser Val Ala Ala Gly Asn Thr His Leu Pro Ala Asn Ser Leu
```
          ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼
```
Ser Pro Ser Ser Trp Ala Gly Ser Pro Ala Asn Gly Ser Ser Val Arg Met Gln Arg Arg Ile  •  Gln
  Val Ala Leu Val Leu Arg Arg Phe Ser Arg Gln Arg Gln Phe Cys Ala Asp Ala Pro Ser Asn Met Ser
Arg Arg Arg Pro Gly Leu Ala Gln Leu Leu Thr Ala Ala Pro Phe Val Cys Arg Gly Ala Phe Glu Asn Phe

FIG. 12H

```
                Eag I
                Eco52 I
                 NgoM I
                  Nae I         Sph I                    Taq II
AAAGAGCGTCACGGCCGGCATCGAGCGCATGCGCTATCTGACCGAAGCACACAAGGCCAGCGAAGGCAAA
++++++++++++++++++++++++++++++++++++++++++++++++++++++++++++++++++++++ 1750
TTTCTCGCAGTGCCGGCCGTAGCTCGCGTACGCGATAGACTGGCTTCGTGTGTTCCGGTCGCTTCCGTTT
```

Lys Glu Arg His Gly Arg His Arg Ala His Ala Leu Ser Asp Arg Ser Thr Gln Gly Gln Arg Arg Gln
 Lys Ser Val Thr Ala Gly Ile Glu Arg Met Arg Tyr Leu Thr Glu Ala His Lys Ala Ser Glu Gly Lys
Lys Arg Ala Ser Arg Pro Ala Ser Ser Ala Cys Ala Ile • Pro Lys His Thr Arg Pro Ala Lys Ala Asn

Phe Ser Arg • Pro Arg Cys Arg Ala Cys Ala Ser Asp Ser Arg Leu Val Cys Pro Trp Arg Leu Cys Val
 Phe Leu Thr Val Ala Pro Met Ser Arg Met Arg • Arg Val Ser Ala Cys Leu Ala Leu Ser Pro Leu
Leu Ala Asp Arg Gly Ala Asp Leu Ala His Ala Ile Gln Gly Phe Cys Val Leu Gly Ala Phe Ala Phe

```
                BscE I
                BssH II
                  BscE I                  Bpm I
                                 Bcg I    Sal I
CCCGAAGCCATCCGTCGCGCGCTGGGCCTGGCGAACGTCCTGAACAAGTCGACCCTGGTGCTCCAGGAGG
++++++++++++++++++++++++++++++++++++++++++++++++++++++++++++++++++++++ 1820
GGGCTTCGGTAGGCAGCGCGCGACCCGGACCGCTTGCAGGACTTGTTCAGCTGGGACCACGAGGTCCTCC
```

Thr Arg Ser His Pro Ser Arg Ala Gly Pro Gly Glu Arg Pro Glu Gln Val Asp Pro Gly Ala Pro Gly Gly
 Pro Glu Ala Ile Arg Arg Ala Leu Gly Leu Ala Asn Val Leu Asn Lys Ser Thr Leu Val Leu Gln Glu
  Pro Lys Pro Ser Val Ala Arg Trp Ala Trp Arg Thr Ser • Thr Ser Arg Pro Trp Cys Ser Arg Arg

Arg Leu Trp Gly Asp Arg Ala Pro Gly Pro Ser Arg Gly Ser Cys Thr Ser Gly Pro Ala Gly Pro Pro
 Gly Ser Ala Met Arg Arg Ala Ser Pro Arg Ala Phe Thr Arg Phe Leu Asp Val Arg Thr Ser Trp Ser Ser
  Gly Phe Gly Asp Thr Ala Arg Gln Ala Gln Arg Val Asp Gln Val Leu Arg Gly Gln His Glu Leu Leu

```
     Bcg I'
     EcoR I                     BspLU11 I
ACGAATTCATCGTCGGCTACCACGCCGAAGATCCCAACATGTTCCCGCTGTATCCCGAACTGTCCCACAT
++++++++++++++++++++++++++++++++++++++++++++++++++++++++++++++++++++++ 1890
TGCTTAAGTAGCAGCCGATGGTGCGGCTTCTAGGGTTGTACAAGGGCGACATAGGGCTTGACAGGGTGTA
```

Arg Ile His Arg Arg Leu Pro Arg Arg Arg Ser Gln His Val Pro Ala Val Ser Arg Thr Val Pro His
Asp Glu Phe Ile Val Gly Tyr His Ala Glu Asp Pro Asn Met Phe Pro Leu Tyr Pro Glu Leu Ser His Met
 Thr Asn Ser Ser Ser Ala Thr Thr Pro Lys Ile Pro Thr Cys Ser Arg Cys Ile Pro Asn Cys Pro Thr

Arg Ile • Arg Arg Ser Gly Arg Arg Leu Asp Trp Cys Thr Gly Ala Thr Asp Arg Val Thr Gly Cys
 Ser Asn Met Thr Pro • Trp Ala Ser Ser Gly Leu Met Asn Gly Ser Tyr Gly Ser Ser Asp Trp Met
Val Phe Glu Asp Asp Ala Val Val Gly Phe Ile Gly Val His Glu Arg Gln Ile Gly Phe Gln Gly Val His

FIG. 12I

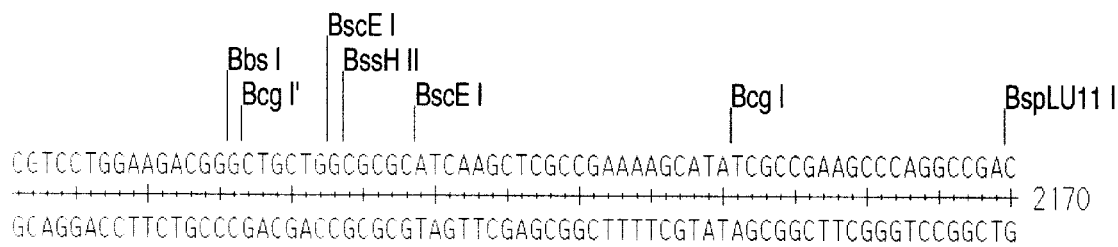
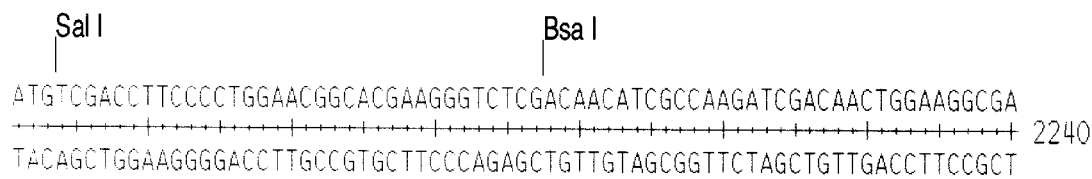
FIG. 12K

Bce83 I

```
GCCGAGCCCTGCAAGGGCCTCAAGGACGCGATGCAGGCGAAATTCTTTACCTTCCTGATCTGTCACGCGA
                                                                      2450
CGGCTCGGGACGTTCCCGGAGTTCCTGCGCTACGTCCGCTTTAAGAAATGGAAGGACTAGACAGTGCGCT
```

Arg Arg Ala Leu Gln Gly Pro Gln Gly Arg Asp Ala Gly Glu Ile Leu Tyr Leu Pro Asp Leu Ser Arg Asp
  Ala Glu Pro Cys Lys Gly Leu Lys Asp Ala Met Gln Ala Lys Phe Phe Thr Phe Leu Ile Cys His Ala
    Pro Ser Pro Ala Arg Ala Ser Arg Thr Arg Cys Arg Arg Asn Ser Leu Pro Ser • Ser Val Thr Arg

Arg Ala Arg Cys Pro Gly • Pro Arg Ser Ala Pro Ser Ile Arg • Arg Gly Ser Arg Asp Arg Ser
Ala Ser Gly Gln Leu Pro Arg Leu Ser Ala Ile Cys Ala Phe Asn Lys Val Lys Arg Ile Gln • Ala Ile
  Gly Leu Gly Ala Leu Ala Glu Leu Val Arg His Leu Arg Phe Glu Lys Gly Glu Gln Asp Thr Val Arg

EcoP15 I

Pvu I  Eco47 III  BsrB I              Bbs I                       BsaX I  Stu I

```
TCGAGCGCTACGCGAGCGGCTACGCCCAGAAGGAAGACACCCTGCTGTGGCCGTACTACAAGGCCTCCGT
                                                                      2520
AGCTCGCGATGCGCTCGCCGATGCGGGTCTTCCTTCTGTGGGACGACACCGGCATGATGTTCCGGAGGCA
```

Arg Ala Leu Arg Glu Arg Leu Arg Pro Glu Gly Arg His Pro Ala Val Ala Val Leu Gln Gly Leu Arg
Ile Glu Arg Tyr Ala Ser Gly Tyr Ala Gln Lys Glu Asp Thr Leu Leu Trp Pro Tyr Tyr Lys Ala Ser Val
  Ser Ser Ala Thr Arg Ala Ala Thr Pro Arg Arg Lys Thr Pro Cys Cys Gly Arg Thr Thr Arg Pro Pro

Arg Ala Ser Arg Ser Arg Ser Arg Gly Ser Pro Leu Cys Gly Ala Thr Ala Thr Ser Cys Pro Arg Arg
    Ser Arg • Ala Leu Pro • Ala Trp Phe Ser Ser Val Arg Ser His Gly Tyr • Leu Ala Glu Thr
Asp Leu Ala Val Arg Ala Ala Val Gly Leu Leu Phe Val Gly Gln Gln Pro Arg Val Val Leu Gly Gly Asp

Sal I                                                         Psp1406 I

```
CGTCGACAAGAAATTCCAGCCGATGAGCCACATGGATGCGGTGGAACTCGTCGAGATGGAACGTTTGAAG
                                                                      2590
GCAGCTGTTCTTTAAGGTCGGCTACTCGGTGTACCTACGCCACCTTGAGCAGCTCTACCTTGCAAACTTC
```

Arg Arg Gln Glu Ile Pro Ala Asp Glu Pro His Gly Cys Gly Gly Thr Arg Arg Asp Gly Thr Phe Glu
  Val Asp Lys Lys Phe Gln Pro Met Ser His Met Asp Ala Val Glu Leu Val Glu Met Glu Arg Leu Lys
Ser Ser Thr Arg Asn Ser Ser Arg • Ala Thr Trp Met Arg Trp Asn Ser Ser Arg Trp Asn Val • Arg

Arg Arg Cys Ser Ile Gly Ala Ser Ser Gly Cys Pro His Pro Pro Val Arg Arg Ser Pro Val Asn Ser Ser
  Thr Ser Leu Phe Asn Trp Gly Ile Leu Trp Met Ser Ala Thr Ser Ser Thr Ser Ile Ser Arg Lys Phe
    Asp Val Leu Phe Glu Leu Arg His Ala Val His Ile Arg His Phe Glu Asp Leu His Phe Thr Gln Leu

FIG. 12M

```
                    Kas I
                    Nar I
                    Ehe I
                    NgoM I        BscE I
                    Bbe I         BssH II              Xma I
                    Nae I         BscE I               Sma I
ATTCCGAGCATGGCGCCGGCAAGTCGCGCGCCTACCGCGAAATCTTCCCGGGGTCGAACGATCTGTTCA
++++++++++++++++++++++++++++++++++++++++++++++++++++++++++++++++++++  2660
TAAAGGCTCGTACCGCGGCCGTTCAGCGCGCGGATGGCGCTTTAGAAGGGCCCCAGCTTGCTAGACAAGT
```

Asp Phe Arg Ala Trp Arg Arg Gln Val Ala Arg Leu Pro Arg Asn Leu Pro Gly Val Glu Arg Ser Val His
 Ile Ser Glu His Gly Ala Gly Lys Ser Arg Ala Tyr Arg Glu Ile Phe Pro Gly Ser Asn Asp Leu Phe
  Phe Pro Ser Met Ala Pro Ala Ser Arg Ala Pro Thr Ala Lys Ser Ser Arg Gly Arg Thr Ile Cys Ser

Lys Arg Ala His Arg Arg Cys Thr Ala Arg Arg Gly Arg Phe Arg Gly Pro Thr Ser Arg Asp Thr  •
  Ile Glu Ser Cys Pro Ala Pro Leu Asp Arg Ala  •  Arg Ser Ile Lys Gly Pro Asp Phe Ser Arg Asn Met
   Asn Gly Leu Met Ala Gly Ala Leu Arg Ala Gly Val Ala Phe Asp Glu Arg Pro Arg Val Ile Gln Glu

Xho I
                                                                              Sci I
                                                                              Taq II
```
TCCTCACCGTCGGCGGCACCAACGCCAAGGGCGAGGACGCCTGCAACGACATGACCGACGCCATCCTCGA
++++++++++++++++++++++++++++++++++++++++++++++++++++++++++++++++++++  2730
AGGAGTGGCAGCCGCCGTGGTTGCGGTTCCCGCTCCTGCGGACGTTGCTGTACTGGCTGCGGTAGGAGCT
```

Pro His Arg Arg Arg His Gln Arg Gln Gly Arg Gly Arg Leu Gln Arg His Asp Arg Arg His Pro Arg
 Ile Leu Thr Val Gly Gly Thr Asn Ala Lys Gly Glu Asp Ala Cys Asn Asp Met Thr Asp Ala Ile Leu Glu
  Ser Ser Pro Ser Ala Ala Pro Thr Pro Arg Ala Arg Thr Pro Ala Thr Thr  •  Pro Thr Pro Ser Ser

Gly  •  Arg Arg Arg Cys Trp Arg Trp Pro Arg Pro Arg Arg Cys Arg Cys Ser Arg Arg Trp Gly Arg
  Arg Val Thr Pro Pro Val Leu Ala Leu Pro Ser Ser Ala Gln Leu Ser Met Val Ser Ala Met Arg Ser
   Asp Glu Gly Asp Ala Ala Gly Val Gly Leu Ala Leu Val Gly Ala Val Val His Gly Val Gly Asp Glu Leu

Eag I
          BamH I    Eco52 I     Bbs I
```
GGCAGCCAAGCGGATCCGCACGGCCGAGCCCTCCATCGTCTTCCGCTATTCCAAGAAGAACCGCGAGAAG
++++++++++++++++++++++++++++++++++++++++++++++++++++++++++++++++++++  2800
CCGTCGGTTCGCCTAGGCGTGCCGGCTCGGGAGGTAGCAGAAGGCGATAAGGTTCTTCTTGGCGCTCTTC
```

Gly Ser Gln Ala Asp Pro His Gly Arg Ala Leu His Arg Leu Pro Leu Phe Gln Glu Glu Pro Arg Glu
 Ala Ala Lys Arg Ile Arg Thr Ala Glu Pro Ser Ile Val Phe Arg Tyr Ser Lys Lys Asn Arg Glu Lys
  Arg Gln Pro Ser Gly Ser Arg Pro Ser Pro Ser Ser Ala Ile Pro Arg Arg Thr Ala Arg Arg

Pro Leu Trp Ala Ser Gly Cys Pro Arg Ala Arg Trp Arg Arg Gly Ser Asn Trp Ser Ser Gly Arg Ser Ser
 Ala Ala Leu Arg Ile Arg Val Ala Ser Gly Glu Met Thr Lys Arg  •  Glu Leu Phe Phe Arg Ser Phe
  Cys Gly Leu Pro Asp Ala Arg Gly Leu Gly Gly Asp Asp Glu Ala Ile Gly Leu Leu Val Ala Leu Leu

FIG. 12N

```
                Bbs I
                |
    ACGCTGCGCTGGGTTTTCGAGTGCATCCGCGACGGACTCGGCTATCCGTCGATCAAGCACGACGAGATCG
    ----+----+----+----+----+----+----+----+----+----+----+----+----+----+  2870
    TGCGACGCGACCCAAAAGCTCACGTAGGCGCTGCCTGAGCCGATAGGCAGCTAGTTCGTGCTGCTCTAGC

Asp Ala Ala Leu Gly Phe Arg Val His Pro Arg Arg Thr Arg Leu Ser Val Asp Gln Ala Arg Arg Asp Arg
    Thr Leu Arg Trp Val Phe Glu Cys Ile Arg Asp Gly Leu Gly Tyr Pro Ser Ile Lys His Asp Glu Ile
      Arg Cys Ala Gly Phe Ser Ser Ala Ser Ala Thr Asp Ser Ala Ile Arg Arg Ser Ser Thr Thr Arg Ser
    ----+----+----+----+----+----+----+----+----+----+----+----+----+----+
    Ala Ala Ser Pro Lys Arg Thr Cys Gly Arg Arg Val Arg Ser Asp Thr Ser  •  Ala Arg Arg Ser Arg
  Val Ser Arg Gln Thr Lys Ser His Met Arg Ser Pro Ser Pro  •  Gly Asp Ile Leu Cys Ser Ser Ile Pro
   Arg Gln Ala Pro Asn Glu Leu Ala Asp Ala Val Ser Glu Ala Ile Arg Arg Asp Leu Val Val Leu Asp

Kas I
                                                              |Nar I
                                                              ||Ehe I
                                          Bgl I               |||Bbe I
                                          |                   ||||
    GCACGGAGCAGATGAAGGAATACGCCAAGTTCAGCCTCAACGGCAACGGCGCCACCGACGAGGAAGCCCA
    ----+----+----+----+----+----+----+----+----+----+----+----+----+----+  2940
    CGTGCCTCGTCTACTTCCTTATGCGGTTCAAGTCGGAGTTGCCGTTGCCGCGGTGGCTGCTCCTTCGGGT

His Gly Ala Asp Glu Gly Ile Arg Gln Val Gln Pro Gln Arg Gln Arg Arg His Arg Arg Gly Ser Pro
  Gly Thr Glu Gln Met Lys Glu Tyr Ala Lys Phe Ser Leu Asn Gly Asn Gly Ala Thr Asp Glu Glu Ala His
    Ala Arg Ser Arg  •  Arg Asn Thr Pro Ser Ser Ala Ser Thr Ala Thr Ala Pro Pro Thr Arg Lys Pro
    ----+----+----+----+----+----+----+----+----+----+----+----+----+----+
   Cys Pro Ala Ser Ser Pro Ile Arg Trp Thr  •  Gly  •  Arg Cys Arg Arg Trp Arg Arg Pro Leu Gly
     Val Ser Cys Ile Phe Ser Tyr Ala Leu Asn Leu Arg Leu Pro Leu Pro Ala Val Ser Ser Ser Ala Trp
   Ala Arg Leu Leu His Leu Phe Val Gly Leu Glu Ala Glu Val Ala Val Ala Gly Gly Val Leu Phe Gly Val

RleA I
              |
    CAACTGGGTCAACGTGCTGTGCATGTCGCCCGGCATCCACGGTCGCCGCAAGACGCAAAAAACCCGTTCG
    ----+----+----+----+----+----+----+----+----+----+----+----+----+----+  3010
    GTTGACCCAGTTGCACGACACGTACAGCGGGCCGTAGGTGCCAGCGGCGTTCTGCGTTTTTTGGGCAAGC

Gln Leu Gly Gln Arg Ala Val His Val Ala Arg His Pro Arg Ser Pro Gln Asp Ala Lys Asn Pro Phe
     Asn Trp Val Asn Val Leu Cys Met Ser Pro Gly Ile His Gly Arg Arg Lys Thr Gln Lys Thr Arg Ser
    Thr Thr Gly Ser Thr Cys Cys Ala Cys Arg Pro Ala Ser Thr Val Ala Ala Arg Arg Lys Lys Pro Val Arg
    ----+----+----+----+----+----+----+----+----+----+----+----+----+----+
   Cys Ser Pro  •  Arg Ala Thr Cys Thr Ala Arg Cys Gly Arg Asp Gly Cys Ser Ala Phe Phe Gly Asn Pro
    Leu Gln Thr Leu Thr Ser His Met Asp Gly Pro Met Trp Pro Arg Arg Leu Val Cys Phe Val Arg Glu
      Val Pro Asp Val His Gln Ala His Arg Gly Ala Asp Val Thr Ala Ala Leu Arg Leu Phe Gly Thr Arg
```

FIG. 12O

```
                      EcoP15 I                          BstX I                                      BsiW I
                      |                                 |                                           |
          GAAGGTGGCGGCTCAATCTTCCCGGCCAAGCTGCTGGAAATCTCGCTCAATGACGGCTACGACTGGTCGT
          +----+----+----+----+----+----+----+----+----+----+----+----+----+----+ 3080
          CTTCCACCGCCGAGTTAGAAGGGCCGGTTCGACGACCTTTAGAGCGAGTTACTGCCGATGCTGACCAGCA
```

Gly Arg Trp Arg Leu Asn Leu Pro Gly Gln Ala Ala Gly Asn Leu Ala Gln • Arg Leu Arg Leu Val Val
 Glu Gly Gly Gly Ser Ile Phe Pro Ala Lys Leu Leu Glu Ile Ser Leu Asn Asp Gly Tyr Asp Trp Ser
  Lys Val Ala Ala Gln Ser Ser Arg Pro Ser Cys Trp Lys Ser Arg Ser Met Thr Ala Thr Thr Gly Arg

Leu His Arg Ser Leu Arg Gly Pro Trp Ala Ala Pro Phe Arg Ala • His Arg Ser Arg Ser Thr Thr
 Ser Pro Pro Pro Glu Ile Lys Gly Ala Leu Ser Ser Ser Ile Glu Ser Leu Ser Pro • Ser Gln Asp Tyr
  Phe Thr Ala Ala • Asp Glu Arg Gly Leu Gln Gln Phe Asp Arg Glu Ile Val Ala Val Val Pro Arg

```
                                   Age I
                                   | Bbs I                       Xmn I                Eco57 I
                                   | |                           |                    |
          ACGCCGACATGCAACTCGGCCCGAAGACCGGTGATCTCTCGTCGCTGAAGTCCTTCGAGGATGTTTGGGA
          +----+----+----+----+----+----+----+----+----+----+----+----+----+----+ 3150
          TGCGGCTGTACGTTGAGCCGGGCTTCTGGCCACTAGAGAGCAGCGACTTCAGGAAGCTCCTACAAACCCT
```

Arg Arg His Ala Thr Arg Pro Glu Asp Arg • Ser Leu Val Ala Glu Val Leu Arg Gly Cys Leu Gly
  Tyr Ala Asp Met Gln Leu Gly Pro Lys Thr Gly Asp Leu Ser Ser Leu Lys Ser Phe Glu Asp Val Trp Glu
   Thr Pro Thr Cys Asn Ser Ala Arg Arg Pro Val Ile Ser Arg Arg • Ser Pro Ser Arg Met Phe Gly

Arg Arg Cys Ala Val Arg Gly Ser Ser Arg His Asp Arg Thr Ala Ser Thr Arg Arg Pro His Lys Pro
  Ala Ser Met Cys Ser Pro Gly Phe Val Pro Ser Arg Glu Asp Ser Phe Asp Lys Ser Ser Thr Gln Ser
   Val Gly Val His Leu Glu Ala Arg Leu Gly Thr Ile Glu Arg Arg Gln Leu Gly Glu Leu Ile Asn Pro Leu

```
          GGCTTTCCGCAAGCAGTATCAATATGCGATCAACCTCTGTATCAGCACCAAGGACGTGTCGCGCTACTTC
          +----+----+----+----+----+----+----+----+----+----+----+----+----+----+ 3220
          CCGAAAGGCGTTCGTCATAGTTATACGCTAGTTGGAGACATAGTCGTGGTTCCTGCACAGCGCGATGAAG
```

Gly Phe Pro Gln Ala Val Ser Ile Cys Asp Gln Pro Leu Tyr Gln His Gln Gly Arg Val Ala Leu Leu
 Ala Phe Arg Lys Gln Tyr Gln Tyr Ala Ile Asn Leu Cys Ile Ser Thr Lys Asp Val Ser Arg Tyr Phe
  Arg Leu Ser Ala Ser Ser Ile Asn Met Arg Ser Thr Ser Val Ser Ala Pro Arg Thr Cys Arg Ala Thr Ser

Pro Lys Gly Cys Ala Thr Asp Ile His Ser • Gly Arg Tyr • Cys Trp Pro Arg Thr Ala Ser Ser Arg
 Ala Lys Arg Leu Cys Tyr • Tyr Ala Ile Leu Arg Gln Ile Leu Val Leu Ser Thr Asp Arg • Lys
  Ser Glu Ala Leu Leu Ile Leu Ile Arg Asp Val Glu Thr Asp Ala Gly Leu Val His Arg Ala Val Glu

FIG. 12P

```
         Eco47 III  Pst I                        Bcg I'
GAGCAGCGCTTCCTGCAGATGCCTTTCGTGTCCGCAATCGACGACGGCTGCATGGAACTCGGGATGGACG
+----+----+----+----+----+----+----+----+----+----+----+----+----+----+ 3290
CTCGTCGCGAAGGACGTCTACGGAAAGCACAGGCGTTAGCTGCTGCCGACGTACCTTGAGCCCTACCTGC
```

Arg Ala Ala Leu Pro Ala Asp Ala Phe Arg Val Arg Asn Arg Arg Arg Leu His Gly Thr Arg Asp Gly Arg
 Glu Gln Arg Phe Leu Gln Met Pro Phe Val Ser Ala Ile Asp Asp Gly Cys Met Glu Leu Gly Met Asp
  Ser Ser Ala Ser Cys Arg Cys Leu Ser Cys Pro Gln Ser Thr Thr Ala Ala Trp Asn Ser Gly Trp Thr
+----+----+----+----+----+----+----+----+----+----+----+----+----+----+
  Ala Ala Ser Gly Ala Ser Ala Lys Arg Thr Arg Leu Arg Arg Arg Ser Cys Pro Val Arg Ser Pro Arg
 Ser Cys Arg Lys Arg Cys Ile Gly Lys Thr Asp Ala Ile Ser Ser Pro Gln Met Ser Ser Pro Ile Ser Ala
Leu Leu Ala Glu Gln Leu His Arg Glu His Gly Cys Asp Val Val Ala Ala His Phe Glu Pro His Val

```
                                                        PshA I
 Bcg I                 Van91 I                          Pvu I           BssS I
CCTGCGCCCTGTCCGAGCAGCCCAATGGCTGGCACAACCCGATCACGACGATCGTCGCGGCGAACTCCCT
+----+----+----+----+----+----+----+----+----+----+----+----+----+----+ 3360
GGACGCGGGACAGGCTCGTCGGGTTACCGACCGTGTTGGGCTAGTGCTGCTAGCAGCGCCGCTTGAGGGA
```

Leu Arg Pro Val Arg Ala Ala Gln Trp Leu Ala Gln Pro Asp His Asp Asp Arg Arg Gly Glu Leu Pro
 Ala Cys Ala Leu Ser Glu Gln Pro Asn Gly Trp His Asn Pro Ile Thr Thr Ile Val Ala Ala Asn Ser Leu
  Pro Ala Pro Cys Pro Ser Ser Pro Met Ala Gly Thr Thr Arg Ser Arg Arg Ser Ser Arg Arg Thr Pro
+----+----+----+----+----+----+----+----+----+----+----+----+----+----+
  Arg Arg Gly Thr Arg Ala Ala Trp His Ser Ala Cys Gly Ser • Ser Ser Arg Arg Pro Ser Ser Gly
 Gln Ala Arg Asp Ser Cys Gly Leu Pro Gln Cys Leu Gly Ile Val Val Ile Thr Ala Ala Phe Glu Arg
Gly Ala Gly Gln Gly Leu Leu Gly Ile Ala Pro Val Val Arg Asp Arg Arg Asp Asp Arg Arg Val Gly Glu

```
 Msp20 I
  Msc I
   Msp20 I                              BseR I
    Xcm I                                Xho I
                                          Sci I
CGTGGCCATCAAGAAACTGGTATTCGAGGAGAAGAAATACACCCTCGAGCAACTCAGCCAAGCGTTGAAG
+----+----+----+----+----+----+----+----+----+----+----+----+----+----+ 3430
GCACCGGTAGTTCTTTGACCATAAGCTCCTCTTCTTTATGTGGGAGCTCGTTGAGTCGGTTCGCAACTTC
```

Arg Gly His Gln Glu Thr Gly Ile Arg Gly Glu Glu Ile His Pro Arg Ala Thr Gln Pro Ser Val Glu
 Val Ala Ile Lys Lys Leu Val Phe Glu Glu Lys Lys Tyr Thr Leu Glu Gln Leu Ser Gln Ala Leu Lys
  Ser Trp Pro Ser Arg Asn Trp Tyr Ser Arg Arg Arg Asn Thr Pro Ser Asn Ser Ala Lys Arg • Arg
+----+----+----+----+----+----+----+----+----+----+----+----+----+----+
  Arg Pro Trp • Ser Val Pro Ile Arg Pro Ser Ser Ile Cys Gly Arg Ala Val • Gly Leu Thr Ser Pro
 Thr Ala Met Leu Phe Ser Thr Asn Ser Ser Phe Phe Tyr Val Arg Ser Cys Ser Leu Trp Ala Asn Phe
His Gly Asp Leu Phe Gln Tyr Glu Leu Leu Leu Phe Val Gly Glu Leu Leu Glu Ala Leu Arg Gln Leu

FIG. 12Q

```
                                                    Kas I
                                                    Nar I
                                                    Ehe I
                              Sal I                 Bbe I
GCGAACTGGGAAGGTTTCGAGGAAATGCGCGTCGACTTCAAGCGGGCGCCGAAGTGGGGCAACGACGATG
++++++++++++++++++++++++++++++++++++++++++++++++++++++++++++++++++++++ 3500
CGCTTGACCCTTCCAAAGCTCCTTTACGCGCAGCTGAAGTTCGCCCGCGGCTTCACCCCGTTGCTGCTAC
```

Gly Glu Leu Gly Arg Phe Arg Gly Asn Ala Arg Arg Leu Gln Ala Gly Ala Glu Val Gly Gln Arg Arg •
 Ala Asn Trp Glu Gly Phe Glu Glu Met Arg Val Asp Phe Lys Arg Ala Pro Lys Trp Gly Asn Asp Asp
  Arg Thr Gly Lys Val Ser Arg Lys Cys Ala Ser Thr Ser Ser Gly Arg Arg Ser Gly Ala Thr Thr Met

Ser Ser Pro Leu Asn Arg Pro Phe Ala Arg Arg Ser • Ala Pro Ala Ser Thr Pro Cys Arg Arg His
Ala Phe Gln Ser Pro Lys Ser Ser Ile Arg Thr Ser Lys Leu Arg Ala Gly Phe His Pro Leu Ser Ser Ser
 Arg Val Pro Phe Thr Glu Leu Phe His Ala Asp Val Glu Leu Pro Arg Arg Leu Pro Ala Val Val Ile

```
                                                              Fsp I
ATTACGCCGACGGTATCATCACCCGCTTCTACGAGGAAATCATCGGCGGCGAAATGCGCAAGATCACCAA
+++++++++++++++++++++++++++++++++++++++++++++++++++++++++++++++++++++ 3570
TAATGCGGCTGCCATAGTAGTGGGCGAAGATGCTCCTTTAGTAGCCGCCGCTTTACGCGTTCTAGTGGTT
```

Leu Arg Arg Arg Tyr His His Pro Leu Leu Arg Gly Asn His Arg Arg Asn Ala Gln Asp His Gln
 Asp Tyr Ala Asp Gly Ile Ile Thr Arg Phe Tyr Glu Glu Ile Ile Gly Gly Glu Met Arg Lys Ile Thr Asn
  Ile Thr Pro Thr Val Ser Ser Pro Ala Ser Thr Arg Lys Ser Ser Ala Ala Lys Cys Ala Arg Ser Pro

Asn Arg Arg Arg Tyr • • Gly Ser Arg Arg Pro Phe • Arg Arg Arg Phe Ala Cys Ser • Trp
 • Ala Ser Pro Ile Met Val Arg Lys • Ser Ser Ile Met Pro Pro Ser Ile Arg Leu Ile Val Leu
  Ile Val Gly Val Thr Asp Asp Gly Ala Glu Val Leu Phe Asp Asp Ala Ala Phe His Ala Leu Asp Gly Val

```
                                         BsrG I                            Bsp120 I
CTACTCTGGTGGTCCGGTCATGCCGACTGGTCAGGCTGTCGGCCTGTACATGGAAGTCGGTTCGCGCACG
+++++++++++++++++++++++++++++++++++++++++++++++++++++++++++++++++++++ 3640
GATGAGACCACCAGGCCAGTACGGCTGACCAGTCCGACAGCCGGACATGTACCTTCAGCCAAGCGCGTGC
```

Leu Leu Trp Trp Ser Gly His Ala Asp Trp Ser Gly Cys Arg Pro Val His Gly Ser Arg Phe Ala His
 Tyr Ser Gly Gly Pro Val Met Pro Thr Gly Gln Ala Val Gly Leu Tyr Met Glu Val Gly Ser Arg Thr
  Thr Thr Leu Val Val Arg Ser Cys Arg Leu Val Arg Leu Ser Ala Cys Thr Trp Lys Ser Val Arg Ala Arg

Ser Ser Gln His Asp Pro • Ala Ser Gln Asp Pro Gln Arg Gly Thr Cys Pro Leu Arg Asn Ala Cys Pro
 • Glu Pro Pro Gly Thr Met Gly Val Pro • Ala Thr Pro Arg Tyr Met Ser Thr Pro Glu Arg Val
  Val Arg Thr Thr Arg Asp His Arg Ser Thr Leu Ser Asp Ala Gln Val His Phe Asp Thr Arg Ala Arg

FIG. 12R

```
              Apa I        Bgl I
              |            |
     GGCCCCACGCCGGACGGGCGCTTCGGGGGTGAAGCGGCAGACGACGGCGGCATTTCTCCCTACATGGGAA
     +----+----+----+----+----+----+----+----+----+----+----+----+----+----+  3710
     CCGGGGTGCGGCCTGCCCGCGAAGCCCCCACTTCGCCGTCTGCTGCCGCCGTAAAGAGGGATGTACCCTT

Gly Pro His Ala Gly Arg Ala Leu Arg Gly  *  Ser Gly Arg Arg Arg Arg His Phe Ser Leu His Gly Asn
      Gly Pro Thr Pro Asp Gly Arg Phe Gly Gly Glu Ala Ala Asp Asp Gly Gly Ile Ser Pro Tyr Met Gly
        Ala Pro Arg Arg Thr Gly Ala Ser Gly Val Lys Arg Gln Thr Thr Ala Ala Phe Leu Pro Thr Trp Glu

Gly Trp Ala Pro Arg Ala Ser Arg Pro His Leu Pro Leu Arg Arg Arg Cys Lys Glu Arg Cys Pro Phe
   Pro Gly Val Gly Ser Pro Arg Lys Pro Pro Ser Ala Ala Ser Ser Pro Pro Met Glu Gly  *  Met Pro Val
      Ala Gly Arg Arg Val Pro Ala Glu Pro Thr Phe Arg Cys Val Val Ala Ala Asn Arg Gly Val His Ser

Bsg I
                                              EcoP15 I                                |   Bsp24 I
                                              |                                       |   |
     CCGACAAGAAGGGGCCGACGGCGGTGTTGCGCTCGGTGTCCAAGGTGCAGAAGAACCAGAAGGGCAACCT
     +----+----+----+----+----+----+----+----+----+----+----+----+----+----+  3780
     GGCTGTTCTTCCCCGGCTGCCGCCACAACGCGAGCCACAGGTTCCACGTCTTCTTGGTCTTCCCGTTGGA

Arg Gln Glu Gly Ala Asp Gly Gly Val Ala Leu Gly Val Gln Gly Ala Glu Glu Pro Glu Gly Gln Pro
   Thr Asp Lys Lys Gly Pro Thr Ala Val Leu Arg Ser Val Ser Lys Val Gln Lys Asn Gln Lys Gly Asn Leu
      Pro Thr Arg Arg Gly Arg Arg Arg Cys Cys Ala Arg Cys Pro Arg Cys Arg Arg Thr Arg Arg Ala Thr

Arg Cys Ser Pro Ala Ser Pro Pro Thr Ala Ser Pro Thr Trp Pro Ala Ser Ser Gly Ser Pro Cys Gly
      Ser Leu Phe Pro Gly Val Ala Thr Asn Arg Glu Thr Asp Leu Thr Cys Phe Phe Trp Phe Pro Leu Arg
        Gly Val Leu Leu Pro Arg Arg Arg His Gln Ala Arg His Gly Leu His Leu Leu Val Leu Ala Val Gln

BspM I
      |      Eco47 III                     Bsp24 I'                  BstB I
      |      |                             |                         Csp45 I
      |      |                             |                         |
     GCTGAACCAGCGCTTGTCGGTGCCGATCATGCGCTCCAAGCATGGCTTCGAAATCTGGAACTCGTACATG
     +----+----+----+----+----+----+----+----+----+----+----+----+----+----+  3850
     CGACTTGGTCGCGAACAGCCACGGCTAGTACGCGAGGTTCGTACCGAAGCTTTAGACCTTGAGCATGTAC

Ala Glu Pro Ala Leu Val Gly Ala Asp His Ala Leu Gln Ala Trp Leu Arg Asn Leu Glu Leu Val His
       Leu Asn Gln Arg Leu Ser Val Pro Ile Met Arg Ser Lys His Gly Phe Glu Ile Trp Asn Ser Tyr Met
         Cys  *  Thr Ser Ala Cys Arg Cys Arg Ser Cys Ala Pro Ser Met Ala Ser Lys Ser Gly Thr Arg Thr  *

Ala Ser Gly Ala Ser Thr Pro Ala Ser  *  Ala Ser Trp Ala His Ser Arg Phe Arg Ser Ser Thr Cys Ser
       Ser Phe Trp Arg Lys Asp Thr Gly Ile Met Arg Glu Leu Cys Pro Lys Ser Ile Gln Phe Glu Tyr Met
         Gln Val Leu Ala Gln Arg His Arg Asp His Ala Gly Leu Met Ala Glu Phe Asp Pro Val Arg Val His
```

FIG. 12S

```
                                                                    BscE I
                               BspD I                               BssH II
          Bbs I                Cla I                                    BscE I
          |                    |                                     |||   |
     AAGACTTGGCACGATCTGAATATCGATCATGTTCAGTTCAATGTCGTCAGCACGGATGAAATGCGCGCTG
     ++++++++++++++++++++++++++++++++++++++++++++++++++++++++++++++++++++++ 3920
     TTCTGAACCGTGCTAGACTTATAGCTAGTACAAGTCAAGTTACAGCAGTCGTGCCTACTTTACGCGCGAC
```

Glu Asp Leu Ala Arg Ser Glu Tyr Arg Ser Cys Ser Val Gln Cys Arg Gln His Gly • Asn Ala Arg Cys
   Lys Thr Trp His Asp Leu Asn Ile Asp His Val Gln Phe Asn Val Val Ser Thr Asp Glu Met Arg Ala
     Arg Leu Gly Thr Ile • Ile Ser Ile Met Phe Ser Ser Met Ser Ser Ala Arg Met Lys Cys Ala Leu

Ser Lys Ala Arg Asp Ser Tyr Arg Asp His Glu Thr • His Arg • Cys Pro His Phe Ala Arg Gln
  Phe Val Gln Cys Ser Arg Phe Ile Ser • Thr • Asn Leu Thr Thr Leu Val Ser Ser Ile Arg Ala Ala
    Leu Ser Pro Val Ile Gln Ile Asp Ile Met Asn Leu Glu Ile Asp Asp Ala Arg Ile Phe His Ala Ser

```
          Fsp I                                               Eco47 III
          |                                                   |
     CGCAGCGCGAACCCGAGAAGCACCATGATCTTATCGTGCGCGTTTCCGGCTACAGCGCTCGGTTCGTAGA
     ++++++++++++++++++++++++++++++++++++++++++++++++++++++++++++++++++++++ 3990
     GCGTCGCGCTTGGGCTCTTCGTGGTACTAGAATAGCACGCGCAAAGGCCGATGTCGCGAGCCAAGCATCT
```

Ala Ala Arg Thr Arg Glu Ala Pro • Ser Tyr Arg Ala Arg Phe Arg Leu Gln Arg Ser Val Arg Arg
 Ala Gln Arg Glu Pro Glu Lys His His Asp Leu Ile Val Arg Val Ser Gly Tyr Ser Ala Arg Phe Val Asp
   Arg Ser Ala Asn Pro Arg Ser Thr Met Ile Leu Ser Cys Ala Phe Pro Ala Thr Ala Leu Gly Ser •

Ala Ala Arg Val Arg Ser Ala Gly His Asp • Arg Ala Arg Lys Arg Ser Cys Arg Glu Thr Arg Leu
     Cys Arg Ser Gly Ser Phe Cys Trp Ser Arg Ile Thr Arg Thr Glu Pro • Leu Ala Arg Asn Thr Ser
  Arg Leu Ala Phe Gly Leu Leu Val Met Ile Lys Asp His Ala Asn Gly Ala Val Ala Ser Pro Glu Tyr Val

```
                                                                       Xho I
                                                                       | Sci I
                                                                       ||
     CATTCCGACCTATGGGCAGAACACCATCATCGCCCGTCAGGAACAGGATTTCAGCGCATCCGATCTCGAG
     ++++++++++++++++++++++++++++++++++++++++++++++++++++++++++++++++++++++ 4060
     GTAAGGCTGGATACCCGTCTTGTGGTAGTAGCGGGCAGTCCTTGTCCTAAAGTCGCGTAGGCTAGAGCTC
```

His Ser Asp Leu Trp Ala Glu His His His Arg Pro Ser Gly Thr Gly Phe Gln Arg Ile Arg Ser Arg
     Ile Pro Thr Tyr Gly Gln Asn Thr Ile Ile Ala Arg Gln Glu Gln Asp Phe Ser Ala Ser Asp Leu Glu
   Thr Phe Arg Pro Met Gly Arg Thr Pro Ser Ser Pro Val Arg Asn Arg Ile Ser Ala His Pro Ile Ser Ser

Cys Glu Ser Arg His Ala Ser Cys Trp • Arg Gly Asp Pro Val Pro Asn • Arg Met Arg Asp Arg Thr
     Met Gly Val • Pro Cys Phe Val Met Met Ala Arg • Ser Cys Ser Lys Leu Ala Asp Ser Arg Ser
       Asn Arg Gly Ile Pro Leu Val Gly Asp Asp Gly Thr Leu Phe Leu Ile Glu Ala Cys Gly Ile Glu Leu

FIG. 12T

Bce83 I

```
TTCCTAAACGTCGAAATCTAGGACAAGCCACTCAAGGGGGGCAGCATCCCGTCCCCCTTTACCTTACGGT
+----+----+----+----+----+----+----+----+----+----+----+----+----+----+ 4130
AAGGATTTGCAGCTTTAGATCCTGTTCGGTGAGTTCCCCCCGTCGTAGGGCAGGGGGAAATGGAATGCCA
```

Val Pro Lys Arg Arg Asn Leu Gly Gln Ala Thr Gln Gly Gly Gln His Pro Val Pro Leu Tyr Leu Thr Val
Phe Leu Asn Val Glu Ile • Asp Lys Pro Leu Lys Gly Gly Ser Ile Pro Ser Pro Phe Thr Leu Arg
Ser • Thr Ser Lys Ser Arg Thr Ser His Ser Arg Gly Ala Ala Ser Arg Pro Pro Leu Pro Tyr Gly

Gly Leu Arg Arg Phe Arg Pro Cys Ala Val • Pro Pro Cys Cys Gly Thr Gly Arg • Arg Val Thr
Asn Arg Phe Thr Ser Ile • Ser Leu Gly Ser Leu Pro Pro Leu Met Gly Asp Gly Lys Val Lys Arg Asn
Glu • Val Asp Phe Asp Leu Val Leu Trp Glu Leu Pro Ala Ala Asp Arg Gly Gly Lys Gly • Pro

```
TGCACGAAAAAACATGGAGGGCAGCAACATGGAAACAGGACAGAATTTGCAAAACCAGCCGCATACCGAG
+----+----+----+----+----+----+----+----+----+----+----+----+----+----+ 4200
ACGTGCTTTTTTGTACCTCCCGTCGTTGTACCTTTGTCCTGTCTTAAACGTTTTGGTCGGCGTATGGCTC
```

Ala Arg Lys Asn Met Glu Gly Ser Asn Met Glu Thr Gly Gln Asn Leu Gln Asn Gln Pro His Thr Glu
Leu His Glu Lys Thr Trp Arg Ala Ala Thr Trp Lys Gln Asp Arg Ile Cys Lys Thr Ser Arg Ile Pro Arg
Cys Thr Lys Lys His Gly Gly Gln Gln His Gly Asn Arg Thr Glu Phe Ala Lys Pro Ala Ala Tyr Arg

Ala Arg Phe Phe Met Ser Pro Leu Leu Met Ser Val Pro Cys Phe Lys Cys Phe Trp Gly Cys Val Ser
Cys Ser Phe Val His Leu Ala Ala Val His Phe Cys Ser Leu Ile Gln Leu Val Leu Arg Met Gly Leu
Gln Val Phe Phe Cys Pro Pro Cys Cys Pro Phe Leu Val Ser Asn Ala Phe Gly Ala Ala Tyr Arg Pro

```
GTGGGTACGGCGAGGCCGTGCCGGAGTTGCAAATGGCAAACCCCCGACCCCACCGATCCGCACCGTGGGC
+----+----+----+----+----+----+----+----+----+----+----+----+----+----+ 4270
CACCCATGCCGCTCCGGCACGGCCTCAACGTTTACCGTTTGGGGGCTGGGGTGGCTAGGCGTGGCACCCG
```

Val Gly Thr Ala Arg Pro Cys Arg Ser Cys Lys Trp Gln Thr Pro Asp Pro Thr Asp Pro His Arg Gly
Trp Val Arg Arg Gly Arg Ala Gly Val Ala Asn Gly Lys Pro Pro Thr Pro Pro Ile Arg Thr Val Gly
Gly Gly Tyr Gly Glu Ala Val Pro Glu Leu Gln Met Ala Asn Pro Arg Pro His Arg Ser Ala Pro Trp Ala

Thr Pro Val Ala Leu Gly His Arg Leu Gln Leu His Cys Val Gly Ser Gly Val Ser Gly Cys Arg Pro Cys
His Thr Arg Arg Pro Arg Ala Pro Thr Ala Phe Pro Leu Gly Gly Val Gly Gly Ile Arg Val Thr Pro
Pro Tyr Pro Ser Ala Thr Gly Ser Asn Cys Ile Ala Phe Gly Arg Gly Trp Arg Asp Ala Gly His Ala

FIG. 12U

```
        BsrD I    Taq II' Nco I                      Bpu10 I      Bpm I
           |        |    |                             |            |
        AATGCACCGCCAACCGGCACGCCATGGGTGGCGTCTGGAAACGCTGGCTTAGGGACGTTGAAAACACGAC
        +----+----+----+----+----+----+----+----+----+----+----+----+----+----+ 4340
        TTACGTGGCGGTTGGCCGTGCGGTACCCACCGCAGACCTTTGCGACCGAATCCCTGCAACTTTTGTGCTG
```

Gln Cys Thr Ala Asn Arg His Ala Met Gly Gly Val Trp Lys Arg Trp Leu Arg Asp Val Glu Asn Thr Thr
  Asn Ala Pro Pro Thr Gly Thr Pro Trp Val Ala Ser Gly Asn Ala Gly Leu Gly Thr Leu Lys Thr Arg
    Met His Arg Gln Pro Ala Arg His Gly Trp Arg Leu Glu Thr Leu Ala • Gly Arg • Lys His Asp

His Val Ala Leu Arg Cys Ala Met Pro Pro Thr Gln Phe Arg Gln Ser Leu Ser Thr Ser Phe Val Val
 Leu Ala Gly Gly Val Pro Val Gly His Thr Ala Asp Pro Phe Ala Pro Lys Pro Val Asn Phe Val Arg Gly
  Ile Cys Arg Trp Gly Ala Arg Trp Pro His Arg Arg Ser Val Ser Ala • Pro Arg Gln Phe Cys Ser

```
        EcoN I
           |BspM I
           | |BssS I                      Tth111 I      Bpm I
           | | |                             |            |
        CTGCTCCAGGCACGAGGAAGGCAAACTAAGTTTCCGCGACCACGTCTGAACACCGGACAGACGTGGTTCA
        +----+----+----+----+----+----+----+----+----+----+----+----+----+----+ 4410
        GACGAGGTCCGTGCTCCTTCCGTTTGATTCAAAGGCGCTGGTGCAGACTTGTGGCCTGTCTGCACCAAGT
```

Cys Ser Arg His Glu Glu Gly Lys Leu Ser Phe Arg Asp His Val • Thr Pro Asp Arg Arg Gly Ser
 Pro Ala Pro Gly Thr Arg Lys Ala Asn • Val Ser Ala Thr Thr Ser Glu His Arg Thr Asp Val Val His
  Leu Leu Gln Ala Arg Gly Arg Gln Thr Lys Phe Pro Arg Pro Arg Leu Asn Thr Gly Gln Thr Trp Phe

Gln Glu Leu Cys Ser Ser Pro Leu Ser Leu Lys Arg Ser Trp Thr Gln Val Gly Ser Leu Arg Pro Glu
  Ala Gly Pro Val Leu Phe Ala Phe • Thr Glu Ala Val Val Asp Ser Cys Arg Val Ser Thr Thr •
 Arg Ser Trp Ala Arg Pro Leu Cys Val Leu Asn Gly Arg Gly Arg Arg Phe Val Pro Cys Val His Asn Val

```
                              Bpm I
                                 |BspH I
                                 | |
        CCTCCAGACCACTGTAGTGATAGATCATGAAAACCTACTCCAGCGCAAATGGCCTGTTCGTCCCGGAAGT
        +----+----+----+----+----+----+----+----+----+----+----+----+----+----+ 4480
        GGAGGTCTGGTGACATCACTATCTAGTACTTTTGGATGAGGTCGCGTTTACCGGACAAGCAGGGCCTTCA
```

Pro Pro Asp His Cys Ser Asp Arg Ser • Lys Pro Thr Pro Ala Gln Met Ala Cys Ser Ser Arg Lys
  Leu Gln Thr Thr Val Val Ile Asp His Glu Asn Leu Leu Gln Arg Lys Trp Pro Val Arg Pro Gly Ser
   Thr Ser Arg Pro Leu • • • Ile Met Lys Thr Tyr Ser Ser Ala Asn Gly Leu Phe Val Pro Glu Val

Gly Gly Ser Trp Gln Leu Ser Leu Asp His Phe Gly Val Gly Ala Cys Ile Ala Gln Glu Asp Arg Phe Asp
  Arg Trp Val Val Thr Thr Ile Ser • Ser Phe Arg Ser Trp Arg Leu His Gly Thr Arg Gly Pro Leu
   Glu Leu Gly Ser Tyr His Tyr Ile Met Phe Val • Glu Leu Ala Phe Pro Arg Asn Thr Gly Ser Thr

FIG. 12V

```
                                                          EcoR V
                          Bcg I      Bcg I'              |    Bcg I'
                          |          |                   |    |
    CGATCCCTACTACTATGTAAGTACGGAAAACCAGAGCTTCCTCGATAAATTTGCAAAGATATCGAAAAAG
    ----+----+----+----+----+----+----+----+----+----+----+----+----+----+ 4550
    GCTAGGGATGATGATACATTCATGCCTTTTGGTCTCGAAGGAGCTATTTAAACGTTTCTATAGCTTTTC
```

Ser Ile Pro Thr Thr Met  •  Val Arg Lys Thr Arg Ala Ser Ser Ile Asn Leu Gln Arg Tyr Arg Lys Ser
  Arg Ser Leu Leu Leu Cys Lys Tyr Gly Lys Pro Glu Leu Pro Arg  •  Ile Cys Lys Asp Ile Glu Lys
    Asp Pro Tyr Tyr Tyr Val Ser Thr Glu Asn Gln Ser Phe Leu Asp Lys Phe Ala Lys Ile Ser Lys Lys

Ile Gly Val Val Ile Tyr Thr Arg Phe Val Leu Ala Glu Glu Ile Phe Lys Cys Leu Tyr Arg Phe Leu
  Arg Asp Arg Ser Ser His Leu Tyr Pro Phe Gly Ser Ser Gly Arg Tyr Ile Gln Leu Ser Ile Ser Phe Ala
    Ser Gly  •   •   •  Thr Leu Val Ser Phe Trp Leu Lys Arg Ser Leu Asn Ala Phe Ile Asp Phe Phe

```
       Bcg I                            Bbs I
       |                                |
    CATCCCGTCAATGTACTGGTGGTCGGCAAACAAGGCTGCGGCAAGTCTTCCCTAGTGCGGCAATACGCCG
    ----+----+----+----+----+----+----+----+----+----+----+----+----+----+ 4620
    GTAGGGCAGTTACATGACCACCAGCCGTTTGTTCCGACGCCGTTCAGAAGGGATCACGCCGTTATGCGGC
```

Ile Pro Ser Met Tyr Trp Trp Ser Ala Asn Lys Ala Ala Ala Ser Leu Pro  •  Cys Gly Asn Thr Pro
Ala Ser Arg Gln Cys Thr Gly Gly Arg Gln Thr Arg Leu Arg Gln Val Phe Pro Ser Ala Ala Ile Arg Arg
  His Pro Val Asn Val Leu Val Val Gly Lys Gln Gly Cys Gly Lys Ser Ser Leu Val Arg Gln Tyr Ala

Met Gly Asp Ile Tyr Gln His Asp Ala Phe Leu Ala Ala Ala Leu Arg Gly  •  His Pro Leu Val Gly
    Asp Arg  •  His Val Pro Pro Arg Cys Val Leu Ser Arg Cys Thr Lys Gly Leu Ala Ala Ile Arg Arg
  Cys Gly Thr Leu Thr Ser Thr Thr Pro Leu Cys Pro Gln Pro Leu Asp Glu Arg Thr Arg Cys Tyr Ala Ala

```
                            BsaB I
                            |
    CCGTCAACAGGCTACCCTTGGCGACCTTCCAGATCGGCATCCTGTCGGAGCCGGGGCAACTGTTTGGTGA
    ----+----+----+----+----+----+----+----+----+----+----+----+----+----+ 4690
    GGCAGTTGTCCGATGGGAACCGCTGGAAGGTCTAGCCGTAGGACAGCCTCGGCCCCGTTGACAAACCACT
```

Pro Ser Thr Gly Tyr Pro Trp Arg Pro Ser Arg Ser Ala Ser Cys Arg Ser Arg Gly Asn Cys Leu Val
  Arg Gln Gln Ala Thr Leu Gly Asp Leu Pro Asp Arg His Pro Val Gly Ala Gly Ala Thr Val Trp  •
    Ala Val Asn Arg Leu Pro Leu Ala Thr Phe Gln Ile Gly Ile Leu Ser Glu Pro Gly Gln Leu Phe Gly Glu

Gly Asp Val Pro  •  Gly Gln Arg Gly Glu Leu Asp Ala Asp Gln Arg Leu Arg Pro Leu Gln Lys Thr Phe
  Arg  •  Cys Ala Val Arg Pro Ser Arg Gly Ser Arg Cys Gly Thr Pro Ala Pro Ala Val Thr Gln His
    Thr Leu Leu Ser Gly Lys Ala Val Lys Trp Ile Pro Met Arg Asp Ser Gly Pro Cys Ser Asn Pro Ser

FIG. 12W

```
                 Bsa I              Bpm I                Ear I                    Mfe I
                 |                  |                    |                        Mun I
                 |                  |                    |                        |
ATACGCGCTGGAGAACGGGGAGACCCGTTACAAGCAGTTCCTCTTCCCCCAGGCCATCCAGACACCCAAT
++++++++++++++++++++++++++++++++++++++++++++++++++++++++++++++++++++ 4760
TATGCGCGACCTCTTGCCCCTCTGGGCAATGTTCGTCAAGGAGAAGGGGGTCCGGTAGGTCTGTGGGTTA
```

Asn Thr Arg Trp Arg Thr Gly Arg Pro Val Thr Ser Ser Ser Ser Ser Pro Arg Pro Ser Arg His Pro Ile
 Ile Arg Ala Gly Glu Arg Gly Asp Pro Leu Gln Ala Val Pro Leu Pro Pro Gly His Pro Asp Thr Gln
  Tyr Ala Leu Glu Asn Gly Glu Thr Arg Tyr Lys Gln Phe Leu Phe Pro Gln Ala Ile Gln Thr Pro Asn

Val Arg Gln Leu Val Pro Leu Gly Thr Val Leu Leu Glu Glu Gly Leu Gly Asp Leu Cys Gly Ile
Ile Arg Ala Pro Ser Arg Pro Ser Gly Asn Cys Ala Thr Gly Arg Gly Gly Pro Trp Gly Ser Val Trp Asn
 Tyr Ala Ser Ser Phe Pro Ser Val Arg • Leu Cys Asn Arg Lys Gly Trp Ala Met Trp Val Gly Leu

```
         Taq II'
         | Ear I                                         BspLU11 I
         | |                                             |
         | |                                             |
TGCGTCATCCACCTTGAAGAGATCAATCGCCCCGAGCATCCGAAGGCGTTGAACATGTTGTTCTCCATTC
++++++++++++++++++++++++++++++++++++++++++++++++++++++++++++++++++++ 4830
ACGCAGTAGGTGGAACTTCTCTAGTTAGCGGGGCTCGTAGGCTTCCGCAACTTGTACAACAAGAGGTAAG
```

Ala Ser Ser Thr Leu Lys Arg Ser Ile Ala Pro Ser Ile Arg Arg Arg • Thr Cys Cys Ser Pro Phe
Leu Arg His Pro Pro • Arg Asp Gln Ser Pro Arg Ala Ser Glu Gly Val Glu His Val Val Leu His Ser
 Cys Val Ile His Leu Glu Glu Ile Asn Arg Pro Glu His Pro Lys Ala Leu Asn Met Leu Phe Ser Ile

Ala Asp Asp Val Lys Phe Leu Asp Ile Ala Gly Leu Met Arg Leu Arg Gln Val His Gln Glu Gly Asn
   Arg • Gly Gly Gln Leu Ser • Asp Gly Arg Ala Asp Ser Pro Thr Ser Cys Thr Thr Arg Trp Glu
Gln Thr Met Trp Arg Ser Ser Ile Leu Arg Gly Ser Cys Gly Phe Ala Asn Phe Met Asn Asn Glu Met Arg

```
                                       EcoICR I
                                       |  Sac I
         EcoP15 I                      |  |
         |                             |  |
         |                             |  |
TCTCCGATGACCGTCAGGTATGGATGGACGAGCTCGGACTGCTGCAAGTAGCGCCCGGAGTCGTTTTCTT
++++++++++++++++++++++++++++++++++++++++++++++++++++++++++++++++++++ 4900
AGAGGCTACTGGCAGTCCATACCTACCTGCTCGAGCCTGACGACGTTCATCGCGGGCCTCAGCAAAAGAA
```

Ser Pro Met Thr Val Arg Tyr Gly Trp Thr Ser Ser Asp Cys Cys Lys • Arg Pro Glu Ser Phe Ser
 Leu Arg • Pro Ser Gly Met Asp Gly Arg Ala Arg Thr Ala Ala Ser Ser Ala Arg Ser Arg Phe Leu
Leu Ser Asp Asp Arg Gln Val Trp Met Asp Glu Leu Gly Leu Leu Gln Val Ala Pro Gly Val Val Phe Phe

Glu Gly Ile Val Thr Leu Tyr Pro His Val Leu Glu Ser Gln Gln Leu Tyr Arg Gly Ser Asp Asn Glu Glu
 Arg Arg His Gly Asp Pro Ile Ser Pro Arg Ala Arg Val Ala Ala Leu Leu Ala Arg Leu Arg Lys Arg
  Glu Ser Ser Arg • Thr His Ile Ser Ser Ser Pro Ser Ser Cys Thr Ala Gly Pro Thr Thr Lys Lys

```
tutE.T1    R K K H E E T V G W P L Q P I L D N I E H L I Q A K A N I R I H I P V I P G F N D S P M D F E D Y I A Y L G R H A A Q L   297
f308.coli  D A P F K Q W T D G N A A R V L D N L K K L A A A G K K I I - - R V P L I Q F N A D E T S V K A I T D F A A - D E L H V   254
pflC.coli  A T Q A R D V V K M N L P R V L E N L R L L V S E G V N V I P - L I P G F T L S R E N M Q Q A L D V L I - P - L N I   238
pflA.coli  D E I H Q N L V G V S N H R T L E F A K Y L A N K N V K V W I R Y V V V P G W S D D D S A H R L G E F - T R D M G N V   194 tutE.T1    D G V D I L N Y H V Y G E G K K Y R S L G R E N E Y Q Y F G V E E N P P E K V V P L A K G L K L A G I T S V T I G G L V G   357
f308.coli  G E I H F L P Y H T L G I N K Y H L L N L P - - - - - Y D A P E K P L D A P E L L D F A Q Q Y A C Q K G L T A T - L R G   308
pflC.coli  R Q I H L L P F H Q Y G E P K K Y R L L G K T - - - W S M K E V P A P S S A D V A T M R E M A E R A G L Q V T - V G G   292
pflA.coli  E K I E L P Y H E L G - - K H K W V A M G E E Y K - - - L D G V K P P K K E T M E R V K G I L E Q Y G H K V - - - - -   244 tutE.T1    I T A D R H K S S R D A G T G C I A   375
f308.coli  - - - - - - - - - - - - - - - - - -   308
pflC.coli  - - - - - - - - - - - - - - - - - -   292
pflA.coli  - - - - - - - - - - - - - - - - M F   246
```

FIG. 13B

US 6,551,814 B1

METHODS FOR BIOREMEDIATION BY DEGRADING TOLUENE

This application for patent under 35 U.S.C. 111(a) claims priority to Provisional Application Ser. No. 60/046,845, filed May 5, 1997 under 35 U.S.C. 111(b). This invention was made with government support under NSF grant MCB9507132 and DARPA grant N00014-92-J-1888. The government has certain rights in the invention.

FIELD OF THE INVENTION

This invention relates to biological treatment of organic compounds, and particularly to the degradation of toluene and toluene analogues.

BACKGROUND

Industrial processes that use or generate toxic organic compounds (e.g., toluene, benzene, xylenes) has lead to the contamination of nearby water and land. Such compounds are among the most water soluble of all gasoline components and can also enter aquatic environments from many sources such as gasoline underground storage tanks, leaks, and spills.

Most approaches to decontamination or "remediation" involve stopping the local dumping of such compounds and transport of the waste to another area for containment. This is costly and does not eliminate the hazard.

As a remediation technology, bioremediation is considerably more attractive. Rather than merely transporting wastes, it offers the possibility of degrading toxic compounds to harmless reaction products by the use of biologicals.

Bioremediation field trials have involved both in-situ and ex-situ treatment methods. Typically, ex-situ treatment involves the transfer of contaminated waste from the site into a treatment tank designed to support microbial growth, i.e., a "bioreactor". The reactor provides for effective mixing of nutrients and control over temperature, pH and aeration to allow optimum microbial growth.

In-situ treatment involves adding biologicals directly to the waste. This avoids the problems associated with handling (e.g., pumping) toxic compounds. However, in-situ treatment has its own problems. Unlike bioreactors, where microbial growth can be monitored and adjusted, in-situ environmental conditions are difficult to measure and control.

Fries et al., "Isolation, characterization and distribution of denitrifying toluene degraders from a variety of habitats," *Appl. Environ. Microbiol.* 60:2802 (1994) generally indicates that biodegradation of benzene, toluene, ethylbenzene and xylenes under aerobic conditions is well known, although the availability of oxygen due to its low solubility in water and low rate of transport in soils and sediments is rate limiting. Fries et al. describes anaerobic respiration of toluene by microorganisms isolated from nature. The microorganisms could grow on 25 ppm toluene and could be fed 50 ppm toluene.

Rates have been determined at 28–30° C. with intact cells from a variety of strains. The rates vary from between 8 to 80 nmoles toluene $min^{-1}$ $mg^{-1}$ protein. A. Frazer et al., "Toluene Metabolism Under Anaerobic Conditions: A Review," *Anaerobe* 1:293 (1995).

There remains a need to develop a bioremediation procedure that can be operated economically on a commercial scale. Such a procedure must be able to degrade organic compounds with high efficiency.

SUMMARY OF THE INVENTION

This invention relates to biological treatment of organic compounds, and particularly to the degradation of toluene and toluene analogues. In one embodiment, the present invention contemplates a method of degrading compounds contained in a liquid or solid waste source, comprising the steps of: a) providing, i) a waste source comprising toluene (and/or a toluene analogue), ii) a reaction containing means, and iii) a compound selected from the group consisting of a functional, cell-free pyruvate formate lyase homologue of a toluene-degrading bacterium and a functional, cell-free pyruvate formate lyase activating homologue of a toluene-degrading bacterium; and b) reacting said homologue and said waste source in said containing means under conditions such that toluene (and/or the toluene analogue) is degraded.

It is not intended that the present invention be limited by the specific toluene-degrading bacterium. In one embodiment, said homologue is derived from an organism of the genus Thauera. In one embodiment, the organism is *Thauera aromatica*.

In another embodiment, said homologue is derived from an organism of the genus Xanthomonas. In one embodiment, the organism is *Xanthomonas maltophilia*.

In yet another embodiment, said homologue is derived from an organism of the genus Geobacter. In one embodiment, the organism is *Geobacter metallireducens*.

In still another embodiment, said homologue is derived from members of the genus Azoarcus. In one embodiment, the organism is *Azoarcus tolulyticus*.

The present invention contemplates the nucleic acid sequences (and constructs comprising said sequences) and amino acid sequences of toluene degrading enzymes as compositions of matter (as well as antibodies to such amino acid sequences). In one embodiment, the present invention contemplates a purified nucleic acid comprising DNA having the sequence as set forth in FIGS. 12A–Y. In one embodiment, said DNA is in a vector. In another embodiment, said vector is a bacterial plasmid. In a particular embodiment, said bacterial plasmid is in a host cell. In one embodiment, said host cell expresses a toluene-degrading enzyme.

The present invention contemplates a functional, cell-free product of the tutD gene having the amino acid sequence as set forth in FIGS. 11A–D. In one embodiment, said product is contained within a reaction containing means. In a preferred embodiment, said reaction containing means is a bioreactor.

It is also not intended that the present invention be limited by the precise amino acid sequence of the homologue. In one embodiment, it is encoded by the tutD gene, a nucleic acid sequence for which is shown in FIGS. 5A–P, and has the amino acid sequence shown in FIGS. 7A–C. In another embodiment, the homologue is an expanded TutD protein having the amino acid shown in FIGS. 11A–D and the corresponding nucleic acid sequence shown in FIGS. 12A–Y. In another embodiment, the homologue is encoded by the tutE gene having a nucleic acid sequence shown in FIGS. 12A–Y, and a corresponding amino acid sequence shown in FIGS. 13A–B.

Additionally, the present invention contemplates a reporter gene fusion product constructed by fusing the tutD gene in frame to a reporter such as lacZ, luxA, or green fluorescence protein. Such constructs can be used to demonstrate regulated expression in response to toluene.

In another embodiment, the present invention contemplates a reporter gene fusion product constructed by fusing the tutE gene in frame to a reporter such as lacZ, luxA, or green fluorescence protein. Such constructs can be used to demonstrate regulated expression in response to toluene.

DEFINITIONS

To facilitate understanding of the invention, a number of terms are defined below.

The term "reaction" or "chemical reaction" means reactions involving chemical reactants, such as organic compounds. A "reaction containing means" refers to anything that can contain a reaction, including but not limited to, tubes, microtiter plates, vessels, and bioreactors. It is not intended that the present invention be limited by a particular reaction containing means. U.S. Pat. No. 5,610,061, U.S. Pat No. 5,585,272, U.S. Pat. No. 5,571,705, U.S. Pat. No. 5,560,737, U.S. Pat. No. 5,057,221 and U.S. Pat. No. 5,037,551 all describe various reaction containing means (including bioreactors) and are hereby incorporated by reference.

"Initiating a reaction" means causing a reaction to take place. Reactions can be initiated by any means (e.g., mixing, heat, wavelengths of light, addition of a catalyst, etc.)

A "solvent" is a liquid substance capable of dissolving or dispersing one or more other substances. It is not intended that the present invention be limited by the nature of the solvent used.

A "waste source" can be a solid or liquid waste source (e.g., paper pulp, pulp mill effluent, sludge, wastewater, petroleum spill, etc.).

"Toluene analogues" are structural analogues of toluene. While it is not intended that the present invention be limited to particular analogues, examples include the o-, m-, and p-isomers of chlorotoluene, fluorotoluene and xylene.

A "pyruvate formate lyase homologue" is defined as a gene product from a toluene-degrading organism, said gene product comprising i) regions of identity with the pyruvate formate lyase from *E. coli* (the-PflD gene Genebank G418519) and/or from *Clostridium pasteurianum* (Genebank G1072361) such that the gene product contains the motif RVSGY (SEQ ID NO:1), RVAGY (SEQ ID NO:2), or VRVSGYSA (SEQ ID NO:3) at the essential glycine (shown in bold and discussed below), and ii) regions of non-identity. The gene product may contain other regions of identity with pyruvate formate lyase from *E. coli* (the PflD gene Genebank G418519) and from *Clostridium pasteurianum* (Genebank G1072361), including but not limited to, the motif TPDGR (SEQ ID NO:4), TPDGRF (SEQ ID NO:5), GPTAVL (SEQ ID NO:6), and GNDDD (SEQ ID NO:7). As noted below, the present invention also identifies other conserved regions, including but not limited to those associated with an essential conserved cysteine.

A "functional" homologue is one where transfer of the gene or expression of the gene product confers the ability to degrade toluene. Functional homologues need not comprise the entire gene product, i.e. functional peptide fragments (portions that are less than the entire gene product) are specifically contemplated.

The term "purified" means separated from some components that are normally present in the native state. Thus, a spectrum of purity is contemplated. At the very basic level, a cell-free preparation is "purified." Similarly, nucleic acid that is even substantially protein-free is "purified." At a more extreme level, the present invention contemplates a particular toluene degrading protein that is substantially free of all other proteins (usually less than 10% and preferably less than 5% of other proteins are present).

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer or oligonucleotide is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarily with the sequence of the template to hybridize and thereby form a template primer complex for synthesis of the extension product of the primer. "Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology.

Even where the sequence of a probe or oligonucleotide is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

Hybridization, regardless of the method used, requires some degree of complementarily between the sequence being assayed (the target sequence) and the fragment of DNA used to perform the test (the probe). (Of course, one can obtain binding without any complementarily but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarily need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art. As indicated by standard references, an estimate of the $T_m$ value may be calculated by the equation:

$$T_m = 81.5° C. + 16.6 \log M + 0.41(\%GC) - 0.61(\% \text{form}) - 500/L$$

where M is the molarity of monovalent cations, % GC is the percentage of guanosine and cytosine nucleotides in the DNA, % form is the percentage of formamide in the hybridization solution, and L=length of the hybrid in base pairs. [See e.g., *Guide to Molecular Cloning Techniques*, Ed. S. L. Berger and A. R. Kimmel, in *Methods in Enzymology* Vol. 152, 401 (1987)]. Other references include more sophisticated computations which take structural as well as sequence characteristics into account for the calculation of $T_m$.

The present invention contemplates utilizing the nucleic acid sequence of the tutD gene to isolate other genes encoding pyruvate formate lyase homologues by hybridizing portions of the tutD gene to total DNA of various toluene-degrading organisms. Preferably, hybridization is carried out at high stringency (i.e., carried out at or near the $T_m$ of the particular duplex). Hybridization can be used to capture other genes. Alternatively, hybridization can be followed by primer extension or PCR.

The present invention also contemplates utilizing the nucleic acid sequence of the tutE gene to isolate other genes encoding pyruvate formate lyase homologues by hybridizing portions of the tutE gene to total DNA of various toluene-degrading organisms. Preferably, hybridization is carried out at high stringency (i.e., carried out at or near the $T_m$ of the particular duplex). Hybridization can be used to capture other genes. Alternatively, hybridization can be followed by primer extension or PCR.

Mullis, et al., U.S. Pat. Nos. 4,683,195 and 4,683,202 (both of which are hereby incorporated by reference), describe a methods for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain are relatively high concentration of a segment of the desired target sequence. The length of the segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired segment of the target sequence become the dominant sequences (in terms of concentration) in the mixture, they are said to be "PCR-amplified."

It is not intended that the present invention be limited to a particular toluene-degrading organism. The present invention contemplates identifying homologues in both known and yet undiscovered toluene-degrading organisms. Known organisms are set forth in the Table 1.

TABLE 1

| Strain Designations | Energy Metabolism |
| --- | --- |
| T | Denitrifying |
| T1 | Denitrifying |
| *Thauera aromatica*, K172 | Denitrifying |
| S100 and S2 | Denitrifying |
| *Azoarcus tolulyticus*, Tol 4 (type strain); others include Td-1, Td-2, Td-3, Td-15, Td-17, Td-19, Td-21 | Denitrifying |
| ToN1, mXyN1, and EbN1 | Denitrifying |
| *Xanthomonas maltophilia*, Sul | Denitrifying |
| *Geobacter metallireducens*, Gs-15 | Denitrifying |
| *Desulfobacula toluolica*, Tol2 | Denitrifying |
| PRTOL1 | Denitrifying |

The term "probe" as used herein refers to a labeled oligonucleotide which forms a duplex structure with a sequence in another nucleic acid, due to complementarily of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It is noted, however, that the invention does not require that a comparison be made between one or more forms of a gene to detect sequence variations.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dump (a naturally occurring dNTP) in a PCR would comprise the use of a nucleotide analog in the PCR. A PCR product generated using dump, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence. A "motif" refers to the corresponding amino acid sequence defining a region of identity following a comparison of two or more amino acid sequences.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, viruses, protozoans, fungi, and ciliates.

The term "microbial gene sequences" refers to gene sequences derived from a microorganism.

The term "bacteria" refers to any bacterial species including abacterial and archaebacterial species.

The term "recombinant DNA molecule" as used herein refers to a DNA molecule which is comprised of segments of DNA joined together by means of molecular biological techniques.

The terms "in operable combination" or "operably linked" as used herein refers to the linkage of nucleic acid sequences in such a manner that a nucleic acid molecule capable of directing the synthesis of a desired protein molecule is produced. When a promoter sequence is operably linked to sequences encoding a protein, the promoter directs the expression of mRNA which can be translated to produce a functional form of the encoded protein. The term also refers to the linkage of amino acid sequences in such a manner that a functional protein is produced.

The term "an oligonucleotide having a nucleotide sequence encoding a gene" means a DNA sequence comprising the coding region of a gene or, in other words, the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The term "recombinant oligonucleotide having a sequence encoding a protein operably linked to a heterologous promoter" or grammatical equivalents indicates that the coding region encoding the protein (e.g., an enzyme) has been joined to a promoter which is not the promoter naturally associated with the coding region in the genome of an organism (i.e., it is linked to an exogenous promoter). The promoter which is naturally associated or linked to a coding region in the genome is referred to as the "endogenous promoter" for that coding region.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element" as used herein refers to a genetic element which controls some aspect of the expression of nucleic acid sequences. For example, a promoter is a regulatory element which facilitates the initiation of transcription of an operably linked coding region.

The term "expression vector" or "vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

Transcriptional control signals in eucaryotes comprise "promoter" and "enhancer" elements. Promoters and enhancers consist of short arrays of DNA sequences that interact specifically with cellular proteins involved in transcription [Maniatis et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss et al., Trends Biochem. Sci. 11:287 (1986) and Maniatis et al., supra (1987)]. For example, the SV40 early gene enhancer is very active in a wide variety of cell types from many mammalian species and has been widely used for the expression of proteins in mammalian cells [Dijkema et al., EMBO J. 4:761 (1985)]. Two other examples of promoter/enhancer elements active in a broad range of mammalian cell types are those from the human elongation factor 1ot gene [Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad Sci. USA 79:6777 (1982)] and the human cytomegalovirus [Boshart et al., Cell 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

DESCRIPTION OF THE DRAWINGS

Figure 2A:
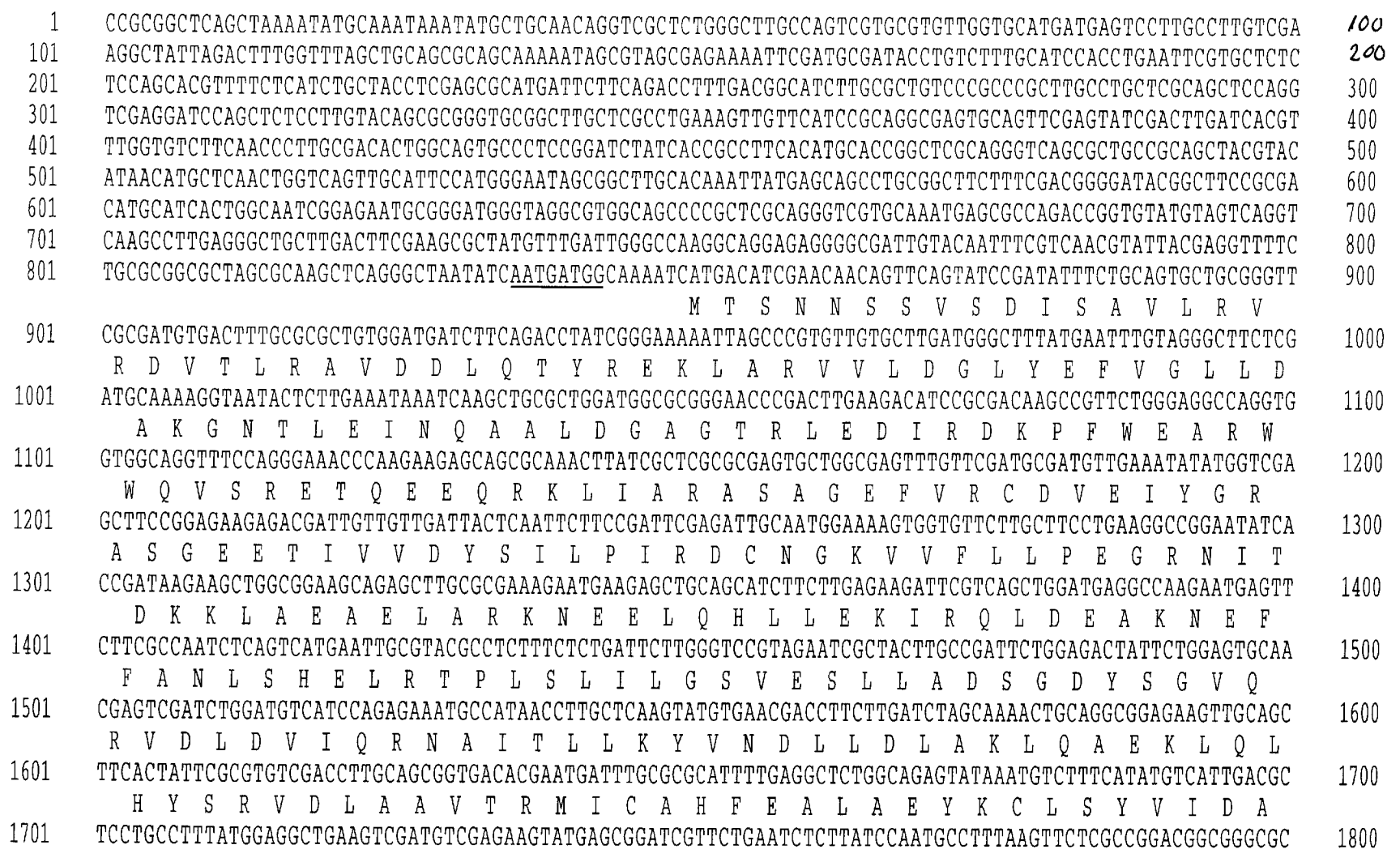
Figure 2C:
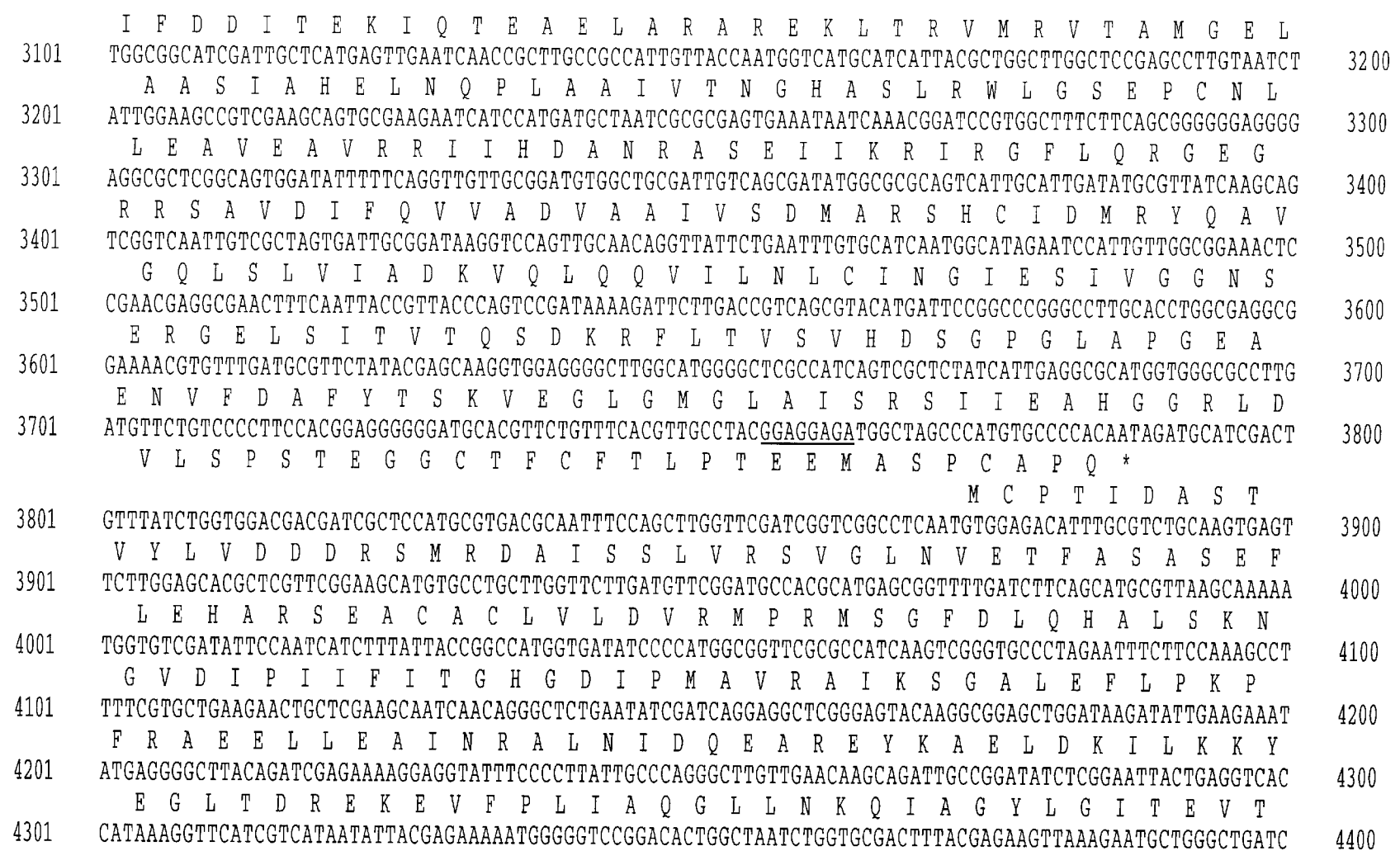
Figure 2D:
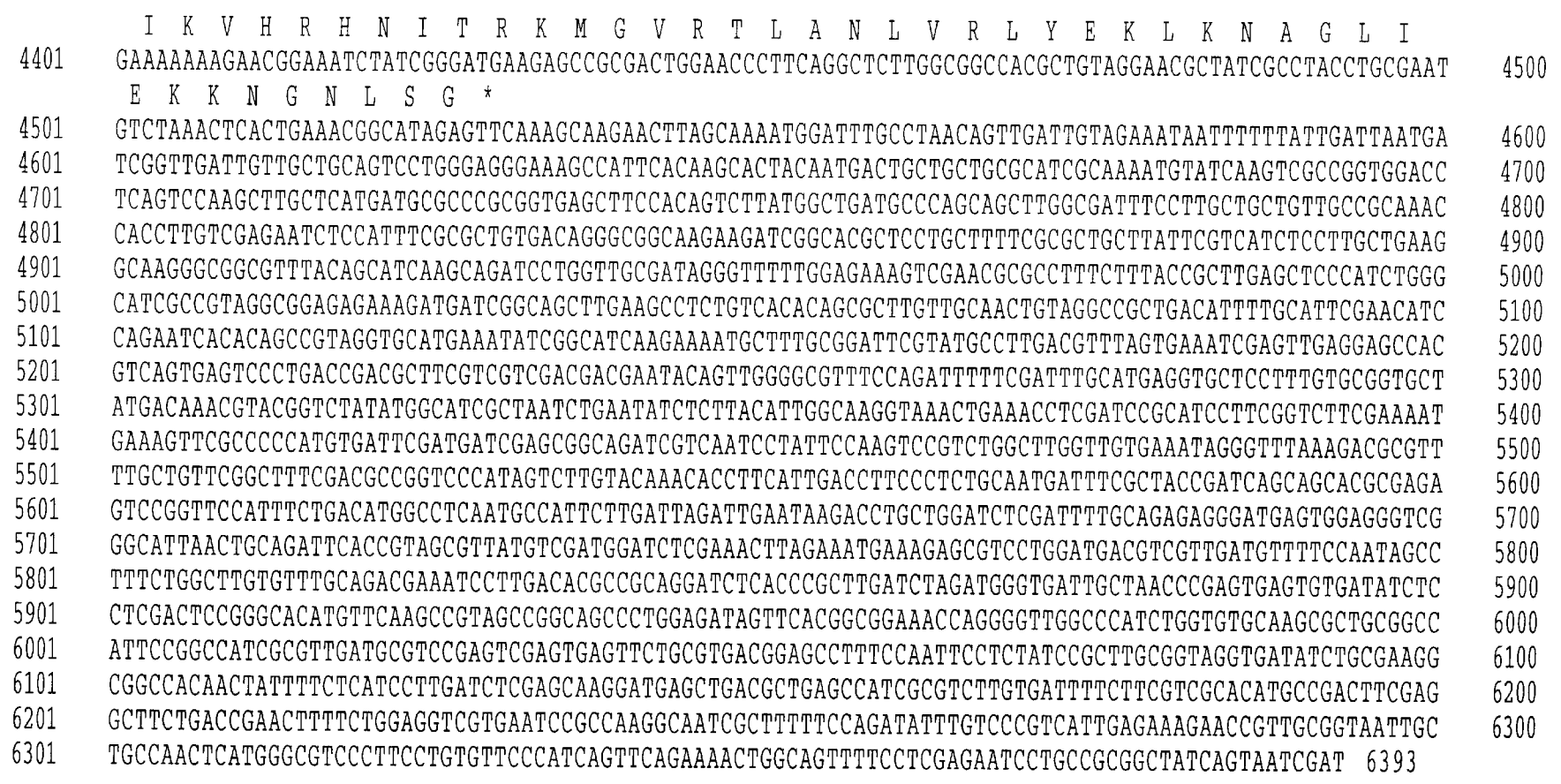

FIGS. 2A–D shows the nucleic acid sequence (SEQ ID NO: 8) of the tutB gene and tutC gene (submitted to the GenBank data base and assigned accession number U57900).

FIG. 3 shows the amino acid sequence of the tutB gene product (SEQ ID NOS:11, 19–23).

FIGS. 4A–B shows the amino acid sequence of the tutC gene product (SEQ ID NO: 10).

FIGS. 6A–C shows part of the nucleic acid sequence of the tutE gene (SEQ ID NO:12).

FIGS. 7A–C shows the amino acid sequence of the tutD gene product (SEQ ID NO:13).

FIG. 9 SEQ ID NOS:31–32 shows the polylinker contained in pRK415.

Figure 11A:
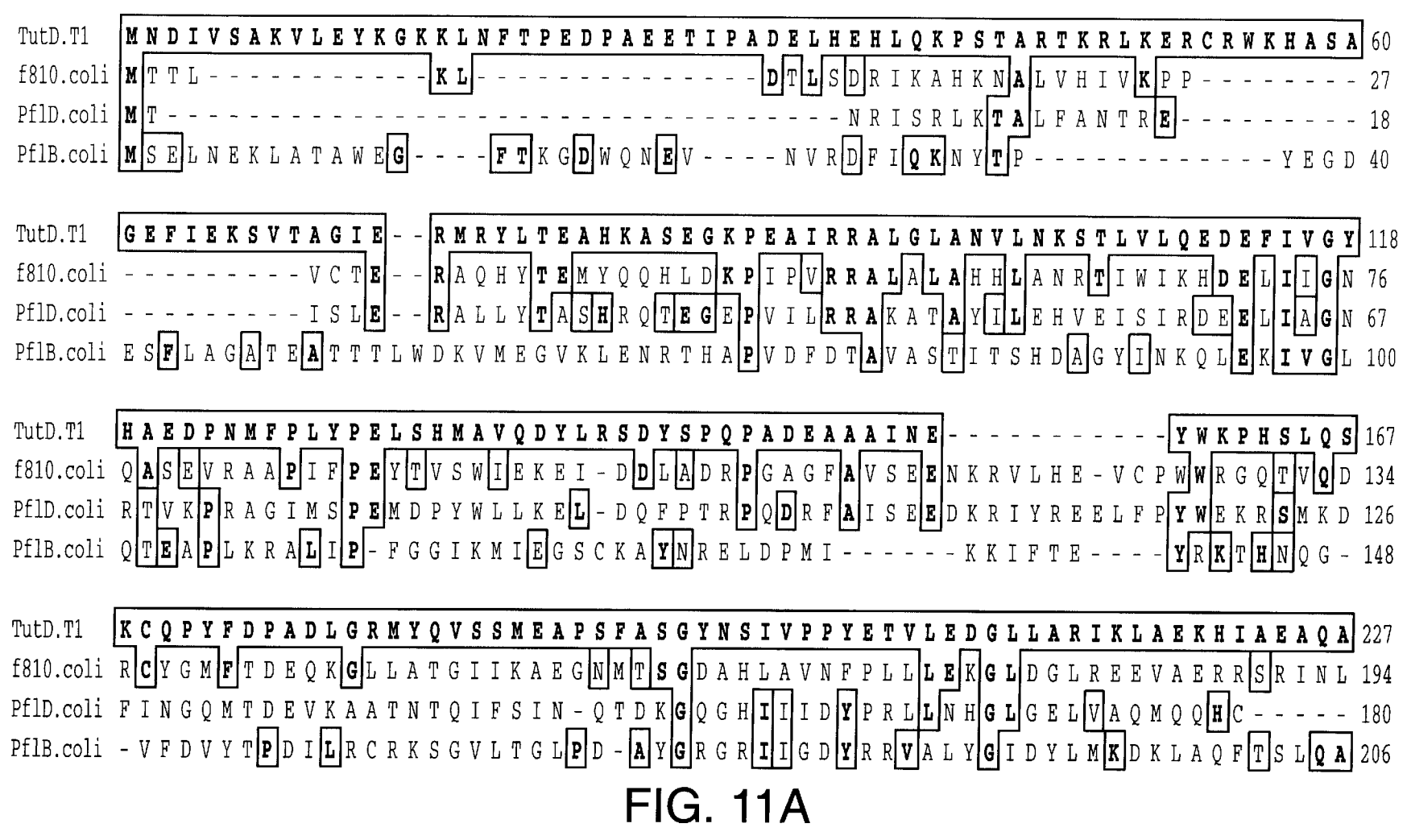
Figure 11B:
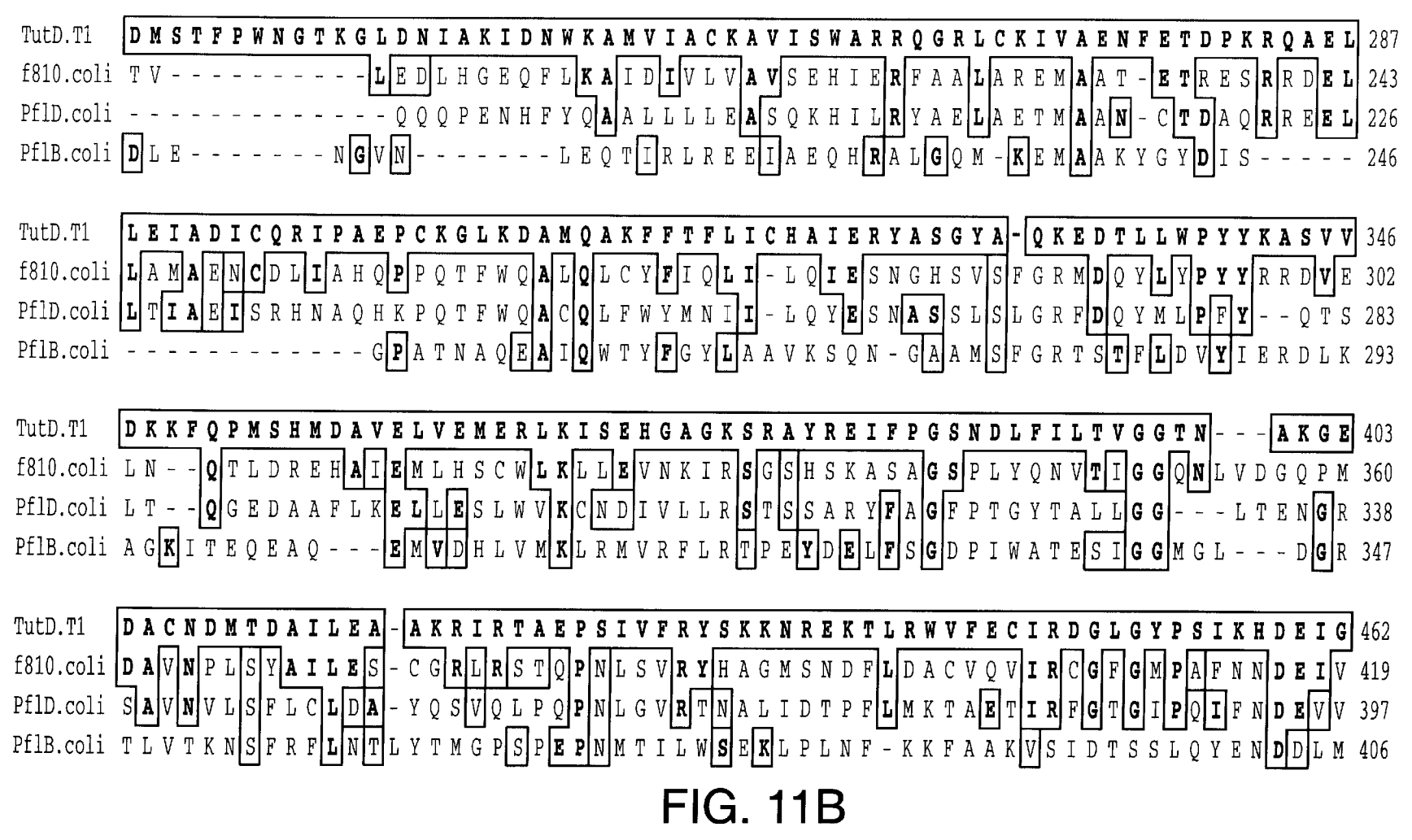
Figure 11C:
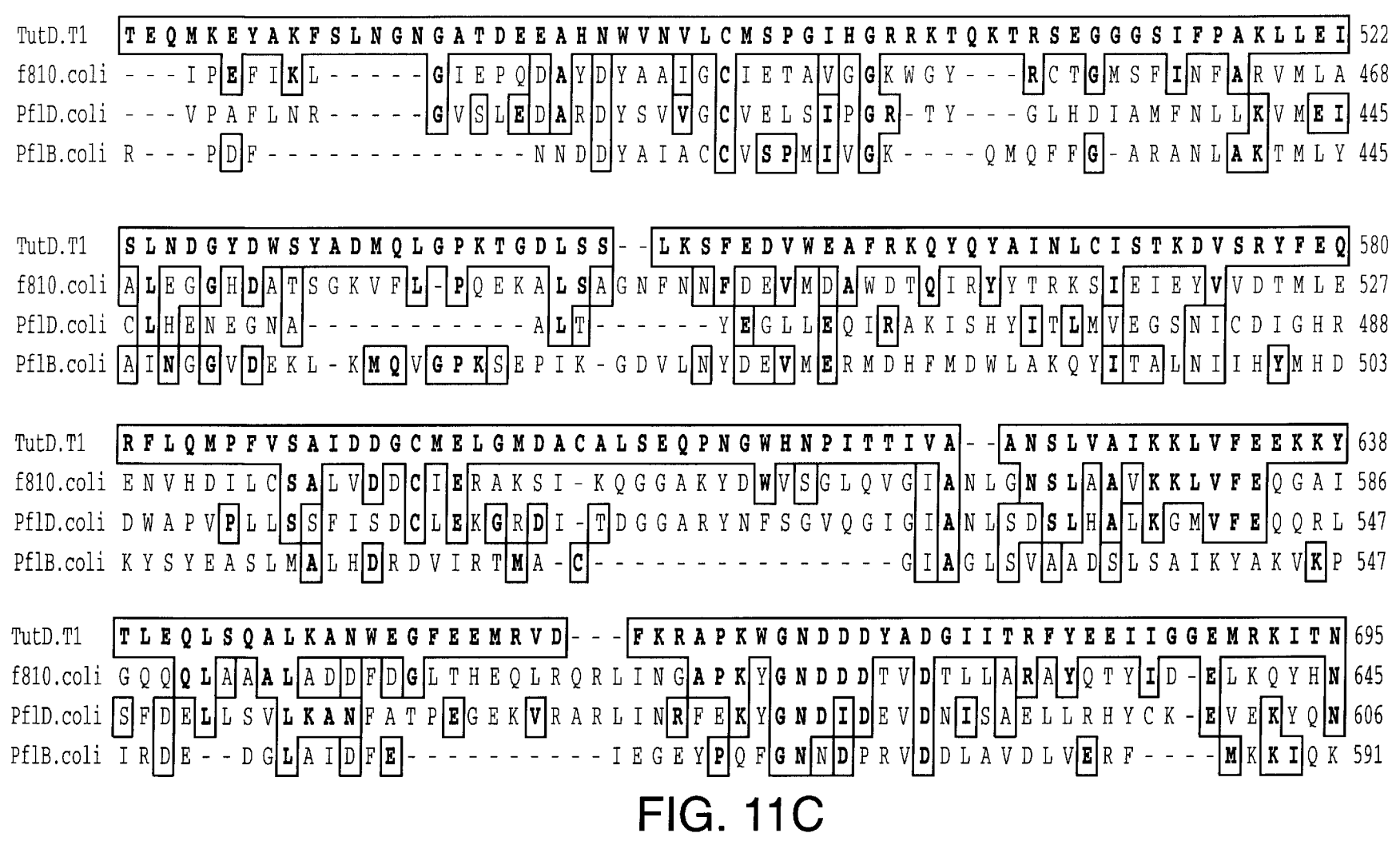
Figure 11D:
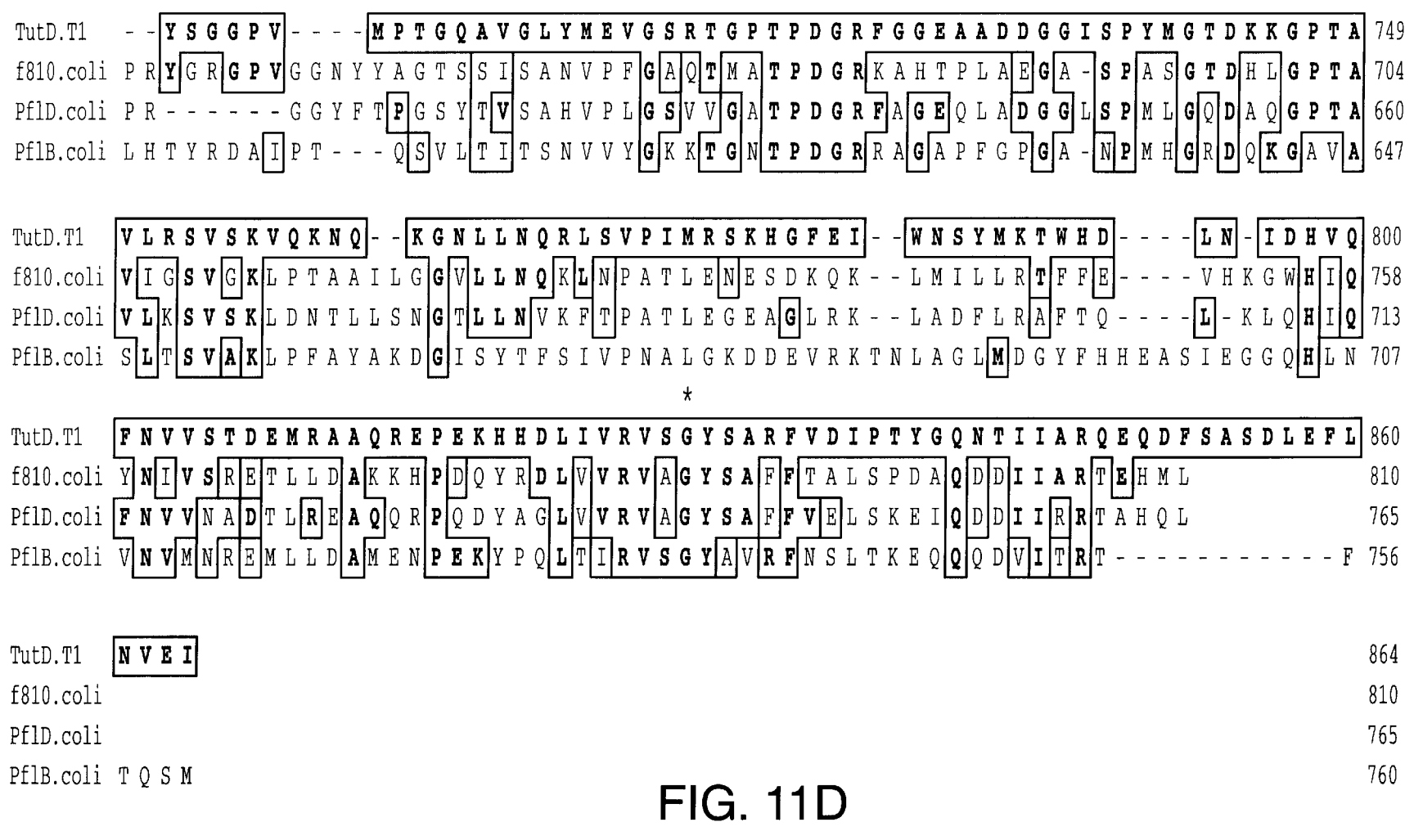

FIGS. 11A–D shows an expanded amino acid sequence of the tutD gene product (SEQ ID NO:14).

FIGS. 13A–B shows the amino acid sequence for the tutE gene product (SEQ ID NO:16).

DESCRIPTION OF THE INVENTION

This invention relates to biological treatment of organic compounds, and particularly to the degradation of toluene. Toluene, along with benzene and xylenes, is a common contaminant of ground and surface water. Toluene has been classified by the U.S. Environmental Protection Agency as a priority pollutant due to its ability to depress the central nervous system and to enhance the effect of known carcinogens.

Anaerobic toluene degrading bacterial strains have been isolated. Most importantly, mutants have been obtained. These mutants fall into two classes, one class that fails to metabolize toluene, and another class that metabolizes toluene but fails to use it as a growth substrate.

Figure 1:
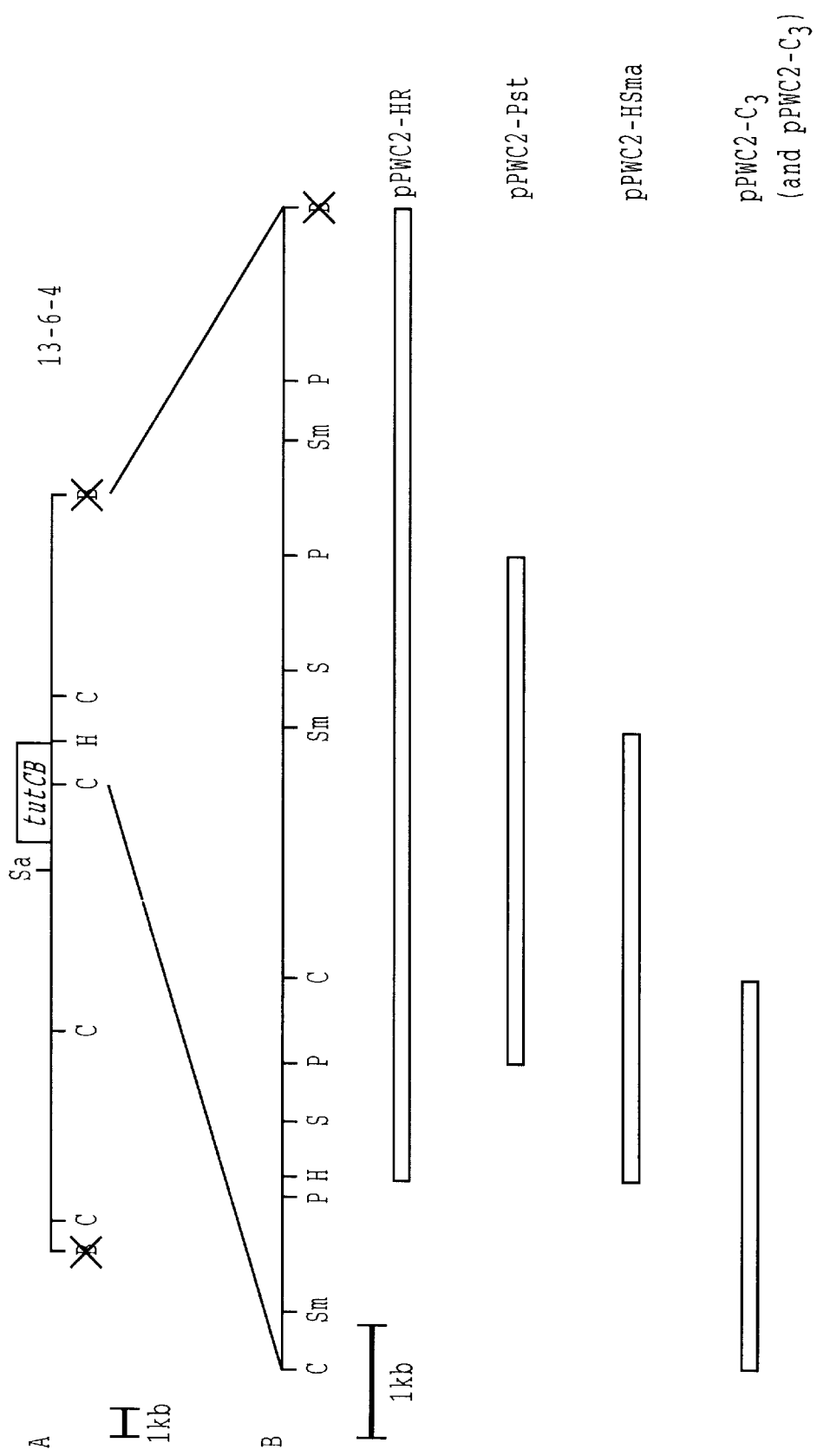
FIG. 1 shows the restriction map of a cosmid clone capable of restoring the ability to grow on toluene in toluene-nondegrading mutants.

A cosmid library was generated from total DNA isolated from the toluene-degrading bacterium strain T1. Triparental matings were used to identify a clone that restored the ability of mutants to grow on toluene and utilize it as a carbon source. This clone has now been characterized (FIG. 1 shows the restriction map). The DNA of this clone has now been sequenced and the genes identified are believed to be both regulatory and structural.

Regulatory Genes

The sequence of the cloned SacII-ClaI-ClaI fragment (approximately 6.4 kb containing the tutB gene and the tutC gene), that fully complements the tutB-16 mutation and carries all the information necessary to restore the ability to utilize toluene, is shown in FIGS. 2A–D (the restriction sites for SacII and ClaI are indicated in FIG. 1 as "Sa" and C" respectively, although not all SacII sites are shown; BamHI, HindII, PstI, SmaI and SalI sites are indicated as "B", "H", "P", "Sm" and "S", respectively). The subclone complements the mutation when inserted into the pRK415 vector (described below) in either orientation. This strongly suggests that the subclone provides all the cis acting factors necessary for gene expression and the vector does not provide any elements essential for expression of the insert.

Figure 3:
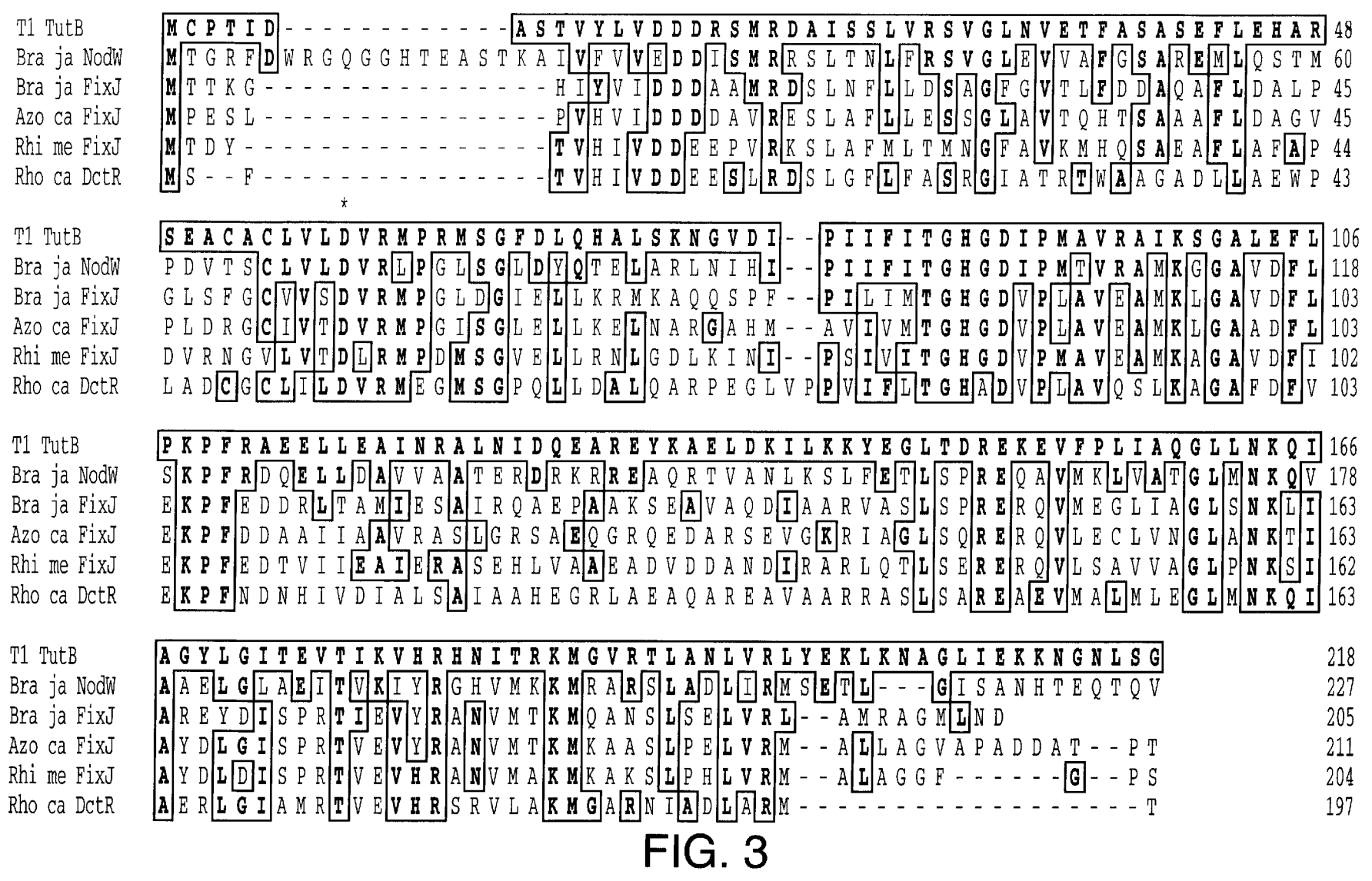

DNA sequence analysis of the fragment has identified an open reading frame that has homology to the nodW gene product of B. japonicum and other proteins presented in FIG. 3 SEQ ID NOS:11, 19–23. All of these proteins hgave been identified as DNA binding regulatory proteins and members of the two component family of signal transduction proteins. All have phosphorylation sites at a conserved aspartic acid residue. The tutB gene product also has an aspartic acid residue in the analogous location, at amino acid 58.

Figure 4A:
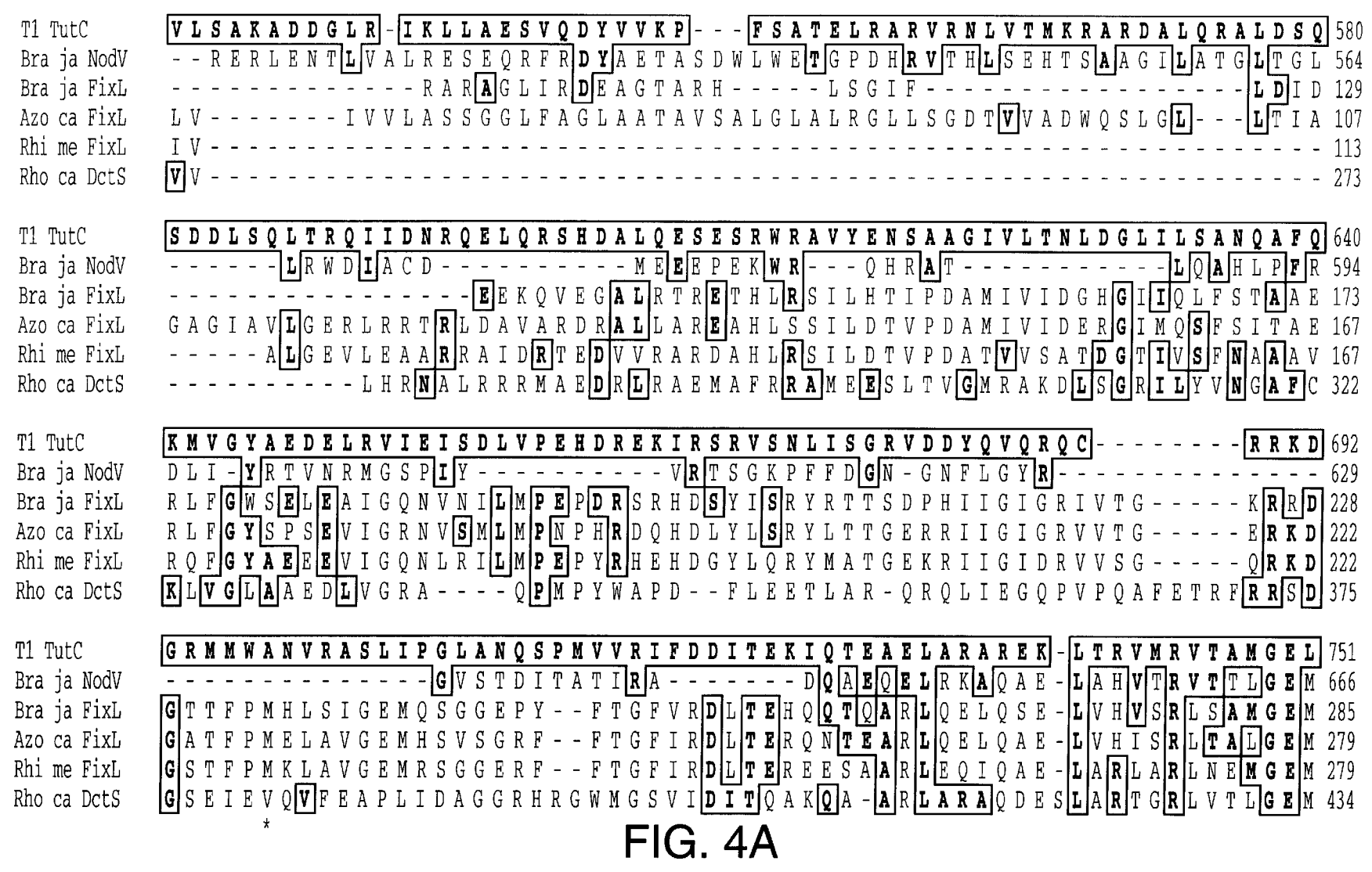
Figure 4B:
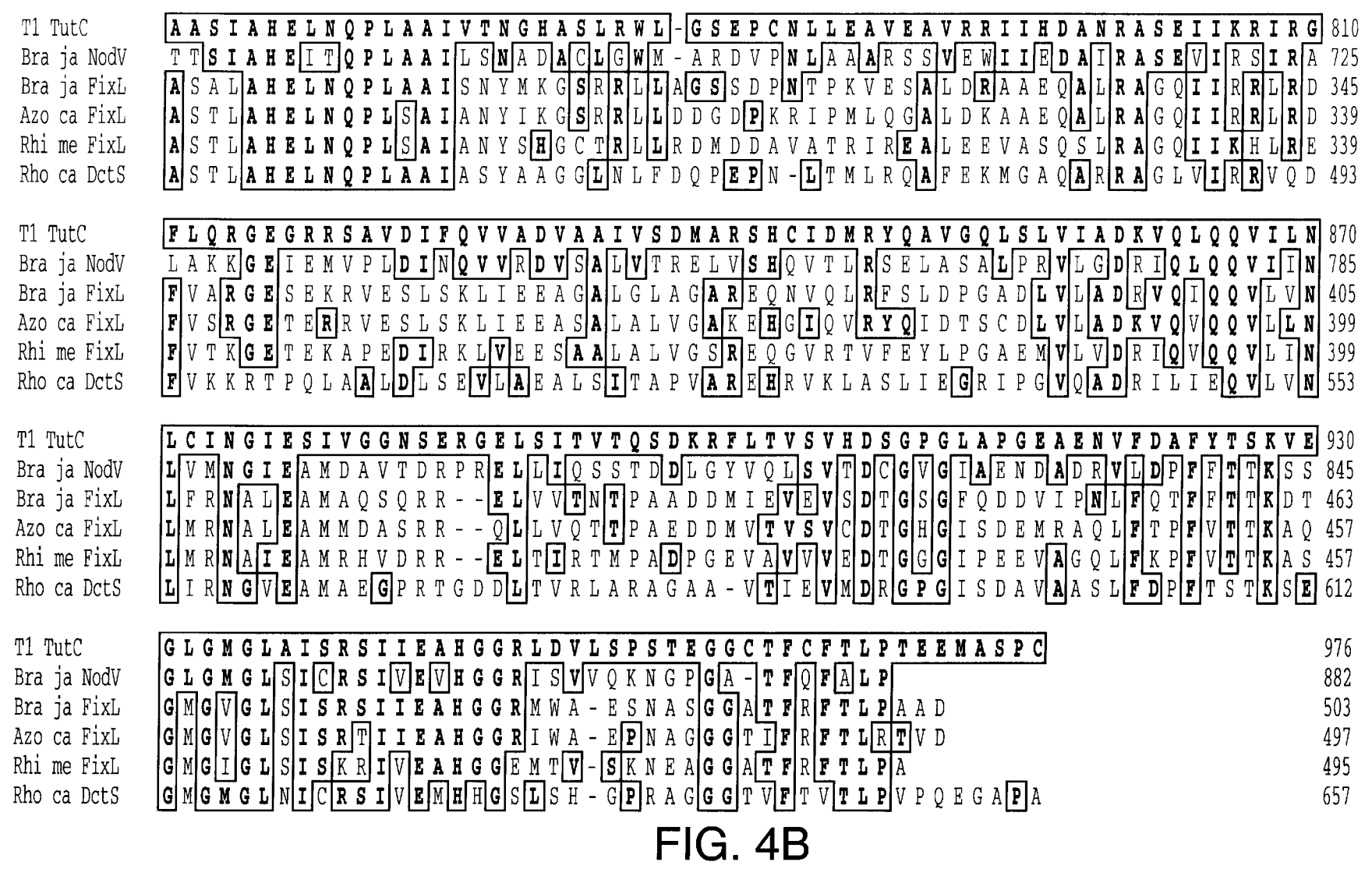

Additional DNA sequence analysis has identified a second open reading frame upstream of the tutB gene. This open reading frame, named tutC, has homology to the nodV gene product of *B. japonicum* and other proteins presented in FIGS. 4A–B. These gene products are proposed to serve as the sensor protein in the two component regulatory system). In their role as sensor proteins, they must autophosphorylate and then transfer the phosphate to the DNA binding protein. The site of autophosphorylation is a histidine residue that is conserved in all the systems. The tutC gene product has a histidine residue in the analogous location at amino acid 757. As can also be seen in FIGS. 4A–B, the homoiogy of the sensor proteins extends only about 400 amino acids. This region is proposed to be the transmitter domain, the part of the protein that sends the regulatory signal to the DNA binding protein. The remainder of the protein presumably serves to detect the signal from the environment and would not be expected to be conserved across the different systems.

The proteins that have the greatest similarity to the tutCB gene products appear to regulate a diverse set of genes. Both FixL/FixJ from *R. meliloti* and from *A. caulinodans* regulate genes involved in nitrogen fixation, while FixL/FixJ from *B. japonicum* are proposed to regulate anaerobic respiratory genes. The nodVW gene products of *B. japonicum* play a role in the nodulation process, while the dctSR gene products of *R. capsulatus* serve as regulators of C4-dicarboxylate transport. It is apparent that these genes function in a similar manner but the classes of genes they regulate have little in common.

Structural Genes

Figure 5B:
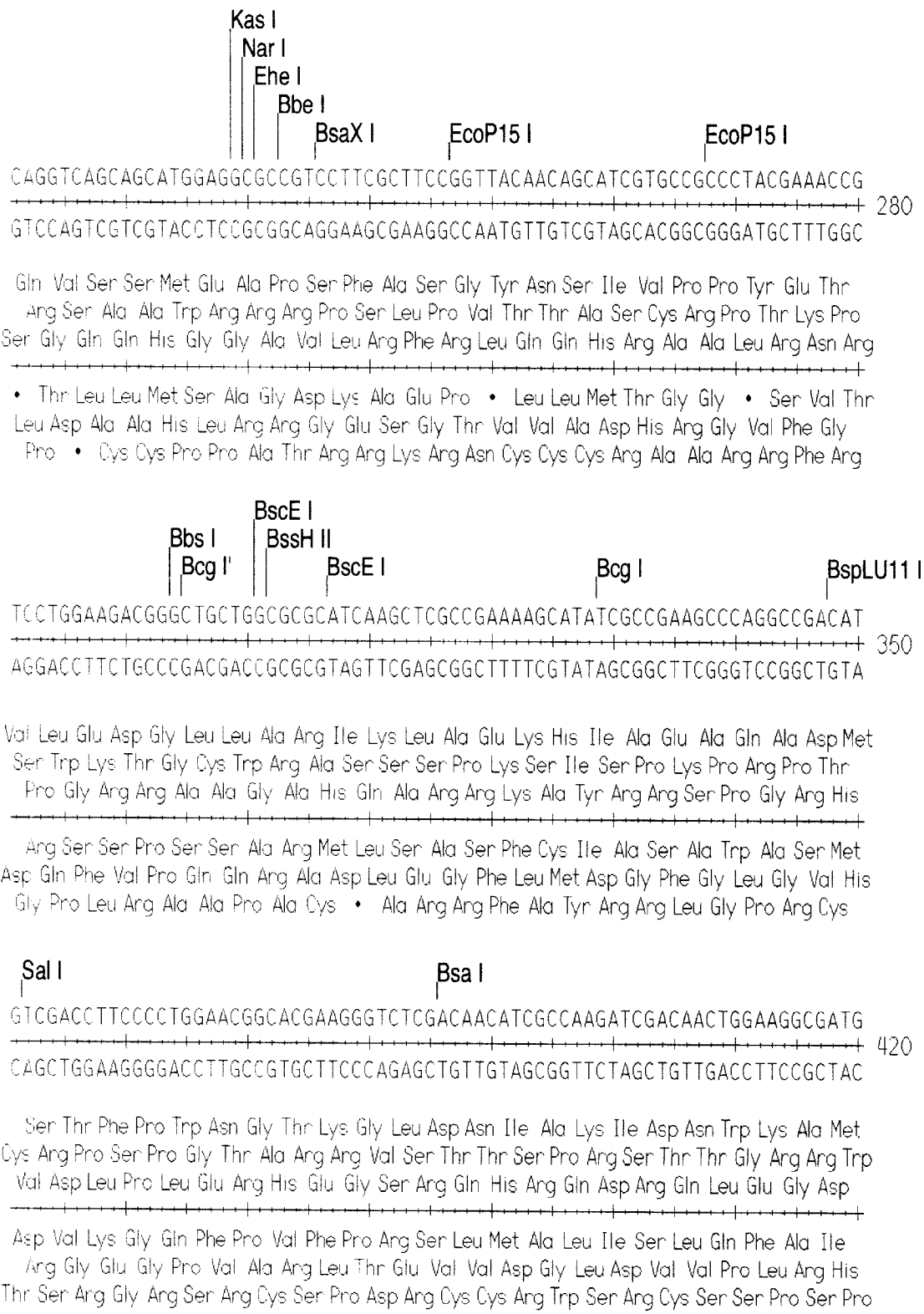
FIGS. 5A–P shows the nucleic acid sequence of the tutD gene (SEQ ID NO: 11).
Figure 5C:
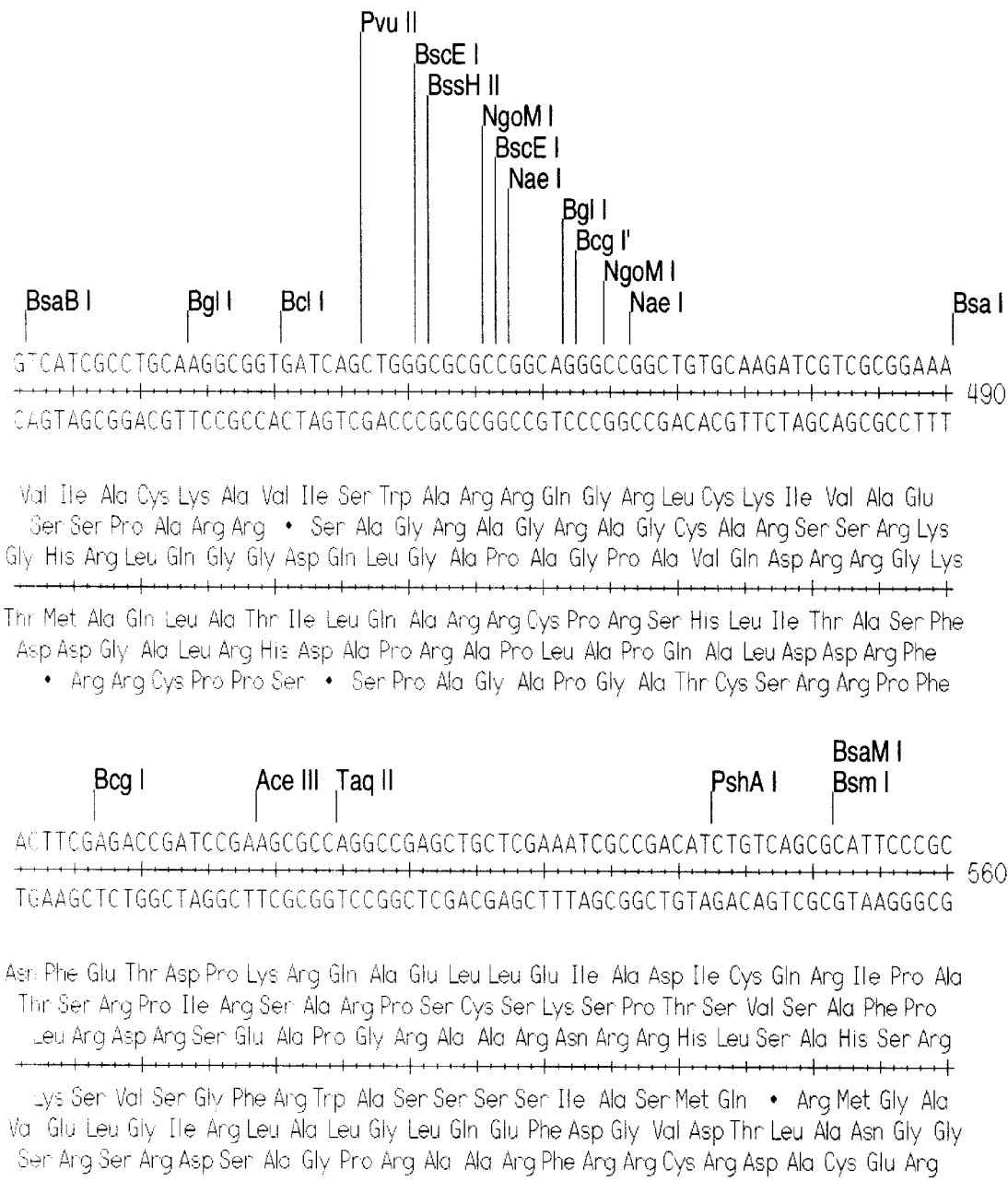
Figure 5E:
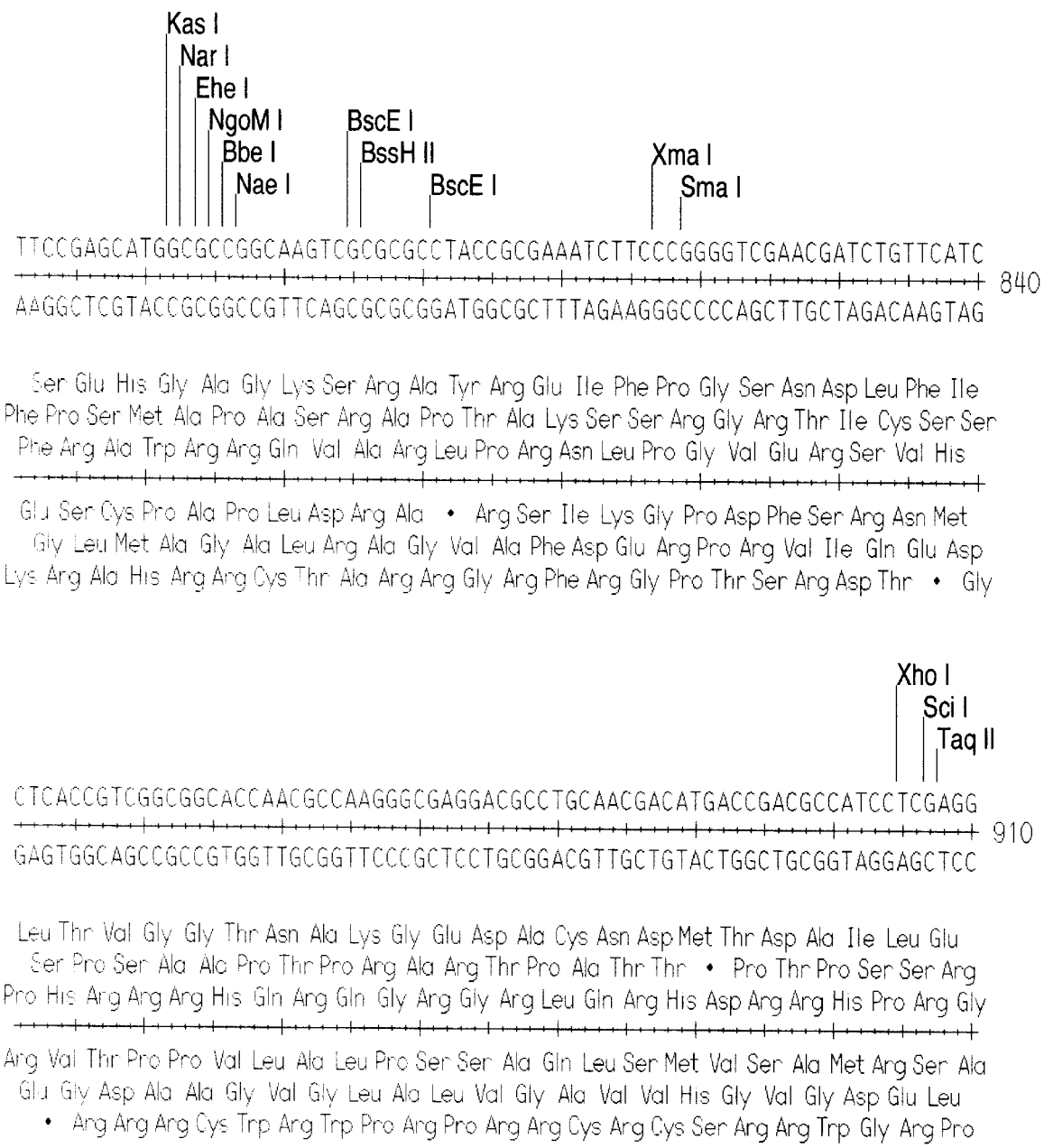
Figure 5K:
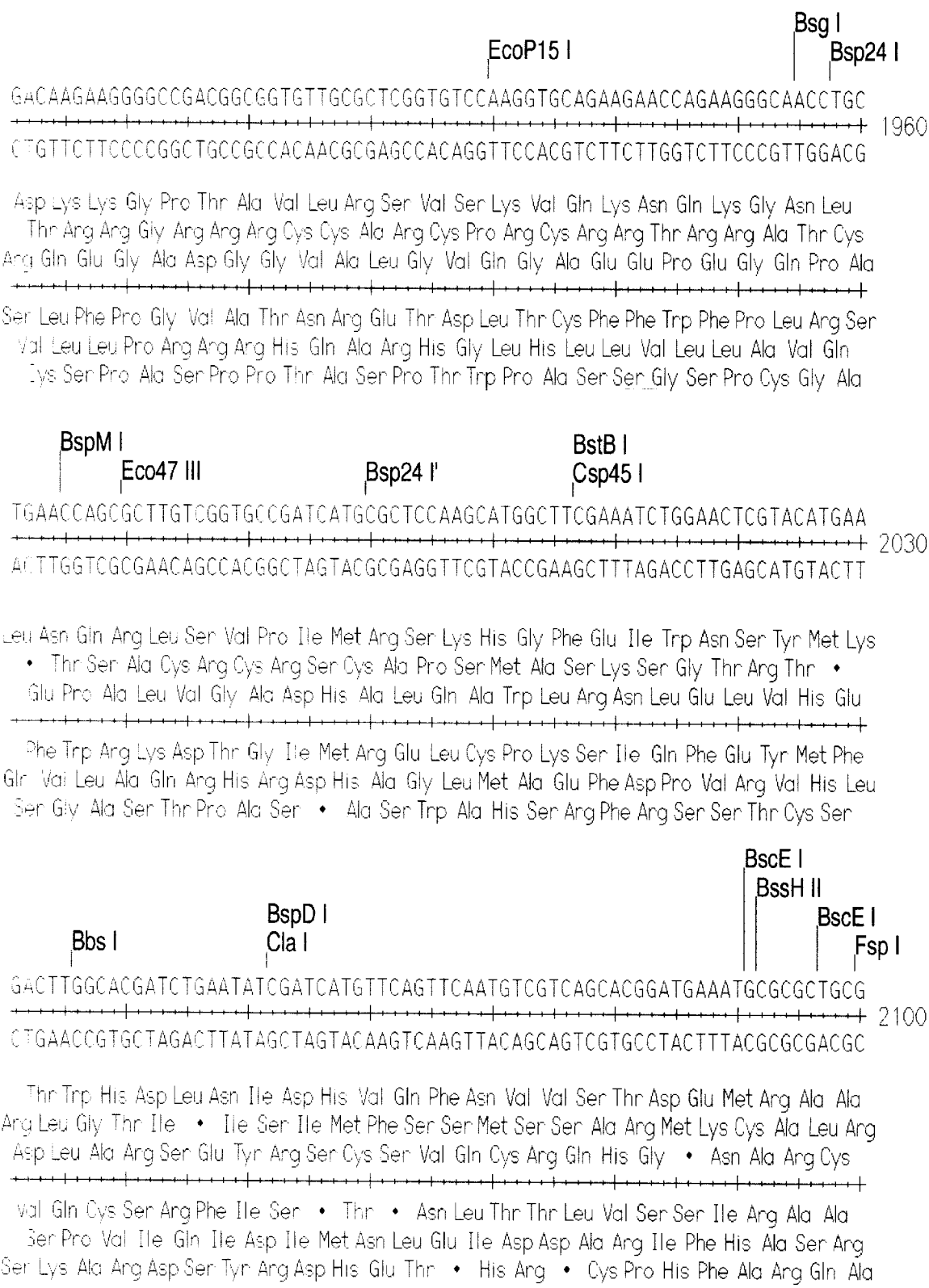
Figure 12G:
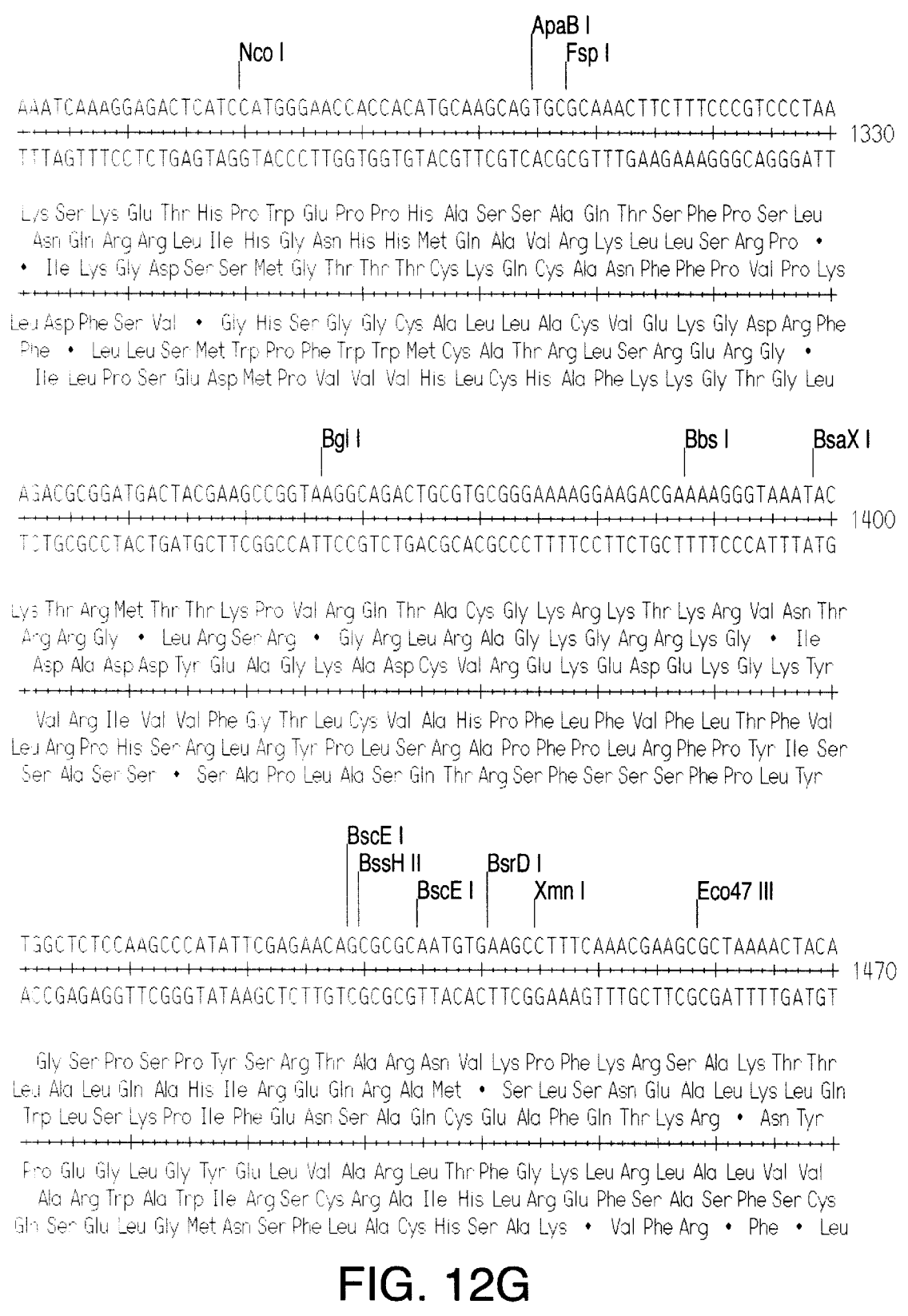
Figure 12J:
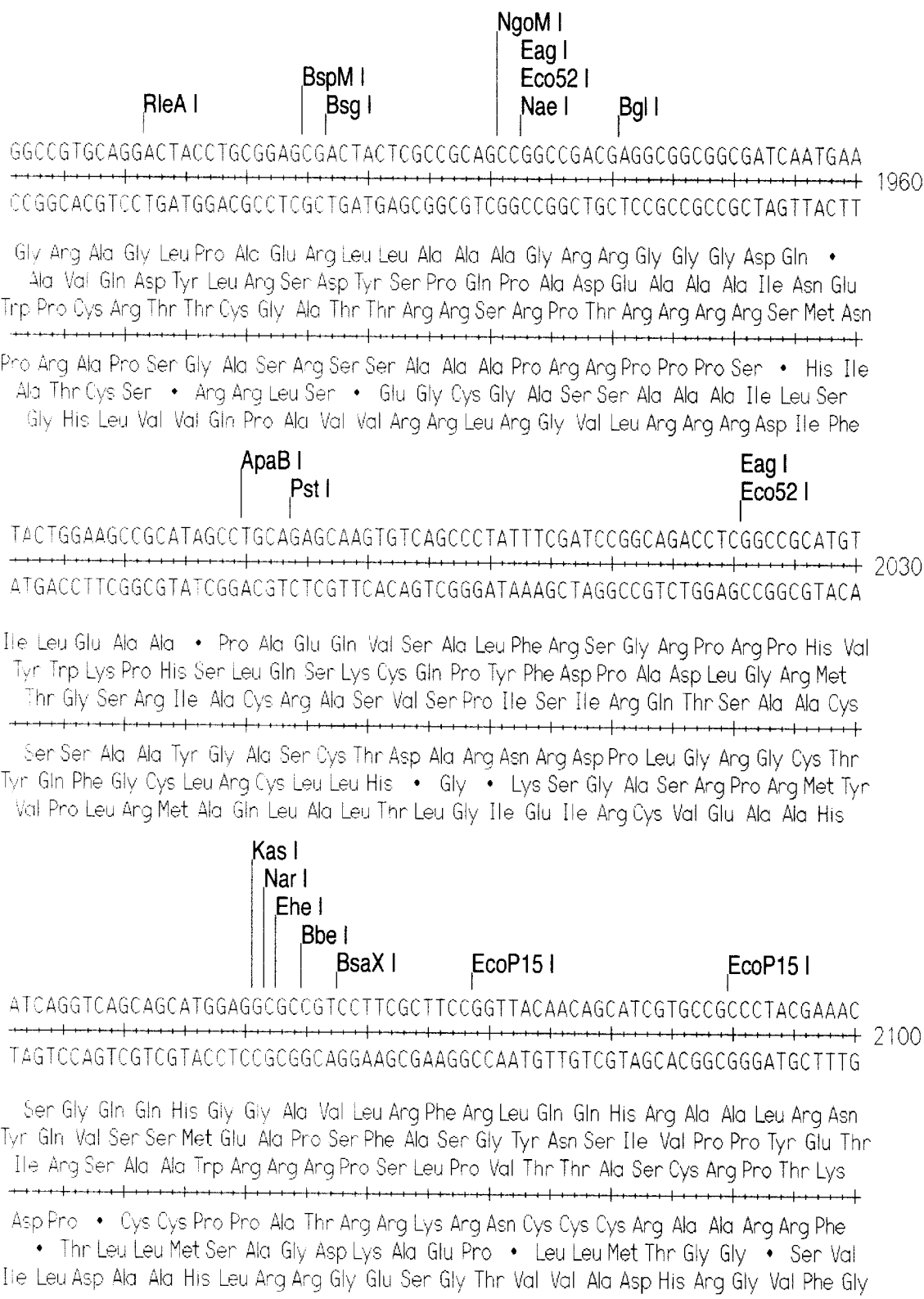
FIGS. 12A–Y shows an expanded nucleic acid sequence encompassing both the tutD and tutE gene (SEQ ID NO:15).
Figure 12L:
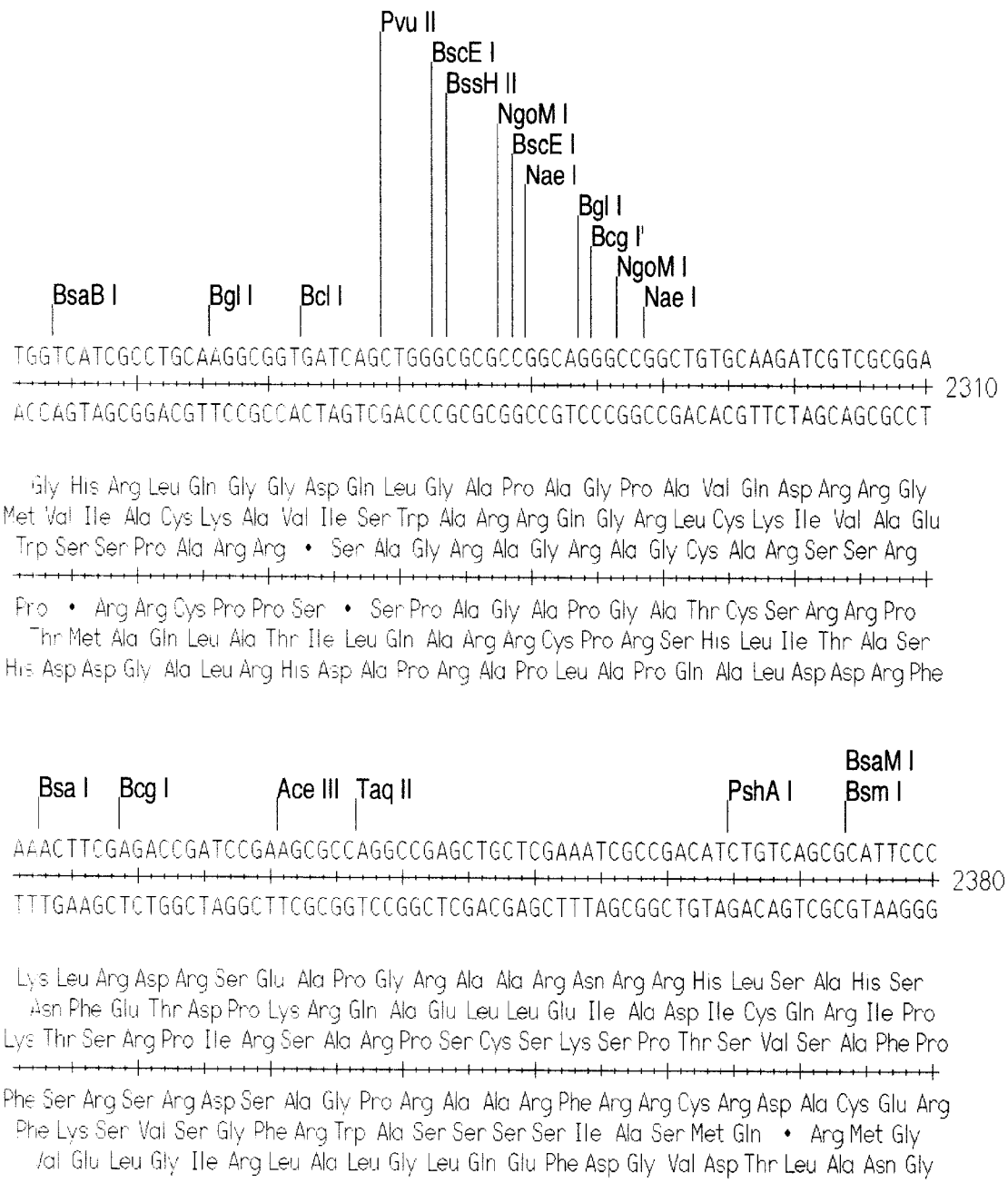
Figure 12Y:

Sequencing of another region of the cosmid clone has revealed the tutD gene (FIGS. 5A–P shows the sequence of an approximately 3.1 kb fragment) and part of the tutE gene (FIGS. 6A–C). An expanded tutD gene is presented in FIGS. 12A–Y (FIGS. 12A–Y shows the sequence of approximately 5 kb fragment) with a corresponding amino acid sequence presented in FIGS. 11A–D (shown aligned with other pyruvate formate lyases). An analysis of this sequence shows that tutD encodes a protein having homologies with the pyruvate formate lyase from *E. coli* (the PflD gene Genebank G418519) and from *Clostridium pasteurianum* (Genebank G1072361) (FIGS. 7A–C). Other pyruvate formate lyases also show homologies (not shown).

Pyruvate formate lyase catalyzes the conversion of pyruvate and CoA to acetyl-CoA and formate, which is the key step of the glucose fermentation route in anaerobically grown *E. coli* cells. See generally, Knappe and Wagner, *Methods Enzymol.* 258:343 (1995). The active form of pyruvate formate-lyase (PFL) from *Escherichia coli* contains a glycyl radical in position 734 of the polypeptide chain which is produced post-translationally by pyruvate formate-lyase-activating enzyme (PFL activase) using S-adenosylmethionine (AdoMet) and dihydroflavodoxin as co-substrates. A. F. Wagner et al., "The free radical in pyruvate formate-lyase is located on glycine-734," *Proc. Natl. Acad. Sci. U.S.A.* 89, 996–1000 (1992). The glycyl radical has been shown to participate in catalysis by guiding the carbon-carbon bond cleavage step along a radical-chemical route. The radical is thought to interact with a cystein residue; indeed, a reversible hydrogen transfer, induced by substrate binding, has been proposed between the Gly-734 resting-state spin localization and Cys-418, whose thiyl radical will function as the "working radical" for substrate processing.

It is not known how the homologue of the present invention functions. However, the comparison shown in FIGS. 7A–C reveals the essential glycine (marked in the FIG. with a '*'). While an understanding of the precise mechanism is not necessary to the successful practice of the invention, it is now known that a cysteine of the tutD gene product is also involved in the transfer that is ultimately directed to the methyl group of toluene (see discussion below). Again, while it is not necessary to the successful practice of the invention, the lack of homology at the 5' end of the tutD gene suggests that this portion of the gene product involves the unique substrate recognition.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade).

Strains And Plasmids

The *Escherichia coli* strains HB101, XL-1 Kan.Blue (Stratagene, LaJolla, Calif.), and XL-1 Blue (Stratagene), used to propagate and transfer DNA, were transformed by the calcium chloride technique or were purchased from the company as competent cells. Strain HB101(pRK2013) (Kan$^R$) contains a helper plasmid that permitted mobilization of cosmids and plasmids into the T1 strain background.

Plasmids used in this study include pLAFR3 for construction of the genomic cosmid library, pRK415 (FIG. 8) for construction of subclones and matings, and the pBluescript vector (Stratagene) for subcloning and preparation of DNA fragments.

Ditta et al. [Plasmid 13(1985) 149–153] constructed the moderately-sized cloning vector pRK404 from pRK290. In order to increase the cloning usefulness of this plasmid, the EcoRI site outside the polylinker was deleted and the pplylinker, derived from pUC9, was replaced by the pUC19 polylinker (FIG. 9 SEQ ID NOS: 31–32). The resulting construct, pRK415 (FIG. 8), permits cloning into all of the polylinker restriction sites of pRK404 as well as the additional unique EcoRI, XbaI, KpnI and SstI sites. The SphI site of the pUC19 polylinker is not generally useful because an SphI site occurs elsewhere in the plasmid. The unique DraI, ApaI, SmaI and Eco RV sites are convenient for mapping the orientation of inserted DNA fragments into the polylinker sites. Since pRK415 retains the lac promoter of pRK404, bacterial genes inserted in the proper orientation into the polylinker should be expressed in *E. coli*. XGal color screening can also be used for plasmid constructions in *E. coli*. pRK415 has proven useful for subdloning and maintaining small DNA fragments in field isolates of *P. syringae pv. glycinea* and other *P. syringae pathovars*. If fragments larger than approx. 5 kb are cloned, however, from a few to more that 50% of the P. syringae exconjugants have been observed to suffer deletions in the inserted DNA.

Figure 8:
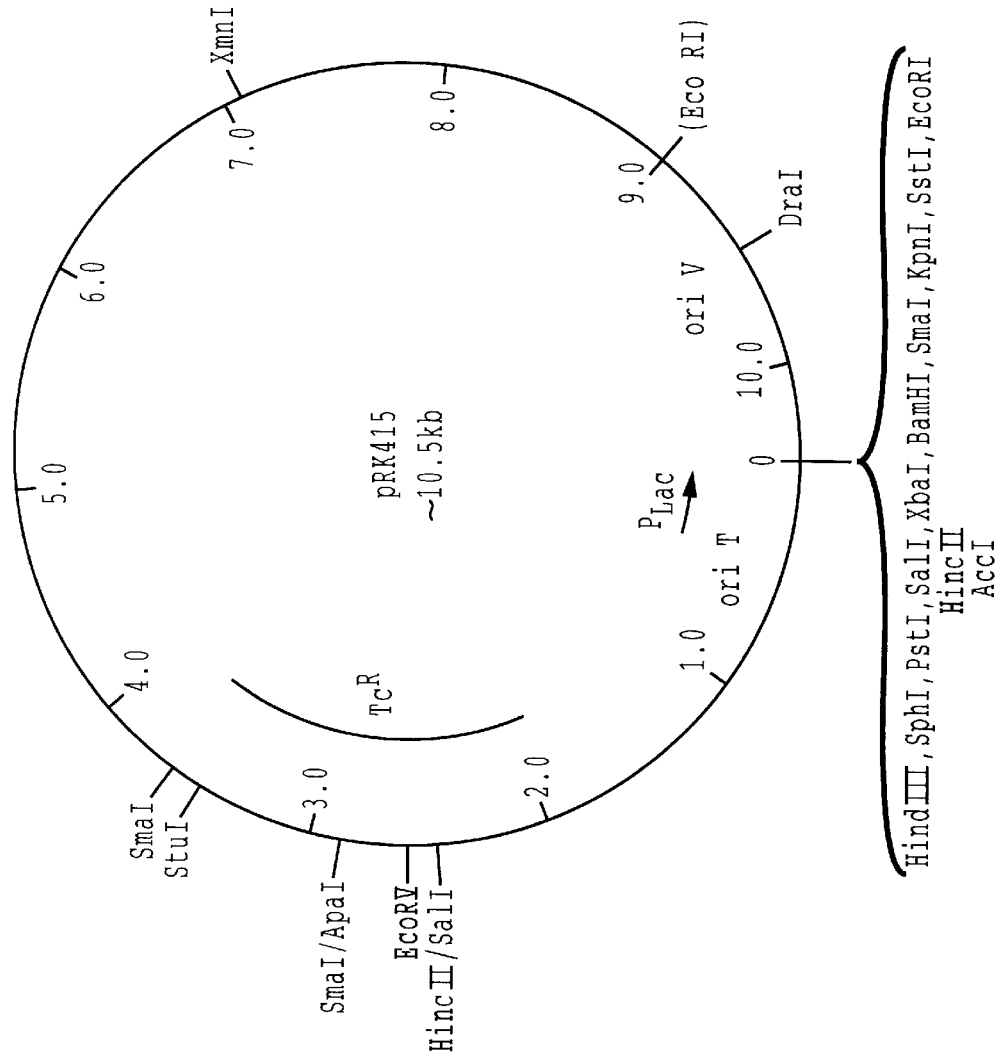
FIG. 8 shows the restriction map for pRK415.

The restriction map for pRK415 is shown in FIG. 8. This DNA was transformed into strain JM-101, a blue colony on XGal medium was retained and the resultant plasmid designated pRK415. The deleted EcoRI site is shown in brackets. Restriction sites separated by a slash occur close together.

Media

Strain T1 and all strains derived from T1 were grown on either Brain Heart Infusion (BHI, Difco Laboratories, Detroit, Mich.) medium or a mineral salts medium (vitamins and yeast extract omitted). Unless otherwise specified, toluene (0.3–0.5 mM) or pyruvic acid (5 mM) were used as the carbon source to supplement the minimal medium. Nitrate was supplied to a concentration of 10 to 20 mM unless otherwise specified. Plates always contained 2% Agar Noble (Difco Laboratories). Liquid media was prepared and placed in serum bottles which were then tightly stoppered with teflon coated butyl rubber and aluminum crimp seals. Anaerobic conditions were generated by evacuation and subsequent filling of the bottles with argon. This process was performed a total of four times. E. coli was grown in Luria-Bertani agar or broth (LB) or on BHI agar plates.

The antibiotics kanamycin (used at 50 mg/ml) and tetracycline (used at 25 mg/ml) were supplied where indicated. A 12.5 mg/ml stock of tetracycline was made in ethanol. Upon addition to minimal media the tetracycline served to select for the cosmid while the ethanol (final concentration of approximately 17 mM) served as the carbon source for the transconjugant strains.

Mutagenesis

Mutagenesis was carried out on strain T2 under aerobic conditions. Strain T1 was grown in a rich medium (BHI+nitrate), washed, and resuspended in 100 mM sodium citrate buffer (pH 5.5) to a cell density of about $3.5 \times 10^8$ cells/ml. The cell suspensions were treated with nitrosoguanidine (final concentration of 50 $\mu$g/ml) and aliquots were removed at various times. The mutagenized cells were harvested by centrifugation and washed with 100 mM potassium phosphate buffer (pH 7.0) to remove the nitrosoguanidine and then resuspended in the phosphate buffer. The treated cells were tittered on BHI plates to establish a killing curve. The treatment group that resulted in about 50% killing was used for the isolation of mutants. Treated cells were diluted in phosphate buffer to yield 100–200 colonies per plate and spread onto minimal medium plates supplemented with nitrate and pyruvic acid. After 5 days of incubation (30° C. anoxic) colonies were replica plated to rich medium and minimal medium with nitrate and toluene supplied in the vapor phase. The plates were placed in an anaerobic incubation jar which was then sealed and filled with hydrogen gas (to 12 psi). In the presence of a palladium catalyst oxygen is removed by reaction with the hydrogen producing water and resulting in an anoxic atmosphere. After 5 days of anaerobic incubation (30° C.) colonies that grew on the rich medium but not on the minimal medium with nitrate and toluene were picked and streaked onto rich plates. The strains were retested for the ability to grow with toluene serving as the sole carbon source in both liquid and solid media. The strains were later tested for the ability to utilize toluene and produce the dead-end products benzylfumaric acid and benzylsuccinic acid in liquid culture.

Chemicals

Tetracycline was purchased from Fluka (Ronkonkoma, N.Y.). Kanamycin and N-methyl-N'-nitro-N-nitrosoguanidine (nitrosoguanidine) were obtained from Sigma (St. Louis, Mo.).

Construction Of Cosmid Library

Strain T1 was grown in 500 ml of minimal+nitrate+ethanol medium under anaerobic conditions and genomic DNA was isolated. The DNA was purified by two successive CsCl gradient centrifugations. A partial digest of the DNA with Sau3AI enzyme was carried out and fragments of 15–25 kb were isolated on a 10–40% glycerol gradient. These fragments were ligated into the BamHI site of pLAFR3. The resulting ligation mix was packaged into phage heads using a Packagene kit from Promega (Madison, Wis.). E. coli strain HB101 was infected with the phage and plated onto LB+tetracycline plates. The resulting 750 colonies were streaked on plates of the same medium and the isolates served as the genomic library for obtaining the cosmid clone.

Triparental Mating

Triparental matings were carried out. Mutants of strain T1 were grown for 3 days in minimal+nitrate+pyruvic acid media. HB101 (or XL-1 Kan Blue) carrying the donor cosmid or plasmid was grown in LB+tetracycline overnight. HB101(pRK2013) was grown in LB+kanamycin overnight. One ml of each culture was centrifuged and resuspended in an equal volume of 100 mM phosphate buffer (pH 7). Ten $\mu$l of each culture was spotted (one on top of the other) onto a BHI+nitrate plate. After a three day incubation at 30° C. in an anoxic environment, the resulting growth was scraped off the plate, resuspended in phosphate buffer, and spotted onto a minimal agar plate containing pyruvic acid, nitrate, ethanol, and tetracycline to select for transconjugants. After another three day incubation, cells from the resultant growth were streaked onto the same media and grown in a sealed jar in the absence of oxygen. After three days of incubation, single transconjugant colonies were isolated from these plates and tested for complementation.

Restriction Mapping And Subcloning

DNA manipulations were carried out as described by Maniatis et al. All enzymes were obtained from New England Biolabs (Beverly, Mass.). Cosmid 13-6-4 was the original clone isolated. Plasmid pPWC1-HSma was constructed in two steps. The first step entailed deleting the HindIII fragment of 13-6-4 (from the HindIII site internal to the insert to the HindIII site (not shown in FIG. 1) in the pLAFR vector just beyond (to the right) the BamHI site) by digestion of 13-6-4 with HindIII and subsequent religation. The resulting cosmid (13-6-4-ΔH) was digested with the enzymes HindIII and SmaI and the 3.8 kb DNA fragment was isolated and inserted into HindIII-SmaI digested pBluescript. The HindIII-SmaI fragment was transferred to pRK415 by cutting both plasmids with the enzymes XbaI and KpnI and then isolating and ligating the fragments. The resulting plasmid was designated pPWC2-HSma (see FIG. 1). Plasmid pPWC1-$C_s$ was constructed by cutting 13-6-4 with ClaI enzyme, isolating the small (3.3 kb) DNA fragment and inserting it into ClaI digested, calf intestinal alkaline phosphatase treated pBluescript. The ClaI fragment was transferred into pRK415 by cutting pPWC1-$C_s$ and the vector with XbaI and KpnI enzymes (to generate pPWC2-$C_s$) or with KpnI and EcoRI enzymes (to generate pPWC2-$C_s'$, the reverse orientation of pPWC2-$C_s$) and ligating.

Restriction mapping was carried out with fragments inserted into the pBluescript vector to facilitate identification of restriction sites and to help place the sites on a restriction map. Digests were run on varying percentages of agarose gels with size standards to estimate the size of the fragments and to locate restriction sites.

Testing For Complementation

Cosmid clones and subclones constructed in pLAFR3 or plasmid subclones constructed in pRK415 were mated into the tutB-16 mutant background via the triparental mating technique. The resultant transconjugant strain was tested to determine if the subclone complements the mutation. First, the transconjugants were streaked onto minimal+nitrate plates in which toluene was supplied in the vapor phase. After 5–7 days of anaerobic incubation (30° C.), the subclones were scored for the ability to restore growth on toluene to the mutants. The transconjugants were also grown in sealed 50 ml serum bottles of minimal+nitrate (10 mM)+ pyruvic acid (1 mM)+toluene (0.4 mM) liquid media with an argon headspace. After 3–4 days of incubation (30° C.) samples were withdrawn for toluene and dead-end product analysis (see below). The clones were scored for the ability to restore toluene utilization (in the presence of pyruvate) in liquid culture and for the ability to restore production of the dead-end metabolites under the same conditions to the mutants. If the transconjugate was positive for all three of these tests, the subdlone was considered to complement the mutation.

Toluene Analysis

One ml samples of the culture to be tested were withdrawn anaerobically and added to 400 ml of pentane containing 1 mM fluorobenzene as an internal standard in a sample vial. One ml of the organic phase (into which toluene had been extracted) was injected using a CTC A200S autosampler (LEAP Technologies, Chapel Hill, N.C.) into an HP5890 gas chromatograph (Hewlett Packard, Palo Alto, Calif.) equipped with a Flame Ionization Detector, a DB-WAX column (J&W Scientific, Folsom, Calif.) and helium as the carrier gas. The injector temperature was set at 250° C., the detector at 300° C., and the column at 35° C. The amount of toluene present in each sample was quantified by comparison to external standards using the Chemstation software (Hewlett Packard).

Analysis Of Dead-End Products

Samples of the culture were withdrawn anaerobically with a sterile syringe flushed with argon. The samples were centrifuged (5 min., microfuge) and the supernatant was filtered through a 0.45 mm filter (Millipore, Bedford, Mass.) into a sample vial. Samples were analyzed by high pressure liquid chromatography using a Beckman System Gold HPLC (Fullerton, Calif.) equipped with a Gilson (Middleton, Wis.) autosampler and a C18 column (250 mm by 4.6 mm, particle size 5 mm, Beckman) with UV detection at 260 nm. The mobile phase was 30:68:2 methanol:water:acetic acid (vol/vol) at a flow rate of 1 ml/min. Peaks were identified by comparison to the external standards benzylmaleic acid and benzylsuccinic acid.

Plasmid DNA Preparation

In general DNA plasmid minipreps were performed. When larger scale preps were needed, Qiagen maxi-preps were carried out (Qiagen, Chatsworth, Calif.) according to the manufacturer's instructions.

DNA Sequence Analysis

DNA was sequenced (both strands) by the dideoxy method of Sanger et al. with (a-$^{35}$S)dATP serving as the label. Sequenase enzyme (modified T7 polymerase) and reagents were obtained in a Sequenase kit from U.S. Biochemicals (Cleveland, Ohio). The Bluescript vector and the T3, T7, –20, and M13 reverse primers used for sequence analysis were obtained from Stratagene. An Erase-a-Base System (Promega, Madison, Wis.) was used to generate deletions of the cloned DNA inserted in the Bluescript vector for sequence analysis. Synthetic oligonucleotide primers were also purchased so that sequence data could be obtained to fill in gaps not covered by the deletions. Searches for protein sequence similarity were carried out against the Swissprot data base (release 32.0) of protein sequences using the FASTA and BLAST programs in the GCG software package (version 7.2) (GCG software, Madison, Wis.). Multiple sequence alignment was performed with the Lasergene software package from DNASTAR (Madison, Wis.).

Site-Directed Mutagenesis

The QuickChange site directed mutagenesis kit (Stratagene) is used to make mutations in the tutD gene. To change the a glycine to an alanine, primers G828AF (GTGCGCGTTTCCGCCTACAGCGCTC SEQ ID NO: 39) and G828AR (GAGCGCTGTAGGCGGAAACGCGCAC SEQ ID NO: 40) are synthesized and used as directed. Plasmid pPWC3-C$_L$-SacII serve as the target for the mutagenesis. The resulting plasmids are sequenced to identify those containing the desired mutation. The 4.9 kb SacI/SacII fragment of three plasmids with the correct change are subcloned into plasmid pRK415 and used to test for complementation of the tutD17 mutation. To change the cysteine at position 492 to an alanine primers C492AF (CAACGTGCTGGCCATGTCGCCCGGCATCC SEQ ID NO: 41) and C492AR (GGATGCCGGGCGACATGCCCAGCACGTTG SEQ ID NO: 42) are synthesized and used in the same manner described above.

EXAMPLE 1

This example describes the isolation and characterization of tut mutants. Cells of strain T1 were grown and mutagenized with nitrosoguanidine as described above. Mutants were isolated from the treatment group that resulted in about 50% killing. Cells were diluted and plated onto minimal medium supplemented with nitrate and pyruvic acid to a density of about 100–200 colonies per plate. After about 5 days of incubation at 30° C. in the absence of oxygen the colonies were replica plated to both rich medium and minimal medium with nitrate and with toluene supplied in the vapor phase. After incubation, colonies that grew on the rich medium but failed to grow on the minimal medium with nitrate and toluene were chosen for further study. Of about 10,000 colonies screened, 32 candidates were isolated in this manner. These 32 mutant candidates were again tested for their ability to grow on minimal medium supplemented with nitrate and toluene both in liquid and on plates. Retesting the candidates identified seven mutants which were truly defective for toluene utilization. These seven were designated tut mutants for their defect in toluene utilization.

The seven tut mutants were tested for their ability to grow on various carbon sources. Four of the mutants are able to use benzoic acid and phenylpropionic acid as a sole carbon source while three are not able to use either substrate. Based on this observation, the first group is predicted to be blocked early in the toluene utilization pathway and were designated tutB mutants. The second group is blocked later in the pathway, probably in benzoic acid utilization. This group was designated tutA. These designations are not meant to imply that all mutants in a particular group are defective in the same gene or in the same step of the pathway, only that they utilize the same range of substrates.

The tut mutants were also tested for their ability to metabolize toluene when provided with both toluene and pyruvic acid in liquid media. Pyruvic acid was added to insure that the transconjugants grew and that there was no selective pressure for reversion of the mutation to occur. Although the tutB-16 mutant metabolized toluene slightly, none of the tutB mutants tested were able to metabolize toluene to the same extent as the wild type control. Similarly, the tutB mutants did not produce significant amounts of the dead-end products benzylsuccinic acid and benzylfumaric acid. Members of the tutA class of mutants were able to both metabolize toluene and produce the dead-end products. This result indicates that the tutB mutants are blocked in a step (or steps) that is common to both the metabolic degradation of toluene and the side reaction that produces the dead-end compounds or in the regulation of such a step (or steps).

EXAMPLE 2

This example describes the generation of T1 DNA library and the isolation of a clone that complements the tutB-16 mutant. It has previously been shown that pLAFR3 derived cosmids can be transferred into and stably maintained in the strain T1 background. Consequently, this vector was chosen for the construction of a genomic DNA library of strain T1. Genomic DNA was isolated from strain T1 as described above. A partial digest of the genomic DNA was carried out with the restriction enzyme Sau3AI and fragments of between 15 and 25 kb were isolated. These fragments were ligated into the BamHI site of pLAFR3. The resulting ligation mix was packaged into lambda phage heads and used to infect *E. coli* strain HB 101. About 750 tetracycline resistant *E. coli* colonies were picked and formed the genomic library used to isolate clones that complement the tut mutations.

The genomic T1 library constructed in pLAFR3 was introduced into a T1 derived strain carrying the tutB-16 mutation via a triparental mating. The donors for all the cosmids were *E. coli* strain HB101 derived strains, while *E. coli* HB101 carrying plasmid pRK2013 served as the helper to mobilize the cosmids. Transconjugants were selected on minimal medium supplemented with nitrate, pyruvic acid, and tetracycline and then screened for the ability to grow with toluene serving as the sole carbon source. One cosmid, designated 13-6-4, restored the ability of the tutB-16 carrying T1 strain to grow on toluene. This cosmid also restored the ability of the mutant strain to metabolize toluene in the presence of pyruvic acid in liquid culture and produce the dead-end products benzylsuccinic acid and benzylfumaric acid in this culture. This cosmid was used for further subdloning and restriction mapping to specifically identify the region containing the complementing gene.

In an effort to determine where on the cosmid the fragment that complements the tutB-16 mutation lies, deletions and subdlones were constructed. All subclones were made in plasmid pRK415, a broad host range tetracycline resistance vector that can be conjugatively transferred into the T1 background in the same manner as pLAFR3 and is stably maintained in this background. FIG. 1 shows a restriction map of cosmid 13-6-4. The relevant region of the cosmid is shown in more detail. The figure includes a number of subclones that were constructed in an effort to identify the region of the cosmid that contains the complementing gene.

Complementation tests were performed for the various subclones shown in FIG. 1 when mated into a T1 strain carrying the tutB-16 mutation. Complementation was assayed in three ways: (1) the ability to grow with toluene serving as the sole carbon source on solid media, (2) the ability to metabolize toluene in the presence of pyruvic acid in liquid media, and (3) the ability to produce the dead-end products benzylsuccinic acid and benzylfumaric acid from toluene in liquid media. The original clone and all complementing subclones were positive (i.e., behaved just as the wild type strain) in all three assays.

The small 3.3 kb ClaI fragment of 13-6-4 when inserted into pRK415 in either orientation is able to complement the tutB-16 mutation. Subclones constructed that do not contain this entire region do not complement this mutation. These results indicate that this 3.3 kb fragment is sufficient to replace the missing activity in the tutB-16 mutant strain.

EXAMPLE 3

This example describes the sequence analysis of the tutCB region. The complete nucleotide sequence of the 3.3 ClaI fragment of 13-6-4 (containing the tutB gene) was determined in both orientations. Analysis of this sequence revealed the presence of a second open reading frame (designated tutC) upstream of the tutB gene. As a result, the sequence was extended to a SacII site about 3 kb upstream of the ClaI site. FIGS. 2A–D presents the complete 6393 bp nucleotide sequence of the tutCB region. The protein translation of the two genes are presented below the DNA sequence in the figure. The TutC protein is 979 amino acids long with a calculated molecular mass of 108.0 da and a calculated pI of 5.2, while the TutB protein is 218 amino acids long with a calculated molecular mass of 24.3 da and a calculated pI of 7.9.

Goldman-Engleman-Steitz hydropathicity analysis failed to detect any membrane spanning regions in either protein but Kyte-Doolittle analysis suggested two possible membrane spanning regions in the TutC protein, amino acids 367–399 and 489–508 (data not shown). The translation of the tutB gene is shown as over-lapping the sequence of the tutC gene by 13 nucleotides. This methinone was chosen as likely to be the first amino acid in the sequence based on the location of a potential Shine-Dalgamo sequence and protein similarity analysis.

The protein sequence of the tutC gene product was compared to the Swissprot protein data base in an effort to identify other proteins with homologous sequences. The results of this analysis are presented in FIGS. 4A–B. The TutC protein shows significant sequence similarity to sensor members of the two component family of signal transduction proteins, a set of bacterial regulatory proteins in which one member senses the environmental conditions of the microorganism and transmits a signal (via phosphorylation) to the other member (a DNA binding protein). The five proteins, all sensor proteins, with the greatest sequence similarity to the tutC gene product are included in FIGS. 4A–B. These proteins (and their percent identity to the tutC gene product) are the products of the nodV gene of *Bradyrhizobium japonicum* (36%), fixL gene of *B. japonicum* (33%), *Azorhizobium caulinodans* (30%), and *Rhizobium meliloti* (30%), and dctS gene of *Rhodobacter capsulatus* (33%).

In a similar manner, the sequence of the tutB gene product was compared to the Swissprot protein data base in an effort to identify other proteins with homologous sequences. The results of this analysis are presented in FIG. 3 SEQ ID NOS: 11, 19–23. The TutB protein shows significant sequence similarity to DNA binding protein members of two component sensor/regulator families. These proteins (and their percent identity to the tutB gene product) are the products of the nodW gene of *B. japonicum* (48%), the fixJ gene of *B. japonicum* (38%), *A. caulinodans* (37%), and *R. meliloti* (39%), and the dctR gene of *R. capsulatus* (38%). Because the similarity between these proteins and TutB extends nearly to the methionine that over-laps the tutC gene product, it is believed that translation begins at this overlapping methionine. Based on the results of the sequence similarity analysis and the previous result that the toluene utilization pathway of strain T1 is inducible, the tutB and tutC gene products are likely involved in the regulation of gene expression (specifically toluene metabolic genes) in response to toluene.

EXAMPLE 4

This example describes the identification and cloning of the tutD and tutE genes. One class of mutants, the tutB class, are unable to grow with toluene serving as the sole carbon source but was able to grow when provided with benzoate. These mutants are also unable to metabolize (at wild type levels) toluene when provided with pyruvate and were unable to produce (at wild type levels) benzylsuccinic acid and a monounsaturated derivative from toluene in liquid media. P. J. Evans, et al., Metabolites formed during anaerobic transformation of toluene and o-xylene and their proposed relationship to the initial steps of toluene mineralization. *AppL. Environ. Microbiol.* 58:496(1992). Hence, it is determined this class of mutants is blocked early in the toluene utilization pathway. A cosmid with a genomic insert of approximately 20 kb (cosmid 13-6-4) is isolated for its ability to complement the tutB16 mutation. P. W. Coschigano et al., Identification and sequence analysis of two regulatory genes involved in anaerobic toluene metabolism by strain T1. *Appl. Environ. Microbiol.* 63:652(1997). This original cosmid clone, along with a number of subclones generated in the characterization of the tutB gene, are tested for their ability to complement the mutations referred to as tutB17 and tutB21, which have phenotypes similar to the tutB16 mutation. These mutations are placed in new complementation groups and are designated tutD17 and tutE21.

Figure 10:
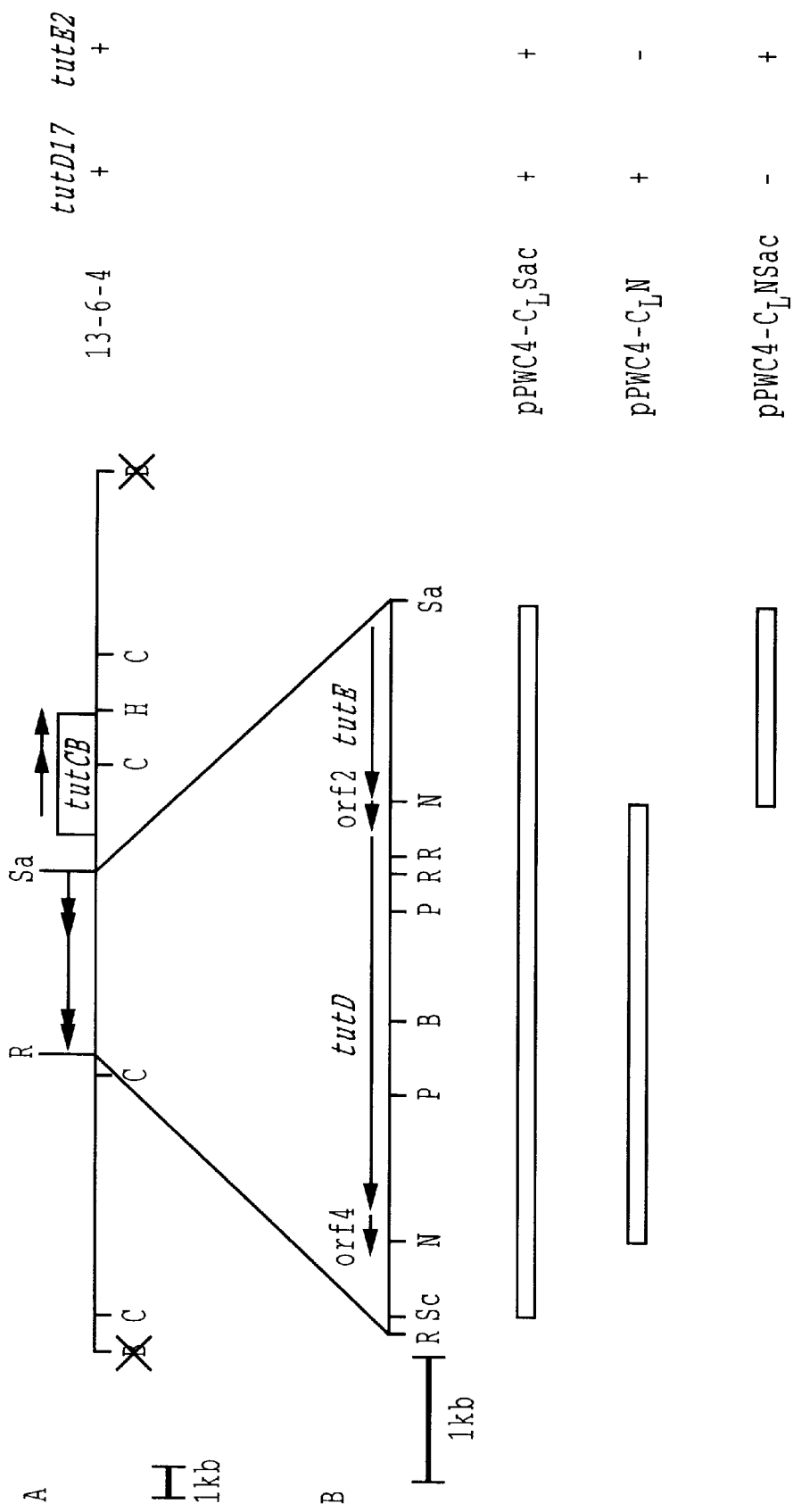
FIG. 10 shows the restriction map of a cosmid clone containing the tutD and tutE genes.

Determining where on the cosmid the fragments that complement the tutD17 and tutE21 mutations are located, a series of subclones are constructed. Subclones are made in plasmid pRK415, a broad host range tetracycline resistant vector that can be conjugatively transferred into the T1 background. FIG. 10 shows a restriction map of cosmid 13-6-4 and a schematic representation of three of the subclones. Each subclone is tested for its ability to complement the tutD17 and tutE21 mutations. Complementation was assayed in three ways: (1) the ability to grow with toluene serving as the sole carbon source on solid media, (2) the ability to metabolize toluene in the presence of pyruvic acid in liquid media, and (3) the ability to produce benzylsuccinic acid and a monounsaturated derivative from toluene in liquid media. P. J. Evans, et al. Metabolites formed during anaerobic transformation of toluene and o-xylene and their proposed relationship to the initial steps of toluene mineralization. *AppL Environ. Microbiol.* 58:496(1997). Restoration of the wild type phenotype in all three assays is required in order for the subclones to be considered as complementing the mutation.

As shown in FIG. 10, the tutD17 mutation and the tutE21 mutation are complemented by mutually exclusive subclones. The 3.0 kb NcoI fragment of 13-6-4 (pPWC4-$C_LN$) is able to complement the tutD17 mutation but not the tutE21 mutation. Conversely, the adjacent 1.3 kb NcoI/SacII fragment (pPWC4-$C_L$NSac) is able to complement the tutE21 mutation but not the tutD17 mutation. These data suggest the 3.0 kb NcoI fragment is sufficient to replace the missing activity in the tutD17 mutant strain and the 1.3 kb NcoI/SacII fragment is sufficient to replace the missing activity in the tutE21 mutant strain; thereby confirming the mutations belong to distinct complementation groups.

EXAMPLE 5

This example describes the complete nucleotide sequence of the 4905 bp SacII/EcoRI fragment of cosmid 13-6-4 (containing the tutD and tutE genes), as determined for both strands. This nucleotide sequence has been deposited in the GenBank (accession number AF036765). Analysis of this sequence reveals the presence of four open reading frames on the same strand of DNA. The first open reading frame, present between the SacII and NcoI sites (subclone pPWC4-$C_L$NSac) and corresponding to the tutE gene, is a sequence of 375 amino acids. The TutE protein has a calculated molecular mass of 41,300 Da and a predicted pI of 6.8.

Two open reading frames are identified on the 3.0 kb NcoI fragment immediately downstream of the tutE gene (subclone pPWC4-$C_LN$). The first of these two open reading frames (designated open reading frame 2) consists of a 60 amino acid sequence which would code for a protein with a calculated molecular mass of 6,900 Da and a predicted pI of 5.2. The translational start begins at the NcoI restriction site and hence no upstream transcriptional regulatory sites or ribosome binding sites for this open reading frame are included on this fragment. Therefore, it is highly unlikely that this open reading frame is responsible for the complementation of the tutD17 mutation observed with this subclone. This observation, along with evidence from the site-directed mutagenesis experiments indicates that ORF2 is not the tutD gene.

The second open reading frame in this fragment is 864 amino acids in length with a calculated molecular mass of 97,600 Da. The predicted pI of this protein is 6.0. Results from the site-directed mutagenesis clearly show that this open reading frame corresponds to the tutD gene.

The fourth open reading frame (designated open reading frame 4) identified in the SacII/EcoRI fragment consists of a sequence of 81 amino acids with a calculated molecular mass of 9,300 Da and a predicted pI of 7.8. The pPWC4-$C_LN$ subclone removes approximately 50% of the C-terminal end of this protein. This result, in conjunction with the evidence presented regarding the third open reading frame, indicates that this 81 amino acid protein is not the tutD gene product.

EXAMPLE 6

This example describes homologies between the protein sequence of the tutD and tutE gene product and proteins in the Genbank protein database. The BLAST program identified a number of similar proteins, all of which are identified as either pyruvate formate-lyases (formate acetyl transferases) or pyruvate formate-lyase homologues. Interestingly, the sequences showing the highest degree of similarity with TutD are the *E. coli* proteins f810 (27% identical to TutD as calculated by the BLAST program) and PflD (26% identical to TutD), both pyruvate formate-lyase homologues. F. R. Blattner, et al. Analysis of the *Escherichia coli* genome. IV. DNA sequence of the region from 89.2 to 92.8 minutes. *Nucleic Acids Res.* 21:5408(1993). F. Blattner, et al, The complete genome sequence of *Escherichia coli* K-12. *Science* (Wash. D.C.). 277:1453(1997).

The sequence similarities between TutD and these two proteins plus PflB (22% identical to TutD), a pyruvate formate-lyase from *E. coli*, are shown in FIGS. 11A–D. R. Rabus, et al., Complete oxidation of toluene under strictly anoxic conditions by a new sulfate-reducing bacterium. *Appl Environ. Microbiol.* 59:1444 (1993). A. F. Wagner, et al. The free radical in pyruvate formate-lyase is located on glycine-734. *Proc.Natl. Acad. Sci. USA*. 89:996(1992). As can be seen in FIGS. 11A–D, the most conserved region is in the carboxyl end of these proteins. There is a highly conserved region around the glycine residue at position 828 of TutD (marked with an asterisk). In the *E. coli* pyruvate formate-lyase, this glycine has been shown to form a free radical which is essential for enzymatic function. Additionally, in a less conserved region there is a cysteine residue at position 492 of TutD (marked with a dagger) that has been shown to transiently form a covalent bond with the acetyl group that is being transferred, an action which is also essential to enzyme function. A. Ogiwara, et al. Construction and analysis of a profile library characterizing groups of structurally known proteins. *Protein Sci.* 5:1991(1996). W. Rödel, et al. Primary structure of *Escherichia coli* pyruvate formate-lyase and pyruvate formate-lyase activating enzyme deduced from the DNA nucleotide sequences. *Eur. J. Biochem.* 177:153(1988). While it is not intended that the instant invention be limited to any one mechanism, the results of this protein sequence similarity analysis suggest a mechanism for TutD where glycine-828 forms a free radical which is necessary for the transient formation of a covalent bond between cysteine-492 and the compound (possibly acetate or fumarate) that is being transferred to the methyl group of toluene (or a toluene metabolite). This mechanism may involve a transient cysteine radical at an undetermined location, as proposed in the *E. coli* pyruvate formate-lyase system. A. F. Wagner, et al. The free radical in pyruvate formate-lyase is located on glycine-734. *Proc.Natl. Acad Sci. USA.* 89:996(1992).

Figure 13A:
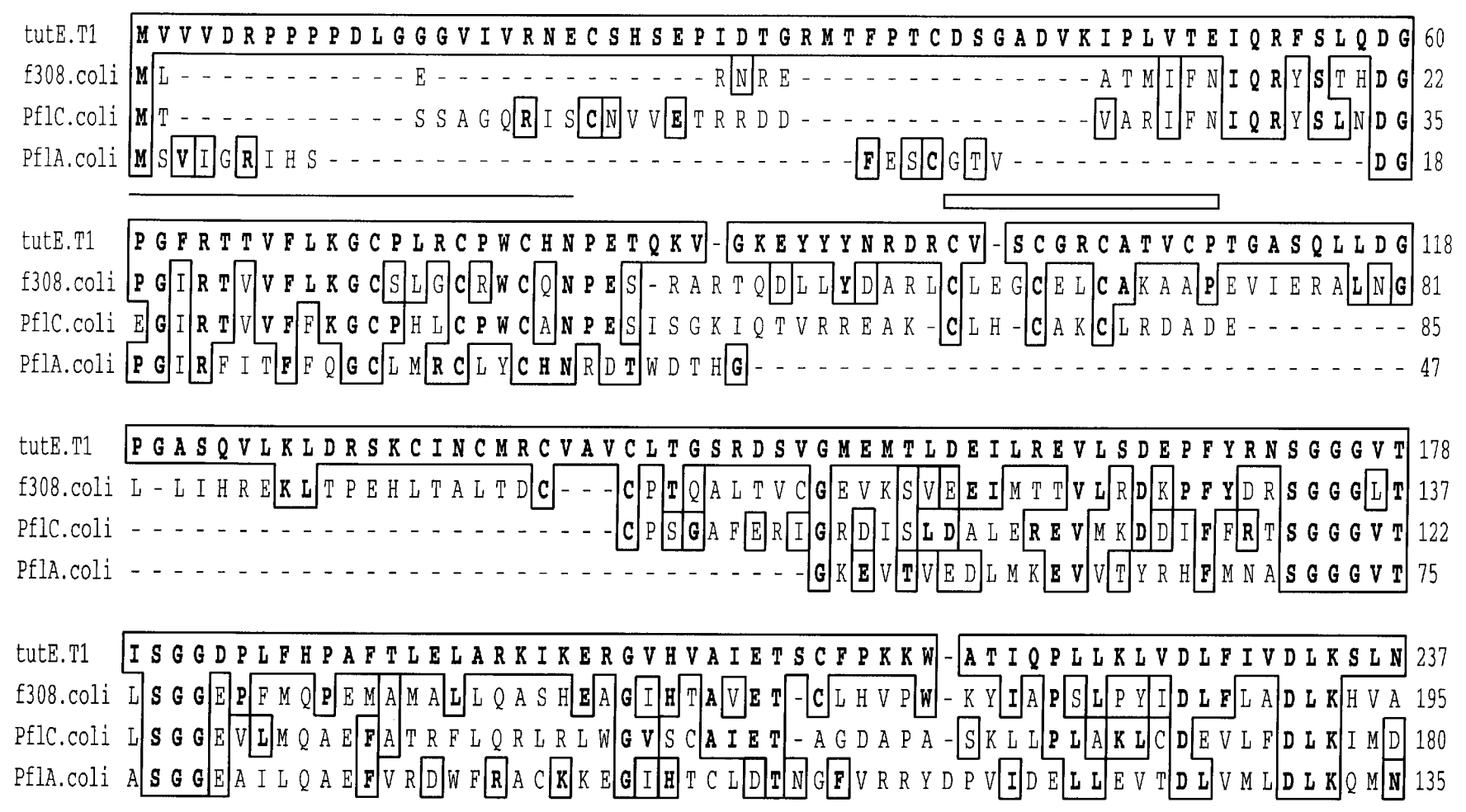

A similar search was performed with the protein sequence of the tutE gene product. The proteins with the highest homology are identified as pyruvate formate-lyase activating enzymes or pyruvate formate-lyase activating enzyme homologues. The sequence similarities between TutE and f308 (34% identical to TutE as calculated by the BLAST program), PflC (32% identical to TutE), and PflA (28% identical to TutE) (all from *E. coli*) are shown in FIGS. 13A–B. Subsequent subjection of the TutE protein sequence to a Motif analysis identified a radical activating region from amino acids 60 to 81 (labeled with a line over it in FIGS. 13A–B). This region which contains potential Fe binding sites (as identified by the Motif analysis) is conserved in the pyruvate formate-lyase activating enzymes. Additionally, the analysis revealed a 4Fe-4S binding domain typically found in ferredoxins (amino acids 98 to 109, labeled with a box over it in FIGS. 13A–B). This region is not very well conserved in the *E. coli* pyruvate formate-lyase activating enzyme and homologues. PflA is missing this region and both f308 and PflC have alterations to the spacing or sequence. The results of this protein sequence similarity analysis are consistent with the predicted role of TutE serving as the activator for TutD and suggest that the activation may involve iron and/or iron-sulfur binding.

EXAMPLE 7

Figure 14:
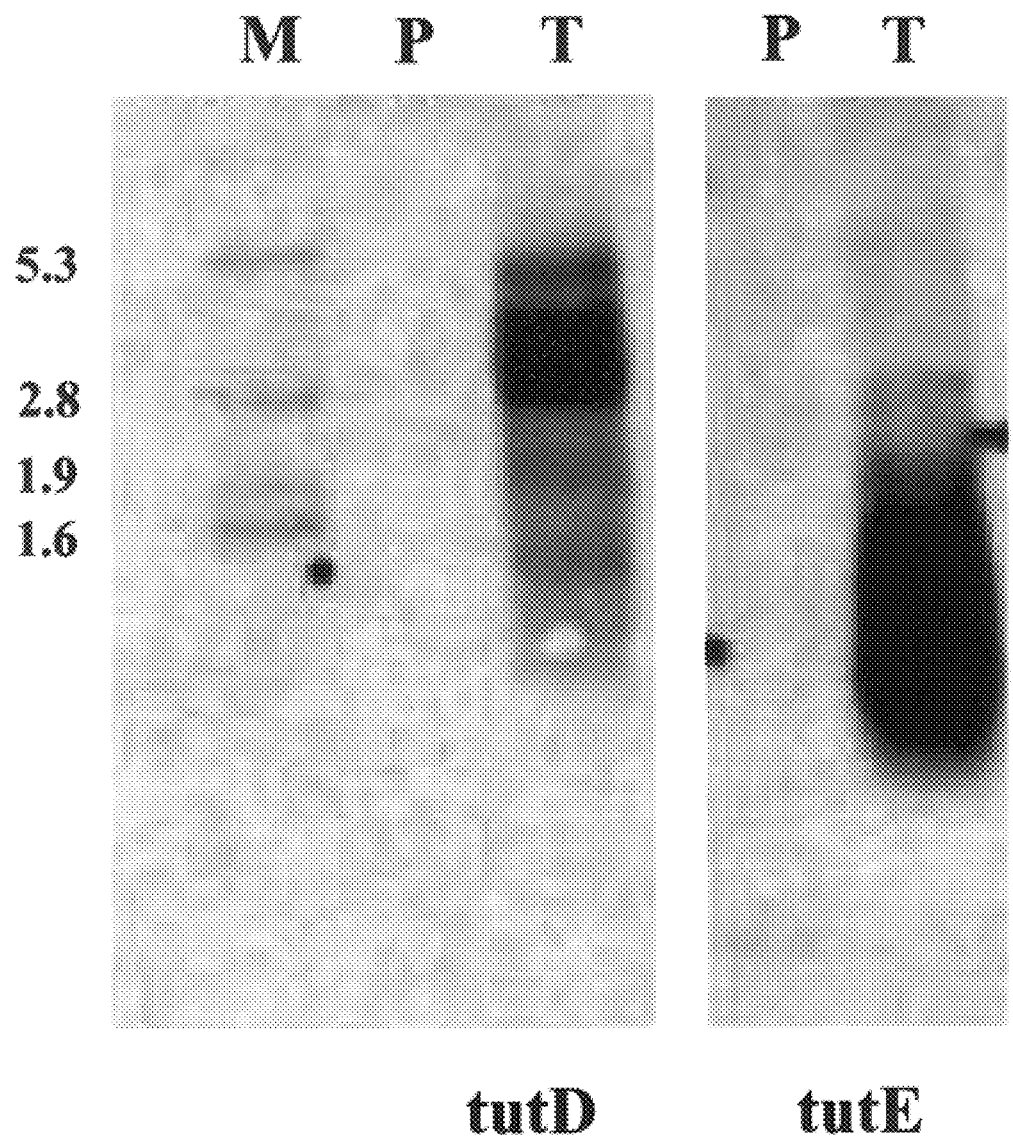
FIG. 14 shows Northern gel results indicating that both tutD and tutE are regulated by toluene.

This example describes various protocols to examine the regulation of the tutD and tutE genes. To confirm that tutD and tute genes are regulated in response to toluene, a Northern blot analysis is performed. Wild type cells of strain T1 are grown in liquid media containing either pyruvate or toluene as the carbon source. RNA is isolated from both of these cultures and subjected to Northern analysis. About 1 micro gram of total RNA from each culture is loaded in each of two lanes on a 1% gel. After electrophoresis the RNA is transferred to a nylon membrane and cut in two. One set of RNA is hybridized to a tutD probe while the other was hybridized to tutE probe. FIG. 14 shows that only cells grown with toluene as the carbon source have tutD and tutE mRNA. It can also be seen that the size of the two messages differ, indicating that the two genes are not contained in one polycistronic mRNA. The fact *that both genes are regulated by toluene suggests that common regulatory protein binding sites is upstream of these and possibly other toluene metabolic genes.

EXAMPLE 8

This example describes the site-directed mutagenesis of TutE protein. Specifically, two cysteine are individually changed to an alanine in an effort to determine if the conserved potential Fe binding site (as identified by the Motif analysis) of TutE plays a role in the enzymatic function of the protein. Three independent isolates of the resulting plasmids (pPWC-$C_L$NSac-C72A, pPWC4-$C_L$NSac-C79A, and pPWC4-$C_L$NSac-C101A) are mated into the strain carrying the tutE21 mutation and the resulting transconjugants are then tested for their ability to complement the mutation. The plasmid carrying the unaltered clone (pPWC-$C_L$NSac) fully complements the tutE21 mutation (utilizing 100% of the toluene provided in the presence in of pyruvate and produces wild type levels of benzylsuccinic acid and a monounsaturated derivative). Neither of the altered plasmids pPWC4-$C_L$NSac-C72A and pPWC4-$C_L$NSac-C79A are able to complement the tutE21 mutation (see Table 2). both of these strains utilize about the same amount of toluene as is utilized by the mutant carrying plasmid pRK415, the vector alone. Likewise, they produce significantly less benzylsuccinic acid and a monounsaturated derivative than the tutE21 mutant strain carrying the unaltered plasmid pPWC4-$C_L$Sac. In fact, they produce about the same amount of these compounds as the mutant carrying plasmid pRK415. Therefore the results in Table 2 clearly demonstrate that cysteine 72 and cysteine 79 are essential for function of the TutE protein. Thus, while it is not intended that the present invention be limited to any one mechanism, the role of iron binding appears to be a mechanistic feature of the TutE protein in its role in toluene metabolism by strain T1.

TABLE 2

| Plasmid | Percent toluene utilized | Percent benzylsuccininic acid like compound produced[c] |
|---|---|---|
| pPWC4-$C_L$NSac[a] | 100 | 100 |
| pRK415[b] | 31.3 ± 5.4 | 8.6 ± 1.2 |
| pPWC4-$C_L$NSac-C72A | 19.5 ± 7.4 | 8.3 ± 0.8 |
| pPWC4-$C_L$NSac-C79A | 31.3 ± 13.8 | 7.8 ± 1.9 |
| pPWC4-$C_L$NSac-C101A | 88.8 ± 13.8 | 55.7 ± 6.1 |

[a] the plasmid carrying the unaltered clone, serving as a positive control.
[b] the vector alone, serving as a negative control.
[c] normalized to 100% for pPWC4-$C_L$NSac, the positive control.

EXAMPLE 9

This example describes the site-directed mutagenesis of TutD protein. To determine if the conserved glycine and cysteine residues of TutD play an essential role in the enzymatic function of the protein has been shown for PflB, both amino acids are individually changed to an alanine as described in materials and methods. W. Plaga, et al. Catalytic-site mapping of pyruvate formate lyase. *Eur. J. Biochem.* 178:445(1988), W. Rödel, et al. Primary structure of *Escherichia coli* pyruvate formate-lyase and pyruvate formate-lyase activating enzyme deduced from the DNA nucleotide sequences. *Eur. J. Biochem.* 177:153(1988). Three independent isolates of the resulting plasmids (pPWC4-$C_L$Sac-G828A and pPWC4-$C_L$Sac-C492A) are mated into the strain carrying the tutD17 mutation and the resulting transconjugants are then tested for their ability to complement the mutation. The plasmid carrying the unaltered clone (pPWC4-$C_L$Sac) fully complements the tutD17 mutation (utilizes 100% of the toluene provided in the presence of pyruvate and produces wild type levels of benzylsuccinic acid and a monounsaturated derivative). Neither of the altered plasmids pPWC4-$C_L$Sac-G828A nor pPWC4-$C_L$Sac-C492A are able to fully complement the tutD17 mutation (see Table 3).

Both of these strains utilized about the same amount of toluene as was utilized by the mutant carrying plasmid pRK415, the vector alone. Likewise, they produce significantly less benzylsuccinic acid and a monounsaturated derivative than the tutD17 mutant strain carrying the unaltered plasmid pPWC4-$C_L$Sac. The mutant carrying plasmid pPWC4-$C_L$Sac-C492A produced about the same amount of these compounds as the mutant carrying plasmid pRK415, while the strain carrying plasmid pPWC4-$C_L$Sac-G828A show higher levels of these compounds than the vector alone but levels much lower than observed with the unaltered plasmid. Since the E. coli pyruvate formate-lyase is known to be a homodimer which requires the formation of only one glycine free radical, the small amount of activity observed in the mutant carrying plasmid pPWC4-$C_L$Sac-G828A may be due to mixed dimers where the free radical forms on the defective chomosomally encoded TutD protein. A. F. Wagner, et al., The free radical in pyruvate formate-lyase is located on glycine-734. Proc. Natl. Acad. Sci. USA. 89:996 (1992). The results in Table 3 clearly demonstrate that glycine 828 and cysteine 492 are essential for function of the TutD protein. While it is not intended the present invention be limited to any one mechanism, the role of a glycine free radical and a covalent substrate-cysteine bond appear to be important mechanistic features of the TutD protein in its role in toluene metabolism by strain T1.

From the above, it should be clear that the present invention provides genes encoding toluene degrading enzymes useful for bioremediation. The genes can be used with an expression vector to over-express the enzymes in a host. In addition, the genes can be used to confer the ability of toluene degradation in an host organism that was not otherwise able to degrade toluene. In this manner, an organism that is native to a waste source (and therefore adapted for competition in the waste source) can be modified to have toluene degrading capabilities. In addition, an organism that is adapted to the laboratory that can overexpress the enzyme in large amounts can be made and used to provide a more efficient system of bioremediation (both in situ and ex-situ).

TABLE 3

| Plasmid | Percent toluene utilized | Percent monounsaturated benzylsuccinic acid derived compound produced[c] |
|---|---|---|
| pPWC4-$C_L$Sac[a] | 100 | 100 |
| pRK415[b] | 23.5 ± 6.4 | 1.3 ± 0.1 |
| pPWC4-$C_L$Sac-G828A | 34.2 ± 9.7 | 13.0 ± 3.8 |
| pPWC4-$C_L$Sac-C492A | 17.7 ± 5.4 | 1.8 ± 0.1 |

[a]The plasmid carrying the unaltered clone, serving as a positive control.
[b]The vector alone, serving as a negative control.
[c]Normalized to 100% for pPWC4-$C_L$NSac, the positive control.

What is claimed is:

1. A method of degrading compounds contained in a liquid or solid waste source, comprising the steps of:
   a) providing
      i) a liquid or solid waste source comprising toluene,
      ii) a reaction containing means,
      iii) a functional, cell-free pyruvate formate lyase obtained from a toluene-degrading bacterium and iv) a functional, cell-free pyruvate formate lyase activating enzyme of a toluene-degrading bacterium; and
   b) reacting said functional, cell-free pyruvate fornate lyase of a toluene-degrading bacterium and said functional, cell-free pyruvate formate lyase activating enzyme of a toluene-degrading bacterium with said liquid or solid waste source in said reaction containing means under conditions such that toluene is degraded.

2. The method of claim 1, wherein said functional, cell-free pyruvate formate lyase obtained from a toluene-degrading bacterium and said functional, cell-free pyruvate formate lyase activating enzyme of a toluene-degrading bacterium are derived from an organism selected from the group consisting of *Thauera aromatica, Xanthomonas maltophilia, Geobacter metallireducens*, and *Azoarcus tolulyticus*.

3. The method of claim 1, wherein said functional, cell-free pyruvate formate lyase obtained from a toluene-degrading bacterium has the amino acid sequence selected from the group consisting of SEQ ID NO: 16, SEQ ID NO: 33, SEQ ID NO: 34 and SEQ ID NO: 35.

4. The method of claim 1, wherein said functional, cell-free pyruvate formate lyase activating enzyme obtained from a toluene-degrading bacterium has the amino acid sequence selected from the group consisting of SEQ ID NO: 18, SEQ ID NO: 36, SEQ ID NO: 37 and SEQ ID NO: 38.

5. The method of claim 1, wherein said reaction containing means is a bioreactor.

6. A method of degrading compounds contained in a liquid or solid waste source, comprising the steps of:
   a) providing i) a liquid or solid waste source comprising toluene, and ii) a functional, cell-free pyruvate formate lyase tutD homologue obtained from a toluene-degrading bacterium selected from the group consisting of *Thauera aromatics, Xanthomonas maltophilia, Geobacter metallireducens*, and *Azoarcus tolulyticus;*
   b) reacting said functional, cell-free pyruvate formate lyase homologue with said liquid or solid waste source under conditions such that toluene is degraded.

7. The method of claim 6, further comprising the step of reacting a functional, cell-free pyruvate fornate lyase activating homologue with said waste source.

8. A method of degrading compounds contained in a liquid or solid waste source, comprising the steps of:
   a) providing
      i) a liquid or solid waste source comprising toluene,
      ii) a reaction containing means,
      iii) a functional, cell-free pyruvate fornate lyase having the amino acid sequence of SEQ ID NO: 16 and iv) a functional, cell-free pyruvate formate lyase activating enzyme having the amino acid sequence of SEQ ID NO: 18; and
   b) reacting said functional, cell-free pyruvate formate lyase and said functional, cell-free pyruvate formate lyase activating enzyme with said liquid or solid waste source in said reaction containing means under conditions such that toluene is degraded.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:1:

Arg Val Ser Gly Tyr
1            5

(2) INFORMATION FOR SEQ ID NO:2:

(i) SEQUENCE CHARACTERISTICS:
      (A) LENGTH: 5 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:2:

Arg Val Ala Gly Tyr
1            5

(2) INFORMATION FOR SEQ ID NO:3:

(i) SEQUENCE CHARACTERISTICS:
      (A) LENGTH: 8 amino acids

```
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:3:

Val Arg Val Ser Gly Tyr Ser Ala
1               5

(2) INFORMATION FOR SEQ ID NO:4:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:4:

Thr Pro Asp Gly Arg
1               5

(2) INFORMATION FOR SEQ ID NO:5:

(i) SEQUENCE CHARACTERISTICS:
          (A) LENGTH: 6 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:5:

Thr Pro Asp Gly Arg Phe
1               5

(2) INFORMATION FOR SEQ ID NO:6:

(i) SEQUENCE CHARACTERISTICS:
          (A) LENGTH: 6 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:6:

Gly Pro Thr Ala Val Leu
1               5

(2) INFORMATION FOR SEQ ID NO:7:

(i) SEQUENCE CHARACTERISTICS:
          (A) LENGTH: 5 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:7:

Gly Asn Asp Asp Asp
1               5

(2) INFORMATION FOR SEQ ID NO:8:

(i) SEQUENCE CHARACTERISTICS:
```

(A) LENGTH: 6393 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:8:

```
CCGCGGCTCA GCTAAAATAT GCAAATAAAT ATGCTGCAAC AGGTCGCTCT GGGCTTGCCA      60
GTCGTGCGTG TTGGTGCATG ATGAGTCCTT GCCTTGTCGA AGGCTATTAG ACTTTGGTTT     120
AGCTGCAGCG CAGCAAAAAT AGCGTAGCGA GAAAATTCGA TGCGATACCT GTCTTTGCAT     180
CCACCTGAAT TCGTGCTCTC TCCAGCACGT TTTCTCATCT GCTACCTCGA GCGCATGATT     240
CTTCAGACCT TTGACGGCAT CTTGCGCTGT CCCGCCCGCT TGCCTGCTCG CAGCTCCAGG     300
TCGAGGATCC AGCTCTCCTT GTACAGCGCG GGTGCGGCTT GCTCGCCTGA AGTTGTTCA      360
TCCGCAGGCG AGTGCAGTTC GAGTATCGAC TTGATCACGT TTGGTGTCTT CAACCCTTGC     420
GACACTGGCA GTGCCCTCCG GATCTATCAC CGCCTTCACA TGCACCGGCT CGCAGGGTCA     480
GCGCTGCCGC AGCTACGTAC ATAACATGCT CAACTGGTCA GTTGCATTCC ATGGGAATAG     540
CGGCTTGCAC AAATTATGAG CAGCCTGCGG CTTCTTTCGA CGGGGATACG GCTTCCGCGA     600
CATGCATCAC TGGCAATCGG AGAATGCGGG ATGGGTAGGC GTGGCAGCCC CGCTCGCAGG     660
GTCGTGCAAA TGAGCGCCAG ACCGGTGTAT GTAGTCAGGT CAAGCCTTGA GGGCTGCTTG     720
ACTTCGAAGC GCTATGTTTG ATTGGGCCAA GGCAGGAGAG GGGCGATTGT ACAATTTCGT     780
CAACGTATTA CGAGGTTTTC TGCGCGGCGC TAGCGCAAGC TCAGGGCTAA TATCAATGAT     840
GGCAAAATCA TGACATCGAA CAACAGTTCA GTATCCGATA TTTCTGCAGT GCTGCGGGTT     900
CGCGATGTGA CTTTGCGCGC TGTGGATGAT CTTCAGACCT ATCGGGAAAA ATTAGCCCGT     960
GTTGTGCTTG ATGGGCTTTA TGAATTTGTA GGGCTTCTCG ATGCAAAAGG TAATACTCTT    1020
GAAATAAATC AAGCTGCGCT GGATGGCGCG GGAACCCGAC TTGAAGACAT CCGCGACAAG    1080
CCGTTCTGGG AGGCCAGGTG GTGGCAGGTT TCCAGGGAAA CCCAAGAAGA GCAGCGCAAA    1140
CTTATCGCTC GCGCGAGTGC TGGCGAGTTT GTTCGATGCG ATGTTGAAAT ATATGGTCGA    1200
GCTTCCGGAG AAGAGACGAT TGTTGTTGAT TACTCAATTC TTCCGATTCG AGATTGCAAT    1260
GGAAAAGTGG TGTTCTTGCT TCCTGAAGGC CGGAATATCA CCGATAAGAA GCTGGCGGAA    1320
GCAGAGCTTG CGCGAAAGAA TGAAGAGCTG CAGCATCTTC TTGAGAAGAT TCGTCAGCTG    1380
GATGAGGCCA AGAATGAGTT CTTCGCCAAT CTCAGTCATG AATTGCGTAC GCCTCTTTCT    1440
CTGATTCTTG GGTCCGTAGA ATCGCTACTT GCCGATTCTG GAGACTATTC TGGAGTGCAA    1500
CGAGTCGATC TGGATGTCAT CCAGAGAAAT GCCATAACCT TGCTCAAGTA TGTGAACGAC    1560
CTTCTTGATC TAGCAAAACT GCAGGCGGAG AAGTTGCAGC TTCACTATTC GCGTGTCGAC    1620
CTTGCAGCGG TGACACGAAT GATTTGCGCG CATTTTGAGG CTCTGGCAGA GTATAAATGT    1680
CTTTCATATG TCATTGACGC TCCTGCCTTT ATGGAGGCTG AAGTCGATGT CGAGAAGTAT    1740
GAGCGGATCG TTCTGAATCT CTTATCCAAT GCCTTTAAGT TCTCGCCGGA CGGCGGGCGC    1800
ATTCGCTGTT CGTTGAGTGC GACTGGTACC GGAAGAATCT TGCTCAGTAT TCAGGACAGT    1860
GGTCCTGGAA TTCCAGCTGA TCAACAGAGT GAAATTTTCG GCCGGTTTCG GCAAGGTGGG    1920
GATATCAAGT CCCGGCAGTT TGGCGGTACG GGCTTGGGTT TGACTATTGT GAAGGATTTT    1980
GTCTGCCTGC ATGGGGGGGT TGTGGTCGTT TCAGACGCTC CGGGAGGCGG GGCTTTATTT    2040
CAGATCGAAT TGCCCAGGAA TGCGCCTTCT GGGGTGTATG TAAATGCGGT TGCAAAGGCT    2100
```

```
GGTGAATTAA GCCCTACATC TTTTGATATC AGCGCATGGG GCCTGGAGGG GCGGAGTGAA    2160

TGGACAAGCG CCGAGGGAGC CAGTGATCGT CCTCGGATCC TGATTGTCGA AGATAACGTC    2220

GATATGCGCT GTTTTATAGG GAGGGTGCTC ATTGACGAGT ATCAGATCAG TGTTGCCGCT    2280

GATGGTGAGC AGGCACTGGA GCTTATTACC TCATCCCCTC CGGATCTGGT CATTACGGAT    2340

CTGATGATGC CCAAGGTCAG CGGTCAGCTT CTGGTCAAAG AGATGCGCTC GAGAGGGGAC    2400

CTAGCCAATG TTCCTATACT CGTGCTTTCG GCCAAGGCGG ATGATGGGTT GAGAATAAAA    2460

TTGCTGGCCG AGTCGGTTCA AGATTATGTT GTCAAGCCAT TCTCGGCTAC GGAGTTGCGA    2520

GCGCGAGTTC GAAATCTTGT TACCATGAAG CGGGCCCGTG ATGCTTTGCA GAGAGCGCTC    2580

GACAGTCAGA GTGACGATTT ATCGCAATTG ACTCGGCAGA TCATCGACAA TCGCCAGGAG    2640

TTGCAGCGAA GCCATGATGC TTTGCAGGAA TCTGAGTCCC GCTGGCGCGC AGTCTATGAG    2700

AATTCTGCTG CAGGTATTGT GTTGACAAAT TTGGACGGCT TGATTTTGTC TGCGAATCAA    2760

GCATTTCAAA AAATGGTTGG CTATGCCGAG GATGAGTTGC GGGTGATTGA AATATCGGAT    2820

CTCGTCCCCG AACATGATCG CGAAAAAATC CGGTCGCGCG TTTCAAATCT GATCAGTGGC    2880

CGCGTCGACG ACTATCAAGT GCAAAGGCAA TGCCGACGAA AGGACGGCCG AATGATGTGG    2940

GCAAATGTGC GAGCATCGCT CATACCTGGG CTGGCCAATC AGTCTCCGAT GGTTGTGAGA    3000

ATTTTTGATG ACATTACCGA AAAGATTCAG ACTGAAGCTG AACTGGCAAG AGCAAGGGAA    3060

AAGTTGACCA GAGTCATGCG TGTTACCGCA ATGGGAGAAT TGGCGGCATC GATTGCTCAT    3120

GAGTTGAATC AACCGCTTGC CGCCATTGTT ACCAATGGTC ATGCATCATT ACGCTGGCTT    3180

GGCTCCGAGC CTTGTAATCT ATTGGAAGCC GTCGAAGCAG TGCGAAGAAT CATCCATGAT    3240

GCTAATCGCG CGAGTGAAAT AATCAAACGG ATCCGTGGCT TTCTTCAGCG GGGGGAGGGG    3300

AGGCGCTCGG CAGTGGATAT TTTTCAGGTT GTTGCGGATG TGGCTGCGAT TGTCAGCGAT    3360

ATGGCGCGCA GTCATTGCAT TGATATGCGT TATCAAGCAG TCGGTCAATT GTCGCTAGTG    3420

ATTGCGGATA AGGTCCAGTT GCAACAGGTT ATTCTGAATT TGTGCATCAA TGGCATAGAA    3480

TCCATTGTTG GCGGAAACTC CGAACGAGGC GAACTTTCAA TTACCGTTAC CCAGTCCGAT    3540

AAAAGATTCT TGACCGTCAG CGTACATGAT TCCGGCCCGG GCCTTGCACC TGGCGAGGCG    3600

GAAAACGTGT TTGATGCGTT CTATACGAGC AAGGTGGAGG GGCTTGGCAT GGGGCTCGCC    3660

ATCAGTCGCT CTATCATTGA GGCGCATGGT GGGCGCCTTG ATGTTCTGTC CCCTTCCACG    3720

GAGGGGGGAT GCACGTTCTG TTTCACGTTG CCTACGGAGG AGATGGCTAG CCCATGTGCC    3780

CCACAATAGA TGCATCGACT GTTTATCTGG TGGACGACGA TCGCTCCATG CGTGACGCAA    3840

TTTCCAGCTT GGTTCGATCG GTCGGCCTCA ATGTGGAGAC ATTTGCGTCT GCAAGTGAGT    3900

TCTTGGAGCA CGCTCGTTCG GAAGCATGTG CCTGCTTGGT TCTTGATGTT CGGATGCCAC    3960

GCATGAGCGG TTTTGATCTT CAGCATGCGT TAAGCAAAAA TGGTGTCGAT ATTCCAATCA    4020

TCTTTATTAC CGGCCATGGT GATATCCCCA TGGCGGTTCG CGCCATCAAG TCGGGTGCCC    4080

TAGAATTTCT TCCAAAGCCT TTTCGTGCTG AAGAACTGCT CGAAGCAATC AACAGGGCTC    4140

TGAATATCGA TCAGGAGGCT CGGGAGTACA AGGCGGAGCT GGATAAGATA TTGAAGAAAT    4200

ATGAGGGGCT TACAGATCGA GAAAAGGAGG TATTTCCCCT TATTGCCCAG GGCTTGTTGA    4260

ACAAGCAGAT TGCCGGATAT CTCGGAATTA CTGAGGTCAC CATAAAGGTT CATCGTCATA    4320

ATATTACGAG AAAAATGGGG GTCCGGACAC TGGCTAATCT GGTGCGACTT TACGAGAAGT    4380

TAAAGAATGC TGGGCTGATC GAAAAAAAGA ACGGAAATCT ATCGGGATGA AGAGCCGCGA    4440
```

```
CTGGAACCCT TCAGGCTCTT GGCGGCCACG CTGTAGGAAC GCTATCGCCT ACCTGCGAAT    4500

GTCTAAACTC ACTGAAACGG CATAGAGTTC AAAGCAAGAA CTTAGCAAAA TGGATTTGCC    4560

TAACAGTTGA TTGTAGAAAT AATTTTTTAT TGATTAATGA TCGGTTGATT GTTGCTGCAG    4620

TCCTGGGAGG GAAAGCCATT CACAAGCACT ACAATGACTG CTGCTGCGCA TCGCAAAATG    4680

TATCAAGTCG CCGGTGGACC TCAGTCCAAG CTTGCTCATG ATGCGCCCGC GGTGAGCTTC    4740

CACAGTCTTA TGGCTGATGC CCAGCAGCTT GGCGATTTCC TTGCTGCTGT TGCCGCAAAC    4800

CACCTTGTCG AGAATCTCCA TTTCGCGCTG TGACAGGGCG GCAAGAAGAT CGGCACGCTC    4860

CTGCTTTTCG CGCTGCTTAT TCGTCATCTC CTTGCTGAAG GCAAGGGCGG CGTTTACAGC    4920

ATCAAGCAGA TCCTGGTTGC GATAGGGTTT TTGGAGAAAG TCGAACGCGC CTTTCTTTAC    4980

CGCTTGAGCT CCCATCTGGG CATCGCCGTA GGCGGAGAGA AGATGATCG GCAGCTTGAA    5040

GCCTCTGTCA CACAGCGCTT GTTGCAACTG TAGGCCGCTG ACATTTTGCA TTCGAACATC    5100

CAGAATCACA CAGCCGTAGG TGCATGAAAT ATCGGCATCA AGAAAATGCT TTGCGGATTC    5160

GTATGCCTTG ACGTTTAGTG AAATCGAGTT GAGGAGCCAC GTCAGTGAGT CCCTGACCGA    5220

CGCTTCGTCG TCGACGACGA ATACAGTTGG GGCGTTTCCA GATTTTTCGA TTTGCATGAG    5280

GTGCTCCTTT GTGCGGTGCT ATGACAAACG TACGGTCTAT ATGGCATCGC TAATCTGAAT    5340

ATCTCTTACA TTGGCAAGGT AAACTGAAAC CTCGATCCGC ATCCTTCGGT CTTCGAAAAT    5400

GAAAGTTCGC CCCCATGTGA TTCGATGATC GAGCGGCAGA TCGTCAATCC TATTCCAAGT    5460

CCGTCTGGCT TGGTTGTGAA ATAGGGTTTA AAGACGCGTT TTGCTGTTCG GCTTTCGACG    5520

CCGGTCCCAT AGTCTTGTAC AAACACCTTC ATTGACCTTC CCTCTGCAAT GATTTCGCTA    5580

CCGATCAGCA GCACGCGAGA GTCCGGTTCC ATTTCTGACA TGGCCTCAAT GCCATTCTTG    5640

ATTAGATTGA ATAAGACCTG CTGGATCTCG ATTTTGCAGA GAGGGATGAG TGGAGGGTCG    5700

GGCATTAACT GCAGATTCAC CGTAGCGTTA TGTCGATGGA TCTCGAAACT TAGAAATGAA    5760

AGAGCGTCCT GGATGACGTC GTTGATGTTT TCCAATAGCC TTTCTGGCTT GTGTTTGCAG    5820

ACGAAATCCT TGACACGCCG CAGGATCTCA CCCGCTTGAT CTAGATGGGT GATTGCTAAC    5880

CCGAGTGAGT GTGATATCTC CTCGACTCCG GGCACATGTT CAAGCCGTAG CCGGCAGCCC    5940

TGGAGATAGT TCACGGCGGA AACCAGGGGT TGGCCCATCT GGTGTGCAAG CGCTGCGGCC    6000

ATTCCGGCCA TCGCGTTGAT GCGTCCGAGT CGAGTGAGTT CTGCGTGACG GAGCCTTTCC    6060

AATTCCTCTA TCCGCTTGCG GTAGGTGATA TCTGCGAAGG CGGCCACAAC TATTTTCTCA    6120

TCCTTGATCT CGAGCAAGGA TGAGCTGACG CTGAGCCATC GCGTCTTGTG ATTTTCTTCG    6180

TCGCACATGC CGACTTCGAG GCTTCTGACC GAACTTTTCT GGAGGTCGTG AATCCGCCAA    6240

GGCAATCGCT TTTTCCAGAT ATTTGTCCCG TCATTGAGAA AGAACCGTTG CGGTAATTGC    6300

TGCCAACTCA TGGGCGTCCC TTCCTGTGTT CCCATCAGTT CAGAAAACTG GCAGTTTTCC    6360

TCGAGAATCC TGCCGCGGCT ATCAGTAATC GAT                                 6393
```

(2) INFORMATION FOR SEQ ID NO:9:

(i) SEQUENCE CHARACTERISTICS:
        (A) LENGTH: 979 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

-continued

```
Met Thr Ser Asn Asn Ser Ser Val Ser Asp Ile Ser Ala Val Leu Arg
1               5                   10                  15

Val Arg Asp Val Thr Leu Arg Ala Val Asp Asp Leu Gln Thr Tyr Arg
            20                  25                  30

Glu Lys Leu Ala Arg Val Val Leu Asp Gly Leu Tyr Glu Phe Val Gly
        35                  40                  45

Leu Leu Asp Ala Lys Gly Asn Thr Leu Glu Ile Asn Gln Ala Ala Leu
    50                  55                  60

Asp Gly Ala Gly Thr Arg Leu Glu Asp Ile Arg Asp Lys Pro Phe Trp
65                  70                  75                  80

Glu Ala Arg Trp Trp Gln Val Ser Arg Glu Thr Gln Glu Gln Arg
                85                  90                  95

Lys Leu Ile Ala Arg Ala Ser Ala Gly Glu Phe Val Arg Cys Asp Val
            100                 105                 110

Glu Ile Tyr Gly Arg Ala Ser Gly Glu Glu Thr Ile Val Val Asp Tyr
            115                 120                 125

Ser Ile Leu Pro Ile Arg Asp Cys Asn Gly Lys Val Val Phe Leu Leu
    130                 135                 140

Pro Glu Gly Arg Asn Ile Thr Asp Lys Lys Leu Ala Glu Ala Glu Leu
145                 150                 155                 160

Ala Arg Lys Asn Glu Glu Leu Gln His Leu Leu Glu Lys Ile Arg Gln
                165                 170                 175

Leu Asp Glu Ala Lys Asn Glu Phe Phe Ala Asn Leu Ser His Glu Leu
            180                 185                 190

Arg Thr Pro Leu Ser Leu Ile Leu Gly Ser Val Glu Ser Leu Leu Ala
        195                 200                 205

Asp Ser Gly Asp Tyr Ser Gly Val Gln Arg Val Asp Leu Asp Val Ile
    210                 215                 220

Gln Arg Asn Ala Ile Thr Leu Leu Lys Tyr Val Asn Asp Leu Leu Asp
225                 230                 235                 240

Leu Ala Lys Leu Gln Ala Glu Lys Leu Gln Leu His Tyr Ser Arg Val
                245                 250                 255

Asp Leu Ala Ala Val Thr Arg Met Ile Cys Ala His Phe Glu Ala Leu
            260                 265                 270

Ala Glu Tyr Lys Cys Leu Ser Tyr Val Ile Asp Ala Pro Ala Phe Met
        275                 280                 285

Glu Ala Glu Val Asp Val Glu Lys Tyr Glu Arg Ile Val Leu Asn Leu
    290                 295                 300

Leu Ser Asn Ala Phe Lys Phe Ser Pro Asp Gly Gly Arg Ile Arg Cys
305                 310                 315                 320

Ser Leu Ser Ala Thr Gly Thr Gly Arg Ile Leu Leu Ser Ile Gln Asp
                325                 330                 335

Ser Gly Pro Gly Ile Pro Ala Asp Gln Gln Ser Glu Ile Phe Gly Arg
            340                 345                 350

Phe Arg Gln Gly Gly Asp Ile Lys Ser Arg Gln Phe Gly Gly Thr Gly
        355                 360                 365

Leu Gly Leu Thr Ile Val Lys Asp Phe Val Cys Leu His Gly Gly Val
    370                 375                 380

Val Val Val Ser Asp Ala Pro Gly Gly Gly Ala Leu Phe Gln Ile Glu
385                 390                 395                 400

Leu Pro Arg Asn Ala Pro Ser Gly Val Tyr Val Asn Ala Val Ala Lys
                405                 410                 415

Ala Gly Glu Leu Ser Pro Thr Ser Phe Asp Ile Ser Ala Trp Gly Leu
```

-continued

```
                420                 425                 430
Glu Gly Arg Ser Glu Trp Thr Ser Ala Glu Gly Ala Ser Asp Arg Pro
            435                 440                 445
Arg Ile Leu Ile Val Glu Asp Asn Val Asp Met Arg Cys Phe Ile Gly
    450                 455                 460
Arg Val Leu Ile Asp Glu Tyr Gln Ile Ser Val Ala Ala Asp Gly Glu
465                 470                 475                 480
Gln Ala Leu Glu Leu Ile Thr Ser Ser Pro Pro Asp Leu Val Ile Thr
                485                 490                 495
Asp Leu Met Met Pro Lys Val Ser Gly Gln Leu Leu Val Lys Glu Met
            500                 505                 510
Arg Ser Arg Gly Asp Leu Ala Asn Val Pro Ile Leu Val Leu Ser Ala
    515                 520                 525
Lys Ala Asp Asp Gly Leu Arg Ile Lys Leu Leu Ala Glu Ser Val Gln
530                 535                 540
Asp Tyr Val Val Lys Pro Phe Ser Ala Thr Glu Leu Arg Ala Arg Val
545                 550                 555                 560
Arg Asn Leu Val Thr Met Lys Arg Ala Arg Asp Ala Leu Gln Arg Ala
                565                 570                 575
Leu Asp Ser Gln Ser Asp Asp Leu Ser Gln Leu Thr Arg Gln Ile Ile
            580                 585                 590
Asp Asn Arg Gln Glu Leu Gln Arg Ser His Asp Ala Leu Gln Glu Ser
    595                 600                 605
Glu Ser Arg Trp Arg Ala Val Tyr Glu Asn Ser Ala Ala Gly Ile Val
        610                 615                 620
Leu Thr Asn Leu Asp Gly Leu Ile Leu Ser Ala Asn Gln Ala Phe Gln
625                 630                 635                 640
Lys Met Val Gly Tyr Ala Glu Asp Glu Leu Arg Val Ile Glu Ile Ser
                645                 650                 655
Asp Leu Val Pro Glu His Asp Arg Glu Lys Ile Arg Ser Arg Val Ser
            660                 665                 670
Asn Leu Ile Ser Gly Arg Val Asp Asp Tyr Gln Val Gln Arg Gln Cys
    675                 680                 685
Arg Arg Lys Asp Gly Arg Met Met Trp Ala Asn Val Arg Ala Ser Leu
690                 695                 700
Ile Pro Gly Leu Ala Asn Gln Ser Pro Met Val Val Arg Ile Phe Asp
705                 710                 715                 720
Asp Ile Thr Glu Lys Ile Gln Thr Glu Ala Glu Leu Ala Arg Ala Arg
                725                 730                 735
Glu Lys Leu Thr Arg Val Met Arg Val Thr Ala Met Gly Glu Leu Ala
            740                 745                 750
Ala Ser Ile Ala His Glu Leu Asn Gln Pro Leu Ala Ala Ile Val Thr
    755                 760                 765
Asn Gly His Ala Ser Leu Arg Trp Leu Gly Ser Glu Pro Cys Asn Leu
770                 775                 780
Leu Glu Ala Val Glu Ala Val Arg Arg Ile Ile His Asp Ala Asn Arg
785                 790                 795                 800
Ala Ser Glu Ile Ile Lys Arg Ile Arg Gly Phe Leu Gln Arg Gly Glu
                805                 810                 815
Gly Arg Arg Ser Ala Val Asp Ile Phe Gln Val Val Ala Asp Val Ala
            820                 825                 830
Ala Ile Val Ser Asp Met Ala Arg Ser His Cys Ile Asp Met Arg Tyr
    835                 840                 845
```

```
Gln Ala Val Gly Gln Leu Ser Leu Val Ile Ala Asp Lys Val Gln Leu
    850                 855                 860
Gln Gln Val Ile Leu Asn Leu Cys Ile Asn Gly Ile Glu Ser Ile Val
865                 870                 875                 880
Gly Gly Asn Ser Glu Arg Gly Glu Leu Ser Ile Thr Val Thr Gln Ser
            885                 890                 895
Asp Lys Arg Phe Leu Thr Val Ser Val His Asp Ser Gly Pro Gly Leu
                900                 905                 910
Ala Pro Gly Glu Ala Glu Asn Val Phe Asp Ala Phe Tyr Thr Ser Lys
        915                 920                 925
Val Glu Gly Leu Gly Met Gly Leu Ala Ile Ser Arg Ser Ile Ile Glu
    930                 935                 940
Ala His Gly Gly Arg Leu Asp Val Leu Ser Pro Ser Thr Glu Gly Gly
945                 950                 955                 960
Cys Thr Phe Cys Phe Thr Leu Pro Thr Glu Glu Met Ala Ser Pro Cys
            965                 970                 975
Ala Pro Gln
```

(2) INFORMATION FOR SEQ ID NO:10:

(i) SEQUENCE CHARACTERISTICS:
        (A) LENGTH: 218 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

```
Met Cys Pro Thr Ile Asp Ala Ser Thr Val Tyr Leu Val Asp Asp Asp
1               5                   10                  15
Arg Ser Met Arg Asp Ala Ile Ser Ser Leu Val Arg Ser Val Gly Leu
            20                  25                  30
Asn Val Glu Thr Phe Ala Ser Ala Ser Glu Phe Leu Glu His Ala Arg
        35                  40                  45
Ser Glu Ala Cys Ala Cys Leu Val Leu Asp Val Arg Met Pro Arg Met
50                  55                  60
Ser Gly Phe Asp Leu Gln His Ala Leu Ser Lys Asn Gly Val Asp Ile
65                  70                  75                  80
Pro Ile Ile Phe Ile Thr Gly His Gly Asp Ile Pro Met Ala Val Arg
                85                  90                  95
Ala Ile Lys Ser Gly Ala Leu Glu Phe Leu Pro Lys Pro Phe Arg Ala
            100                 105                 110
Glu Glu Leu Leu Glu Ala Ile Asn Arg Ala Leu Asn Ile Asp Gln Glu
        115                 120                 125
Ala Arg Glu Tyr Lys Ala Glu Leu Asp Lys Ile Leu Lys Lys Tyr Glu
    130                 135                 140
Gly Leu Thr Asp Arg Glu Lys Glu Val Phe Pro Leu Ile Ala Gln Gly
145                 150                 155                 160
Leu Leu Asn Lys Gln Ile Ala Gly Tyr Leu Gly Ile Thr Glu Val Thr
                165                 170                 175
Ile Lys Val His Arg His Asn Ile Thr Arg Lys Met Gly Val Arg Thr
            180                 185                 190
Leu Ala Asn Leu Val Arg Leu Tyr Glu Lys Leu Lys Asn Ala Gly Leu
        195                 200                 205
```

```
Ile Glu Lys Lys Asn Gly Asn Leu Ser Gly
    210                 215
```

(2) INFORMATION FOR SEQ ID NO:11:

(i) SEQUENCE CHARACTERISTICS:
        (A) LENGTH: 218 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

```
Met Cys Pro Thr Ile Asp Ala Ser Thr Val Tyr Leu Val Asp Asp
1               5                   10                  15

Arg Ser Met Arg Asp Ala Ile Ser Ser Leu Val Arg Ser Val Gly Leu
            20                  25                  30

Asn Val Glu Thr Phe Ala Ser Ala Ser Glu Phe Leu Glu His Ala Arg
            35                  40                  45

Ser Glu Ala Cys Ala Cys Leu Val Leu Asp Val Arg Met Pro Arg Met
65  50              55                  60

Ser Gly Phe Asp Leu Gln His Ala Leu Ser Lys Asn Gly Val Asp Ile
65              70                  75                  80

Pro Ile Ile Phe Ile Thr Gly His Gly Asp Ile Pro Met Ala Val Arg
                85                  90                  95

Ala Ile Lys Ser Gly Ala Leu Glu Phe Leu Pro Lys Pro Phe Arg Ala
            100                 105                 110

Glu Glu Leu Leu Glu Ala Ile Asn Arg Ala Leu Asn Ile Asp Gln Glu
            115                 120                 125

Ala Arg Glu Tyr Lys Ala Glu Leu Asp Lys Ile Leu Lys Lys Tyr Glu
    130                 135                 140

Gly Leu Thr Asp Arg Glu Lys Glu Val Phe Pro Leu Ile Ala Gln Gly
145             150                 155                 160

Leu Leu Asn Lys Gln Ile Ala Gly Tyr Leu Gly Ile Thr Glu Val Thr
                165                 170                 175

Ile Lys Val His Arg His Asn Ile Thr Arg Lys Met Gly Val Arg Thr
            180                 185                 190

Leu Ala Asn Leu Val Arg Leu Tyr Glu Lys Leu Lys Asn Ala Gly Leu
        195                 200                 205

Ile Glu Lys Lys Asn Gly Asn Leu Ser Gly
    210                 215
```

(2) INFORMATION FOR SEQ ID NO:12:

(i) SEQUENCE CHARACTERISTICS:
        (A) LENGTH: 452 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

```
Val Leu Ser Ala Lys Ala Asp Asp Gly Leu Arg Ile Lys Leu Leu Ala
1               5                   10                  15

Glu Ser Val Gln Asp Tyr Val Val Lys Pro Phe Ser Ala Thr Glu Leu
            20                  25                  30

Arg Ala Arg Val Arg Asn Leu Val Thr Met Lys Arg Ala Arg Asp Ala
            35                  40                  45
```

```
Leu Gln Arg Ala Leu Asp Ser Gln Ser Asp Leu Ser Gln Leu Thr
    50                  55                  60
Arg Gln Ile Ile Asp Asn Arg Gln Glu Leu Gln Arg Ser His Asp Ala
 65              70                  75                  80
Leu Gln Glu Ser Glu Ser Arg Trp Arg Ala Val Tyr Glu Asn Ser Ala
                 85                  90                  95
Ala Gly Ile Val Leu Thr Asn Leu Asp Gly Leu Ile Leu Ser Ala Asn
                100                 105                 110
Gln Ala Phe Gln Lys Met Val Gly Tyr Ala Glu Asp Glu Leu Arg Val
        115                 120                 125
Ile Glu Ile Ser Asp Leu Val Pro Glu His Asp Arg Glu Lys Ile Arg
        130                 135                 140
Ser Arg Val Ser Asn Leu Ile Ser Gly Arg Val Asp Asp Tyr Gln Val
145                 150                 155                 160
Gln Arg Gln Cys Arg Arg Lys Asp Gly Arg Met Met Trp Ala Asn Val
                165                 170                 175
Arg Ala Ser Leu Ile Pro Gly Leu Ala Asn Gln Ser Pro Met Val Val
                180                 185                 190
Arg Ile Phe Asp Asp Ile Thr Glu Lys Ile Gln Thr Glu Ala Glu Leu
        195                 200                 205
Ala Arg Ala Arg Glu Lys Leu Thr Arg Val Met Arg Val Thr Ala Met
        210                 215                 220
Gly Glu Leu Ala Ala Ser Ile Ala His Glu Leu Asn Gln Pro Leu Ala
225                 230                 235                 240
Ala Ile Val Thr Asn Gly His Ala Ser Leu Arg Trp Leu Gly Ser Glu
                245                 250                 255
Pro Cys Asn Leu Leu Glu Ala Val Glu Ala Val Arg Arg Ile Ile His
                260                 265                 270
Asp Ala Asn Arg Ala Ser Glu Ile Ile Lys Arg Ile Arg Gly Phe Leu
        275                 280                 285
Gln Arg Gly Glu Gly Arg Arg Ser Ala Val Asp Ile Phe Gln Val Val
        290                 295                 300
Ala Asp Val Ala Ala Ile Val Ser Asp Met Ala Arg Ser His Cys Ile
305                 310                 315                 320
Asp Met Arg Tyr Gln Ala Val Gly Gln Leu Ser Leu Val Ile Ala Asp
                325                 330                 335
Lys Val Gln Leu Gln Gln Val Ile Leu Asn Leu Cys Ile Asn Gly Ile
                340                 345                 350
Glu Ser Ile Val Gly Gly Asn Ser Glu Arg Gly Glu Leu Ser Ile Thr
        355                 360                 365
Val Thr Gln Ser Asp Lys Arg Phe Leu Thr Val Ser Val His Asp Ser
        370                 375                 380
Gly Pro Gly Leu Ala Pro Gly Glu Ala Glu Asn Val Phe Asp Ala Phe
385                 390                 395                 400
Tyr Thr Ser Lys Val Glu Gly Leu Gly Met Gly Leu Ala Ile Ser Arg
                405                 410                 415
Ser Ile Ile Glu Ala His Gly Gly Arg Leu Asp Val Leu Ser Pro Ser
                420                 425                 430
Thr Glu Gly Gly Cys Thr Phe Cys Phe Thr Leu Pro Thr Glu Glu Met
        435                 440                 445
Ala Ser Pro Cys
    450
```

(2) INFORMATION FOR SEQ ID NO:13:

(i) SEQUENCE CHARACTERISTICS:
        (A) LENGTH: 3106 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

```
GAATTCATCG TCGGCTACCA CGCCGAAGAT CCCAACATGT TCCCGCTGTA TCCCGAACTG      60

TCCCACATGG CCGTGCAGGA CTACCTGCGG AGCGACTACT CGCCGCAGCC GGCCGACGAG     120

GCGGCGGCGA TCAATGAATA CTGGAAGCCG CATAGCCTGC AGAGCAAGTG TCAGCCCTAT     180

TTCGATCCGG CAGACCTCGG CCGCATGTAT CAGGTCAGCA GCATGGAGGC GCCGTCCTTC     240

GCTTCCGGTT ACAACAGCAT CGTGCCGCCC TACGAAACCG TCCTGGAAGA CGGGCTGCTG     300

GCGCGCATCA AGCTCGCCGA AAAGCATATC GCCGAAGCCC AGGCCGACAT GTCGACCTTC     360

CCCTGGAACG GCACGAAGGG TCTCGACAAC ATCGCCAAGA TCGACAACTG GAAGGCGATG     420

GTCATCGCCT GCAAGGCGGT GATCAGCTGG GCGCGCCGGC AGGGCCGGCT GTGCAAGATC     480

GTCGCGGAAA ACTTCGAGAC CGATCCGAAG CGCCAGGCCG AGCTGCTCGA AATCGCCGAC     540

ATCTGTCAGC GCATTCCCGC CGAGCCCTGC AAGGGCCTCA AGGACGCGAT GCAGGCGAAA     600

TTCTTTACCT TCCTGATCTG TCACGCGATC GAGCGCTACG CGAGCGGCTA CGCCCAGAAG     660

GAAGACACCC TGCTGTGGCC GTACTACAAG GCCTCCGTCG TCGACAAGAA ATTCCAGCCG     720

ATGAGCCACA TGGATGCGGT GGAACTCGTC GAGATGGAAC GTTTGAAGAT TTCCGAGCAT     780

GGCGCCGGCA AGTCGCGCGC CTACCGCGAA ATCTTCCCGG GGTCGAACGA TCTGTTCATC     840

CTCACCGTCG GCGGCACCAA CGCCAAGGGC GAGGACGCCT GCAACGACAT GACCGACGCC     900

ATCCTCGAGG CAGCCAAGCG GATCCGCACG GCCGAGCCCT CCATCGTCTT CCGCTATTCC     960

AAGAAGAACC GCGAGAAGAC GCTGCGCTGG GTTTTCGAGT GCATCCGCGA CGGACTCGGC    1020

TATCCGTCGA TCAAGCACGA CGAGATCGGC ACGGAGCAGA TGAAGGAATA CGCCAAGTTC    1080

AGCCTCAACG GCAACGGCGC CACCGACGAG GAAGCCCACA ACTGGGTCAA CGTGCTGTGC    1140

ATGTCGCCCG GCATCCACGG TCGCCGCAAG ACGCAAAAAA CCCGTTCGGA AGGTGGCGGC    1200

TCAATCTTCC CGGCCAAGCT GCTGGAAATC TCGCTCAATG ACGGCTACGA CTGGTCGTAC    1260

GCCGACATGC AACTCGGCCC GAAGACCGGT GATCTCTCGT CGCTGAAGTC CTTCGAGGAT    1320

GTTTGGGAGG CTTTCCGCAA GCAGTATCAA TATGCGATCA ACCTCTGTAT CAGCACCAAG    1380

GACGTGTCGC GCTACTTCGA GCAGCGCTTC CTGCAGATGC CTTTCGTGTC CGCAATCGAC    1440

GACGGCTGCA TGGAACTCGG GATGGACGCC TGCGCCCTGT CCGAGCAGCC CAATGGCTGG    1500

CACAACCCGA TCACGACGAT CGTCGCGGCG AACTCCCTCG TGGCCATCAA GAAACTGGTA    1560

TTCGAGGAGA AGAAATACAC CCTCGAGCAA CTCAGCCAAG CGTTGAAGGC GAACTGGGAA    1620

GGTTTCGAGG AAATGCGCGT CGACTTCAAG CGGGCGCCGA AGTGGGCAA CGACGATGAT    1680

TACGCCGACG GTATCATCAC CCGCTTCTAC GAGGAAATCA TCGGCGGCGA AATGCGCAAG    1740

ATCACCAACT ACTCTGGTGG TCCGGTCATG CCGACTGGTC AGGCTGTCGG CCTGTACATG    1800

GAAGTCGGTT CGCGCACGGG CCCCACGCCG ACGGGCGCT TCGGGGGTGA AGCGGCAGAC    1860

GACGGCGGCA TTTCTCCCTA CATGGGAACC GACAAGAAGG GGCCGACGGC GGTGTTGCGC    1920

TCGGTGTCCA AGGTGCAGAA GAACCAGAAG GGCAACCTGC TGAACCAGCG CTTGTCGGTG    1980
```

```
CCGATCATGC GCTCCAAGCA TGGCTTCGAA ATCTGGAACT CGTACATGAA GACTTGGCAC      2040

GATCTGAATA TCGATCATGT TCAGTTCAAT GTCGTCAGCA CGGATGAAAT GCGCGCTGCG      2100

CAGCGCGAAC CCGAGAAGCA CCATGATCTT ATCGTGCGCG TTTCCGGCTA CAGCGCTCGG      2160

TTCGTAGACA TTCCGACCTA TGGGCAGAAC ACCATCATCG CCCGTCAGGA ACAGGATTTC      2220

AGCGCATCCG ATCTCGAGTT CCTAAACGTC GAAATCTAGG ACAAGCCACT CAAGGGGGGC      2280

AGCATCCCGT CCCCCTTTAC CTTACGGTTG CACGAAAAAA CATGGAGGGC AGCAACATGG      2340

AAACAGGACA GAATTTGCAA AACCAGCCGC ATACCGAGGT GGGTACGGCG AGGCCGTGCC      2400

GGAGTTGCAA ATGGCAAACC CCCGACCCCA CCGATCCGCA CCGTGGGCAA TGCACCGCCA      2460

ACCGGCACGC CATGGGTGGC GTCTGGAAAC GCTGGCTTAG GGACGTTGAA AACACGACCT      2520

GCTCCAGGCA CGAGGAAGGC AAACTAAGTT TCCGCGACCA CGTCTGAACA CCGGACAGAC      2580

GTGGTTCACC TCCAGACCAC TGTAGTGATA GATCATGAAA ACCTACTCCA GCGCAAATGG      2640

CCTGTTCGTC CCGGAAGTCG ATCCCTACTA CTATGTAAGT ACGGAAAACC AGAGCTTCCT      2700

CGATAAATTT GCAAGATAT CGAAAAAGCA TCCCGTCAAT GTACTGGTGG TCGGCAAACA       2760

AGGCTGCGGC AAGTCTTCCC TAGTGCGGCA ATACGCCGCC GTCAACAGGC TACCCTTGGC      2820

GACCTTCCAG ATCGGCATCC TGTCGGAGCC GGGGCAACTG TTTGGTGAAT ACGCGCTGGA      2880

GAACGGGGAG ACCCGTTACA AGCAGTTCCT CTTCCCCCAG GCCATCCAGA CACCCAATTG      2940

CGTCATCCAC CTTGAAGAGA TCAATCGCCC CGAGCATCCG AAGGCGTTGA ACATGTTGTT      3000

CTCCATTCTC TCCGATGACC GTCAGGTATG GATGGACGAG CTCGGACTGC TGCAAGTAGC      3060

GCCCGGAGTC GTTTTCTTCG CAACGCTCAA CGAAGGGTCC GAATTC                    3106
```

(2) INFORMATION FOR SEQ ID NO:14:

(i) SEQUENCE CHARACTERISTICS:
        (A) LENGTH: 557 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

```
ATACGGCGAC GCAGCGCATG CAATTGATGC ACTTGCTGCG GTCGAGCTTA AGCACCTGCT        60

TGCGCCCGGT CCATCAAGAA GCTGCGATGC ACCGGTTGGG CAGACCGTTG CACACCGTCC       120

GCAGCTCACG CAACGATCAC GGTTGTAATA GTATTCCTTG CCCACCTTTT GGGTTTCAGG       180

GTTGTGGCAC CACGGACATC TCAATGGGCA ACCCTTCAAG AACACCGTCG TCCGNAATCC       240

AGGACCGTCT TGCAGGCTAA AACGCTGTAT TTCGGTGACT AATGGAATTT TCACGTCAGC       300

CCCAGAATCG CATGTTGGAA ACGTCATCCG TCCGGTATCA ATCGGCTCGC TGTGCGAGCA       360

TTCATTTCGA ACGATTACGC CTCCGCCCAA ATCCGGCGGC GGAGGCCGAT CCACCACGAC       420

CATAGAAGTG AATCTTGTAA GGGTTCATTG AACTTCCGCC CTGCTGGCGG CGTCAATAAG       480

TGCGATCACC AGTCGGTGTG GTGATTTCCC TCATGTATTC GTTTGTCACC GCGGCTCAGC       540

TAAAATATGC AAATAAA                                                      557
```

(2) INFORMATION FOR SEQ ID NO:15:

(i) SEQUENCE CHARACTERISTICS:
        (A) LENGTH: 740 amino acids
        (B) TYPE: amino acid -continued

```
    (C) STRANDEDNESS: Not Relevant
    (D) TOPOLOGY: linear (ii) MOLECULE TYPE: protein (xi) SEQUENCE DESCRIPTION: SEQ ID NO:15:

Met Phe Pro Leu Tyr Pro Glu Leu Ser His Met Ala Val Gln Asp Tyr
1               5                   10                  15

Leu Arg Ser Asp Tyr Ser Pro Gln Pro Ala Asp Glu Ala Ala Ala Ile
                20                  25                  30

Asn Glu Tyr Trp Lys Pro His Ser Leu Gln Ser Lys Cys Gln Pro Tyr
            35                  40                  45

Phe Asp Pro Ala Asp Leu Gly Arg Met Tyr Gln Val Ser Ser Met Glu
    50                  55                  60

Ala Pro Ser Phe Ala Ser Gly Tyr Asn Ser Ile Val Pro Pro Tyr Glu
65                  70                  75                  80

Thr Val Leu Glu Asp Gly Leu Leu Ala Arg Ile Lys Leu Ala Glu Lys
                85                  90                  95

His Ile Ala Glu Ala Gln Ala Asp Met Ser Thr Phe Pro Trp Asn Gly
            100                 105                 110

Thr Lys Gly Leu Asp Asn Ile Ala Lys Ile Asp Asn Trp Lys Ala Met
        115                 120                 125

Val Ile Ala Cys Lys Ala Val Ile Ser Trp Ala Arg Arg Gln Gly Arg
130                 135                 140

Leu Cys Lys Ile Val Ala Glu Asn Phe Glu Thr Asp Pro Lys Arg Gln
145                 150                 155                 160

Ala Glu Leu Leu Glu Ile Ala Asp Ile Cys Gln Arg Ile Pro Ala Glu
                165                 170                 175

Pro Cys Lys Gly Leu Lys Asp Ala Met Gln Ala Lys Phe Phe Thr Phe
            180                 185                 190

Leu Ile Cys His Ala Ile Glu Arg Tyr Ala Ser Gly Tyr Ala Gln Lys
        195                 200                 205

Glu Asp Thr Leu Leu Trp Pro Tyr Tyr Lys Ala Ser Val Val Asp Lys
    210                 215                 220

Lys Phe Gln Pro Met Ser His Met Asp Ala Val Glu Leu Val Glu Met
225                 230                 235                 240

Glu Arg Leu Lys Ile Ser Glu His Gly Ala Gly Lys Ser Arg Ala Tyr
                245                 250                 255

Arg Glu Ile Phe Pro Gly Ser Asn Asp Leu Phe Ile Leu Thr Val Gly
            260                 265                 270

Gly Thr Asn Ala Lys Gly Glu Asp Ala Cys Asn Asp Met Thr Asp Ala
        275                 280                 285

Ile Leu Glu Ala Ala Lys Arg Ile Arg Thr Ala Glu Pro Ser Ile Val
290                 295                 300

Phe Arg Tyr Ser Lys Lys Asn Arg Glu Lys Thr Leu Arg Trp Val Phe
305                 310                 315                 320

Glu Cys Ile Arg Asp Gly Leu Gly Tyr Pro Ser Ile Lys His Asp Glu
                325                 330                 335

Ile Gly Thr Glu Gln Met Lys Gly Tyr Ala Lys Phe Ser Leu Asn Gly
            340                 345                 350

Asn Gly Ala Thr Asp Glu Glu Ala His Asn Trp Val Asn Val Leu Cys
        355                 360                 365

Met Ser Pro Gly Ile His Gly Arg Lys Thr Gln Lys Thr Arg Ser
370                 375                 380
```

-continued

```
Glu Gly Gly Gly Ser Ile Phe Pro Ala Lys Leu Leu Glu Ile Ser Leu
385                 390                 395                 400

Asn Asp Gly Tyr Asp Trp Ser Tyr Ala Asp Met Gln Leu Gly Pro Lys
            405                 410                 415

Thr Gly Asp Leu Ser Ser Leu Lys Ser Phe Glu Asp Val Trp Glu Ala
            420                 425                 430

Phe Arg Lys Gln Tyr Gln Tyr Ala Ile Asn Leu Cys Ile Ser Thr Lys
            435                 440                 445

Asp Val Ser Arg Tyr Phe Glu Gln Arg Phe Leu Gln Met Pro Phe Val
450                 455                 460

Ser Ala Ile Asp Asp Gly Cys Met Glu Leu Gly Met Asp Ala Cys Ala
465                 470                 475                 480

Leu Ser Glu Gln Pro Asn Gly Trp His Asn Pro Ile Thr Thr Ile Val
            485                 490                 495

Ala Ala Asn Ser Leu Val Ala Ile Lys Lys Leu Val Phe Glu Glu Lys
            500                 505                 510

Lys Tyr Thr Leu Glu Gln Leu Ser Gln Ala Leu Lys Ala Asn Trp Glu
            515                 520                 525

Gly Phe Glu Glu Met Arg Val Asp Phe Lys Arg Ala Pro Lys Trp Gly
            530                 535                 540

Asn Asp Asp Tyr Ala Asp Gly Ile Ile Thr Arg Phe Tyr Glu Glu
545                 550                 555                 560

Ile Ile Gly Gly Glu Met Arg Lys Ile Thr Asn Tyr Ser Gly Gly Pro
                565                 570                 575

Val Met Pro Thr Gly Gln Ala Val Gly Leu Tyr Met Glu Val Gly Ser
            580                 585                 590

Arg Thr Gly Pro Thr Pro Asp Gly Arg Phe Gly Gly Glu Ala Ala Asp
            595                 600                 605

Asp Gly Gly Ile Ser Pro Tyr Met Gly Thr Asp Lys Lys Gly Pro Thr
            610                 615                 620

Ala Val Leu Arg Ser Val Ser Lys Val Gln Lys Asn Gln Lys Gly Asn
625                 630                 635                 640

Leu Leu Asn Gln Arg Leu Ser Val Pro Ile Met Arg Ser Lys His Gly
                645                 650                 655

Phe Glu Ile Trp Asn Ser Tyr Met Lys Thr Trp His Asp Leu Asn Ile
                660                 665                 670

Asp His Val Gln Phe Asn Val Val Ser Thr Asp Glu Met Arg Ala Ala
            675                 680                 685

Gln Arg Glu Pro Glu Lys His His Asp Leu Ile Val Arg Val Ser Gly
690                 695                 700

Tyr Ser Ala Arg Phe Val Asp Ile Pro Thr Tyr Gly Gln Asn Thr Ile
705                 710                 715                 720

Ile Ala Arg Gln Glu Gln Asp Phe Ser Ala Ser Asp Leu Glu Phe Leu
                725                 730                 735

Asn Val Glu Ile
            740

(2) INFORMATION FOR SEQ ID NO:16:

(i) SEQUENCE CHARACTERISTICS:
        (A) LENGTH: 864 amino acids
        (B) TYPE: amino acid
        (C) STRANDEDNESS: Not Relevant
        (D) TOPOLOGY: linear (ii) MOLECULE TYPE: protein
```

(xi) SEQUENCE DESCRIPTION: SEQ ID NO:16:

```
Met Asn Asp Ile Val Ser Ala Lys Val Leu Glu Tyr Lys Gly Lys Lys
1               5                   10                  15

Leu Asn Phe Thr Pro Glu Asp Pro Ala Glu Glu Thr Ile Pro Ala Asp
                20                  25                  30

Glu Leu His Glu His Leu Gln Lys Pro Ser Thr Ala Arg Thr Lys Arg
            35                  40                  45

Leu Lys Glu Arg Cys Arg Trp Lys His Ala Ser Ala Gly Glu Phe Ile
50                      55                  60

Glu Lys Ser Val Thr Ala Gly Ile Glu Arg Met Arg Tyr Leu Thr Glu
65                  70                  75                  80

Ala His Lys Ala Ser Glu Gly Lys Pro Glu Ala Ile Arg Arg Ala Leu
                85                  90                  95

Gly Leu Ala Asn Val Leu Asn Lys Ser Thr Leu Val Leu Gln Glu Asp
            100                 105                 110

Glu Phe Ile Val Gly Tyr His Ala Glu Asp Pro Asn Met Phe Pro Leu
        115                 120                 125

Tyr Pro Glu Leu Ser His Met Ala Val Gln Asp Tyr Leu Arg Ser Asp
130                 135                 140

Tyr Ser Pro Gln Pro Ala Asp Glu Ala Ala Ile Asn Glu Tyr Trp
145                 150                 155                 160

Lys Pro His Ser Leu Gln Ser Lys Cys Gln Pro Tyr Phe Asp Pro Ala
                165                 170                 175

Asp Leu Gly Arg Met Tyr Gln Val Ser Ser Met Glu Ala Pro Ser Phe
            180                 185                 190

Ala Ser Gly Tyr Asn Ser Ile Val Pro Pro Tyr Glu Thr Val Leu Glu
        195                 200                 205

Asp Gly Leu Leu Ala Arg Ile Lys Leu Ala Glu Lys His Ile Ala Glu
        210                 215                 220

Ala Gln Ala Asp Met Ser Thr Phe Pro Trp Asn Gly Thr Lys Gly Leu
225                 230                 235                 240

Asp Asn Ile Ala Lys Ile Asp Asn Trp Lys Ala Met Val Ile Ala Cys
                245                 250                 255

Lys Ala Val Ile Ser Trp Ala Arg Arg Gln Gly Arg Leu Cys Lys Ile
            260                 265                 270

Val Ala Glu Asn Phe Glu Thr Asp Pro Lys Arg Gln Ala Glu Leu Leu
        275                 280                 285

Glu Ile Ala Asp Ile Cys Gln Arg Ile Pro Ala Glu Pro Cys Lys Gly
290                 295                 300

Leu Lys Asp Ala Met Gln Ala Lys Phe Phe Thr Phe Leu Ile Cys His
305                 310                 315                 320

Ala Ile Glu Arg Tyr Ala Ser Gly Tyr Ala Gln Lys Glu Asp Thr Leu
                325                 330                 335

Leu Trp Pro Tyr Tyr Lys Ala Ser Val Val Asp Lys Lys Phe Gln Pro
            340                 345                 350

Met Ser His Met Asp Ala Val Glu Leu Val Glu Met Glu Arg Leu Lys
        355                 360                 365

Ile Ser Glu His Gly Ala Gly Lys Ser Arg Ala Tyr Arg Glu Ile Phe
        370                 375                 380

Pro Gly Ser Asn Asp Leu Phe Ile Leu Thr Val Gly Thr Asn Ala
385                 390                 395                 400

Lys Gly Glu Asp Ala Cys Asn Asp Met Thr Asp Ala Ile Leu Glu Ala
```

-continued

```
                    405                 410                 415
Ala Lys Arg Ile Arg Thr Ala Glu Pro Ser Ile Val Phe Arg Tyr Ser
                420                 425                 430
Lys Lys Asn Arg Glu Lys Thr Leu Arg Trp Val Phe Glu Cys Ile Arg
                435                 440                 445
Asp Gly Leu Gly Tyr Pro Ser Ile Lys His Asp Glu Ile Gly Thr Glu
            450                 455                 460
Gln Met Lys Glu Tyr Ala Lys Phe Ser Leu Asn Gly Asn Gly Ala Thr
465                 470                 475                 480
Asp Glu Glu Ala His Asn Trp Val Asn Val Leu Cys Met Ser Pro Gly
                485                 490                 495
Ile His Gly Arg Arg Lys Thr Gln Lys Thr Arg Ser Glu Gly Gly Gly
                500                 505                 510
Ser Ile Phe Pro Ala Lys Leu Leu Glu Ile Ser Leu Asn Asp Gly Tyr
            515                 520                 525
Asp Trp Ser Tyr Ala Asp Met Gln Leu Gly Pro Lys Thr Gly Asp Leu
            530                 535                 540
Ser Ser Leu Lys Ser Phe Glu Asp Val Trp Ala Phe Arg Lys Gln
545                 550                 555                 560
Tyr Gln Tyr Ala Ile Asn Leu Cys Ile Ser Thr Lys Asp Val Ser Arg
                565                 570                 575
Tyr Phe Glu Gln Arg Phe Leu Gln Met Pro Phe Val Ser Ala Ile Asp
            580                 585                 590
Asp Gly Cys Met Glu Leu Gly Met Asp Ala Cys Ala Leu Ser Glu Gln
            595                 600                 605
Pro Asn Gly Trp His Asn Pro Ile Thr Thr Ile Val Ala Ala Asn Ser
            610                 615                 620
Leu Val Ala Ile Lys Lys Leu Val Phe Glu Glu Lys Lys Tyr Thr Leu
625                 630                 635                 640
Glu Gln Leu Ser Gln Ala Leu Lys Ala Asn Trp Glu Gly Phe Glu Glu
                645                 650                 655
Met Arg Val Asp Phe Lys Arg Ala Pro Lys Trp Gly Asn Asp Asp
                660                 665                 670
Tyr Ala Asp Gly Ile Ile Thr Arg Phe Tyr Glu Glu Ile Ile Gly Gly
            675                 680                 685
Glu Met Arg Lys Ile Thr Asn Tyr Ser Gly Gly Pro Val Met Pro Thr
690                 695                 700
Gly Gln Ala Val Gly Leu Tyr Met Glu Val Gly Ser Arg Thr Gly Pro
705                 710                 715                 720
Thr Pro Asp Gly Arg Phe Gly Gly Glu Ala Ala Asp Asp Gly Gly Ile
                725                 730                 735
Ser Pro Tyr Met Gly Thr Asp Lys Lys Gly Pro Thr Ala Val Leu Arg
            740                 745                 750
Ser Val Ser Lys Val Gln Lys Asn Gln Lys Gly Asn Leu Leu Asn Gln
            755                 760                 765
Arg Leu Ser Val Pro Ile Met Arg Ser Lys His Gly Phe Glu Ile Trp
            770                 775                 780
Asn Ser Tyr Met Lys Thr Trp His Asp Leu Asn Ile Asp His Val Gln
785                 790                 795                 800
Phe Asn Val Val Ser Thr Asp Glu Met Arg Ala Ala Gln Arg Glu Pro
                805                 810                 815
Glu Lys His His Asp Leu Ile Val Arg Val Ser Gly Tyr Ser Ala Arg
            820                 825                 830
```

```
Phe Val Asp Ile Pro Thr Tyr Gly Gln Asn Thr Ile Ile Ala Arg Gln
                835                 840                 845

Glu Gln Asp Phe Ser Ala Ser Asp Leu Glu Phe Leu Asn Val Glu Ile
    850                 855                 860
```

(2) INFORMATION FOR SEQ ID NO:17:

(i) SEQUENCE CHARACTERISTICS:
        (A) LENGTH: 4928 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

```
TTTATTTGCA TATTTTAGCT GAGCCGCGGT GACAAACGAA TACATGAGGG AAATCACCAC      60

ACCGACTGGT GATCGCACTT ATTGACGCCG CCAGCAGGGC GGAAGTTCAA TGAACCCTTA     120

CAAGATTCAC TTCTATGGTC GTGGTGGATC GGCCTCCGCC GCCGGATTTG GCGGAGGCG      180

TAATCGTTCG AAATGAATGC TCGCACAGCG AGCCGATTGA TACCGGACGG ATGACGTTTC     240

CAACATGCGA TTCTGGGGCT GACGTGAAAA TTCCATTAGT CACCGAAATA CAGCGTTTTA     300

GCCTGCAAGA CGGTCCTGGA TTCCGGACGA CGGTGTTCTT GAAGGGTTGC CCATTGAGAT     360

GTCCGTGGTG CCACAACCCT GAAACCCAAA AGGTGGGCAA GGAATACTAT TACAACCGTG     420

ATCGTTGCGT GAGCTGCGGA CGGTGTGCAA CGGTCTGCCC AACCGGTGCA TCGCAGCTTC     480

TTGATGGACC GGGCGCAAGC CAGGTGCTTA AGCTCGACCG CAGCAAGTGC ATCAATTGCA     540

TGCGCTGCGT CGCCGTATGC CTCACCGGTA GCCGCGACTC TGTCGGGATG GAAATGACAC     600

TCGACGAGAT TTTGCGCGAG GTCTTGTCCG ATGAGCCTTT CTACCGCAAT AGCGGGGCG      660

GAGTGACGAT CAGCGGAGGC GATCCTCTCT TCCACCCTGC ATTCACATTG AACTAGCGC      720

GCAAGATCAA GGAACGCGGC GTCCATGTCG CGATCGAGAC TTCCTGCTTC CCAAAAAAAT     780

GGGCGACTAT CCAGCCGCTA CTTAAACTCG TCGATCTTTT CATCGTCGAC CTGAAATCGC     840

TGAATCGGAA AAAGCATGAG GAAACTGTTG GCTGGCCACT GCAACCCATA CTCGACAATA     900

TCGAGCATCT CATACAAGCC AAGGCCAATA TCCGCATACA CATTCCTGTA ATCCCTGGAT     960

TCAACGACTC ACCAATGGAT TTCGAGGATT ACATCGCTTA CTTGGGTCGC CATGCCGCGC    1020

AGCTGGATGG CGTAGACATT CTAAATTATC ACGTCTATGG AGAAGGCAAG TACCGCTCCT    1080

TGGGCCGGGA AAATGAATAC CAGTATTTTG GCGTGGAAGA GAACCCACCC GAAAAGGTAG    1140

TGCCACTCGC GAAAGGTTTG AAACTCGCCG GCATCACGAG CGTAACGATC GGCGGGTTGG    1200

TCGGATCAC AGCGGACAGA CACAAGAGTA GTCGCGACGC TGGGACTGGG TGTATTGCAT    1260

AAATCAAAGG AGACTCATCC ATGGGAACCA CCACATGCAA GCAGTGCGCA AACTTCTTTC    1320

CCGTCCCTAA AGACGCGGAT GACTACGAAG CCGGTAAGGC AGACTGCGTG CGGGAAAAGG    1380

AAGACGAAAA GGGTAAATAC TGGCTCTCCA AGCCCATATT CGAGAACAGC GCGCAATGTG    1440

AAGCCTTTCA AACGAAGCGC TAAAACTACA GATCAAGGAG ACCGCCATGA ACGACATCGT    1500

AAGCGCCAAG GTTCTGGAAT ATAAAGGAAA GAAGCTCAAT TTCACGCCGG AAGATCCGGC    1560

TGAAGAGACA ATTCCGGCCG ACGAGTTGCA CGAGCATCTG CAAAAGCCTT CGACGGCGAG    1620

GACCAAGCGC CTGAAGGAGC GTTGCCGCTG GAAACACGCA TCTGCCGGCG AATTCATTGA    1680

AAAGAGCGTC ACGGCCGGCA TCGAGCGCAT GCGCTATCTG ACCGAAGCAC ACAAGGCCAG    1740
```

```
CGAAGGCAAA CCCGAAGCCA TCCGTCGCGC GCTGGGCCTG GCGAACGTCC TGAACAAGTC      1800

GACCCTGGTG CTCCAGGAGG ACGAATTCAT CGTCGGCTAC CACGCCGAAG ATCCCAACAT      1860

GTTCCCGCTG TATCCCGAAC TGTCCCACAT GGCCGTGCAG GACTACCTGC GGAGCGACTA      1920

CTCGCCGCAG CCGGCCGACG AGGCGGCGGC GATCAATGAA TACTGGAAGC CGCATAGCCT      1980

GCAGAGCAAG TGTCAGCCCT ATTTCGATCC GGCAGACCTC GGCCGCATGT ATCAGGTCAG      2040

CAGCATGGAG GCGCCGTCCT TCGCTTCCGG TTACAACAGC ATCGTGCCGC CTACGAAAC       2100

CGTCCTGGAA GACGGGCTGC TGGCGCGCAT CAAGCTCGCC GAAAAGCATA TCGCCGAAGC      2160

CCAGGCCGAC ATGTCGACCT TCCCCTGGAA CGGCACGAAG GGTCTCGACA ACATCGCCAA      2220

GATCGACAAC TGGAAGGCGA TGGTCATCGC CTGCAAGGCG GTGATCAGCT GGGCGCGCCG      2280

GCAGGGCCGG CTGTGCAAGA TCGTCGCGGA AAACTTCGAG ACCGATCCGA AGCGCCAGGC      2340

CGAGCTGCTC GAAATCGCCG ACATCTGTCA GCGCATTCCC GCCGAGCCCT GCAAGGGCCT      2400

CAAGGACGCG ATGCAGGCGA AATTCTTTAC CTTCCTGATC TGTCACGCGA TCGAGCGCTA      2460

CGCGAGCGGC TACGCCCAGA AGGAAGACAC CCTGCTGTGG CCGTACTACA AGGCCTCCGT      2520

CGTCGACAAG AAATTCCAGC CGATGAGCCA CATGGATGCG GTGGAACTCG TCGAGATGGA      2580

ACGTTTGAAG ATTTCCGAGC ATGGCGCCGG CAAGTCGCGC GCCTACCGCG AAATCTTCCC      2640

GGGGTCGAAC GATCTGTTCA TCCTCACCGT CGGCGGCACC AACGCCAAGG GCGAGGACGC      2700

CTGCAACGAC ATGACCGACG CCATCCTCGA GGCAGCCAAG CGGATCCGCA CGGCCGAGCC      2760

CTCCATCGTC TTCCGCTATT CCAAGAAGAA CCGCGAGAAG ACGCTGCGCT GGGTTTTCGA      2820

GTGCATCCGC GACGGACTCG GCTATCCGTC GATCAAGCAC GACGAGATCG GCACGGAGCA      2880

GATGAAGGAA TACGCCAAGT TCAGCCTCAA CGGCAACGGC GCCACCGACG AGGAAGCCCA      2940

CAACTGGGTC AACGTGCTGT GCATGTCGCC CGGCATCCAC GGTCGCCGCA AGACGCAAAA      3000

AACCCGTTCG GAAGGTGGCG GCTCAATCTT CCCGGCCAAG CTGCTGGAAA TCTCGCTCAA      3060

TGACGGCTAC GACTGGTCGT ACGCCGACAT GCAACTCGGC CCGAAGACCG GTGATCTCTC      3120

GTCGCTGAAG TCCTTCGAGG ATGTTTGGGA GGCTTTCCGC AAGCAGTATC AATATGCGAT      3180

CAACCTCTGT ATCAGCACCA AGGACGTGTC GCGCTACTTC GAGCAGCGCT CCTGCAGAT       3240

GCCTTTCGTG TCCGCAATCG ACGACGGCTG CATGGAACTC GGGATGGACG CCTGCGCCCT      3300

GTCCGAGCAG CCCAATGGCT GGCACAACCC GATCACGACG ATCGTCGCGG CGAACTCCCT      3360

CGTGGCCATC AAGAAACTGG TATTCGAGGA GAAGAAATAC ACCCTCGAGC AACTCAGCCA      3420

AGCGTTGAAG GCGAACTGGG AAGGTTTCGA GGAAATGCGC GTCGACTTCA GCGGGCGCC       3480

GAAGTGGGGC AACGACGATG ATTACGCCGA CGGTATCATC ACCCGCTTCT ACGAGGAAAT      3540

CATCGGCGGC GAAATGCGCA AGATCACCAA CTACTCTGGT GGTCCGGTCA TGCCGACTGG      3600

TCAGGCTGTC GGCCTGTACA TGGAAGTCGG TTCGCGCACG GCCCCACGC GGACGGGCG       3660

CTTCGGGGGT GAAGCGGCAG ACGACGGCGG CATTTCTCCC TACATGGGAA CCGACAAGAA      3720

GGGGCCGACG GCGGTGTTGC GCTCGGTGTC CAAGGTGCAG AAGAACCAGA AGGGCAACCT      3780

GCTGAACCAG CGCTTGTCGG TGCCGATCAT GCGCTCCAAG CATGGCTTCG AAATCTGGAA      3840

CTCGTACATG AAGACTTGGC ACGATCTGAA TATCGATCAT GTTCAGTTCA ATGTCGTCAG      3900

CACGGATGAA ATGCGCGCTG CGCAGCGCGA ACCCGAGAAG CACCATGATC TTATCGTGCG      3960

CGTTTCCGGC TACAGCGCTC GGTTCGTAGA CATTCCGACC TATGGGCAGA ACACCATCAT      4020

CGCCCGTCAG GAACAGGATT TCAGCGCATC CGATCTCGAG TTCCTAAACG TCGAAATCTA      4080

GGACAAGCCA CTCAAGGGGG GCAGCATCCC GTCCCCCTTT ACCTTACGGT TGCACGAAAA      4140
```

```
AACATGGAGG GCAGCAACAT GGAAACAGGA CAGAATTTGC AAAACCAGCC GCATACCGAG    4200

GTGGGTACGG CGAGGCCGTG CCGGAGTTGC AAATGGCAAA CCCCCGACCC CACCGATCCG    4260

CACCGTGGGC AATGCACCGC CAACCGGCAC GCCATGGGTG GCGTCTGGAA ACGCTGGCTT    4320

AGGGACGTTG AAAACACGAC CTGCTCCAGG CACGAGGAAG GCAAACTAAG TTTCCGCGAC    4380

CACGTCTGAA CACCGGACAG ACGTGGTTCA CCTCCAGACC ACTGTAGTGA TAGATCATGA    4440

AAACCTACTC CAGCGCAAAT GGCCTGTTCG TCCCGGAAGT CGATCCCTAC TACTATGTAA    4500

GTACGGAAAA CCAGAGCTTC CTCGATAAAT TTGCAAAGAT ATCGAAAAAG CATCCCGTCA    4560

ATGTACTGGT GGTCGGCAAA CAAGGCTGCG GCAAGTCTTC CCTAGTGCGG CAATACGCCG    4620

CCGTCAACAG GCTACCCTTG GCGACCTTCC AGATCGGCAT CCTGTCGGAG CCGGGGCAAC    4680

TGTTTGGTGA ATACGCGCTG GAGAACGGGG AGACCCGTTA CAAGCAGTTC CTCTTCCCCC    4740

AGGCCATCCA GACACCCAAT TGCGTCATCC ACCTTGAAGA GATCAATCGC CCCGAGCATC    4800

CGAAGGCGTT GAACATGTTG TTCTCCATTC TCTCCGATGA CCGTCAGGTA TGGATGGACG    4860

AGCTCGGACT GCTGCAAGTA GCGCCCGGAG TCGTTTTCTT CGCAACGCTC AACGAAGGGT    4920

CCGAATTC                                                            4928
```

(2) INFORMATION FOR SEQ ID NO:18:

(i) SEQUENCE CHARACTERISTICS:
        (A) LENGTH: 375 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

```
Met Val Val Asp Arg Pro Pro Pro Asp Leu Gly Gly Gly Val
1               5                  10                  15

Ile Val Arg Asn Glu Cys Ser His Ser Glu Pro Ile Asp Thr Gly Arg
            20                  25                  30

Met Thr Phe Pro Thr Cys Asp Ser Gly Ala Asp Val Lys Ile Pro Leu
        35                  40                  45

Val Thr Glu Ile Gln Arg Phe Ser Leu Gln Asp Gly Pro Gly Phe Arg
    50                  55                  60

Thr Thr Val Phe Leu Lys Gly Cys Pro Leu Arg Cys Pro Trp Cys His
65                  70                  75                  80

Asn Pro Glu Thr Gln Lys Val Gly Lys Glu Tyr Tyr Asn Arg Asp
                85                  90                  95

Arg Cys Val Ser Cys Gly Arg Cys Ala Thr Val Cys Pro Thr Gly Ala
            100                 105                 110

Ser Gln Leu Leu Asp Gly Pro Gly Ala Ser Gln Val Leu Lys Leu Asp
        115                 120                 125

Arg Ser Lys Cys Ile Asn Cys Met Arg Cys Val Ala Val Cys Leu Thr
    130                 135                 140

Gly Ser Arg Asp Ser Val Gly Met Glu Met Thr Leu Asp Glu Ile Leu
145                 150                 155                 160

Arg Glu Val Leu Ser Asp Glu Pro Phe Tyr Arg Asn Ser Gly Gly Gly
                165                 170                 175

Val Thr Ile Ser Gly Gly Asp Pro Leu Phe His Pro Ala Phe Thr Leu
            180                 185                 190

Glu Leu Ala Arg Lys Ile Lys Glu Arg Gly Val His Val Ala Ile Glu
```

-continued

```
                195                 200                 205
Thr Ser Cys Phe Pro Lys Lys Trp Ala Thr Ile Gln Pro Leu Leu Lys
    210                 215                 220

Leu Val Asp Leu Phe Ile Val Asp Leu Lys Ser Leu Asn Arg Lys Lys
225                 230                 235                 240

His Glu Glu Thr Val Gly Trp Pro Leu Gln Pro Ile Leu Asp Asn Ile
                245                 250                 255

Glu His Leu Ile Gln Ala Lys Ala Asn Ile Arg Ile His Ile Pro Val
            260                 265                 270

Ile Pro Gly Phe Asn Asp Ser Pro Met Asp Phe Glu Asp Tyr Ile Ala
        275                 280                 285

Tyr Leu Gly Arg His Ala Ala Gln Leu Asp Gly Val Asp Ile Leu Asn
    290                 295                 300

Tyr His Val Tyr Gly Glu Gly Lys Tyr Arg Ser Leu Gly Arg Glu Asn
305                 310                 315                 320

Glu Tyr Gln Tyr Phe Gly Val Glu Glu Asn Pro Pro Glu Lys Val Val
                325                 330                 335

Pro Leu Ala Lys Gly Leu Lys Leu Ala Gly Ile Thr Ser Val Thr Ile
            340                 345                 350

Gly Gly Leu Val Gly Ile Thr Ala Asp Arg His Lys Ser Ser Arg Asp
        355                 360                 365

Ala Gly Thr Gly Cys Ile Ala
    370                 375

(2) INFORMATION FOR SEQ ID NO:19:

(i) SEQUENCE CHARACTERISTICS:
        (A) LENGTH: 227 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

Met Thr Gly Arg Phe Asp Trp Arg Gly Gln Gly Gly His Thr Glu Ala
1               5                   10                  15

Ser Thr Lys Ala Ile Val Phe Val Val Glu Asp Asp Ile Ser Met Arg
                20                  25                  30

Arg Ser Leu Thr Asn Leu Phe Arg Ser Val Gly Leu Glu Val Val Ala
            35                  40                  45

Phe Gly Ser Ala Arg Glu Met Leu Gln Ser Thr Met Pro Asp Val Thr
        50                  55                  60

Ser Cys Leu Val Leu Asp Val Arg Leu Pro Gly Leu Ser Gly Leu Asp
65                  70                  75                  80

Tyr Gln Thr Glu Leu Ala Arg Leu Asn Ile His Ile Pro Ile Ile Phe
                85                  90                  95

Ile Thr Gly His Gly Asp Ile Pro Met Thr Val Arg Ala Met Lys Gly
            100                 105                 110

Gly Ala Val Asp Phe Leu Ser Lys Pro Phe Arg Asp Gln Glu Leu Leu
        115                 120                 125

Asp Ala Val Val Ala Ala Thr Glu Arg Asp Arg Lys Arg Arg Glu Ala
    130                 135                 140

Gln Arg Thr Val Ala Asn Leu Lys Ser Leu Phe Glu Thr Leu Ser Pro
145                 150                 155                 160

Arg Glu Gln Ala Val Met Lys Leu Val Ala Thr Gly Leu Met Asn Lys
```

165                 170                 175
Gln Val Ala Ala Glu Leu Gly Leu Ala Glu Ile Thr Val Lys Ile Tyr
                180                 185                 190

Arg Gly His Val Met Lys Lys Met Arg Ala Arg Ser Leu Ala Asp Leu
            195                 200                 205

Ile Arg Met Ser Glu Thr Leu Gly Ile Ser Ala Asn His Thr Glu Gln
        210                 215                 220

Thr Gln Val
225

(2) INFORMATION FOR SEQ ID NO:20:

(i) SEQUENCE CHARACTERISTICS:
        (A) LENGTH: 205 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

Met Thr Thr Lys Gly His Ile Tyr Val Ile Asp Asp Ala Ala Met
1               5                   10                  15

Arg Asp Ser Leu Asn Phe Leu Asp Ser Ala Gly Phe Gly Val Thr
                20                  25                  30

Leu Phe Asp Asp Ala Gln Ala Phe Leu Asp Ala Leu Pro Gly Leu Ser
            35                  40                  45

Phe Gly Cys Val Val Ser Asp Val Arg Met Pro Gly Leu Asp Gly Ile
        50                  55                  60

Glu Leu Leu Lys Arg Met Lys Ala Gln Gln Ser Pro Phe Pro Ile Leu
65                  70                  75                  80

Ile Met Thr Gly His Gly Asp Val Pro Leu Ala Val Glu Ala Met Lys
                85                  90                  95

Leu Gly Ala Val Asp Phe Leu Glu Lys Pro Phe Glu Asp Asp Arg Leu
            100                 105                 110

Thr Ala Met Ile Glu Ser Ala Ile Arg Gln Ala Glu Pro Ala Ala Lys
        115                 120                 125

Ser Glu Ala Val Ala Gln Asp Ile Ala Ala Arg Val Ala Ser Leu Ser
    130                 135                 140

Pro Arg Glu Arg Gln Val Met Glu Gly Leu Ile Ala Gly Leu Ser Asn
145                 150                 155                 160

Lys Leu Ile Ala Arg Glu Tyr Asp Ile Ser Pro Arg Thr Ile Glu Val
                165                 170                 175

Tyr Arg Ala Asn Val Met Thr Lys Met Gln Ala Asn Ser Leu Ser Glu
            180                 185                 190

Leu Val Arg Leu Ala Met Arg Ala Gly Met Leu Asn Asp
        195                 200                 205

(2) INFORMATION FOR SEQ ID NO:21:

(i) SEQUENCE CHARACTERISTICS:
        (A) LENGTH: 211 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

```
Met Pro Glu Ser Leu Pro Val His Val Ile Asp Asp Asp Ala Val
 1               5                  10                  15

Arg Glu Ser Leu Ala Phe Leu Leu Glu Ser Ser Gly Leu Ala Val Thr
                20                  25                  30

Gln His Thr Ser Ala Ala Ala Phe Leu Asp Ala Gly Val Pro Leu Asp
                35                  40                  45

Arg Gly Cys Ile Val Thr Asp Val Arg Met Pro Gly Ile Ser Gly Leu
        50                  55                  60

Glu Leu Leu Lys Glu Leu Asn Ala Arg Gly Ala His Met Ala Val Ile
 65                  70                  75                  80

Val Met Thr Gly His Gly Asp Val Pro Leu Ala Val Glu Ala Met Lys
                 85                  90                  95

Leu Gly Ala Ala Asp Phe Leu Glu Lys Pro Phe Asp Asp Ala Ala Ile
                100                 105                 110

Ile Ala Ala Val Arg Ala Ser Leu Gly Arg Ser Ala Glu Gln Gly Arg
                115                 120                 125

Gln Glu Asp Ala Arg Ser Glu Val Gly Lys Arg Ile Ala Gly Leu Ser
        130                 135                 140

Gln Arg Glu Arg Gln Val Leu Glu Cys Leu Val Asn Gly Leu Ala Asn
145                 150                 155                 160

Lys Thr Ile Ala Tyr Asp Leu Gly Ile Ser Pro Arg Thr Val Glu Val
                165                 170                 175

Tyr Arg Ala Asn Val Met Thr Lys Met Lys Ala Ala Ser Leu Pro Glu
                180                 185                 190

Leu Val Arg Met Ala Leu Leu Ala Gly Val Ala Pro Ala Asp Asp Ala
        195                 200                 205

Thr Pro Thr
    210

(2) INFORMATION FOR SEQ ID NO:22:

(i) SEQUENCE CHARACTERISTICS:
        (A) LENGTH: 204 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

Met Thr Asp Tyr Thr Val His Ile Val Asp Asp Glu Glu Pro Val Arg
 1               5                  10                  15

Lys Ser Leu Ala Phe Met Leu Thr Met Asn Gly Phe Ala Val Lys Met
                20                  25                  30

His Gln Ser Ala Glu Ala Phe Leu Ala Phe Ala Pro Asp Val Arg Asn
                35                  40                  45

Gly Val Leu Val Thr Asp Leu Arg Met Pro Asp Met Ser Gly Val Glu
        50                  55                  60

Leu Leu Arg Asn Leu Gly Asp Leu Lys Ile Asn Ile Pro Ser Ile Val
 65                  70                  75                  80

Ile Thr Gly His Gly Asp Val Pro Met Ala Val Glu Ala Met Lys Ala
                 85                  90                  95

Gly Ala Val Asp Phe Ile Glu Lys Pro Phe Glu Asp Thr Val Ile Ile
                100                 105                 110

Glu Ala Ile Glu Arg Ala Ser Glu His Leu Val Ala Ala Glu Ala Asp
                115                 120                 125
```

```
Val Asp Asp Ala Asn Asp Ile Arg Ala Arg Leu Gln Thr Leu Ser Glu
    130                 135                 140

Arg Glu Arg Gln Val Leu Ser Ala Val Val Ala Gly Leu Pro Asn Lys
145                 150                 155                 160

Ser Ile Ala Tyr Asp Leu Asp Ile Ser Pro Arg Thr Val Glu Val His
                165                 170                 175

Arg Ala Asn Val Met Ala Lys Met Lys Ala Lys Ser Leu Pro His Leu
                180                 185                 190

Val Arg Met Ala Leu Ala Gly Gly Phe Gly Pro Ser
            195                 200
```

(2) INFORMATION FOR SEQ ID NO:23:

(i) SEQUENCE CHARACTERISTICS:
        (A) LENGTH: 197 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:23:

```
Met Ser Phe Thr Val His Ile Val Asp Asp Glu Glu Ser Leu Arg Asp
1               5                   10                  15

Ser Leu Gly Phe Leu Phe Ala Ser Arg Gly Ile Ala Thr Arg Thr Trp
                20                  25                  30

Ala Ala Gly Ala Asp Leu Leu Ala Glu Trp Pro Leu Ala Asp Cys Gly
            35                  40                  45

Cys Leu Ile Leu Asp Val Arg Met Glu Gly Met Ser Gly Pro Gln Leu
50                  55                  60

Leu Asp Ala Leu Gln Ala Arg Pro Glu Gly Leu Val Pro Pro Val Ile
65                  70                  75                  80

Phe Leu Thr Gly His Ala Asp Val Pro Leu Ala Val Gln Ser Leu Lys
                85                  90                  95

Ala Gly Ala Phe Asp Phe Val Gly Lys Pro Phe Asn Asp Asn His Ile
            100                 105                 110

Val Asp Ile Ala Leu Ser Ala Ile Ala Ala His Glu Gly Arg Leu Ala
            115                 120                 125

Glu Ala Gln Ala Arg Glu Ala Val Ala Arg Arg Ala Ser Leu Ser
        130                 135                 140

Ala Arg Glu Ala Glu Val Met Ala Leu Met Leu Glu Gly Leu Met Asn
145                 150                 155                 160

Lys Gln Ile Ala Glu Arg Leu Gly Ile Ala Met Arg Thr Val Glu Val
                165                 170                 175

His Arg Ser Arg Val Leu Ala Lys Met Gly Ala Arg Asn Ile Ala Asp
                180                 185                 190

Leu Ala Arg Met Thr
            195
```

(2) INFORMATION FOR SEQ ID NO:24:

(i) SEQUENCE CHARACTERISTICS:
        (A) LENGTH: 376 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:24:

```
Arg Glu Arg Leu Glu Asn Thr Leu Val Ala Leu Arg Glu Ser Glu Gln
  1               5                  10                  15

Arg Phe Arg Asp Tyr Ala Glu Thr Ala Ser Asp Trp Leu Trp Glu Thr
             20                  25                  30

Gly Pro Asp His Arg Val Thr His Leu Ser Glu His Thr Ser Ala Ala
             35                  40                  45

Gly Ile Leu Ala Thr Gly Leu Thr Gly Leu Leu Arg Trp Asp Ile Ala
         50                  55                  60

Cys Asp Met Glu Glu Pro Glu Lys Trp Arg Gln His Arg Ala Thr
 65              70                  75                  80

Leu Gln Ala His Leu Pro Phe Arg Asp Leu Ile Tyr Arg Thr Val Asn
                 85                  90                  95

Arg Met Gly Ser Pro Ile Tyr Val Arg Thr Ser Gly Lys Pro Phe Phe
                100                 105                 110

Asp Gly Asn Gly Asn Phe Leu Gly Tyr Arg Gly Val Ser Thr Asp Ile
                115                 120                 125

Thr Ala Thr Ile Arg Ala Asp Gln Ala Glu Gln Glu Leu Arg Lys Ala
            130                 135                 140

Gln Ala Glu Leu Ala His Val Thr Arg Val Thr Thr Leu Gly Glu Met
145                 150                 155                 160

Thr Thr Ser Ile Ala His Glu Ile Thr Gln Pro Leu Ala Ala Ile Leu
                165                 170                 175

Ser Asn Ala Asp Ala Cys Leu Gly Trp Met Ala Arg Asp Val Pro Asn
            180                 185                 190

Leu Ala Ala Ala Arg Ser Ser Val Glu Trp Ile Ile Glu Asp Ala Ile
            195                 200                 205

Arg Ala Ser Glu Val Ile Arg Ser Ile Arg Ala Leu Ala Lys Lys Gly
210                 215                 220

Glu Ile Glu Met Val Pro Leu Asp Ile Asn Gln Val Val Arg Asp Val
225                 230                 235                 240

Ser Ala Leu Val Thr Arg Glu Leu Val Ser His Gln Val Thr Leu Arg
                245                 250                 255

Ser Glu Leu Ala Ser Ala Leu Pro Arg Val Leu Gly Asp Arg Ile Gln
            260                 265                 270

Leu Gln Gln Val Ile Ile Asn Leu Val Met Asn Gly Ile Glu Ala Met
            275                 280                 285

Asp Ala Val Thr Asp Arg Pro Arg Glu Leu Leu Ile Gln Ser Ser Thr
            290                 295                 300

Asp Asp Leu Gly Tyr Val Gln Leu Ser Val Thr Asp Cys Gly Val Gly
305                 310                 315                 320

Ile Ala Glu Asn Asp Ala Asp Arg Val Leu Asp Pro Phe Phe Thr Thr
                325                 330                 335

Lys Ser Ser Gly Leu Gly Met Gly Leu Ser Ile Cys Arg Ser Ile Val
            340                 345                 350

Glu Val His Gly Gly Arg Ile Ser Val Val Gln Lys Asn Gly Pro Gly
            355                 360                 365

Ala Thr Phe Gln Phe Ala Leu Pro
            370                 375

(2) INFORMATION FOR SEQ ID NO:25:

(i) SEQUENCE CHARACTERISTICS:
         (A) LENGTH: 399 amino acids
         (B) TYPE: amino acid
```

(C) STRANDEDNESS: Not Relevant
        (D) TOPOLOGY: linear (ii) MOLECULE TYPE: protein (xi) SEQUENCE DESCRIPTION: SEQ ID NO:25:

Arg Ala Arg Ala Gly Leu Ile Arg Asp Glu Ala Gly Thr Ala Arg His
1               5                   10                  15

Leu Ser Gly Ile Phe Leu Asp Ile Asp Glu Glu Lys Gln Val Glu Gly
            20                  25                  30

Ala Leu Arg Thr Arg Glu Thr His Leu Arg Ser Ile Leu His Thr Ile
        35                  40                  45

Pro Asp Ala Met Ile Val Ile Asp Gly His Gly Ile Ile Gln Leu Phe
50                  55                  60

Ser Thr Ala Ala Glu Arg Leu Phe Gly Trp Ser Glu Leu Glu Ala Ile
65              70                  75                  80

Gly Gln Asn Val Asn Ile Leu Met Pro Glu Pro Asp Arg Ser Arg His
                85                  90                  95

Asp Ser Tyr Ile Ser Arg Tyr Arg Thr Thr Ser Asp Pro His Ile Ile
                100                 105                 110

Gly Ile Gly Arg Ile Val Thr Gly Lys Arg Arg Asp Gly Thr Thr Phe
            115                 120                 125

Pro Met His Leu Ser Ile Gly Glu Met Gln Ser Gly Gly Glu Pro Tyr
130                 135                 140

Phe Thr Gly Phe Val Arg Asp Leu Thr Glu His Gln Gln Thr Gln Ala
145                 150                 155                 160

Arg Leu Gln Glu Leu Gln Ser Glu Leu Val His Val Ser Arg Leu Ser
                165                 170                 175

Ala Met Gly Glu Met Ala Ser Ala Leu Ala His Glu Leu Asn Gln Pro
            180                 185                 190

Leu Ala Ala Ile Ser Asn Tyr Met Lys Gly Ser Arg Arg Leu Leu Ala
        195                 200                 205

Gly Ser Ser Asp Pro Asn Thr Pro Lys Val Glu Ser Ala Leu Asp Arg
210                 215                 220

Ala Ala Glu Gln Ala Leu Arg Ala Gly Gln Ile Ile Arg Arg Leu Arg
225                 230                 235                 240

Asp Phe Val Ala Arg Gly Glu Ser Glu Lys Arg Val Glu Ser Leu Ser
                245                 250                 255

Lys Leu Ile Glu Glu Ala Gly Ala Leu Gly Leu Ala Gly Ala Arg Glu
            260                 265                 270

Gln Asn Val Gln Leu Arg Phe Ser Leu Asp Pro Gly Ala Asp Leu Val
        275                 280                 285

Leu Ala Asp Arg Val Gln Ile Gln Gln Val Leu Val Asn Leu Phe Arg
290                 295                 300

Asn Ala Leu Glu Ala Met Ala Gln Ser Gln Arg Arg Glu Leu Val Val
305                 310                 315                 320

Thr Asn Thr Pro Ala Ala Asp Met Ile Glu Val Glu Val Ser Asp
                325                 330                 335

Thr Gly Ser Gly Phe Gln Asp Val Ile Pro Asn Leu Phe Gln Thr
            340                 345                 350

Phe Phe Thr Thr Lys Asp Thr Gly Met Gly Val Gly Leu Ser Ile Ser
        355                 360                 365

Arg Ser Ile Ile Glu Ala His Gly Gly Arg Met Trp Ala Glu Ser Asn
370                 375                 380

```
Ala Ser Gly Gly Ala Thr Phe Arg Phe Thr Leu Pro Ala Ala Asp
385                 390                 395
```

(2) INFORMATION FOR SEQ ID NO:26:

(i) SEQUENCE CHARACTERISTICS:
        (A) LENGTH: 440 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:26:

```
Leu Val Ile Val Val Leu Ala Ser Ser Gly Gly Leu Phe Ala Gly Leu
1               5                   10                  15

Ala Ala Thr Ala Val Ser Ala Leu Gly Leu Ala Leu Arg Gly Leu Leu
                20                  25                  30

Ser Gly Asp Thr Val Val Ala Asp Trp Gln Ser Leu Gly Leu Leu Thr
                35                  40                  45

Ile Ala Gly Ala Gly Ile Ala Val Leu Gly Glu Arg Leu Arg Arg Thr
            50                  55                  60

Arg Leu Asp Ala Val Ala Arg Asp Arg Ala Leu Leu Ala Arg Glu Ala
65                  70                  75                  80

His Leu Ser Ser Ile Leu Asp Thr Val Pro Asp Ala Met Ile Val Ile
                85                  90                  95

Asp Glu Arg Gly Ile Met Gln Ser Phe Ser Ile Thr Ala Glu Arg Leu
                100                 105                 110

Phe Gly Tyr Ser Pro Ser Glu Val Ile Gly Arg Asn Val Ser Met Leu
                115                 120                 125

Met Pro Asn Pro His Arg Asp Gln His Asp Leu Tyr Leu Ser Arg Tyr
            130                 135                 140

Leu Thr Thr Gly Glu Arg Arg Ile Ile Gly Ile Gly Arg Val Val Thr
145                 150                 155                 160

Gly Glu Arg Lys Asp Gly Ala Thr Phe Pro Met Glu Leu Ala Val Gly
                165                 170                 175

Glu Met His Ser Val Ser Gly Arg Phe Phe Thr Gly Phe Ile Arg Asp
                180                 185                 190

Leu Thr Glu Arg Gln Asn Thr Glu Ala Arg Leu Gln Glu Leu Gln Ala
            195                 200                 205

Glu Leu Val His Ile Ser Arg Leu Thr Ala Leu Gly Glu Met Ala Ser
                210                 215                 220

Thr Leu Ala His Glu Leu Asn Gln Pro Leu Ser Ala Ile Ala Asn Tyr
225                 230                 235                 240

Ile Lys Gly Ser Arg Arg Leu Leu Asp Asp Gly Asp Pro Lys Arg Ile
                245                 250                 255

Pro Met Leu Gln Gly Ala Leu Asp Lys Ala Ala Glu Gln Ala Leu Arg
            260                 265                 270

Ala Gly Gln Ile Ile Arg Arg Leu Arg Asp Phe Val Ser Arg Gly Glu
                275                 280                 285

Thr Glu Arg Arg Val Glu Ser Leu Ser Lys Leu Ile Glu Glu Ala Ser
            290                 295                 300

Ala Leu Ala Leu Val Gly Ala Lys Glu His Gly Ile Gln Val Arg Tyr
305                 310                 315                 320

Gln Ile Asp Thr Ser Cys Asp Leu Val Leu Ala Asp Lys Val Gln Val
                325                 330                 335
```

```
Gln Gln Val Leu Leu Asn Leu Met Arg Asn Ala Leu Glu Ala Met Met
            340                 345                 350

Asp Ala Ser Arg Arg Gln Leu Leu Val Gln Thr Thr Pro Ala Glu Asp
            355                 360                 365

Asp Met Val Thr Val Ser Val Cys Asp Thr Gly His Gly Ile Ser Asp
            370                 375                 380

Glu Met Arg Ala Gln Leu Phe Thr Pro Phe Val Thr Thr Lys Ala Gln
385                 390                 395                 400

Gly Met Gly Val Gly Leu Ser Ile Ser Arg Thr Ile Ile Glu Ala His
            405                 410                 415

Gly Gly Arg Ile Trp Ala Glu Pro Asn Ala Gly Gly Thr Ile Phe
            420                 425                 430

Arg Phe Thr Leu Arg Thr Val Asp
            435                 440

(2) INFORMATION FOR SEQ ID NO:27:

(i) SEQUENCE CHARACTERISTICS:
        (A) LENGTH: 385 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:27:

Ile Val Ala Leu Gly Glu Val Leu Glu Ala Ala Arg Arg Ala Ile Asp
1               5                   10                  15

Arg Thr Glu Asp Val Val Arg Ala Arg Asp Ala His Leu Arg Ser Ile
            20                  25                  30

Leu Asp Thr Val Pro Asp Ala Thr Val Val Ser Ala Thr Asp Gly Thr
            35                  40                  45

Ile Val Ser Phe Asn Ala Ala Ala Val Arg Gln Phe Gly Tyr Ala Glu
            50                  55                  60

Glu Glu Val Ile Gly Gln Asn Leu Arg Ile Leu Met Pro Glu Pro Tyr
65                  70                  75                  80

Arg His Glu His Asp Gly Tyr Leu Gln Arg Tyr Met Ala Thr Gly Glu
            85                  90                  95

Lys Arg Ile Ile Gly Ile Asp Arg Val Val Ser Gly Gln Arg Lys Asp
            100                 105                 110

Gly Ser Thr Phe Pro Met Lys Leu Ala Val Gly Glu Met Arg Ser Gly
            115                 120                 125

Gly Glu Arg Phe Phe Thr Gly Phe Ile Arg Asp Leu Thr Glu Arg Glu
            130                 135                 140

Glu Ser Ala Ala Arg Leu Glu Gln Ile Gln Ala Glu Leu Ala Arg Leu
145                 150                 155                 160

Ala Arg Leu Asn Glu Met Gly Glu Met Ala Ser Thr Leu Ala His Glu
            165                 170                 175

Leu Asn Gln Pro Leu Ser Ala Ile Ala Asn Tyr Ser His Gly Cys Thr
            180                 185                 190

Arg Leu Leu Arg Asp Met Asp Asp Ala Val Ala Thr Arg Ile Arg Glu
            195                 200                 205

Ala Leu Glu Glu Val Ala Ser Gln Ser Leu Arg Ala Gly Gln Ile Ile
            210                 215                 220

Lys His Leu Arg Glu Phe Val Thr Lys Gly Glu Thr Glu Lys Ala Pro
225                 230                 235                 240
```

-continued

```
Glu Asp Ile Arg Lys Leu Val Glu Ser Ala Ala Leu Ala Leu Val
                245                 250                 255

Gly Ser Arg Glu Gln Gly Val Arg Thr Val Phe Glu Tyr Leu Pro Gly
            260                 265                 270

Ala Glu Met Val Leu Val Asp Arg Ile Gln Val Gln Gln Val Leu Ile
        275                 280                 285

Asn Leu Met Arg Asn Ala Ile Glu Ala Met Arg His Val Asp Arg Arg
    290                 295                 300

Glu Leu Thr Ile Arg Thr Met Pro Ala Asp Pro Gly Glu Val Ala Val
305                 310                 315                 320

Val Val Glu Asp Thr Gly Gly Ile Pro Glu Val Ala Gly Gln
                325                 330                 335

Leu Phe Lys Pro Phe Val Thr Thr Lys Ala Ser Gly Met Gly Ile Gly
                340                 345                 350

Leu Ser Ile Ser Lys Arg Ile Val Glu Ala His Gly Glu Met Thr
            355                 360                 365

Val Ser Lys Asn Glu Ala Gly Gly Ala Thr Phe Arg Phe Thr Leu Pro
            370                 375                 380

Ala
385

(2) INFORMATION FOR SEQ ID NO:28:

(i) SEQUENCE CHARACTERISTICS:
        (A) LENGTH: 387 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:28:

Val Val Leu His Arg Asn Ala Leu Arg Arg Arg Met Ala Glu Asp Arg
1               5                   10                  15

Leu Arg Ala Glu Met Ala Phe Arg Ala Met Glu Glu Ser Leu Thr
            20                  25                  30

Val Gly Met Arg Ala Lys Asp Leu Ser Gly Arg Ile Leu Tyr Val Asn
        35                  40                  45

Gly Ala Phe Cys Lys Leu Val Gly Leu Ala Ala Glu Asp Leu Val Gly
    50                  55                  60

Arg Ala Gln Pro Met Pro Tyr Trp Ala Pro Asp Phe Leu Glu Glu Thr
65              70                  75                  80

Leu Ala Arg Gln Arg Gln Leu Ile Glu Gly Gln Pro Val Pro Gln Ala
            85                  90                  95

Phe Glu Thr Arg Phe Arg Arg Ser Asp Gly Ser Glu Ile Glu Val Gln
                100                 105                 110

Val Phe Glu Ala Pro Leu Ile Asp Ala Gly Gly Arg His Arg Gly Trp
        115                 120                 125

Met Gly Ser Val Ile Asp Ile Thr Gln Ala Lys Gln Ala Ala Arg Leu
    130                 135                 140

Ala Arg Ala Gln Asp Glu Ser Leu Ala Arg Thr Gly Arg Leu Val Thr
145                 150                 155                 160

Leu Gly Glu Met Ala Ser Thr Leu Ala His Glu Leu Asn Gln Pro Leu
                165                 170                 175

Ala Ala Ile Ala Ser Tyr Ala Ala Gly Gly Leu Asn Leu Phe Asp Gln
            180                 185                 190
```

```
Pro Glu Pro Asn Leu Thr Met Leu Arg Gln Ala Phe Glu Lys Met Gly
            195                 200                 205

Ala Gln Ala Arg Arg Ala Gly Leu Val Ile Arg Arg Val Gln Asp Phe
    210                 215                 220

Val Lys Lys Arg Thr Pro Gln Leu Ala Ala Leu Asp Leu Ser Glu Val
225                 230                 235                 240

Leu Ala Glu Ala Leu Ser Ile Thr Ala Pro Val Ala Arg Glu His Arg
                245                 250                 255

Val Lys Leu Ala Ser Leu Ile Glu Gly Arg Ile Pro Gly Val Gln Ala
            260                 265                 270

Asp Arg Ile Leu Ile Glu Gln Val Leu Val Asn Leu Ile Arg Asn Gly
        275                 280                 285

Val Glu Ala Met Ala Glu Gly Pro Arg Thr Gly Asp Asp Leu Thr Val
    290                 295                 300

Arg Leu Ala Arg Ala Gly Ala Ala Val Thr Ile Glu Val Met Asp Arg
305                 310                 315                 320

Gly Pro Gly Ile Ser Asp Ala Val Ala Ala Ser Leu Phe Asp Pro Phe
                325                 330                 335

Thr Ser Thr Lys Ser Glu Gly Met Gly Met Gly Leu Asn Ile Cys Arg
            340                 345                 350

Ser Ile Val Glu Met His His Gly Ser Leu Ser His Gly Pro Arg Ala
        355                 360                 365

Gly Gly Gly Thr Val Phe Thr Val Thr Leu Pro Val Pro Gln Glu Gly
    370                 375                 380

Ala Pro Ala
385

(2) INFORMATION FOR SEQ ID NO:29:

(i) SEQUENCE CHARACTERISTICS:
        (A) LENGTH: 765 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:29:

Met Thr Asn Arg Ile Ser Arg Leu Lys Thr Ala Leu Phe Ala Asn Thr
1               5                   10                  15

Arg Glu Ile Ser Leu Glu Arg Ala Leu Leu Tyr Thr Ala Ser His Arg
            20                  25                  30

Gln Thr Glu Gly Glu Pro Val Ile Leu Arg Arg Ala Lys Ala Thr Ala
        35                  40                  45

Tyr Ile Leu Glu His Val Glu Ile Ser Ile Arg Asp Glu Glu Leu Ile
    50                  55                  60

Ala Gly Asn Arg Thr Val Lys Pro Arg Ala Gly Ile Met Ser Pro Glu
65                  70                  75                  80

Met Asp Pro Tyr Trp Leu Leu Lys Glu Leu Asp Gln Phe Pro Thr Arg
                85                  90                  95

Pro Gln Asp Arg Phe Ala Ile Ser Glu Glu Asp Lys Arg Ile Tyr Arg
            100                 105                 110

Glu Glu Leu Phe Pro Tyr Trp Glu Lys Arg Ser Met Lys Asp Phe Ile
        115                 120                 125

Asn Gly Gln Met Thr Asp Glu Val Lys Ala Ala Thr Asn Thr Gln Ile
    130                 135                 140
```

-continued

```
Phe Ser Ile Asn Gln Thr Asp Lys Gly Gln Gly His Ile Ile Asp
145                 150                 155                 160

Tyr Pro Arg Leu Leu Asn His Gly Leu Gly Glu Leu Val Ala Gln Met
            165                 170                 175

Gln Gln His Cys Gln Gln Gln Pro Glu Asn His Phe Tyr Gln Ala Ala
            180                 185                 190

Leu Leu Leu Leu Glu Ala Ser Gln Lys His Ile Leu Arg Tyr Ala Glu
            195                 200                 205

Leu Ala Glu Thr Met Ala Ala Asn Cys Thr Asp Ala Gln Arg Arg Glu
            210                 215                 220

Glu Leu Leu Thr Ile Ala Glu Ile Ser Arg His Asn Ala Gln His Lys
225                 230                 235                 240

Pro Gln Thr Phe Trp Gln Ala Cys Gln Leu Phe Trp Tyr Met Asn Ile
            245                 250                 255

Ile Leu Gln Tyr Glu Ser Asn Ala Ser Ser Leu Ser Leu Gly Arg Phe
            260                 265                 270

Asp Gln Tyr Met Leu Pro Phe Tyr Gln Thr Ser Leu Thr Gln Gly Glu
            275                 280                 285

Asp Ala Ala Phe Leu Lys Glu Leu Leu Glu Ser Leu Trp Val Lys Cys
290                 295                 300

Asn Asp Ile Val Leu Leu Arg Ser Thr Ser Ser Ala Arg Tyr Phe Ala
305                 310                 315                 320

Gly Phe Pro Thr Gly Tyr Thr Ala Leu Leu Gly Gly Leu Thr Glu Asn
            325                 330                 335

Gly Arg Ser Ala Val Asn Val Leu Ser Phe Leu Cys Leu Asp Ala Tyr
            340                 345                 350

Gln Ser Val Gln Leu Pro Gln Pro Asn Leu Gly Val Arg Thr Asn Ala
            355                 360                 365

Leu Ile Asp Thr Pro Phe Leu Met Lys Thr Ala Glu Thr Ile Arg Phe
            370                 375                 380

Gly Thr Gly Ile Pro Gln Ile Phe Asn Asp Glu Val Val Pro Ala
385                 390                 395                 400

Phe Leu Asn Arg Gly Val Ser Leu Glu Asp Ala Arg Asp Tyr Ser Val
            405                 410                 415

Val Gly Cys Val Glu Leu Ser Ile Pro Gly Arg Thr Tyr Gly Leu His
            420                 425                 430

Asp Ile Ala Met Phe Asn Leu Leu Lys Val Met Glu Ile Cys Leu His
            435                 440                 445

Glu Asn Glu Gly Asn Ala Ala Leu Thr Tyr Glu Gly Leu Leu Glu Gln
450                 455                 460

Ile Arg Ala Lys Ile Ser His Tyr Ile Thr Leu Met Val Glu Gly Ser
465                 470                 475                 480

Asn Ile Cys Asp Ile Gly His Arg Asp Trp Ala Pro Val Pro Leu Leu
            485                 490                 495

Ser Ser Phe Ile Ser Asp Cys Leu Glu Lys Gly Arg Asp Ile Thr Asp
            500                 505                 510

Gly Gly Ala Arg Tyr Asn Phe Ser Gly Val Gln Gly Ile Gly Ile Ala
            515                 520                 525

Asn Leu Ser Asp Ser Leu His Ala Leu Lys Gly Met Val Phe Glu Gln
            530                 535                 540

Gln Arg Leu Ser Phe Asp Glu Leu Leu Ser Val Leu Lys Ala Asn Phe
545                 550                 555                 560

Ala Thr Pro Glu Gly Glu Lys Val Arg Ala Arg Leu Ile Asn Arg Phe
```

-continued

```
                  565                 570                 575
Glu Lys Tyr Gly Asn Asp Ile Asp Glu Val Asp Asn Ile Ser Ala Glu
                  580                 585                 590

Leu Leu Arg His Tyr Cys Lys Glu Val Glu Lys Tyr Gln Asn Pro Arg
            595                 600                 605

Gly Gly Tyr Phe Thr Pro Gly Ser Tyr Thr Val Ser Ala His Val Pro
        610                 615                 620

Leu Gly Ser Val Val Gly Ala Thr Pro Asp Gly Arg Phe Ala Gly Glu
625                 630                 635                 640

Gln Leu Ala Asp Gly Gly Leu Ser Pro Met Leu Gly Gln Asp Ala Gln
                645                 650                 655

Gly Pro Thr Ala Val Leu Lys Ser Val Ser Lys Leu Asp Asn Thr Leu
            660                 665                 670

Leu Ser Asn Gly Thr Leu Leu Asn Val Lys Phe Thr Pro Ala Thr Leu
        675                 680                 685

Glu Gly Glu Ala Gly Leu Arg Lys Leu Ala Asp Phe Leu Arg Ala Phe
690                 695                 700

Thr Gln Leu Lys Leu Gln His Ile Gln Phe Asn Val Val Asn Ala Asp
705                 710                 715                 720

Thr Leu Arg Glu Ala Gln Gln Arg Pro Gln Asp Tyr Ala Gly Leu Val
                725                 730                 735

Val Arg Val Ala Gly Tyr Ser Ala Phe Phe Val Glu Leu Ser Lys Glu
            740                 745                 750

Ile Gln Asp Asp Ile Ile Arg Arg Thr Ala His Gln Leu
        755                 760                 765

(2) INFORMATION FOR SEQ ID NO:30:

(i) SEQUENCE CHARACTERISTICS:
        (A) LENGTH: 740 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:30:

Met Phe Lys Gln Trp Glu Gly Phe Gln Asp Gly Glu Trp Thr Asn Asp
1               5                   10                  15

Val Asn Val Arg Asp Phe Ile Gln Lys Asn Tyr Lys Glu Tyr Thr Gly
                20                  25                  30

Asp Lys Ser Phe Leu Lys Gly Pro Thr Glu Lys Thr Lys Lys Val Trp
            35                  40                  45

Asp Lys Ala Val Ser Leu Ile Leu Glu Glu Leu Lys Lys Gly Ile Leu
        50                  55                  60

Asp Val Asp Thr Glu Thr Ile Ser Gly Ile Asn Ser Phe Lys Pro Gly
65                  70                  75                  80

Tyr Leu Asp Lys Asp Asn Glu Val Ile Val Gly Phe Gln Thr Asp Ala
                85                  90                  95

Pro Leu Lys Arg Ile Thr Asn Pro Phe Gly Gly Ile Arg Met Ala Glu
            100                 105                 110

Gln Ser Leu Lys Glu Tyr Gly Phe Lys Ile Ser Asp Glu Met His Asn
        115                 120                 125

Ile Phe Thr Asn Tyr Arg Lys Thr His Asn Gln Gly Val Phe Asp Ala
        130                 135                 140

Tyr Ser Glu Glu Thr Arg Ile Ala Arg Ser Ala Gly Val Leu Thr Gly
```

-continued

```
145                 150                 155                 160
Leu Pro Asp Ala Tyr Gly Arg Gly Arg Ile Gly Asp Tyr Arg Arg
                165                 170                 175

Val Ala Leu Tyr Gly Ile Asp Phe Leu Ile Gln Glu Lys Lys Asp
                180                 185                 190

Leu Ser Asn Leu Lys Gly Asp Met Leu Asp Glu Leu Ile Arg Leu Arg
                195                 200                 205

Glu Glu Val Ser Glu Gln Ile Arg Ala Leu Asp Glu Ile Lys Lys Met
    210                 215                 220

Ala Leu Ser Tyr Gly Val Asp Ile Ser Arg Pro Ala Val Asn Ala Lys
225                 230                 235                 240

Glu Ala Ala Gln Phe Leu Tyr Phe Gly Tyr Leu Ala Gly Val Lys Glu
                245                 250                 255

Asn Asn Gly Ala Ala Met Ser Leu Gly Arg Thr Ser Thr Phe Leu Asp
                260                 265                 270

Ile Tyr Ile Glu Arg Asp Leu Glu Gln Gly Leu Ile Thr Glu Asp Glu
                275                 280                 285

Ala Gln Glu Val Ile Asp Gln Phe Ile Ile Lys Leu Arg Leu Val Arg
    290                 295                 300

His Leu Arg Thr Pro Glu Tyr Asn Glu Leu Phe Ala Gly Asp Pro Thr
305                 310                 315                 320

Trp Val Thr Glu Ser Ile Ala Gly Val Gly Ile Asp Gly Arg Ser Leu
                325                 330                 335

Val Thr Lys Asn Ser Phe Arg Tyr Leu His Thr Leu Ile Asn Leu Gly
                340                 345                 350

Ser Ala Pro Glu Pro Asn Met Thr Val Leu Trp Ser Glu Asn Leu Pro
                355                 360                 365

Glu Ser Phe Lys Lys Phe Cys Ala Glu Met Ser Ile Leu Thr Asp Ser
    370                 375                 380

Ile Gln Tyr Glu Asn Asp Asp Ile Met Arg Pro Ile Tyr Gly Asp Asp
385                 390                 395                 400

Tyr Ala Ile Ala Cys Cys Val Ser Ala Met Arg Val Gly Lys Asp Met
                405                 410                 415

Gln Phe Phe Gly Ala Arg Cys Asn Leu Ala Lys Cys Leu Leu Leu Ala
                420                 425                 430

Ile Asn Gly Gly Val Asp Glu Lys Lys Gly Ile Lys Val Val Pro Asp
                435                 440                 445

Ile Glu Pro Ile Thr Asp Glu Val Leu Asp Tyr Glu Lys Val Lys Glu
    450                 455                 460

Asn Tyr Phe Lys Val Leu Glu Tyr Met Ala Gly Leu Tyr Val Asn Thr
465                 470                 475                 480

Met Asn Ile Ile His Phe Met His Asp Lys Tyr Ala Tyr Glu Ala Ser
                485                 490                 495

Gln Met Ala Leu His Asp Thr Lys Val Gly Arg Leu Met Ala Phe Gly
                500                 505                 510

Ile Ala Gly Phe Ser Val Ala Ala Asp Ser Leu Ser Ala Ile Arg Tyr
                515                 520                 525

Ala Lys Val Lys Pro Ile Arg Glu Asn Gly Ile Thr Val Asp Phe Val
    530                 535                 540

Lys Glu Gly Asp Phe Pro Lys Tyr Gly Asn Asp Asp Arg Val Asp
545                 550                 555                 560

Ser Ile Ala Val Glu Ile Val Glu Lys Phe Ser Asp Glu Leu Lys Lys
                565                 570                 575
```

```
His Pro Thr Tyr Arg Asn Ala Lys His Thr Leu Ser Val Leu Thr Ile
            580                 585                 590

Thr Ser Asn Val Met Tyr Gly Lys Lys Thr Gly Thr Thr Pro Asp Gly
        595                 600                 605

Arg Lys Val Gly Glu Pro Leu Ala Pro Gly Ala Asn Pro Met His Gly
    610                 615                 620

Arg Asp Met Glu Gly Ala Leu Ala Ser Leu Asn Ser Val Ala Lys Val
625                 630                 635                 640

Pro Tyr Val Cys Cys Glu Asp Gly Val Ser Asn Thr Phe Ser Ile Val
                645                 650                 655

Pro Asp Ala Leu Gly Asn Asp His Asp Val Arg Ile Asn Asn Leu Val
                660                 665                 670

Ser Ile Met Gly Gly Tyr Phe Gly Gln Gly Ala His His Leu Asn Val
                675                 680                 685

Asn Val Leu Asn Arg Glu Thr Leu Ile Asp Ala Met Asn Asn Pro Asp
            690                 695                 700

Lys Tyr Pro Thr Leu Thr Ile Arg Val Ser Gly Tyr Ala Val Asn Phe
705                 710                 715                 720

Asn Arg Leu Ser Lys Asp His Gln Lys Glu Val Ile Ser Arg Thr Phe
                725                 730                 735

His Glu Lys Leu
            740
```

(2) INFORMATION FOR SEQ ID NO:31:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..147

(xi) SEQUENCE DESCRIPTION: SEQ ID NO:31:

```
ATG ACC ATG ATT ACG CCA AGC TTG CAT GCA TCG GTA CCG GGC CCC CCC      48
Met Thr Met Ile Thr Pro Ser Leu His Ala Ser Val Pro Gly Pro Pro
 1               5                  10                  15

TCG AGG TCG ACG GTA TCG ATA AGC TTG ATA TCG AAT TCC TGC AGC CCG      96
Ser Arg Ser Thr Val Ser Ile Ser Leu Ile Ser Asn Ser Cys Ser Pro
             20                  25                  30

GGG GAT CCA CTA GTT CTA GAG CGG CCG CCA CCG CGG TGG AGC TCG AAT     144
Gly Asp Pro Leu Val Leu Glu Arg Pro Pro Pro Arg Trp Ser Ser Asn
         35                  40                  45

TCA                                                                 147
Ser
```

(2) INFORMATION FOR SEQ ID NO:32:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO:32:

```
Met Thr Met Ile Thr Pro Ser Leu His Ala Ser Val Pro Gly Pro Pro
 1               5                  10                  15

Ser Arg Ser Thr Val Ser Ile Ser Leu Ile Ser Asn Ser Cys Ser Pro
                20                  25                  30

Gly Asp Pro Leu Val Leu Glu Arg Pro Pro Pro Arg Trp Ser Ser Asn
            35                  40                  45

Ser
```

(2) INFORMATION FOR SEQ ID NO:33:

(i) SEQUENCE CHARACTERISTICS:
        (A) LENGTH: 810 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:33:

```
Met Thr Thr Leu Lys Leu Asp Thr Leu Ser Asp Arg Ile Lys Ala His
 1               5                  10                  15

Lys Asn Ala Leu Val His Ile Val Lys Pro Val Cys Thr Glu Arg
                20                  25                  30

Ala Gln His Tyr Thr Glu Met Tyr Gln Gln His Leu Asp Lys Pro Ile
                35                  40                  45

Pro Val Arg Arg Ala Leu Ala Leu Ala His His Leu Ala Asn Arg Thr
            50                  55                  60

Ile Trp Ile Lys His Asp Glu Leu Ile Ile Gly Asn Gln Ala Ser Glu
65                  70                  75                  80

Val Arg Ala Ala Pro Ile Phe Pro Glu Tyr Thr Val Ser Trp Ile Glu
                85                  90                  95

Lys Glu Ile Asp Asp Leu Ala Asp Arg Pro Gly Ala Gly Phe Ala Val
                100                 105                 110

Ser Glu Glu Asn Lys Arg Val Leu His Glu Val Cys Pro Trp Trp Arg
                115                 120                 125

Gly Gln Thr Val Gln Asp Arg Cys Tyr Gly Met Phe Thr Asp Glu Gln
            130                 135                 140

Lys Gly Leu Leu Ala Thr Gly Ile Ile Lys Ala Glu Gly Asn Met Thr
145                 150                 155                 160

Ser Gly Asp Ala His Leu Ala Val Asn Phe Pro Leu Leu Glu Lys
                165                 170                 175

Gly Leu Asp Gly Leu Arg Glu Val Ala Glu Arg Ser Arg Ile
            180                 185                 190

Asn Leu Thr Val Leu Glu Asp Leu His Gly Glu Gln Phe Leu Lys Ala
                195                 200                 205

Ile Asp Ile Val Leu Val Ala Val Ser Glu His Ile Glu Arg Phe Ala
    210                 215                 220

Ala Leu Ala Arg Glu Met Ala Ala Thr Glu Thr Arg Glu Ser Arg Arg
225                 230                 235                 240

Asp Glu Leu Leu Ala Met Ala Glu Asn Cys Asp Leu Ile Ala His Gln
                245                 250                 255

Pro Pro Gln Thr Phe Trp Gln Ala Leu Gln Leu Cys Tyr Phe Ile Gln
                260                 265                 270

Leu Ile Leu Gln Ile Glu Ser Asn Gly His Ser Val Ser Phe Gly Arg
            275                 280                 285

Met Asp Gln Tyr Leu Tyr Pro Tyr Tyr Arg Arg Asp Val Glu Leu Asn
```

```
            290                 295                 300
Gln Thr Leu Asp Arg Glu His Ala Ile Glu Met Leu His Ser Cys Trp
305                 310                 315                 320

Leu Lys Leu Leu Glu Val Asn Lys Ile Arg Ser Gly Ser His Ser Lys
                325                 330                 335

Ala Ser Ala Gly Ser Pro Leu Tyr Gln Asn Val Thr Ile Gly Gly Gln
                340                 345                 350

Asn Leu Val Asp Gly Gln Pro Met Asp Ala Val Asn Pro Leu Ser Tyr
                355                 360                 365

Ala Ile Leu Glu Ser Cys Gly Arg Leu Arg Ser Thr Gln Pro Asn Leu
            370                 375                 380

Ser Val Arg Tyr His Ala Gly Met Ser Asn Asp Phe Leu Asp Ala Cys
385                 390                 395                 400

Val Gln Val Ile Arg Cys Gly Phe Gly Met Pro Ala Phe Asn Asn Asp
                405                 410                 415

Glu Ile Val Ile Pro Glu Phe Ile Lys Leu Gly Ile Glu Pro Gln Asp
                420                 425                 430

Ala Tyr Asp Tyr Ala Ala Ile Gly Cys Ile Glu Thr Ala Val Gly Gly
                435                 440                 445

Lys Trp Gly Tyr Arg Cys Thr Gly Met Ser Phe Ile Asn Phe Ala Arg
450                 455                 460

Val Met Leu Ala Ala Leu Glu Gly His Asp Ala Thr Ser Gly Lys
465                 470                 475                 480

Val Phe Leu Pro Gln Glu Lys Ala Leu Ser Ala Gly Asn Phe Asn Asn
                485                 490                 495

Phe Asp Glu Val Met Asp Ala Trp Asp Thr Gln Ile Arg Tyr Tyr Thr
                500                 505                 510

Arg Lys Ser Ile Glu Ile Glu Tyr Val Val Asp Thr Met Leu Glu Glu
                515                 520                 525

Asn Val His Asp Ile Leu Cys Ser Ala Leu Val Asp Asp Cys Ile Glu
                530                 535                 540

Arg Ala Lys Ser Ile Lys Gln Gly Gly Ala Lys Tyr Asp Trp Val Ser
545                 550                 555                 560

Gly Leu Gln Val Gly Ile Ala Asn Leu Gly Asn Ser Leu Ala Ala Val
                565                 570                 575

Lys Lys Leu Val Phe Glu Gln Gly Ala Ile Gly Gln Gln Leu Ala
                580                 585                 590

Ala Ala Leu Ala Asp Asp Phe Asp Gly Leu Thr His Glu Gln Leu Arg
                595                 600                 605

Gln Arg Leu Ile Asn Gly Ala Pro Lys Tyr Gly Asn Asp Asp Thr
                610                 615                 620

Val Asp Thr Leu Leu Ala Arg Ala Tyr Gln Thr Tyr Ile Asp Glu Leu
625                 630                 635                 640

Lys Gln Tyr His Asn Pro Arg Tyr Arg Gly Pro Val Gly Gly Asn
                645                 650                 655

Tyr Tyr Ala Gly Thr Ser Ser Ile Ser Ala Asn Val Pro Phe Gly Ala
                660                 665                 670

Gln Thr Met Ala Thr Pro Asp Gly Arg Lys Ala His Thr Pro Leu Ala
                675                 680                 685

Glu Gly Ala Ser Pro Ala Ser Gly Thr Asp His Leu Gly Pro Thr Ala
                690                 695                 700

Val Ile Gly Ser Val Gly Lys Leu Pro Thr Ala Ala Ile Leu Gly Gly
705                 710                 715                 720
```

```
Val Leu Leu Asn Gln Lys Leu Asn Pro Ala Thr Leu Glu Asn Glu Ser
                725                 730                 735

Asp Lys Gln Lys Leu Met Ile Leu Leu Arg Thr Phe Phe Glu Val His
            740                 745                 750

Lys Gly Trp His Ile Gln Tyr Asn Ile Val Ser Arg Glu Thr Leu Leu
        755                 760                 765

Asp Ala Lys Lys His Pro Asp Gln Tyr Arg Asp Leu Val Val Arg Val
    770                 775                 780

Ala Gly Tyr Ser Ala Phe Phe Thr Ala Leu Ser Pro Asp Ala Gln Asp
785                 790                 795                 800

Asp Ile Ile Ala Arg Thr Glu His Met Leu
                805                 810

(2) INFORMATION FOR SEQ ID NO:34:

(i) SEQUENCE CHARACTERISTICS:
        (A) LENGTH: 765 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:34:

Met Thr Asn Arg Ile Ser Arg Leu Lys Thr Ala Leu Phe Ala Asn Thr
1                 5                   10                  15

Arg Glu Ile Ser Leu Glu Arg Ala Leu Leu Tyr Thr Ala Ser His Arg
                20                  25                  30

Gln Thr Glu Gly Glu Pro Val Ile Leu Arg Arg Ala Lys Ala Thr Ala
            35                  40                  45

Tyr Ile Leu Glu His Val Glu Ile Ser Ile Arg Asp Glu Glu Leu Ile
    50                  55                  60

Ala Gly Asn Arg Thr Val Lys Pro Arg Ala Gly Ile Met Ser Pro Glu
65                  70                  75                  80

Met Asp Pro Tyr Trp Leu Leu Lys Glu Leu Asp Gln Phe Pro Thr Arg
                85                  90                  95

Pro Gln Asp Arg Phe Ala Ile Ser Glu Glu Asp Lys Arg Ile Tyr Arg
            100                 105                 110

Glu Glu Leu Phe Pro Tyr Trp Glu Lys Arg Ser Met Lys Asp Phe Ile
        115                 120                 125

Asn Gly Gln Met Thr Asp Glu Val Lys Ala Ala Thr Asn Thr Gln Ile
    130                 135                 140

Phe Ser Ile Asn Gln Thr Asp Lys Gly Gln Gly His Ile Ile Ile Asp
145                 150                 155                 160

Tyr Pro Arg Leu Leu Asn His Gly Leu Gly Glu Leu Val Ala Gln Met
                165                 170                 175

Gln Gln His Cys Gln Gln Pro Glu Asn His Phe Tyr Gln Ala Ala
            180                 185                 190

Leu Leu Leu Leu Glu Ala Ser Gln Lys His Ile Leu Arg Tyr Ala Glu
        195                 200                 205

Leu Ala Glu Thr Met Ala Ala Asn Cys Thr Asp Ala Gln Arg Arg Glu
    210                 215                 220

Glu Leu Leu Thr Ile Ala Glu Ile Ser Arg His Asn Ala Gln His Lys
225                 230                 235                 240

Pro Gln Thr Phe Trp Gln Ala Cys Gln Leu Phe Trp Tyr Met Asn Ile
                245                 250                 255
```

-continued

```
Ile Leu Gln Tyr Glu Ser Asn Ala Ser Ser Leu Ser Leu Gly Arg Phe
            260                 265                 270
Asp Gln Tyr Met Leu Pro Phe Tyr Gln Thr Ser Leu Thr Gln Gly Glu
            275                 280                 285
Asp Ala Ala Phe Leu Lys Glu Leu Leu Glu Ser Leu Trp Val Lys Cys
            290                 295                 300
Asn Asp Ile Val Leu Leu Arg Ser Thr Ser Ser Ala Arg Tyr Phe Ala
305                 310                 315                 320
Gly Phe Pro Thr Gly Tyr Thr Ala Leu Leu Gly Gly Leu Thr Glu Asn
                325                 330                 335
Gly Arg Ser Ala Val Asn Val Leu Ser Phe Leu Cys Leu Asp Ala Tyr
            340                 345                 350
Gln Ser Val Gln Leu Pro Gln Pro Asn Leu Gly Val Arg Thr Asn Ala
            355                 360                 365
Leu Ile Asp Thr Pro Phe Leu Met Lys Thr Ala Glu Thr Ile Arg Phe
            370                 375                 380
Gly Thr Gly Ile Pro Gln Ile Phe Asn Asp Glu Val Val Pro Ala
385                 390                 395                 400
Phe Leu Asn Arg Gly Val Ser Leu Glu Asp Ala Arg Asp Tyr Ser Val
                405                 410                 415
Val Gly Cys Val Glu Leu Ser Ile Pro Gly Arg Thr Tyr Gly Leu His
            420                 425                 430
Asp Ile Ala Met Phe Asn Leu Leu Lys Val Met Glu Ile Cys Leu His
            435                 440                 445
Glu Asn Glu Gly Asn Ala Ala Leu Thr Tyr Glu Gly Leu Leu Glu Gln
450                 455                 460
Ile Arg Ala Lys Ile Ser His Tyr Ile Thr Leu Met Val Glu Gly Ser
465                 470                 475                 480
Asn Ile Cys Asp Ile Gly His Arg Asp Trp Ala Pro Val Pro Leu Leu
                485                 490                 495
Ser Ser Phe Ile Ser Asp Cys Leu Glu Lys Gly Arg Asp Ile Thr Asp
            500                 505                 510
Gly Gly Ala Arg Tyr Asn Phe Ser Gly Val Gln Gly Ile Gly Ile Ala
            515                 520                 525
Asn Leu Ser Asp Ser Leu His Ala Leu Lys Gly Met Val Phe Glu Gln
530                 535                 540
Gln Arg Leu Ser Phe Asp Glu Leu Leu Ser Val Leu Lys Ala Asn Phe
545                 550                 555                 560
Ala Thr Pro Glu Gly Glu Lys Val Arg Ala Arg Leu Ile Asn Arg Phe
                565                 570                 575
Glu Lys Tyr Gly Asn Asp Ile Asp Glu Val Asp Asn Ile Ser Ala Glu
            580                 585                 590
Leu Leu Arg His Tyr Cys Lys Glu Val Glu Lys Tyr Gln Asn Pro Arg
            595                 600                 605
Gly Gly Tyr Phe Thr Pro Gly Ser Tyr Thr Val Ser Ala His Val Pro
            610                 615                 620
Leu Gly Ser Val Val Gly Ala Thr Pro Asp Gly Arg Phe Ala Gly Glu
625                 630                 635                 640
Gln Leu Ala Asp Gly Gly Leu Ser Pro Met Leu Gly Gln Asp Ala Gln
                645                 650                 655
Gly Pro Thr Ala Val Leu Lys Ser Val Ser Lys Leu Asp Asn Thr Leu
            660                 665                 670
```

```
Leu Ser Asn Gly Thr Leu Leu Asn Val Lys Phe Thr Pro Ala Thr Leu
            675                 680                 685

Glu Gly Glu Ala Gly Leu Arg Lys Leu Ala Asp Phe Leu Arg Ala Phe
        690                 695                 700

Thr Gln Leu Lys Leu Gln His Ile Gln Phe Asn Val Val Asn Ala Asp
705                 710                 715                 720

Thr Leu Arg Glu Ala Gln Gln Arg Pro Gln Asp Tyr Ala Gly Leu Val
                725                 730                 735

Val Arg Val Ala Gly Tyr Ser Ala Phe Phe Val Glu Leu Ser Lys Glu
            740                 745                 750

Ile Gln Asp Asp Ile Ile Arg Arg Thr Ala His Gln Leu
            755                 760                 765

(2) INFORMATION FOR SEQ ID NO:35:

(i) SEQUENCE CHARACTERISTICS:
        (A) LENGTH: 760 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:35:

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
        50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
        130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
        210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255
```

```
Gln Trp Thr Tyr Phe Gly Tyr Leu Ala Ala Val Lys Ser Gln Asn Gly
              260                 265                 270

Ala Ala Met Ser Phe Gly Arg Thr Ser Thr Phe Leu Asp Val Tyr Ile
            275                 280                 285

Glu Arg Asp Leu Lys Ala Gly Lys Ile Thr Glu Gln Glu Ala Gln Glu
        290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
            355                 360                 365

Glu Pro Asn Met Thr Ile Leu Trp Ser Glu Lys Leu Pro Leu Asn Phe
        370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
            435                 440                 445

Gly Gly Val Asp Glu Lys Leu Lys Met Gln Val Gly Pro Lys Ser Glu
            450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
        530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
        610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
```

```
                675                 680                 685
Leu Met Asp Gly Tyr Phe His His Glu Ala Ser Ile Glu Gly Gly Gln
        690                 695             700
His Leu Asn Val Asn Val Met Asn Arg Glu Met Leu Leu Asp Ala Met
705                 710                 715                 720
Glu Asn Pro Glu Lys Tyr Pro Gln Leu Thr Ile Arg Val Ser Gly Tyr
            725                 730                 735
Ala Val Arg Phe Asn Ser Leu Thr Lys Glu Gln Gln Gln Asp Val Ile
            740                 745                 750
Thr Arg Thr Phe Thr Gln Ser Met
            755                 760

(2) INFORMATION FOR SEQ ID NO:36:

(i) SEQUENCE CHARACTERISTICS:
        (A) LENGTH: 308 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:36:

Met Leu Glu Arg Asn Arg Glu Ala Thr Met Ile Phe Asn Ile Gln Arg
1               5                   10                  15
Tyr Ser Thr His Asp Gly Pro Gly Ile Arg Thr Val Val Phe Leu Lys
                20                  25                  30
Gly Cys Ser Leu Gly Cys Arg Trp Cys Gln Asn Pro Glu Ser Arg Ala
            35                  40                  45
Arg Thr Gln Asp Leu Leu Tyr Asp Ala Arg Leu Cys Leu Glu Gly Cys
        50                  55                  60
Glu Leu Cys Ala Lys Ala Ala Pro Glu Val Ile Glu Arg Ala Leu Asn
65                  70                  75                  80
Gly Leu Leu Ile His Arg Glu Lys Leu Thr Pro Glu His Leu Thr Ala
                85                  90                  95
Leu Thr Asp Cys Cys Pro Thr Gln Ala Leu Thr Val Cys Gly Glu Val
                100                 105                 110
Lys Ser Val Glu Glu Ile Met Thr Thr Val Leu Arg Asp Lys Pro Phe
            115                 120                 125
Tyr Asp Arg Ser Gly Gly Gly Leu Thr Leu Ser Gly Gly Glu Pro Phe
        130                 135                 140
Met Gln Pro Glu Met Ala Met Ala Leu Leu Gln Ala Ser His Glu Ala
145                 150                 155                 160
Gly Ile His Thr Ala Val Glu Thr Cys Leu His Val Pro Trp Lys Tyr
                165                 170                 175
Ile Ala Pro Ser Leu Pro Tyr Ile Asp Leu Phe Leu Ala Asp Leu Lys
                180                 185                 190
His Val Ala Asp Ala Pro Phe Lys Gln Trp Thr Asp Gly Asn Ala Ala
            195                 200                 205
Arg Val Leu Asp Asn Leu Lys Lys Leu Ala Ala Gly Lys Lys Ile
        210                 215                 220
Ile Ile Arg Val Pro Leu Ile Gln Gly Phe Asn Ala Asp Glu Thr Ser
225                 230                 235                 240
Val Lys Ala Ile Thr Asp Phe Ala Ala Asp Glu Leu His Val Gly Glu
                245                 250                 255
Ile His Phe Leu Pro Tyr His Thr Leu Gly Ile Asn Lys Tyr His Leu
```

```
                    260                 265                 270
Leu Asn Leu Pro Tyr Asp Ala Pro Glu Lys Pro Leu Asp Ala Pro Glu
        275                 280                 285

Leu Leu Asp Phe Ala Gln Gln Tyr Ala Cys Gln Lys Gly Leu Thr Ala
    290                 295                 300

Thr Leu Arg Gly
305

(2) INFORMATION FOR SEQ ID NO:37:

(i) SEQUENCE CHARACTERISTICS:
        (A) LENGTH: 292 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:37:

Met Thr Ser Ser Ala Gly Gln Arg Ile Ser Cys Asn Val Val Glu Thr
1               5                   10                  15

Arg Arg Asp Asp Val Ala Arg Ile Phe Asn Ile Gln Arg Tyr Ser Leu
            20                  25                  30

Asn Asp Gly Glu Gly Ile Arg Thr Val Val Phe Phe Lys Gly Cys Pro
        35                  40                  45

His Leu Cys Pro Trp Cys Ala Asn Pro Glu Ser Ile Ser Gly Lys Ile
    50                  55                  60

Gln Thr Val Arg Arg Glu Ala Lys Cys Leu His Cys Ala Lys Cys Leu
65                  70                  75                  80

Arg Asp Ala Asp Glu Cys Pro Ser Gly Ala Phe Glu Arg Ile Gly Arg
                85                  90                  95

Asp Ile Ser Leu Asp Ala Leu Glu Arg Glu Val Met Lys Asp Asp Ile
            100                 105                 110

Phe Phe Arg Thr Ser Gly Gly Val Thr Leu Ser Gly Gly Glu Val
        115                 120                 125

Leu Met Gln Ala Glu Phe Ala Thr Arg Phe Leu Gln Arg Leu Arg Leu
    130                 135                 140

Trp Gly Val Ser Cys Ala Ile Glu Thr Ala Gly Asp Ala Pro Ala Ser
145                 150                 155                 160

Lys Leu Leu Pro Leu Ala Lys Leu Cys Asp Glu Val Leu Phe Asp Leu
                165                 170                 175

Lys Ile Met Asp Ala Thr Gln Ala Arg Asp Val Val Lys Met Asn Leu
            180                 185                 190

Pro Arg Val Leu Glu Asn Leu Arg Leu Val Ser Glu Gly Val Asn
        195                 200                 205

Val Ile Pro Arg Leu Pro Leu Ile Pro Gly Phe Thr Leu Ser Arg Glu
    210                 215                 220

Asn Met Gln Gln Ala Leu Asp Val Leu Ile Pro Leu Asn Ile Arg Gln
225                 230                 235                 240

Ile His Leu Leu Pro Phe His Gln Tyr Gly Glu Pro Lys Tyr Arg Leu
                245                 250                 255

Leu Gly Lys Thr Trp Ser Met Lys Glu Val Pro Ala Pro Ser Ser Ala
            260                 265                 270

Asp Val Ala Thr Met Arg Glu Met Ala Glu Arg Ala Gly Leu Gln Val
        275                 280                 285

Thr Val Gly Gly
```

290

(2) INFORMATION FOR SEQ ID NO:38:

(i) SEQUENCE CHARACTERISTICS:
        (A) LENGTH: 246 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:38:

```
Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
            20                  25                  30

Arg Cys Leu Tyr Cys His Asn Arg Asp Thr Trp Asp Thr His Gly Gly
                35                  40                  45

Lys Glu Val Thr Val Glu Asp Leu Met Lys Glu Val Val Thr Tyr Arg
        50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
            115                 120                 125

Leu Asp Leu Lys Gln Met Asn Asp Glu Ile His Gln Asn Leu Val Gly
        130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220

Pro Lys Lys Glu Thr Met Glu Arg Val Lys Gly Ile Leu Glu Gln Tyr
225                 230                 235                 240

Gly His Lys Val Met Phe
            245
```

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:39:

GTGCGCGTTT CCGCCTACAG CGCTC                                          25

(2) INFORMATION FOR SEQ ID NO:40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:40:

GAGCGCTGTA GGCGGAAACG CGCAC                              25

(2) INFORMATION FOR SEQ ID NO:41:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

CAACGTGCTG GCCATGTCGC CCGGCATCC                         29

(2) INFORMATION FOR SEQ ID NO:42:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

GGATGCCGGG CGACATGCCC AGCACGTTG                         29